US012540192B2

(12) United States Patent
Tavernier et al.

(10) Patent No.: US 12,540,192 B2
(45) Date of Patent: Feb. 3, 2026

(54) CD20 BINDING SINGLE DOMAIN ANTIBODIES

(71) Applicants: VIB VZW, Ghent (BE); Universiteit Gent, Ghent (BE)

(72) Inventors: Jan Tavernier, Balegem (BE); Anje Cauwels, Merelbeke (BE); José Van Der Heyden, Munte (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 926 days.

(21) Appl. No.: 17/557,729

(22) Filed: Dec. 21, 2021

(65) Prior Publication Data

US 2022/0185904 A1 Jun. 16, 2022

Related U.S. Application Data

(63) Continuation of application No. 16/082,300, filed as application No. PCT/EP2017/055312 on Mar. 7, 2017, now Pat. No. 11,248,057.

(30) Foreign Application Priority Data

Mar. 7, 2016 (EP) .................................... 16158962
Apr. 20, 2016 (EP) .................................... 16166206

(51) Int. Cl.

| | |
|---|---|
| ***C07K 16/28*** | (2006.01) |
| ***A61K 31/704*** | (2006.01) |
| ***A61K 33/243*** | (2019.01) |
| ***A61K 39/00*** | (2006.01) |
| ***A61K 39/395*** | (2006.01) |
| ***A61K 45/06*** | (2006.01) |
| ***A61P 35/00*** | (2006.01) |
| ***A61P 37/06*** | (2006.01) |
| ***C07K 14/56*** | (2006.01) |
| ***C07K 14/715*** | (2006.01) |
| ***C07K 16/30*** | (2006.01) |
| *A61K 38/00* | (2006.01) |

(52) U.S. Cl.

CPC ........ *C07K 16/2887* (2013.01); *A61K 31/704* (2013.01); *A61K 33/243* (2019.01); *A61K 39/001124* (2018.08); *A61K 39/3955* (2013.01); *A61K 45/06* (2013.01); *A61P 35/00* (2018.01); *A61P 37/06* (2018.01); *C07K 14/56* (2013.01); *C07K 14/7156* (2013.01); *C07K 16/3061* (2013.01); *A61K 38/00* (2013.01); *A61K 2039/505* (2013.01); *C07K 2317/33* (2013.01); *C07K 2317/569* (2013.01); *C07K 2319/00* (2013.01)

(58) Field of Classification Search

None

See application file for complete search history.

(56) References Cited

U.S. PATENT DOCUMENTS

| | | | |
|---|---|---|---|
| 5,914,254 | A | 6/1999 | Mascarenhas et al. |
| 8,980,267 | B2 | 3/2015 | Grewal et al. |
| 9,139,634 | B2 | 9/2015 | Morrison et al. |
| 9,534,056 | B2 | 1/2017 | Grewal et al. |
| 2010/0172868 | A1 | 7/2010 | Morrison et al. |
| 2010/0297076 | A1 | 11/2010 | Morrison et al. |
| 2011/0081341 | A1 | 4/2011 | Honjo et al. |
| 2011/0104112 | A1 | 5/2011 | Morrison et al. |
| 2011/0224407 | A1 | 9/2011 | Langer et al. |
| 2011/0274658 | A1 | 11/2011 | Silver et al. |
| 2013/0183298 | A1 | 7/2013 | Le et al. |
| 2014/0348789 | A1 | 11/2014 | Tavernier et al. |
| 2015/0139951 | A1 | 5/2015 | Grewal et al. |

FOREIGN PATENT DOCUMENTS

| | | | |
|---|---|---|---|
| WO | 9102754 | A1 | 3/1991 |
| WO | 2003033720 | A2 | 4/2003 |
| WO | 2006053883 | A1 | 5/2006 |
| WO | 2006115800 | A2 | 11/2006 |
| WO | 2008014612 | A1 | 2/2008 |
| WO | 2008124086 | A2 | 10/2008 |
| WO | 2009003145 | A1 | 12/2008 |
| WO | 2009039409 | A1 | 3/2009 |
| WO | 2010036918 | A2 | 4/2010 |
| WO | 2010066740 | A1 | 6/2010 |
| WO | 2011020783 | A2 | 2/2011 |
| WO | 2011029870 | A1 | 3/2011 |
| WO | 2012/096924 | A1 | 7/2012 |
| WO | 2012170072 | A1 | 12/2012 |
| WO | 2013059885 | A2 | 5/2013 |
| WO | 2013107791 | A1 | 7/2013 |
| WO | 2013134138 | A1 | 9/2013 |
| WO | WO 2014164680 | A1 | 10/2014 |
| WO | 2015007536 | A1 | 1/2015 |
| WO | 2015007542 | A1 | 1/2015 |

(Continued)

OTHER PUBLICATIONS

International Search Report, PCT Appl. No. PCT/EP2017/055312, dated Sep. 14, 2017, 6 pages.
Acres, B., et al., "Fusokine Interleukin-2/Interleukin-18, a Novel Potent Innate and Adaptive Immune Stimulator with Decreased Toxicity", Cancer Res., vol. 65, No. 20, (2005), pp. 9536-9546.
Baba, M., et al., "Identification of CCR6, the Specific Receptor for a Novel Lymphocyte-Directed CC Chemokine LARC", The Journal of Biological Chemistry vol. 272, No. 23, (1997), pp. 14893-14898.
Bork "Powers and Pitfalls in Sequence Analysis: The 70% Hurdle", Genome Research, vol. 10 (2000), pp. 398-400.
Bork et al., "Go hunting in sequence databases but watch out for the traps." Trends in Genetics vol. 12 (1996), pp. 425-427.

(Continued)

*Primary Examiner* — Gary B Nickol
*Assistant Examiner* — Cheom-Gil Cheong
(74) *Attorney, Agent, or Firm* — Morgan, Lewis & Bockius LLP

(57) ABSTRACT

The present application relates, in part, to agents that bind CD20 and their use as therapeutic agents. The present application further relates to pharmaceutical compositions comprising the CD20 binding agents and their use in the treatment of various diseases.

16 Claims, 30 Drawing Sheets

Specification includes a Sequence Listing.

(56) References Cited

FOREIGN PATENT DOCUMENTS

| | | | |
|---|---|---|---|
| WO | WO 2015007520 | A1 | 1/2015 |
| WO | WO 2015007903 | A1 | 1/2015 |
| WO | 2017077382 | A1 | 5/2017 |

OTHER PUBLICATIONS

Boschert et al., Single chain TNF derivatives with individually mutated receptor binding sites reveal differential stoichiometry of ligand receptor complex formation for TNFR1 and TNFR2. Cellular Signalling 22 (7):1088-1096, 2010.
Bremer et al., Superior activity of fusion protein scFvRit:sFasL over cotreatment with rituximab and Fas agonists. Cancer Res. 68:597-604, 2008.
Camacho, N.P., et al., "Structure of an Interleukin-1β Mutant With Reduced Bioactivity Shows Multiple Subtle Changes In Conformation That Affect Protein-Protein Recognition", Biochemistry, vol. 32, No. 34, (1993), pp. 8749-8757.
Coulstock, E., et al., "Liver-Targeting of Interferon-Alpha with Tissue Specific Domain Antibodies." PLOS ONE, vol. 8, No. 2, (2013), pp. 1-11.
De Bruyn, M., et al., "Antibody-Based Fusion Proteins to Target Death Receptors in Cancer", Cancer Letters, vol. 332, (2013), pp. 175-183.
Deffar et al., "Nanobodies—The New Concept in Antibody Engineering" African Journal of Biotechnology, 2009, vol. 8 No. 12, pp. 2645-2652.
Dijkmans, R., et al., "Murine Interferon-γ/Interleukin-1 Fusion Proteins Used as Antigens for the Generation of Hybridomas Producing Monoclonal Anti-Interleukin-1 Antibodies", Cytokine, vol. 3, No. 2, (1991), pp. 134-140.
Dimitrov, D. S., "Engineered CH2 Domains (Nanoantibodies)", mAbs, Landes Bioscience, vol. 1, No. 1, (2009), pp. 26-28.
Frey, K., et al., "Antibody-Based Targeting of Interferon-Alpha to the Tumor Neovasculature: A Critical Evaluation", Integrative Biology, vol. 3, (2011), p. 468-478.
Garlanda et al., "The Interleukin-1 Family: Back to the Future", Immunity, Dec. 12, 2013, 39(6) 1003-1018.
Joller, N., et al: "Two Adjacent Trimeric Fas Ligands are Required for Fas Signaling and Formation of a Death-Inducing Signaling Complex", Molecular and Cellular Biology, vol. 23, No. 4, (2003), pp. 1428-1440.
Huang, T., et al., "A Trimeric Anti-HER2/neu ScFv and Tumor Necrosis Factor-[alpha] Fusion Protein Induces HER2/Neu Signaling and Facilitates Repair of Injured Epithelia", The Journal of Pharmacology and Experimental Therapeutics, vol. 316, No. 3, (2006), pp. 983-991.
Krippner-Heidenreich, A., et al: "Single-Chain TNF, a TNF Derivative with Enhanced Stability and Antitumoral Activity", The Journal of Immunology, vol. 180, (2008), pp. 8176-8183.
Masci, P. et al., "New and Modified Interferon alfas: Preclinical and Clinical Data", Current Oncology Reports, vol. 5, (2003), pp. 108-113.
Ngo et al., "Computational Complexity, Protein Structure Prediction, and the Levinthal Paradox. The Protein Folding Problem and Tertiary Structure Prediction", Edited by: Mertz et al., (Birkhauser, Boston), (1994), pp. 492-495.
Pan, M., et al., "Mutation of the IFNAR-1 Receptor Binding Site of Human IFN-[alpha]2 Generates Type I IFN Competitive Antagonists", Biochemistry, vol. 47, (2008), pp. 12018-12027.
Patris, et al., "Nanoimmunoassay onto a screen printed electrode for HER2 breast cancer biomarker determination", Talanta, 2014, vol. 130 pp. 164-170.
Penafuerte, C., et al., "The Human Ortholog of Granulocyte Macrophage Colony-Stimulating Factor and Interleukin-2 Fusion Protein Induces Potent Ex Vivo Natural Killer Cell Activation and Maturation", Cancer Res, vol. 69, No. 23, (2009), pp. 9020-9028.
Rafei, M., et al., "A MCP1 Fusokine with CCR2-Specific Tumoricidal Activity", Molecular Cancer, vol. 10, No. 121, (2011), pp. 1-11.
Rafei, M., et al., "An Engineered GM-CSF-CCL2 Fusokine Is A Potent Inhibitor of CCR2-Driven Inflammation as Demonstrated in a Murine Model of Inflammatory Arthritis", The Journal of Immunology, vol. 183, (2009), pp. 1759-1766.
Roisman, LC., et al., "Structure of the Interferon-Receptor Complex Determined by Distant Constraints from Double Mutant Cycles and Flexible Docking", PNAS, vol. 98, No. 23, (2001), pp. 13231-13236.
Rovero S et al., "Insertion of the DNA for the 163-171 Peptide of IL 1β Enables a DNA Vaccine Encoding p185neu to Inhibit Mammary Carcinogenesis in Her-2/neu Transgenic BALB/c Mice", Gene Therapy, vol. 8, (2001), pp. 447-452.
Schutyser, E., et al., "The CC Chemokine CCL20 and its Receptor CCR6", Cytokine & Growth Factor Reviews, vol. 14, (2003), pp. 409-426.
Vaneycken, et al., "Preclinical Screening of Anti-HER2 Nanobodies for Molecular Imaging of Breast Cancer", The FASEB Journal, 2011, vol. 25, pp. 2433-2446.
Weber, H., et al., "Single Amino Acid Changes that Render Human IFN-[alpha]2 Biologically Active on Mouse Cells", The EMBO Journal, vol. 6, No. 3, (1987), pp. 591-598.
Wells, "Additivity of mutational effects in proteins." Biochemistry, vol. 29, No. 37, (1990), pp. 8509-8517.
Wesolowski et al., "Single Domain Antibodies: Promising Experimental and Therapeutic Tools in Infection and Immunity", Med Microbiol Immunol. 2009, vol. 198 pp. 157-174.
Barbara, J A et al., "Dissociation of TNF-alpha cytotoxic and proinflammatory activities by p55 receptor- and p75 receptor-selective TNF-alpha mutants," EMBO Journal, vol. 13, No. 4, (1994) pp. 843-850.
Garcin, Genevieve et al., "High Efficiency cell-specific targeting of cytokine activity," Nature Communications, vol. 5, No. 8 (2014).
Loetscher, H et al., "Human Tumor Necrosis Factor alpha (TNFalpha) Mutants with Exclusive Specificity for the 55-kDa or 75-kDa TNF Receptors," Journal of Biological Chemistry, American Society For Biochemistry and Molecular Biology, US, vol. 268, No. 35 (1993) pp. 26350-26357.
Uchida, et al., "Mouse CD20 expression and function, International Immunology", vol. 16, Issue 1, pp. 119-129 (2004).
Mitchell, et al., "Comparative analysis of nanobody sequence and structure data." Proteins: Structure, Function, and Bioinformatics 86.7, pp. 697-706 (2018).
Caljon, et al., "Affinity is an important determinant of the anti-trypanosome activity of nanobodies." PLoS neglected tropical diseases 6.11, e1902 (2012).
Liu, et al., "Selection and characterization of single domain antibodies against human CD20." Molecular immunology vol. 78, 146-154 (2016).

Figure 2 continued

```
2HCD16  : GTATCTGCAAATGAACAGCCTGAAACCTGAGGATACGGCCGTTTATTACTGTGCAGCCCCCGTTTCGTA---CGGTAGTCAGTGGCTTGCGG------------------------AC : 327
2HCD22  : GTATCTGCAAATGAACAGCCTGAAACCTGAGGATACGGCCGTTTATTACTGTGCAGCCCCCGTTTCGTA---CGGTAGTCAGTGGCTTGCGG------------------------AC : 327
2HCD42  : GTATCTGCAAATGAACAGCCTGAAACCTGAGGATACGGCCGTTTATTACTGTGCAGCCCCCGTTTCGTA---CGGTAGTCAGTGGCTTGCGG------------------------AC : 327
2HCD73  : GTATCTGCAAATGAACAGCCTGAAACCTGAGGATACGGCCGTTTATTACTGTGCAGCCCCCGTTTCGTA---CGGTAGTCAGTGGCTTGCGG------------------------AC : 327
2HCD35  : GCATCTGCAAATGAACAGCCTGAAACCTGAGGATACGGCCGTTTATTACTGTGCAGCCCCCGTTTCGTA---CGGTAGTCAGTGGCTTGCGG------------------------AC : 327
2HCD81  : GTATCTGCAAATGAACAGCCTGAAACCTGAGGACACGGCCGTTTATTACTGTGCAGCCCCCGTTTCGTA---CGGTAGTAGCTGGCTTGCGG------------------------AC : 327
R3CD105 : GTATCTGCAAATGAACAGCCTGAAACCTGAGGACACGGCCGTTTATTACTGTGCAGCTCCTTTATCGTA---CGGCAGTACCTGGTTAGCTG------------------------AC : 327
R3CD18  : GTATCTGCAAATGAACAGACTGAAACCTGAGGACACGGCCGTTTATTACTGTGCAGGAGGCGTTTCCTT---CGGTAGTAGGTGGTTGTCCG------------------------AC : 327
2HCD17  : GTATCTGCAAATGAACAGCCTGAAACCTGAGGACACGGCCGTTTATTACTGTGCAGCAAATCCTACGTA---CAGTGGTGGCTGGCACGCGG------------------------AA : 327
2HCD40  : GTATCTGCAAATGAACAGCCTGAAACCTGAGGACACGGCCGTTTATTACTGTGCAGCAAATCCTACGTA---CAGTGGTGGCTGGCACGCGG------------------------AA : 327
2HCD88  : GTATCTGCAAATGAACAGCCTGAAACCTGAGGACACGGCCGTTTATTACTGTGCAGCAAATCCTACGTA---CAGTGGTGGCTGGCACGCGG------------------------AA : 327
2HCD59  : GTATCTGCAAATGAACAGCCTGAAACCTGAGGACACGGCCGTTTATTACTGTGCAGCAAATCCTACGTA---CAGTGGTGGCTGGCACGCGG------------------------AA : 327
2HCD68  : GTATCTGCAAATGAACAGCCTGAAACCTGAGGACACGGCCGTTTATTACTGTGCAGCAAATCCTACGTA---CAGTGGTGGCTGGCACGCGG------------------------AA : 327
R3CD7   : GTATCTGCAAATGAACAGCCTGAAACCTGAGGACACGGCCGTTTATTATTGTGCAGCAGGGGTTTCGTA---CGGTAGTAGGTGGTTGGGGG------------------------AT : 327
2HCD25  : GTATCTGCAAATGAACAGCCTGAAACCTGAGGACACGGCCGTTTATTACTGCGCAGCAAATCCTACGTA---CGGTAGTGACTGGAACGCGG------------------------AA : 318
2HCD78  : GTATCTGCAAATGAACAGCCTGAAACCTGAGGACACGGCCGTTTATTACTGCGCAGCAAATCCTACGTA---CGGTAGTGACTGGAACGCGG------------------------AA : 318
2HCD43  : GTATCTGCTAATGAACAGCCTGAAACCTGAGGACACGGCCGTTTATTACTGTGCAGCCGAACGAACATGGGTCAGTAATTACTACTGTTCAGGCGACGGAGACGGATATGACTATGAC : 354

                360         *        380         *        400         *        420         *        440         *
2HCD16  : TACTGGGGCCAGGGGACCCAGGTCACCGTCTCCTCAGCGGCCGCATACCCGTACGACGTTCCGGACTACGGTTCCCACCACCATCACCATCACTAG : 423 (SEQ ID NO:1)
2HCD22  : TACTGGGGCCAGGGGACCCAGGTCACCGTCTCCTCAGCGGCCGCATACCCGTACGACGTTCCGGACTACGGTTCCCACCACCATCACCATCACTAG : 423 (SEQ ID NO:2)
2HCD42  : TACTGGGGCCAGGGGACCCAGGTCACCGTCTCCTCAGCGGCCGCATACCCGTACGACGTTCCGGACTACGGTTCCCACCACCATCACCATCACTAG : 423 (SEQ ID NO:3)
2HCD73  : TACTGGGGCCAGGGGACCCAGGTCACCGTCTCCTCAGCGGCCGCATACCCGTACGACGTTCCGGACTACGGTTCCCACCACCATCACCATCACTAG : 423 (SEQ ID NO:4)
2HCD35  : TACTGGGGCCAGGGGACCCAGGTCACCGTCTCCTCAGCGGCCGCATACCCGTACGACGTTCCGGACTACGGTTCCCACCACCATCACCATCACTAG : 423 (SEQ ID NO:5)
2HCD81  : TACTGGGGCCAGGGGACCCAGGTCACCGTCTCCTCAGCGGCCGCATACCCGTACGACGTTCCGGACTACGGTTCCCACCACCATCACCATCACTAG : 423 (SEQ ID NO:6)
R3CD105 : TACTGGGGCCAGGGGACCCAGGTCACCGTCTCCTCAGCGGCCGCATACCCGTACGACGTTCCGGACTACGGTTCCCACCACCATCACCATCACTAG : 423 (SEQ ID NO:7)
R3CD18  : TACTGGGGCCAGGGGACCCAGGTCACCGTCTCCTCAGCGGCCGCATACCCGTACGACGTTCCGGACTACGGTTCCCACCACCATCACCATCACTAG : 423 (SEQ ID NO:8)
2HCD17  : TACTGGGGCCAGGGGACCCAGGTCACCGTCTCCTCAGCGGCCGCATACCCGTACGACGTTCCGGACTACGGTTCCCACCACCATCACCATCACTAG : 423 (SEQ ID NO:9)
2HCD40  : TACTGGGGCCAGGGGACCCAGGTCACCGTCTCCTCAGCGGCCGCATACCCGTACGACGTTCCGGACTACGGTTCCCACCACCATCACCATCACTAG : 423 (SEQ ID NO:10)
2HCD88  : TACTGGGGCCAGGGGACCCAGGTCACCGTCTCCTCAGCGGCCGCATACCCGTACGACGTTCCGGACTACGGTTCCCACCACCATCACCATCACTAG : 423 (SEQ ID NO:11)
2HCD59  : TACTGGGGCCAGGGGACCCAGGTCACCGTCTCCTCAGCGGCCGCATACCCGTACGACGTTCCGGACTACGGTTCCCACCACCATCACCATCACTAG : 423 (SEQ ID NO:12)
2HCD68  : TACTGGGGCCAGGGGACCCAGGTCACCGTCTCCTCAGCGGCCGCATACCCGTACGACGTTCCGGACTACGGTTCCCACCACCATCACCATCACTAG : 423 (SEQ ID NO:13)
R3CD7   : TACTGGGGCCAGGGGACCCAGGTCACCGTCTCCTCAGCGGCCGCATACCCGTACGACGTTCCGGACTACGGTTCCCACCACCATCACCATCACTAG : 423 (SEQ ID NO:14)
2HCD25  : AATTGGGGCCAGGGGACCCAGGTCACCGTCTCCTCAGCGGCCGCATACCCGTACGACGTTCCGGACTACGGTTCCCACCACCATCACCATCACTAG : 414 (SEQ ID NO:15)
2HCD78  : AATTGGGGCCAGGGGACCCAGGTCACCGTCTCCTCAGCGGCCGCATACCCGTACGACGTTCCGGACTACGGTTCCCACCACCATCACCATCACTAG : 414 (SEQ ID NO:16)
2HCD43  : TACTGGGGCCAGGGGACCCAGGTCACCGTCTCCTCAGCGGCCGCATACCCGTACGACGTTCCGGACTACGGTTCCCACCACCATCACCATCACTAG : 450 (SEQ ID NO:17)
```

Figure 6 continued

```
                    240         *        260         *        280         *        300         *        320         *        340         *
2MC57      : GTGTATCTGCAAATGAACAGCCTGAAACCTGAGGACACGGCCGTTTATTACTGTGCAATGC--CCCGTACCTGGGGGGAGTTTCCACCTACCCAGTATGACTCGTGGGGCCAGGGGA : 349
R3MUC17    : GTGTATCTGCAAATGAACAGCCTGAAACCTGAGGACACGGCCGTTTATTACTGTGCAGCAC--CCCGTACCTGGGGGGAGTTTCCACCTACCCAGTATGACTCGTGGGGCCAGGGGA : 349
R2MUC70    : GTGTATCTGCAAATGAACAGCCTGAAACCTGAGGACACGGCCGTTTATTACTGTGCAGCAC--CCCGTACCTGGGGGGAGTTTCCACCTACCCAGTATGACTCGTGGGGCCAGGGGA : 349
R3MUC66    : GTGTATCTGCAAATGAACAGCCTGAGACCTGAGGACACGGCCGTTTATTACTGTGCAGCAC--CCCGTACCTGGGGGGAGTTTCCACCTACCCAGTATGACTCGTGGGGCCAGGGGA : 349
R3MUC57    : GTGTATCTGCAAATGAACAGCCTGAAACCTGAGGACACGGCCGTTTATTACTGTGCAGCAC--CCCGTACCTGGGGGGAGTTTCCACCTACCCAGTATGACTCGTGGGGCCAGGGGA : 349
R3MUC56    : GTGTATCTGCAAATGAACAGCCTGAAACCTGAGGACACGGCCGTTTATTACTGTGCAGCAC--CCCGTACCTGGGGGGAGTTTCCACCTACCCAGTATGACTCGTGGGGCCAGGGGA : 349
R2MUC85    : GTGTATCTGCAAATGAACAGCCTGAAACCTGAGGACACGGCCGTTTATTACTGTGCAGCAC--CCCGTACCTGGGGGGAGTTTCCACCTACCCAGTATGACTCGTGGGGCCAGGGGA : 349
R3MUC58    : GTGTATCTGCAAATGAACAGCCTGAAACCTGAGGACACGGCCGTTTATTACTGTGCAGCAC--CCCGTACCTGGGGGGAGTTTCCACCTACCCAGTATGACTCGTGGGGCCAGGGGA : 349
R2MUC21    : GTGTATCTGCAAATGAACAGCCTGAAACCTGAGGACACGGCCGTTTATTACTGTGCAGCAC--CCCGTACCTGGGGGGAGTTTCCACCTACCCAGTATGACTCGTGGGGCCAGGGGA : 349
R3MUC75    : GTGTATCTGCAAATGAACAGCCTGAAACCTGAGGACACGGCCGTTTATTACTGTGCAGCAC--CCCGTACCTGGGGGGAGTTTCCACCTACCCAGTATGACTCGTGGGGCCAGGGGA : 349
R3MUC22    : GTGTATCTGCAAATGAACAGCCTGAAACCTGAGGACACGGCCGTTTATTACTGTGCAGCAC--CCCGTACCTGGGGGGAGTTTCCACCTACCCAGTATGACTCGTGGGGCCAGGGGA : 349
2MC52      : GTGTATCTGCAAATGAACAGCCTGAAACCTGAGGACACGGCCGTTTATTACTGTGCGTCAC--CCCGTACCTGGGGGGAGTTTCCACCTACTCAGTATGACTCGTGGGGCCAGGGGA : 349
R2MUC36    : GTGTATCTGTCAATGAATAGCCTGAAACCTGAGGACACGGCCGTTTATTATTGTGCAGCTG--ATCGAAGCATTGAGG---TCCAAATCGGGATTATGACTACTGGGGCCGGGGGA : 346
2MC51      : GTGTATCTGCAAATGAACAGCCTGAAACCTGAGGACACGGCCGTTTATTACTGTGTAGCTG--GCAAGTACGGTATGAAGTGGAGGGATGGCGC---TGACTACTGGGGCCAGGGGA : 346
2MC39      : GTGTATCTGCAAATGAACAGCCTGAAACCTGAGGACACGGCCGTTTATTACTGTGCAGCTG--GCAAGTACGGTATGAAGTGGAGGGATGGCGC---TGACTACTGGGGCCAGGGGA : 346
2MC82      : GTGTATCTGCAAATGAACAGCCTGAAACCTGAGGACACGGCCGTTTATTACTGTGCAGCTG--GCAAGTACGGTATGAAGTGGAGGGATGGCGC---TGACTACTGGGGCCAGGGGA : 346
2MC38      : GTGTATCTGCAAATGAACAGCCTGAAACCTGAGGACACGGCCGTTTATTACTGTGTAGCTG--GCAAGTACGGTATGAAGTGGAGGGATGGCGC---TGACTACTGGGGCCAGGGGA : 346
2MC20      : GTGTATCTGCAAATGAACAGCCTGAAACCTGAGGACACGGCCGTTTATTACTGTGCAGCTG--GCAAGTACGGTATGAAGTGGAGGGATGGCGC---TGACTACTGGGGCCAGGGGA : 346
2MC42      : GTGTATCTGCAAATGAACAGCCTGAAACCTGAGGACACGGCCGTTTATTACTGTGCAGCTG--GCAAGTACGGTATGAAGTGGAGGGATGGCGC---TGACTACTGGGGCCAGGGGA : 346
R3MCD137   : ATGTATCTGCAAATGGACAGCCTGGAACCTGAGGACACGGCCGTGTATTACTGTTACATAGTACTGCCTACTGGGGGGGAAGCGCCATG------GACTACTGGGGCGAAGGGA : 343
R3MCD22    : ATGTATCTGCAAATGGACAGCCTGAAACCTGAGGACACGGCCGTGTATTACTGCTACATAGTACTGACTACTGGGGGGGAAGCGCCATG------GACTACTGGGGCCAAGGGA : 343

                    360         *        380         *        400         *        420         *
2MC57      : CCCAGGTCACCGTCTCCTCAGCGGCCGCATACCCGTACGACGTTCCGGACTACGGTTCCCACCACCATCACCATCACTAG : 429 (SEQ ID NO:64)
R3MUC17    : CCCAGGTCACCGTCTCCTCAGCGGCCGCATACCCGTACGACGTTCCGGACTACGGTTCCCACCACCATCACCATCACTAG : 429 (SEQ ID NO:65)
R2MUC70    : CCCAGGTCACCGTCTCCTCAGCGGCCGCATACCCGTACGACGTTCCGGACTACGGTTCCCACCACCATCACCATCACTAG : 429 (SEQ ID NO:66)
R3MUC66    : CCCAGGTCACCGTCTCCTCAGCGGCCGCATACCCGTACGACGTTCCGGACTACGGTTCCCACCACCATCACCATCACTAG : 429 (SEQ ID NO:67)
R3MUC57    : CCCAGGTCACCGTCTCCTCAGCGGCCGCATACCCGTACGACGTTCCGGACTACGGTTCCCACCACCATCACCATCACTAG : 429 (SEQ ID NO:68)
R3MUC56    : CCCAGGTCACCGTCTCCTCAGCGGCCGCATACCCGTACGACGTTCCGGACTACGGTTCCCACCACCATCACCATCACTAG : 429 (SEQ ID NO:69)
R2MUC85    : CCCAGGTCACCGTCTCCTCAGCGGCCGCATACCCGTACGACGTTCCGGACTACGGTTCCCACCACCATCACCATCACTAG : 429 (SEQ ID NO:70)
R3MUC58    : CCCAGGTCACCGTCTCCTCAGCGGCCGCATACCCGTACGACGTTCCGGACTACGGTTCCCACCACCATCACCATCACTAG : 429 (SEQ ID NO:71)
R2MUC21    : CCCAGGTCACCGTCTCCTCAGCGGCCGCATACCCGTACGACGTTCCGGACTACGGTTCCCACCACCATCACCATCACTAG : 429 (SEQ ID NO:72)
R3MUC75    : CCCAGGTCACCGTCTCCTCAGCGGCCGCATACCCGTACGACGTTCCGGACTACGGTTCCCACCACCATCACCATCACTAG : 429 (SEQ ID NO:73)
R3MUC22    : CCCAGGTCACCGTCTCCTCAGCGGCCGCATACCCGTACGACGTTCCGGACTACGGTTCCCACCACCATCACCATCACTAG : 429 (SEQ ID NO:74)
2MC52      : CCCAGGTCACCGTCTCCTCAGCGGCCGCATACCCGTACGACGTTCCGGACTACGGTTCCCACCACCATCACCATCACTAG : 429 (SEQ ID NO:75)
R2MUC36    : CCCAGGTCACCGTCTCCTCAGCGGCCGCATACCCGTACGACGTTCCGGACTACGGTTCCCACCACCATCACCATCACTAG : 426 (SEQ ID NO:76)
2MC51      : CCCAGGTCACCGTCTCCTCAGCGGCCGCATACCCGTACGACGTTCCGGACTACGGTTCCCACCACCATCACCATCACTAG : 426 (SEQ ID NO:77)
2MC39      : CCCAGGTCACCGTCTCCTCAGCGGCCGCATACCCGTACGACGTTCCGGACTACGGTTCCCACCACCATCACCATCACTAG : 426 (SEQ ID NO:78)
2MC82      : CCCAGGTCACCGTCTCCTCAGCGGCCGCATACCCGTACGACGTTCCGGACTACGGTTCCCACCACCATCACCATCACTAG : 426 (SEQ ID NO:79)
2MC38      : CCCAGGTCACCGTCTCCTCAGCGGCCGCATACCCGTACGACGTTCCGGACTACGGTTCCCACCACCATCACCATCACTAG : 426 (SEQ ID NO:80)
2MC20      : CCCAGGTCACCGTCTCCTCAGCGGCCGCATACCCGTACGACGTTCCGGACTACGGTTCCCACCACCATCACCATCACTAG : 426 (SEQ ID NO:81)
2MC42      : CCCAGGTCACCGTCTCCTCAGCGGCCGCATACCCGTACGACGTTCCGGACTACGGTTCCCACCACCATCACCATCACTAG : 426 (SEQ ID NO:82)
R3MCD137   : CCCAGGTCACCGTCTCCTCAGCGGCCGCATACCCGTACGACGTTCCGGACTACGGTTCCCACCACCATCACCATCACTAG : 423 (SEQ ID NO:83)
R3MCD22    : CCCAGGTCACCGTCTCCTCAGCGGCCGCATACCCGTACGACGTTCCGGACTACGGTTCCCACCACCATCACCATCACTAG : 423 (SEQ ID NO:84)
```

A.

B.

SEQUENCE LISTING

```
<160> NUMBER OF SEQ ID NOS: 222

<210> SEQ ID NO 1
<211> LENGTH: 423
<212> TYPE: DNA
<213> ORGANISM: Homo sapiens

<400> SEQUENCE: 1

caggtgcagc tgcaggagtc tgggggagga ttggtgcagg ctgggggctc tctgagactc      60

tcctgtgcag cctctggacg caccttcagt agacagtcca tgggctggtt ccgccaggct     120

ccagggaagg agcgtgagtt tgtagcagtc attacctgga gtggtggcag cccatattat     180

gcagactccg tgaggggccg attcaccatc tccagagaca acgccaagaa caccgtgtat     240

ctgcaaatga acagcctgaa acctgaggat acggccgttt attactgtgc agccccccgtt    300

tcgtacggta gtcagtggct tgcggactac tggggccagg ggacccaggt caccgtctcc     360

tcagcggccg catacccgta cgacgttccg gactacggtt cccaccacca tcaccatcac     420

tag                                                                   423


<210> SEQ ID NO 2
<211> LENGTH: 423
<212> TYPE: DNA
<213> ORGANISM: Homo sapiens
```

<400> SEQUENCE: 2
caggtgcagc tgcaggagtc tggggggagga ttggtgcagg ctggggactc tctgagactc 60
tcctgtgcag cctctggacg caccttcagt agacagtcca tgggctggtt ccgccaggct 120
ccagggaagg agcgtgagtt tgtagcagtc attacctgga gtggtggcag cccatattat 180
gcagactccg tgaagggccg attcaccatc tccagagaca acgccaagaa caccgtgtat 240
ctgcaaatga acagcctgaa acctgaggat acggccgttt attactgtgc agcccccgtt 300
tcgtacggta gtcagtggct tgcggactac tggggccagg ggacccaggt caccgtctcc 360
tcagcggccg catacccgta cgacgttccg gactacggtt cccaccacca tcaccatcac 420
tag 423

<210> SEQ ID NO 3
<211> LENGTH: 423
<212> TYPE: DNA
<213> ORGANISM: Homo sapiens

<400> SEQUENCE: 3
caggtgcagc tgcaggagtc tggggggagga ttggtgcagg ctgggggctc tctgagactc 60
tcctgtgcag cctctggacg caccttcagt agctatgcca tgggctggtt ccgccaggct 120
ccagggaagg agcgtgagtt tgtagcagtc attacctgga gtggtggcag cccatattat 180
gcagactccg tgaggggccg attcaccatc tccagagaca acgccaagaa caccgtgtat 240
ctgcaaatga acagcctgaa acctgaggat acggccgttt attactgtgc agcccccgtt 300
tcgtacggta gtcagtggct tgcggactac tggggccagg ggacccaggt caccgtctcc 360
tcagcggccg catacccgta cgacgttccg gactacggtt cccaccacca tcaccatcac 420
tag 423

<210> SEQ ID NO 4
<211> LENGTH: 423
<212> TYPE: DNA
<213> ORGANISM: Homo sapiens

<400> SEQUENCE: 4
caggtgcagc tgcaggagtc tggggggagga ttggtgcaag ctgggggctc tctgagactc 60
tcctgtgcag cctctggacg caccttcagt agacagtcca tgggctggtt ccgccaggct 120
ccaggggagg agcgtgagtt tgtagcagtc attacctgga gtggtggcag cccatattat 180
gcagactccg tgaggggccg attcaccatc tccagagaca acgccaagaa caccgtgtat 240
ctgcaaatga acagcctgaa acctgaggat acggccgttt attactgtgc agcccccgtt 300
tcgtacggka gtcagtggct tgcggactac tggggccagg ggacccaggt caccgtctcc 360
tcagcggccg catacccgta cgacgttccg gactacggtt cccaccacca tcaccatcac 420
tag 423

<210> SEQ ID NO 5
<211> LENGTH: 423
<212> TYPE: DNA
<213> ORGANISM: Homo sapiens

<400> SEQUENCE: 5
caggtgcagc tgcaggagtc tggaggagga ttggtgcagg ctgggggctc tctgagactc 60
tcctgtgcag cctctggacg caccttcagt ggacagtcca tgggctggtt ccgccaggct 120
ccagggaagg agcgtgagtt tgtagcagtc attacctgga gtggtggcag cccatattat 180
gcagactccg tgaggggccg attcaccatc tccagagaca acgccaagaa caccgtgcat 240
ctgcaaatga acagcctgaa acctgaggat acggccgttt attactgtgc agcccccgtt 300
tcgtacggta gtcagtggct tgcggactac tggggccagg ggacccaggt caccgtctcc 360
tcagcggccg catacccgta cgacgttccg gactacggtt cccaccacca tcaccatcac 420
tag 423

<210> SEQ ID NO 6
<211> LENGTH: 423
<212> TYPE: DNA
<213> ORGANISM: Homo sapiens

<400> SEQUENCE: 6
caggtgcagc tgcaggagtc tgggggagga ttggtgcagg ctgggggctc tctgagactc 60
tcctgtgcag cctctggacg caccttcagt agctataaca tgggctggtt ccgccaggct 120
ccagggaagg agcgtgagtt tgtagcagtt attagctgga gtggtggtag cccatactat 180
gcggactccg tgaagggccg attcaccatc tccagagaca acgccaagaa cacggtgtat 240
ctgcaaatga acagcctgaa acctgaggac acggccgttt attactgtgc agcccccgtt 300
tcgtacggta gtagctggct tgcggactac tggggccagg ggacccaggt caccgtctcc 360
tcagcggccg catacccgta cgacgttccg gactacggtt cccaccacca tcaccatcac 420
tag 423

<210> SEQ ID NO 7
<211> LENGTH: 423
<212> TYPE: DNA
<213> ORGANISM: Homo sapiens

<400> SEQUENCE: 7
caggtgcagc tgcaggagtc tgggggagga ttggtgcagg ctgggggctc tctgagactc 60
tcctgtgcag cctctggacg caccttcagt aattataaca tgggctggtt ccgccaggct 120
ccagggaagg agcgtgagtt tgtagcagct attgactgga gtggtggtag cccatactat 180
gcagcctccg tgaggggccg attcaccatc tccagagaca acgccgagaa cacggtgtat 240
ctgcaaatga acagcctgaa acctgaggac acggccgttt attactgtgc agctccttta 300
tcgtacggca gtacctggtt agctgactac tggggccagg ggacccaggt caccgtctcc 360
tcagcggccg catacccgta cgacgttccg gactacggtt cccaccacca tcaccatcac 420
tag 423

<210> SEQ ID NO 8
<211> LENGTH: 423
<212> TYPE: DNA
<213> ORGANISM: Homo sapiens

<400> SEQUENCE: 8
caggtgcagc tgcaggagtc tggaggagga ttggtgcagg ctgggggctc tctgagactc 60
tcctgtgcag cctctggacg caccttcagt aactctaaca tgggctggtt ccgccaggct 120
ccagggaagg agcgtgagtt tgtagcagtt attgactgga gtggtggtag cccatactat 180
acagactccg tgaggggccg attcaccatc tccagagaca acgccaagaa cacggtgtat 240
ctgcaaatga acagactgaa acctgaggac acggccgttt attactgtgc aggaggcgtt 300
tccttcggta gtaggtggtt gtccgactac tggggccagg ggacccaggt caccgtctcc 360
tcagcggccg catacccgta cgacgttccg gactacggtt cccaccacca tcaccatcac 420
tag 423

<210> SEQ ID NO 9
<211> LENGTH: 423
<212> TYPE: DNA
<213> ORGANISM: Homo sapiens

<400> SEQUENCE: 9
caggtgcagc tgcaggagtc tgggggagga ttggtgcagg ctgggggctc tctgagactc 60
tcctgtgcag cctctggacg caccgtcggc agctattcca tgggctggtt ccgccaggct 120
ccagggaagg agcgtgagtt tgtagcagct gttatctgga gtggtgctag tccatactat 180
gcagactccg tgaagggccg attcaccatc tccagagaca acgccaagaa cacggtgtat 240
ctgcaaatga acagcctgaa acctgaggac acggccgttt attactgtgc agcaaatcct 300
acgtacagtg gtggctggca cgcggaatac tggggccagg ggacccaggt caccgtctcc 360
tcagcggccg catacccgta cgacgttccg gactacggtt cccaccacca tcaccatcac 420
tag 423

<210> SEQ ID NO 10
<211> LENGTH: 423
<212> TYPE: DNA
<213> ORGANISM: Homo sapiens

<400> SEQUENCE: 10
caggtgcagc tgcaggagtc tgggggagga ttggtgcagg ctgggggctc tctgagactc 60
tcctgtgcag cctctggacg caccgtcggc agctattcca tgggctggtt ccgccaggct 120
ccagggaagg agcgtgagtt tgtagcagct gttacctgga gtggtgctag tccatactat 180
gcagactccg tgaagggccg attcaccatc tccagagaca acgccaagaa cacggtgtat 240
ctgcaaatga acagcctgaa acctgaggac acggccgttt attactgtgc agcaaatcct 300
acgtacagtg gtggctggca cgcggaatac tggggccagg ggacccaggt caccgtctcc 360
tcagcggccg catacccgta cgacgttccg gactacggtt cccaccacca tcaccatcac 420
tag 423

<210> SEQ ID NO 11
<211> LENGTH: 423
<212> TYPE: DNA
<213> ORGANISM: Homo sapiens

<400> SEQUENCE: 11
caggtgcagc tgcaggagtc tgggggagga ttggtgcagg ctggggactc tctgagactc 60
tcctgtgcag cctctggacg caccgtcggc agctattcca tgggctggtt ccgccaggct 120
ccagggaagg agcgtgagtt tgtagcagct gttacctgga gtggtgctag tccatactat 180
gcagactccg tgaagggccg attcaccatc tccagagaca acgccaagaa cacggtgtat 240
ctgcaaatga acagcctgaa acctgaggac acggccgttt attactgtgc agcaaatcct 300
acgtacagtg gtggctggca cgcggaatac tggggccagg ggacccaggt caccgtctcc 360
tcagcggccg catacccgta cgacgttccg gactacggtt cccaccacca tcaccatcac 420
tag 423

<210> SEQ ID NO 12

<211> LENGTH: 423
<212> TYPE: DNA
<213> ORGANISM: Homo sapiens

<400> SEQUENCE: 12
caggtgcagc tgcaggagtc tgggggaggt tcggagcagc cggggggctc tctgagactc 60
tcctgtgcag cctctggacg caccgtcggc agctattcca tgggctggtt ccgccaggct 120
ccagggaagg agcgtgagtt tgtagcagct gttacccgga gtggtgctag tccatactat 180
gcagactccg tgaagggccg attcaccatc tccagagaca acgccaagaa cacggtgtat 240
ctgcaaatga acagcctgaa acctgaggac acggccgttt attactgtgc agcaaatcct 300
acgtacagtg gtggctggca cgcggaatac tggggccagg ggacccaggt caccgtctcc 360
tcagcggccg catacccgta cgacgttccg gactacggtt cccaccacca tcaccatcac 420
tag 423

<210> SEQ ID NO 13
<211> LENGTH: 423
<212> TYPE: DNA
<213> ORGANISM: Homo sapiens

<400> SEQUENCE: 13
caggtgcagc tgcaggagtc tgggggaggc ttggtgcagc ctggggggtc tctgagactc 60
tcctgtgcag cctctagatt cactttggat tattatgcca taggctggtt ccgccaggcc 120
ccagggaagg agcgtgagtt tgtagcagct gttacctgga gtggtgctag tccatactat 180
gcagactccg tgaagggccg attcaccatc tccagagaca acgccaagaa cacggtgtat 240
ctgcaaatga acagcctgaa acctgaggac acggccgttt attactgtgc agcaaatcct 300
acgtacagtg gtggctggca cgcggaatac tggggccagg ggacccaggt caccgtctcc 360
tcagcggccg catacccgta cgacgttccg gactacggtt cccaccacca tcaccatcac 420
tag 423

<210> SEQ ID NO 14
<211> LENGTH: 423
<212> TYPE: DNA
<213> ORGANISM: Homo sapiens

<400> SEQUENCE: 14
caggtgcagc tgcaggagtc tgggggaggc ttggtgcagg ctggggggtc tctgagactc 60
tcctgtgcag cctctggacg ctccttcagt agcgttaaca tgggctggtt ccgccaggct 120
ccagggaagg agcgtgagtt cgtagcggtt attgactgga gtggcggtag cccatactat 180
acagactccg tgaggggccg attcaccatc tccagagaca actccaagaa cacggtgtat 240
ctgcaaatga acagcctgaa acctgaggac acggccgttt attattgtgc agcaggggtt 300
tcgtacggta gtaggtggtt gggggattac tggggccagg ggacccaggt caccgtctcc 360
tcagcggccg catacccgta cgacgttccg gactacggtt cccaccacca tcaccatcac 420
tag 423

<210> SEQ ID NO 15
<211> LENGTH: 414
<212> TYPE: DNA
<213> ORGANISM: Homo sapiens

<400> SEQUENCE: 15
caggtgcagc tgcaggagtc tgggggagga ttggcgcagg ctgggggctc tctgagactc 60
tcctgtgcag cctctggacg taccttcagt atgggctggt tccgccaggc tccggggaag 120
gagcgtgagt ttgtagcagc aattacctat agtggtggta gtccgtacta tgcgtcgtcc 180
gtgaggggcc gattcaccat ctccagagac aacgccaaga acacggtgta tctgcaaatg 240
aacagcctga aacctgagga cacggccgtt tattactgcg cagcaaatcc tacgtacggt 300
agtgactgga acgcggaaaa ttggggccag gggacccagg tcaccgtctc ctcagcggcc 360
gcatacccgt acgacgttcc ggactacggt tcccaccacc atcaccatca ctag 414

<210> SEQ ID NO 16
<211> LENGTH: 414
<212> TYPE: DNA
<213> ORGANISM: Homo sapiens

<400> SEQUENCE: 16
caggtgcagc tgcaggagtc tggaggaggc ttggtgcagc ccgggggctc tctgagactc 60
tcctgtgcag cctctggacg taccttcagt atgggctggt tccgccaggc tccggggaag 120
gagcgtgagt ttgtagcagc aattacctat agtggtggta gtccgtacta tgcgtcgtcc 180
gtgaggggcc gattcaccat ctccagagac aacgccaaga acacggtgta tctgcaaatg 240
aacagcctga aacctgagga cacggccgtt tattactgcg cagcaaatcc tacgtacggt 300
agtgactgga acgcggaaaa ttggggccag gggacccagg tcaccgtctc ctcagcggcc 360
gcatacccgt acgacgttcc ggactacggt tcccaccacc atcaccatca ctag 414

<210> SEQ ID NO 17
<211> LENGTH: 450
<212> TYPE: DNA
<213> ORGANISM: Homo sapiens

<400> SEQUENCE: 17
caggtgcagc tgcaggagtc tgggggaggc ttggtgcagc ctggggggtc tctgagactc 60
tcctgtacag cctctggatt cactttggat tattatgcca taggctggct ccgccaggcc 120
ccagggaagg agcgtgaggg ggtctcatgt attagtagta gtggtggtag cacaaactat 180
gcagactccg tgaagggccg attcaccatc tccagagaca acgccaagaa cacggtgtat 240
ctgctaatga acagcctgaa acctgaggac acggccgttt attactgtgc agccgaacga 300
acatgggtca gtaattacta ctgttcaggc gacggagacg gatatgacta tgactactgg 360
ggccagggga cccaggtcac cgtctcctca gcggccgcat acccgtacga cgttccggac 420
tacggttccc accaccatca ccatcactag 450

<210> SEQ ID NO 18
<211> LENGTH: 140
<212> TYPE: PRT
<213> ORGANISM: Lama glama

<400> SEQUENCE: 18

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Phe Ser Arg Gln
20 25 30

Ser Met Gly Trp Phe Arg Gln Ala Pro Gly Lys Glu Arg Glu Phe Val
35 40 45

Ala Val Ile Thr Trp Ser Gly Gly Ser Pro Tyr Tyr Ala Asp Ser Val
50 55 60

Arg Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Pro Val Ser Tyr Gly Ser Gln Trp Leu Ala Asp Tyr Trp Gly
100 105 110

Gln Gly Thr Gln Val Thr Val Ser Ser Ala Ala Ala Tyr Pro Tyr Asp
115 120 125

Val Pro Asp Tyr Gly Ser His His His His His His
130 135 140

<210> SEQ ID NO 19
<211> LENGTH: 140
<212> TYPE: PRT
<213> ORGANISM: Lama glama

<400> SEQUENCE: 19

Gln Val Gln Leu Gln Glu Ser Gly Gly Gly Leu Val Gln Ala Gly Asp
1 5 10 15

Ser Leu Arg Leu Ser Cys Ala Ala Ser Gly Arg Thr Phe Ser Arg Gln
20 25 30

Ser Met Gly Trp Phe Arg Gln Ala Pro Gly Lys Glu Arg Glu Phe Val
35 40 45

Ala Val Ile Thr Trp Ser Gly Gly Ser Pro Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Pro Val Ser Tyr Gly Ser Gln Trp Leu Ala Asp Tyr Trp Gly
100 105 110

Gln Gly Thr Gln Val Thr Val Ser Ser Ala Ala Ala Tyr Pro Tyr Asp
115 120 125

Val Pro Asp Tyr Gly Ser His His His His His His
130 135 140

<210> SEQ ID NO 20
<211> LENGTH: 140
<212> TYPE: PRT
<213> ORGANISM: Lama glama

<400> SEQUENCE: 20

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Phe Ser Gly Gln
20 25 30

Ser Met Gly Trp Phe Arg Gln Ala Pro Gly Lys Glu Arg Glu Phe Val
35 40 45

Ala Val Ile Thr Trp Ser Gly Gly Ser Pro Tyr Tyr Ala Asp Ser Val
50 55 60

Arg Gly Arg Phe Thr Ile Ser Arg Asp Asn Ala Lys Asn Thr Val His
65 70 75 80

Leu Gln Met Asn Ser Leu Lys Pro Glu Asp Thr Ala Val Tyr Tyr Cys
85 90 95

```
Ala Ala Pro Val Ser Tyr Gly Ser Gln Trp Leu Ala Asp Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140
```

<210> SEQ ID NO 21
<211> LENGTH: 140
<212> TYPE: PRT
<213> ORGANISM: Lama glama

<400> SEQUENCE: 21

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Val Ile Thr Trp Ser Gly Gly Ser Pro Tyr Tyr Ala Asp Ser Val
    50                  55                  60

Arg Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Pro Val Ser Tyr Gly Ser Gln Trp Leu Ala Asp Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140
```

<210> SEQ ID NO 22
<211> LENGTH: 140
<212> TYPE: PRT
<213> ORGANISM: Lama glama

<400> SEQUENCE: 22

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Arg Gln
            20                  25                  30

Ser Met Gly Trp Phe Arg Gln Ala Pro Gly Glu Glu Arg Glu Phe Val
        35                  40                  45

Ala Val Ile Thr Trp Ser Gly Gly Ser Pro Tyr Tyr Ala Asp Ser Val
    50                  55                  60

Arg Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Pro Val Ser Tyr Gly Ser Gln Trp Leu Ala Asp Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140
```

<210> SEQ ID NO 23
<211> LENGTH: 140
<212> TYPE: PRT
<213> ORGANISM: Lama glama

<400> SEQUENCE: 23

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Phe Ser Ser Tyr
20 25 30

Asn Met Gly Trp Phe Arg Gln Ala Pro Gly Lys Glu Arg Glu Phe Val
35 40 45

Ala Val Ile Ser Trp Ser Gly Gly Ser Pro Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Pro Val Ser Tyr Gly Ser Ser Trp Leu Ala Asp Tyr Trp Gly
100 105 110

Gln Gly Thr Gln Val Thr Val Ser Ser Ala Ala Ala Tyr Pro Tyr Asp
115 120 125

Val Pro Asp Tyr Gly Ser His His His His His His
130 135 140

<210> SEQ ID NO 24
<211> LENGTH: 140
<212> TYPE: PRT
<213> ORGANISM: Lama glama

<400> SEQUENCE: 24

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Phe Ser Asn Tyr
20 25 30

Asn Met Gly Trp Phe Arg Gln Ala Pro Gly Lys Glu Arg Glu Phe Val
35 40 45

Ala Ala Ile Asp Trp Ser Gly Gly Ser Pro Tyr Tyr Ala Ala Ser Val
50 55 60

Arg Gly Arg Phe Thr Ile Ser Arg Asp Asn Ala Glu Asn Thr Val Tyr
65 70 75 80

Leu Gln Met Asn Ser Leu Lys Pro Glu Asp Thr Ala Val Tyr Tyr Cys
85 90 95

Ala Ala Pro Leu Ser Tyr Gly Ser Thr Trp Leu Ala Asp Tyr Trp Gly
100 105 110

Gln Gly Thr Gln Val Thr Val Ser Ser Ala Ala Ala Tyr Pro Tyr Asp
115 120 125

Val Pro Asp Tyr Gly Ser His His His His His His
130 135 140

<210> SEQ ID NO 25
<211> LENGTH: 140
<212> TYPE: PRT
<213> ORGANISM: Lama glama

<400> SEQUENCE: 25

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Asn Ser
            20                  25                  30

Asn Met Gly Trp Phe Arg Gln Ala Pro Gly Lys Glu Arg Glu Phe Val
        35                  40                  45

Ala Val Ile Asp Trp Ser Gly Gly Ser Pro Tyr Tyr Thr Asp Ser Val
    50                  55                  60

Arg Gly Arg Phe Thr Ile Ser Arg Asp Asn Ala Lys Asn Thr Val Tyr
65                  70                  75                  80

Leu Gln Met Asn Arg Leu Lys Pro Glu Asp Thr Ala Val Tyr Tyr Cys
                85                  90                  95

Ala Gly Gly Val Ser Phe Gly Ser Arg Trp Leu Ser Asp Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140
```

<210> SEQ ID NO 26
<211> LENGTH: 140
<212> TYPE: PRT
<213> ORGANISM: Lama glama

<400> SEQUENCE: 26

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ser Phe Ser Ser Val
            20                  25                  30

Asn Met Gly Trp Phe Arg Gln Ala Pro Gly Lys Glu Arg Glu Phe Val
        35                  40                  45

Ala Val Ile Asp Trp Ser Gly Gly Ser Pro Tyr Tyr Thr Asp Ser Val
    50                  55                  60

Arg Gly Arg Phe Thr Ile Ser Arg Asp Asn Ser Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Val Ser Tyr Gly Ser Arg Trp Leu Gly Asp Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140
```

<210> SEQ ID NO 27
<211> LENGTH: 137
<212> TYPE: PRT
<213> ORGANISM: Lama glama

<400> SEQUENCE: 27

```
Gln Val Gln Leu Gln Glu Ser Gly Gly Gly Leu Ala Gln Ala Gly Gly
1               5                   10                  15

Ser Leu Arg Leu Ser Cys Ala Ala Ser Gly Arg Thr Phe Ser Met Gly
            20                  25                  30
```

Trp Phe Arg Gln Ala Pro Gly Lys Glu Arg Glu Phe Val Ala Ala Ile
35 40 45

Thr Tyr Ser Gly Gly Ser Pro Tyr Tyr Ala Ser Ser Val Arg Gly Arg
50 55 60

Phe Thr Ile Ser Arg Asp Asn Ala Lys Asn Thr Val Tyr Leu Gln Met
65 70 75 80

Asn Ser Leu Lys Pro Glu Asp Thr Ala Val Tyr Tyr Cys Ala Ala Asn
85 90 95

Pro Thr Tyr Gly Ser Asp Trp Asn Ala Glu Asn Trp Gly Gln Gly Thr
100 105 110

Gln Val Thr Val Ser Ser Ala Ala Ala Tyr Pro Tyr Asp Val Pro Asp
115 120 125

Tyr Gly Ser His His His His His His
130 135

<210> SEQ ID NO 28
<211> LENGTH: 137
<212> TYPE: PRT
<213> ORGANISM: Lama glama

<400> SEQUENCE: 28

Gln Val Gln Leu Gln Glu Ser Gly Gly Gly Leu Val Gln Pro Gly Gly
1 5 10 15

Ser Leu Arg Leu Ser Cys Ala Ala Ser Gly Arg Thr Phe Ser Met Gly
20 25 30

Trp Phe Arg Gln Ala Pro Gly Lys Glu Arg Glu Phe Val Ala Ala Ile
35 40 45

Thr Tyr Ser Gly Gly Ser Pro Tyr Tyr Ala Ser Ser Val Arg Gly Arg
50 55 60

Phe Thr Ile Ser Arg Asp Asn Ala Lys Asn Thr Val Tyr Leu Gln Met
65 70 75 80

Asn Ser Leu Lys Pro Glu Asp Thr Ala Val Tyr Tyr Cys Ala Ala Asn
85 90 95

Pro Thr Tyr Gly Ser Asp Trp Asn Ala Glu Asn Trp Gly Gln Gly Thr
100 105 110

Gln Val Thr Val Ser Ser Ala Ala Ala Tyr Pro Tyr Asp Val Pro Asp
115 120 125

Tyr Gly Ser His His His His His His
130 135

<210> SEQ ID NO 29
<211> LENGTH: 140
<212> TYPE: PRT
<213> ORGANISM: Lama glama

<400> SEQUENCE: 29

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Val Gly Ser Tyr
20 25 30

Ser Met Gly Trp Phe Arg Gln Ala Pro Gly Lys Glu Arg Glu Phe Val
35 40 45

Ala Ala Val Ile Trp Ser Gly Ala Ser Pro Tyr Tyr Ala Asp Ser Val
50 55 60

Lys Gly Arg Phe Thr Ile Ser Arg Asp Asn Ala Lys Asn Thr Val Tyr
65 70 75 80

```
Leu Gln Met Asn Ser Leu Lys Pro Glu Asp Thr Ala Val Tyr Tyr Cys
                85                  90                  95

Ala Ala Asn Pro Thr Tyr Ser Gly Gly Trp His Ala Glu Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140


<210> SEQ ID NO 30
<211> LENGTH: 140
<212> TYPE: PRT
<213> ORGANISM: Lama glama

<400> SEQUENCE: 30

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Val Gly Ser Tyr
            20                  25                  30

Ser Met Gly Trp Phe Arg Gln Ala Pro Gly Lys Glu Arg Glu Phe Val
        35                  40                  45

Ala Ala Val Thr Trp Ser Gly Ala Ser Pro Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asn Pro Thr Tyr Ser Gly Gly Trp His Ala Glu Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140


<210> SEQ ID NO 31
<211> LENGTH: 140
<212> TYPE: PRT
<213> ORGANISM: Lama glama

<400> SEQUENCE: 31

Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Thr Val Gly Ser Tyr
            20                  25                  30

Ser Met Gly Trp Phe Arg Gln Ala Pro Gly Lys Glu Arg Glu Phe Val
        35                  40                  45

Ala Ala Val Thr Trp Ser Gly Ala Ser Pro Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asn Pro Thr Tyr Ser Gly Gly Trp His Ala Glu Tyr Trp Gly
            100                 105                 110

Gln Gly Thr Gln Val Thr Val Ser Ser Ala Ala Ala Tyr Pro Tyr Asp
        115                 120                 125
```

Val Pro Asp Tyr Gly Ser His His His His His His
130 135 140

<210> SEQ ID NO 32
<211> LENGTH: 140
<212> TYPE: PRT
<213> ORGANISM: Lama glama

<400> SEQUENCE: 32

Gln Val Gln Leu Gln Glu Ser Gly Gly Gly Ser Glu Gln Pro Gly Gly
1 5 10 15

Ser Leu Arg Leu Ser Cys Ala Ala Ser Gly Arg Thr Val Gly Ser Tyr
20 25 30

Ser Met Gly Trp Phe Arg Gln Ala Pro Gly Lys Glu Arg Glu Phe Val
35 40 45

Ala Ala Val Thr Arg Ser Gly Ala Ser Pro Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Asn Pro Thr Tyr Ser Gly Gly Trp His Ala Glu Tyr Trp Gly
100 105 110

Gln Gly Thr Gln Val Thr Val Ser Ser Ala Ala Ala Tyr Pro Tyr Asp
115 120 125

Val Pro Asp Tyr Gly Ser His His His His His His
130 135 140

<210> SEQ ID NO 33
<211> LENGTH: 140
<212> TYPE: PRT
<213> ORGANISM: Lama glama

<400> SEQUENCE: 33

Gln Val Gln Leu Gln Glu Ser Gly Gly Gly Leu Val Gln Pro Gly Gly
1 5 10 15

Ser Leu Arg Leu Ser Cys Ala Ala Ser Arg Phe Thr Leu Asp Tyr Tyr
20 25 30

Ala Ile Gly Trp Phe Arg Gln Ala Pro Gly Lys Glu Arg Glu Phe Val
35 40 45

Ala Ala Val Thr Trp Ser Gly Ala Ser Pro Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Asn Pro Thr Tyr Ser Gly Gly Trp His Ala Glu Tyr Trp Gly
100 105 110

Gln Gly Thr Gln Val Thr Val Ser Ser Ala Ala Ala Tyr Pro Tyr Asp
115 120 125

Val Pro Asp Tyr Gly Ser His His His His His His
130 135 140

<210> SEQ ID NO 34
<211> LENGTH: 149
<212> TYPE: PRT
<213> ORGANISM: Lama glama

<400> SEQUENCE: 34

Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Thr Leu Asp Tyr Tyr
            20                  25                  30

Ala Ile Gly Trp Leu Arg Gln Ala Pro Gly Lys Glu Arg Glu Gly Val
        35                  40                  45

Ser Cys Ile Ser Ser Ser Gly Gly Ser Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Leu Met Asn Ser Leu Lys Pro Glu Asp Thr Ala Val Tyr Tyr Cys
                85                  90                  95

Ala Ala Glu Arg Thr Trp Val Ser Asn Tyr Tyr Cys Ser Gly Asp Gly
            100                 105                 110

Asp Gly Tyr Asp Tyr Asp Tyr Trp Gly Gln Gly Thr Gln Val Thr Val
        115                 120                 125

Ser Ser Ala Ala Ala Tyr Pro Tyr Asp Val Pro Asp Tyr Gly Ser His
    130                 135                 140

His His His His His
145

<210> SEQ ID NO 35
<211> LENGTH: 10
<212> TYPE: PRT
<213> ORGANISM: Lama glama

<400> SEQUENCE: 35

Gly Arg Thr Phe Ser Arg Gln Ser Met Gly
1               5                   10

<210> SEQ ID NO 36
<211> LENGTH: 10
<212> TYPE: PRT
<213> ORGANISM: Lama glama

<400> SEQUENCE: 36

Gly Arg Thr Phe Ser Gly Gln Ser Met Gly
1               5                   10

<210> SEQ ID NO 37
<211> LENGTH: 10
<212> TYPE: PRT
<213> ORGANISM: Lama glama

<400> SEQUENCE: 37

Gly Arg Thr Phe Ser Ser Tyr Ala Met Gly
1               5                   10

<210> SEQ ID NO 38
<211> LENGTH: 10
<212> TYPE: PRT
<213> ORGANISM: Lama glama

<400> SEQUENCE: 38

Gly Arg Thr Phe Ser Ser Tyr Asn Met Gly
1               5                   10

<210> SEQ ID NO 39
<211> LENGTH: 10

<212> TYPE: PRT
<213> ORGANISM: Lama glama

<400> SEQUENCE: 39

Gly Arg Thr Phe Ser Asn Tyr Asn Met Gly
1 5 10

<210> SEQ ID NO 40
<211> LENGTH: 10
<212> TYPE: PRT
<213> ORGANISM: Lama glama

<400> SEQUENCE: 40

Gly Arg Thr Phe Ser Asn Ser Asn Met Gly
1 5 10

<210> SEQ ID NO 41
<211> LENGTH: 10
<212> TYPE: PRT
<213> ORGANISM: Lama glama

<400> SEQUENCE: 41

Gly Arg Ser Phe Ser Ser Val Asn Met Gly
1 5 10

<210> SEQ ID NO 42
<211> LENGTH: 7
<212> TYPE: PRT
<213> ORGANISM: Lama glama

<400> SEQUENCE: 42

Gly Arg Thr Phe Ser Met Gly
1 5

<210> SEQ ID NO 43
<211> LENGTH: 10
<212> TYPE: PRT
<213> ORGANISM: Lama glama

<400> SEQUENCE: 43

Gly Arg Thr Val Gly Ser Tyr Ser Met Gly
1 5 10

<210> SEQ ID NO 44
<211> LENGTH: 10
<212> TYPE: PRT
<213> ORGANISM: Lama glama

<400> SEQUENCE: 44

Arg Phe Thr Leu Asp Tyr Tyr Ala Ile Gly
1 5 10

<210> SEQ ID NO 45
<211> LENGTH: 10
<212> TYPE: PRT
<213> ORGANISM: Lama glama

<400> SEQUENCE: 45

Gly Phe Thr Leu Asp Tyr Tyr Ala Ile Gly
1 5 10

<210> SEQ ID NO 46
<211> LENGTH: 17
<212> TYPE: PRT
<213> ORGANISM: Lama glama

<400> SEQUENCE: 46

Val Ile Thr Trp Ser Gly Gly Ser Pro Tyr Tyr Ala Asp Ser Val Arg
1 5 10 15

Gly

<210> SEQ ID NO 47
<211> LENGTH: 17
<212> TYPE: PRT
<213> ORGANISM: Lama glama

<400> SEQUENCE: 47

Val Ile Thr Trp Ser Gly Gly Ser Pro Tyr Tyr Ala Asp Ser Val Lys
1 5 10 15

Gly

<210> SEQ ID NO 48
<211> LENGTH: 17
<212> TYPE: PRT
<213> ORGANISM: Lama glama

<400> SEQUENCE: 48

Val Ile Ser Trp Ser Gly Gly Ser Pro Tyr Tyr Ala Asp Ser Val Lys
1 5 10 15

Gly

<210> SEQ ID NO 49
<211> LENGTH: 17
<212> TYPE: PRT
<213> ORGANISM: Lama glama

<400> SEQUENCE: 49

Ala Ile Asp Trp Ser Gly Gly Ser Pro Tyr Tyr Ala Ala Ser Val Arg
1 5 10 15

Gly

<210> SEQ ID NO 50
<211> LENGTH: 17
<212> TYPE: PRT
<213> ORGANISM: Lama glama

<400> SEQUENCE: 50

Val Ile Asp Trp Ser Gly Gly Ser Pro Tyr Tyr Thr Asp Ser Val Arg
1 5 10 15

Gly

<210> SEQ ID NO 51
<211> LENGTH: 17
<212> TYPE: PRT
<213> ORGANISM: Lama glama

<400> SEQUENCE: 51

Ala Ile Thr Tyr Ser Gly Gly Ser Pro Tyr Tyr Ala Ser Ser Val Arg
1 5 10 15

Gly

<210> SEQ ID NO 52
<211> LENGTH: 17
<212> TYPE: PRT
<213> ORGANISM: Lama glama

<400> SEQUENCE: 52

Ala Val Ile Trp Ser Gly Ala Ser Pro Tyr Tyr Ala Asp Ser Val Lys
1 5 10 15

Gly

<210> SEQ ID NO 53
<211> LENGTH: 17
<212> TYPE: PRT
<213> ORGANISM: Lama glama

<400> SEQUENCE: 53

Ala Val Thr Trp Ser Gly Ala Ser Pro Tyr Tyr Ala Asp Ser Val Lys
1 5 10 15

Gly

<210> SEQ ID NO 54
<211> LENGTH: 17
<212> TYPE: PRT
<213> ORGANISM: Lama glama

<400> SEQUENCE: 54

Ala Val Thr Arg Ser Gly Ala Ser Pro Tyr Tyr Ala Asp Ser Val Lys
1 5 10 15

Gly

<210> SEQ ID NO 55
<211> LENGTH: 17
<212> TYPE: PRT
<213> ORGANISM: Lama glama

<400> SEQUENCE: 55

Cys Ile Ser Ser Ser Gly Gly Ser Thr Asn Tyr Ala Asp Ser Val Lys
1 5 10 15

Gly

<210> SEQ ID NO 56
<211> LENGTH: 12
<212> TYPE: PRT
<213> ORGANISM: Lama glama

<400> SEQUENCE: 56

Pro Val Ser Tyr Gly Ser Gln Trp Leu Ala Asp Tyr
1 5 10

<210> SEQ ID NO 57
<211> LENGTH: 12
<212> TYPE: PRT
<213> ORGANISM: Lama glama

<400> SEQUENCE: 57

Pro Val Ser Tyr Gly Ser Ser Trp Leu Ala Asp Tyr
1 5 10

<210> SEQ ID NO 58
<211> LENGTH: 12
<212> TYPE: PRT
<213> ORGANISM: Lama glama

<400> SEQUENCE: 58

Pro Leu Ser Tyr Gly Ser Thr Trp Leu Ala Asp Tyr
1 5 10

<210> SEQ ID NO 59
<211> LENGTH: 12
<212> TYPE: PRT
<213> ORGANISM: Lama glama

<400> SEQUENCE: 59

Gly Val Ser Phe Gly Ser Arg Trp Leu Ser Asp Tyr
1 5 10

<210> SEQ ID NO 60
<211> LENGTH: 12
<212> TYPE: PRT
<213> ORGANISM: Lama glama

<400> SEQUENCE: 60

Gly Val Ser Tyr Gly Ser Arg Trp Leu Gly Asp Tyr
1 5 10

<210> SEQ ID NO 61
<211> LENGTH: 12
<212> TYPE: PRT
<213> ORGANISM: Lama glama

<400> SEQUENCE: 61

Asn Pro Thr Tyr Gly Ser Asp Trp Asn Ala Glu Asn
1 5 10

<210> SEQ ID NO 62
<211> LENGTH: 12
<212> TYPE: PRT
<213> ORGANISM: Lama glama

<400> SEQUENCE: 62

Asn Pro Thr Tyr Ser Gly Gly Trp His Ala Glu Tyr
1 5 10

<210> SEQ ID NO 63
<211> LENGTH: 20
<212> TYPE: PRT
<213> ORGANISM: Lama glama

<400> SEQUENCE: 63

Glu Arg Thr Trp Val Ser Asn Tyr Tyr Cys Ser Gly Asp Gly Asp Gly
1 5 10 15

Tyr Asp Tyr Asp
20

<210> SEQ ID NO 64
<211> LENGTH: 429
<212> TYPE: DNA
<213> ORGANISM: Lama glama

<400> SEQUENCE: 64
caggtgcagc tgcaggagtc tggggggagga ttggtgcagg ctgggggctc tctgagactc 60
tcctgtgcag cctctggacg cgacttcgct acctattcca tggcctggtt ccgccaggct 120
ccagggaagg agcgtgagtc tgtagcgaca attagctgga gtggtcaacg tacacgctat 180
gcggactccg tgaagggccg attcaccatc tccagagaca acgccaagaa cacggtgtat 240
ctgcaaatga acagcctgaa acctgaggac acggccgttt attactgtgc aatgccccgt 300
acctgggggg agtttccacc tacccagtat gactcgtggg gccaggggac ccaggtcacc 360
gtctcctcag cggccgcata cccgtacgac gttccggact acggttccca ccaccatcac 420
catcactag 429

<210> SEQ ID NO 65
<211> LENGTH: 429
<212> TYPE: DNA
<213> ORGANISM: Lama glama

<400> SEQUENCE: 65
caggtgcagc tgcaggagtc tgggggagga ttggtgccgg ctgggggctc tctgagactc 60
tcctgtgcag cctctggacg cgacttcgct acctattcca tggcctggtt ccgccaggct 120
ccagggaagg agcgtgagtc tgtagcgaca attagctgga gtggtcaacg tacacgctat 180
gcggactccg tgaagggccg attcaccatc tccagagaca acgccaagaa cacggtgtat 240
ctgcaaatga acagcctgaa acctgaggac acggccgttt attactgtgc agcaccccgt 300
acctgggggg agtttccacc tacccagtat gactcgtggg gccaggggac ccaggtcacc 360
gtctcctcag cggccgcata cccgtacgac gttccggact acggttccca ccaccatcac 420
catcactag 429

<210> SEQ ID NO 66
<211> LENGTH: 429
<212> TYPE: DNA
<213> ORGANISM: Lama glama

<400> SEQUENCE: 66
caggtgcagc tgcaggagtc tggaggagga ttggtgcagg ctgggggctc tctgagactc 60
tcctgtgcag cctctggacg cgacttcgct acctattcca tggcctggtt ccgccaggct 120
ccagggaagg agcgtgagtc tgtagcgaca attagctgga gtggtcaacg tacacgctat 180
gcggactccg tgaagggccg attcaccatc tccagagaca acgccaagaa cacggtgtat 240
ctgcaaatga acagcctgaa acctgaggac acggccgttt attactgtgc agcaccccgt 300
acctgggggg agtttccacc tacccagtat gactcgtggg gccaggggac ccaggtcacc 360
gtctcctcag cggccgcata cccgtacgac gttccggact acggttccca ccaccatcac 420
catcactag 429

<210> SEQ ID NO 67
<211> LENGTH: 429
<212> TYPE: DNA
<213> ORGANISM: Lama glama

<400> SEQUENCE: 67
caggtgcagc tgcaggagtc tgggggagga ttggtgcagg ctgggggctc tctgagactc 60
tcctgtgcag cctctggacg cgacttcgct acctattcca tgacctggtt ccgccaggct 120
ccagggaagg agcgtgagtc tgtagcgaca attagctgga gtggtcaacg tacacgctat 180
gcggactccg tgaagggccg attcaccatc tccagagaca acgccaagaa cacggtgtat 240
ctgcaaatga acagcctgag acctgaggac acggccgttt attactgtgc agcaccccgt 300
acctgggggg agtttccacc tacccagtat gactcgtggg gccaggggac ccaggtcacc 360
gtctcctcag cggccgcata cccgtacgac gttccggact acggttccca ccaccatcac 420
catcactag 429

<210> SEQ ID NO 68

<211> LENGTH: 429
<212> TYPE: DNA
<213> ORGANISM: Lama glama

<400> SEQUENCE: 68
caggtgcagc tgcaggagtc tgggggagga ttggtgcagg ctgggggctc tctgagactc 60
tcctgtgcag cctctggacg cgacttcgct acctattcca tggcctggtt ccgccaggct 120
ccaggggagg agcgtgagtc tgtagcgacg attagctgga gtggtcaacg tacacgctat 180
gcggactccg tgaagggccg attcaccatc tccagagaca acgccaagaa cacggtgtat 240
ctgcaaatga acagcctgaa acctgaggac acggccgttt attactgtgc agcaccccgt 300
acctgggggg agtttccacc tacccagtat gactcgtggg gccaggggac ccaggtcacc 360
gtctcctcag cggccgcata cccgtacgac gttccggact acggttccca ccaccatcac 420
catcactag 429

<210> SEQ ID NO 69
<211> LENGTH: 429
<212> TYPE: DNA
<213> ORGANISM: Lama glama

<400> SEQUENCE: 69
caggtgcagc tgcaggagtc tgggggaggt ttggtgcagg ctggggactc tctgagactc 60
tcctgcgcag cctctggacg cgacttcgct acctattcca tggcctggtt ccgccaggct 120
ccagggaagg agcgtgagtc tgtagcgaca attagctgga gtggtcaacg tacacgctat 180
gcggactccg tgaagggccg attcaccatc tccagagaca acgccaagaa cacggtgtat 240
ctgcaaatga acagcctgaa acctgaggac acggccgttt attactgtgc agcaccccgt 300
acctgggggg agtttccacc tacccagtat gactcgtggg gccaggggac ccaggtcacc 360
gtctcctcag cggccgcata cccgtacgac gttccggact acggttccca ccaccatcac 420
catcactag 429

<210> SEQ ID NO 70
<211> LENGTH: 429
<212> TYPE: DNA
<213> ORGANISM: Lama glama

<400> SEQUENCE: 70
caggtgcagc tgcaggagtc tgggggggc ttggtgcagc ctgggggtc tctgagactc 60 tcctgtgcaa cctctggacg cgacttcgct acctattcca tggcctggtt ccgccaggct 120
ccagggaagg agcgtgagtc tgtagcgaca attagctgga gtggtcaacg tacacgctat 180
gcggactccg tgaagggccg attcaccatc tccagagaca acgccaagaa cacggtgtat 240
ctgcaaatga acagcctgaa acctgaggac acggccgttt attactgtgc agcaccccgt 300
acctgggggg agtttccacc tacccagtat gactcgtggg gccaggggac ccaggtcacc 360
gtctcctcag cggccgcata cccgtacgac gttccggact acggttccca ccaccatcac 420
catcactag 429

<210> SEQ ID NO 71
<211> LENGTH: 429
<212> TYPE: DNA
<213> ORGANISM: Lama glama

<400> SEQUENCE: 71
caggtgcagc tgcaggagtc tgggggaggc ttggtgcagc ctggggggtc tctgagactc 60
tcctgtgcag cctctggacg cgacttcgct acctattcca tggcctggtt ccgccaggct 120
ccagggaagg agcgtgagtc tgtagcgaca attagctgga gtggtcaacg tacacgctat 180
gcggactccg tgaagggccg attcaccatc tccagagaca acgccaagaa cacggtgtat 240
ctgcaaatga acagcctgaa acctgaggac acggccgttt attactgtgc agcaccccgt 300
acctgggggg agtttccacc tacccagtat gactcgtggg gccaggggac ccaggtcacc 360
gtctcctcag cggccgcata cccgtacgac gttccggact acggttccca ccaccatcac 420
catcactag 429

<210> SEQ ID NO 72
<211> LENGTH: 429
<212> TYPE: DNA
<213> ORGANISM: Lama glama

<400> SEQUENCE: 72
caggtgcagc tgcaggagtc tgggggaggc ttggtgcagg ctggggactc tctgagactc 60
tcctgtgcag cctctggacg cgacttcagt acctattcca tgggctggtt ccgccaggct 120
ccagggaagg agcgtgagtc tgtagcgaca attagctgga gtggtcaacg tacacgctat 180
gcggactccg tgaaaggccg attcaccatc tccagagaca acgccaagaa cacggtgtat 240
ctgcaaatga acagcctgaa acctgaggac acggccgttt attactgtgc agcaccccgt 300
acctgggggg agtttccacc tacccagtat gactcgtggg gccaggggac ccaggtcacc 360
gtctcctcag cggccgcata cccgtacgac gttccggact acggttccca ccaccatcac 420
catcactag 429

<210> SEQ ID NO 73
<211> LENGTH: 429
<212> TYPE: DNA
<213> ORGANISM: Lama glama

<400> SEQUENCE: 73
caggtgcagc tgcaggagtc tgggggaggc tcggtgcaga ctgggggctc tctgagactc 60
tcctgtgcag cctctggacg cgacttcagt acctattcca tgggctggtt ccgccaggct 120
ccagggaagg agcgtgagtc tgtagcgaca attagctgga gtggtcaacg tacacgctat 180
gcggactccg tgaagggccg attcaccatc tccagagaca acgccaagaa cacggtgtat 240
ctgcaaatga acagcctgaa acctgaggac acggccgttt attactgtgc agcaccccgt 300
acctgggggg agtttccacc tacccagtat gactcgtggg gccaggggac ccaggtcacc 360
gtctcctcag cggccgcata cccgtacgac gttccggact acggttccca ccaccatcac 420
catcactag 429

<210> SEQ ID NO 74
<211> LENGTH: 429
<212> TYPE: DNA
<213> ORGANISM: Lama glama

<400> SEQUENCE: 74
caggtgcagc tgcaggagtc tggaggagga ttggtgcagg ctgggggctc tctgagactc 60
tcctgtgcag cctctggacg caccttcagt acatattcca tgggctggtt ccgccaggct 120
ccagggaagg agcgtgagtt tgtagcgatt attagctgga gtggtcaacg tacacgctat 180
gcggactccg tgaagggccg attcaccatc tccagagaca acgccaagaa cacggtgtat 240
ctgcaaatga acagcctgaa acctgaggac acggccgttt attactgtgc agcaccccgt 300
acctgggggg agtttccacc tacccagtat gactcgtggg gccaggggac ccaggtcacc 360
gtctcctcag cggccgcata cccgtacgac gttccggact acggttccca ccaccatcac 420
catcactag 429

<210> SEQ ID NO 75
<211> LENGTH: 429
<212> TYPE: DNA
<213> ORGANISM: Lama glama

<400> SEQUENCE: 75
caggtgcagc tgcaggagtc tgggggagga ttggtgcagg ctgggggctc tctgagactc 60
tcctgtgtag cctctggacg caccttcaat acctattcca tgggctggtt ccgccaggct 120
ccagggaagg agcgtgagtt tgtagcgtct attagctgga gtggtcaacg ttcacgctat 180
gcggactccg tgaagggccg attcaccatc tccagagaca acgccaagaa cacggtgtat 240
ctgcaaatga acagcctgaa acctgaggac acggccgttt attactgtgc gtcaccccgt 300
acctgggggg agtttccacc tactcagtat gactcgtggg gccaggggac ccaggtcacc 360
gtctcctcag cggccgcata cccgtacgac gttccggact acggttccca ccaccatcac 420
catcactag 429

<210> SEQ ID NO 76
<211> LENGTH: 426
<212> TYPE: DNA
<213> ORGANISM: Lama glama

<400> SEQUENCE: 76
caggtgcagc tgcaggagtc tgggggagga ttggtgcagg ctgagggctc tctgagactc 60
tcgtgtgcag cctctggacg cacccgtgat gccaatgcca tgggctggtt ccgccaggct 120
ccagggaagg agcgtgagtt agtagcagct attagctgga gtggtagtag gacatactat 180
gcagactccg tgaagggccg attcaccatc tccagagaca atgtcatgca cacggtgtat 240
ctgtcaatga atagcctgaa acctgaggac acggccgttt attattgtgc agctgatcga 300
agcattgagg tccaaatcgc ggattatgac tactggggcc gggggaccca ggtcaccgtc 360
tcctcagcgg ccgcataccc gtacgacgtt ccggactacg gttcccacca ccatcaccat 420
cactag 426

<210> SEQ ID NO 77
<211> LENGTH: 426
<212> TYPE: DNA
<213> ORGANISM: Lama glama

<400> SEQUENCE: 77
caggtgcagc tgcaggagtc tgggggagga ttggcgcagg ctgggaactc tctgagaatc 60
tcttgtgtag cctctggaaa caccttcgac acacgtgcca tgggctggtt ccgccaggct 120
ccagggaagg agcgtgagtt tgtagcggcg attagtcgga gtagtttcaa cacatactac 180
tccgactccg tgacgggccg attcaccatc tccagagaca acgccaagaa cacggtgtat 240
ctgcaaatga acagcctgaa acctgaggac acggccgttt attactgtgt agctggcaag 300
tacggtatga agtggaggga tggcgctgac tactggggcc aggggaccca ggtcaccgtc 360
tcctcagcgg ccgcataccc gtacgacgtt ccggactacg gttcccacca ccatcaccat 420
cactag 426

<210> SEQ ID NO 78
<211> LENGTH: 426
<212> TYPE: DNA
<213> ORGANISM: Lama glama

<400> SEQUENCE: 78
caggtgcagc tgcaggagtc tgggggagga ttggcgcagg ctgggaactc tctgagaatc 60
tcttgtgtag cctctggaaa caccttcgac acacgtgcca tgggctggtt ccgccaggct 120
ccagggaagg agcgtgagtt tgtagcggcg attagtcgga gtagtttcaa cacatactac 180
tccgactccg tgacgggccg attcaccatc tccagagaca acgccaagaa cacggtgtat 240
ctgcaaatga acagcctgaa acctgaggac acggccgttt attactgtgc agctggcaag 300
tacggtatga agtggaggga tggcgctgac tactggggcc aggggaccca ggtcaccgtc 360
tcctcagcgg ccgcataccc gtacgacgtt ccggactacg gttcccacca ccatcaccat 420
cactag 426

<210> SEQ ID NO 79
<211> LENGTH: 426
<212> TYPE: DNA
<213> ORGANISM: Lama glama

<400> SEQUENCE: 79
caggtgcagc tgcaggagtc tgggggaggc ttggcgcagg aggggggtc cctgagactc 60 tcttgtgtag cctctggaaa caccttcgac acacgtgcca tgggctggtt ccgccaggct 120
ccagggaagg agcgtgagtt tgtagcggcg attagtcgga gtagtttcaa cacatactac 180
tccgactccg tgacgggccg attcaccatc tccagagaca acgccaagaa catggtgtat 240
ctgcaaatga acagcctgaa acctgaggac acggccgttt attactgtgc agctggcaag 300
tacggtatga agtggaggga tggcgctgac tactggggcc aggggaccca ggtcaccgtc 360
tcctcagcgg ccgcataccc gtacgacgtt ccggactacg gttcccacca ccatcaccat 420
cactag 426

<210> SEQ ID NO 80
<211> LENGTH: 426
<212> TYPE: DNA
<213> ORGANISM: Lama glama

<400> SEQUENCE: 80
caggtgcagc tgcaggagtc tggaggaggc ttggtgcagg ctggggagtc tctgagaatc 60
tcttgtgtag cctctggaaa caccttcgac acacgtgcca tgggctggtt ccgccaggct 120
ccagggaagg agcgtgagtt tgtagcggcg attagtcgga gtagtttcaa cacatactac 180
tccgactccg tgacgggccg attcaccatc tccagagaca acgccaagaa cacggtgtat 240
ctgcaaatga acagcctgaa acctgaggac acggccgttt attactgtgt agctggcaag 300
tacggtatga agtggaggga tggcgctgac tactggggcc aggggaccca ggtcaccgtc 360
tcctcagcgg ccgcataccc gtacgacgtt ccggactacg gttcccacca ccatcaccat 420
cactag 426

<210> SEQ ID NO 81

<211> LENGTH: 426
<212> TYPE: DNA
<213> ORGANISM: Lama glama

<400> SEQUENCE: 81
caggtgcagc tgcaggagtc tgggggagga ttggtgcaga ctgggggctc tctgagactc 60
tcctgtgcag cctctggaaa caccttcgac acacgtgcca tgggctggtt ccgccaggct 120
ccagggaagg agcgtgagtt tgtagcggcg attagtcgga gtagtttcaa cacatactac 180
tccgactccg tgacgggccg attcaccatc tccagagaca acgccaagaa cacggtgtat 240
ctgcaaatga acagcctgaa acctgaggac acggccgttt attactgtgc agctggcaag 300
tacggtatga agtggaggga tggcgctgac tactggggcc aggggaccca ggtcaccgtc 360
tcctcagcgg ccgcataccc gtacgacgtt ccggactacg gttcccacca ccatcaccat 420
cactag 426

<210> SEQ ID NO 82
<211> LENGTH: 426
<212> TYPE: DNA
<213> ORGANISM: Lama glama

<400> SEQUENCE: 82
caggtgcagc tgcaggagtc tgggggagga tcggtacaga ctgggggcac tctgacactc 60
tcttgtgtag cctctggaaa caccttcgac acacgtgcca tgggctggtt ccgccaggct 120
ccaggggagg agcgtgagtt tgtagcggcg attagtcgga gtagtttcaa cacatactac 180
tccgactccg tgacgggccg attcaccatc tccagagaca acgccaagaa cacggtgtat 240
ctgcaaatga acagcctgaa acctgaggac acggccgttt attactgtgc agctggcaag 300
tacggtatga agtggaggga tggcgctgac tactggggcc aggggaccca ggtcaccgtc 360
tcctcagcgg ccgcataccc gtacgacgtt ccggactacg gttcccacca ccatcaccat 420
cactag 426

<210> SEQ ID NO 83
<211> LENGTH: 423
<212> TYPE: DNA
<213> ORGANISM: Lama glama

<400> SEQUENCE: 83
caggtgcagc tgcaggagtc tgggggagga tcggtgcagg ctgggggttc tctgagactc 60
tcctgtgcag cctccggaag caccttcagt atcaaggcca tggggtggta ccgccaggct 120
ccagggaagc agcgcgagtt ggtcgcagct tttattagtg gtcgtggtag tacaaagtat 180
gcagactccg tgaagggccg attcgccatc tccagagaca atgccaagaa cacgatgtat 240
ctgcaaatgg acagcctgga acctgaggac acggccgtgt attactgtta catagtactg 300
cctactgggg ggggaagcgc catggactac tggggcgaag ggacccaggt caccgtctcc 360
tcagcggccg catacccgta cgacgttccg gactacggtt cccaccacca tcaccatcac 420
tag 423

<210> SEQ ID NO 84
<211> LENGTH: 423
<212> TYPE: DNA
<213> ORGANISM: Lama glama

<400> SEQUENCE: 84
caggtgcagc tgcaggagtc tgggggaggc gtcgtgcagg ctgggggttc tctgagactc 60
tcctgtgcag cctccggaag caccttcagt atcaaggcca tggggtggta ccgccaggct 120
ccagggaagc agcgcgactt ggtcgcaggt ttcattagtg gtcgtggtag tgcaaagtat 180
gcagactccg tgaagggccg attcgccatc tccagagaca atgccaagaa cacgatgtat 240
ctgcaaatgg acagcctgaa acctgaggac acggccgtgt attactgcta catagtactg 300
actactgggg ggggaagcgc catggactac tggggccaag ggacccaggt caccgtctcc 360
tcagcggccg catacccgta cgacgttccg gactacggtt cccaccacca tcaccatcac 420
tag 423

<210> SEQ ID NO 85
<211> LENGTH: 142
<212> TYPE: PRT
<213> ORGANISM: Lama glama

<400> SEQUENCE: 85

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Asp Phe Ala Thr Tyr
20 25 30

Ser Met Ala Trp Phe Arg Gln Ala Pro Gly Lys Glu Arg Glu Ser Val
35 40 45

Ala Thr Ile Ser Trp Ser Gly Gln Arg Thr Arg Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Met Pro Arg Thr Trp Gly Glu Phe Pro Pro Thr Gln Tyr Asp Ser
100 105 110

Trp Gly Gln Gly Thr Gln Val Thr Val Ser Ser Ala Ala Ala Tyr Pro
115 120 125

Tyr Asp Val Pro Asp Tyr Gly Ser His His His His His His
130 135 140

<210> SEQ ID NO 86
<211> LENGTH: 142
<212> TYPE: PRT
<213> ORGANISM: Lama glama

<400> SEQUENCE: 86

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Asp Phe Ala Thr Tyr
20 25 30

Ser Met Ala Trp Phe Arg Gln Ala Pro Gly Lys Glu Arg Glu Ser Val
35 40 45

Ala Thr Ile Ser Trp Ser Gly Gln Arg Thr Arg Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

```
Ala Ala Pro Arg Thr Trp Gly Glu Phe Pro Pro Thr Gln Tyr Asp Ser
            100                 105                 110

Trp Gly Gln Gly Thr Gln Val Thr Val Ser Ser Ala Ala Ala Tyr Pro
        115                 120                 125

Tyr Asp Val Pro Asp Tyr Gly Ser His His His His His His
    130                 135                 140


<210> SEQ ID NO 87
<211> LENGTH: 142
<212> TYPE: PRT
<213> ORGANISM: Lama glama

<400> SEQUENCE: 87

Gln Val Gln Leu Gln Glu Ser Gly Gly Gly Leu Val Pro Ala Gly Gly
1               5                   10                  15

Ser Leu Arg Leu Ser Cys Ala Ala Ser Gly Arg Asp Phe Ala Thr Tyr
            20                  25                  30

Ser Met Ala Trp Phe Arg Gln Ala Pro Gly Lys Glu Arg Glu Ser Val
        35                  40                  45

Ala Thr Ile Ser Trp Ser Gly Gln Arg Thr Arg Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Pro Arg Thr Trp Gly Glu Phe Pro Pro Thr Gln Tyr Asp Ser
            100                 105                 110

Trp Gly Gln Gly Thr Gln Val Thr Val Ser Ser Ala Ala Ala Tyr Pro
        115                 120                 125

Tyr Asp Val Pro Asp Tyr Gly Ser His His His His His His
    130                 135                 140


<210> SEQ ID NO 88
<211> LENGTH: 142
<212> TYPE: PRT
<213> ORGANISM: Lama glama

<400> SEQUENCE: 88

Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Asp Phe Ala Thr Tyr
            20                  25                  30

Ser Met Ala Trp Phe Arg Gln Ala Pro Gly Lys Glu Arg Glu Ser Val
        35                  40                  45

Ala Thr Ile Ser Trp Ser Gly Gln Arg Thr Arg Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Pro Arg Thr Trp Gly Glu Phe Pro Pro Thr Gln Tyr Asp Ser
            100                 105                 110

Trp Gly Gln Gly Thr Gln Val Thr Val Ser Ser Ala Ala Ala Tyr Pro
        115                 120                 125

Tyr Asp Val Pro Asp Tyr Gly Ser His His His His His His
    130                 135                 140
```

<210> SEQ ID NO 89
<211> LENGTH: 142
<212> TYPE: PRT
<213> ORGANISM: Lama glama

<400> SEQUENCE: 89

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Asp Phe Ala Thr Tyr
            20                  25                  30

Ser Met Ala Trp Phe Arg Gln Ala Pro Gly Glu Glu Arg Glu Ser Val
        35                  40                  45

Ala Thr Ile Ser Trp Ser Gly Gln Arg Thr Arg Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Pro Arg Thr Trp Gly Glu Phe Pro Pro Thr Gln Tyr Asp Ser
            100                 105                 110

Trp Gly Gln Gly Thr Gln Val Thr Val Ser Ser Ala Ala Ala Tyr Pro
        115                 120                 125

Tyr Asp Val Pro Asp Tyr Gly Ser His His His His His His
    130                 135                 140
```

<210> SEQ ID NO 90
<211> LENGTH: 142
<212> TYPE: PRT
<213> ORGANISM: Lama glama

<400> SEQUENCE: 90

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Asp Phe Ala Thr Tyr
            20                  25                  30

Ser Met Ala Trp Phe Arg Gln Ala Pro Gly Lys Glu Arg Glu Ser Val
        35                  40                  45

Ala Thr Ile Ser Trp Ser Gly Gln Arg Thr Arg Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Pro Arg Thr Trp Gly Glu Phe Pro Pro Thr Gln Tyr Asp Ser
            100                 105                 110

Trp Gly Gln Gly Thr Gln Val Thr Val Ser Ser Ala Ala Ala Tyr Pro
        115                 120                 125

Tyr Asp Val Pro Asp Tyr Gly Ser His His His His His His
    130                 135                 140
```

<210> SEQ ID NO 91
<211> LENGTH: 142
<212> TYPE: PRT
<213> ORGANISM: Lama glama

<400> SEQUENCE: 91

Gln Val Gln Leu Gln Glu Ser Gly Gly Gly Leu Val Gln Pro Gly Gly
1 5 10 15

Ser Leu Arg Leu Ser Cys Ala Thr Ser Gly Arg Asp Phe Ala Thr Tyr
20 25 30

Ser Met Ala Trp Phe Arg Gln Ala Pro Gly Lys Glu Arg Glu Ser Val
35 40 45

Ala Thr Ile Ser Trp Ser Gly Gln Arg Thr Arg Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Pro Arg Thr Trp Gly Glu Phe Pro Pro Thr Gln Tyr Asp Ser
100 105 110

Trp Gly Gln Gly Thr Gln Val Thr Val Ser Ser Ala Ala Ala Tyr Pro
115 120 125

Tyr Asp Val Pro Asp Tyr Gly Ser His His His His His His
130 135 140

<210> SEQ ID NO 92
<211> LENGTH: 142
<212> TYPE: PRT
<213> ORGANISM: Lama glama

<400> SEQUENCE: 92

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Asp Phe Ala Thr Tyr
20 25 30

Ser Met Thr Trp Phe Arg Gln Ala Pro Gly Lys Glu Arg Glu Ser Val
35 40 45

Ala Thr Ile Ser Trp Ser Gly Gln Arg Thr Arg Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Arg Pro Glu Asp Thr Ala Val Tyr Tyr Cys
85 90 95

Ala Ala Pro Arg Thr Trp Gly Glu Phe Pro Pro Thr Gln Tyr Asp Ser
100 105 110

Trp Gly Gln Gly Thr Gln Val Thr Val Ser Ser Ala Ala Ala Tyr Pro
115 120 125

Tyr Asp Val Pro Asp Tyr Gly Ser His His His His His His
130 135 140

<210> SEQ ID NO 93
<211> LENGTH: 142
<212> TYPE: PRT
<213> ORGANISM: Lama glama

<400> SEQUENCE: 93

Gln Val Gln Leu Gln Glu Ser Gly Gly Gly Leu Val Gln Ala Gly Asp
1 5 10 15

Ser Leu Arg Leu Ser Cys Ala Ala Ser Gly Arg Asp Phe Ser Thr Tyr
20 25 30

-continued

```
Ser Met Gly Trp Phe Arg Gln Ala Pro Gly Lys Glu Arg Glu Ser Val
        35                  40                  45

Ala Thr Ile Ser Trp Ser Gly Gln Arg Thr Arg Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Pro Arg Thr Trp Gly Glu Phe Pro Pro Thr Gln Tyr Asp Ser
            100                 105                 110

Trp Gly Gln Gly Thr Gln Val Thr Val Ser Ser Ala Ala Ala Tyr Pro
        115                 120                 125

Tyr Asp Val Pro Asp Tyr Gly Ser His His His His His His
    130                 135                 140


<210> SEQ ID NO 94
<211> LENGTH: 142
<212> TYPE: PRT
<213> ORGANISM: Lama glama

<400> SEQUENCE: 94

Gln Val Gln Leu Gln Glu Ser Gly Gly Gly Leu Val Gln Ala Gly Gly
1               5                   10                  15

Ser Leu Arg Leu Ser Cys Val Ala Ser Gly Arg Thr Phe Asn Thr Tyr
            20                  25                  30

Ser Met Gly Trp Phe Arg Gln Ala Pro Gly Lys Glu Arg Glu Phe Val
        35                  40                  45

Ala Ser Ile Ser Trp Ser Gly Gln Arg Ser Arg Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ser Pro Arg Thr Trp Gly Glu Phe Pro Pro Thr Gln Tyr Asp Ser
            100                 105                 110

Trp Gly Gln Gly Thr Gln Val Thr Val Ser Ser Ala Ala Ala Tyr Pro
        115                 120                 125

Tyr Asp Val Pro Asp Tyr Gly Ser His His His His His His
    130                 135                 140


<210> SEQ ID NO 95
<211> LENGTH: 142
<212> TYPE: PRT
<213> ORGANISM: Lama glama

<400> SEQUENCE: 95

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Thr Tyr
            20                  25                  30

Ser Met Gly Trp Phe Arg Gln Ala Pro Gly Lys Glu Arg Glu Phe Val
        35                  40                  45

Ala Ile Ile Ser Trp Ser Gly Gln Arg Thr Arg Tyr Ala Asp Ser Val
    50                  55                  60

Lys Gly Arg Phe Thr Ile Ser Arg Asp Asn Ala Lys Asn Thr Val Tyr
65                  70                  75                  80
```

```
Leu Gln Met Asn Ser Leu Lys Pro Glu Asp Thr Ala Val Tyr Tyr Cys
                85                  90                  95

Ala Ala Pro Arg Thr Trp Gly Glu Phe Pro Pro Thr Gln Tyr Asp Ser
            100                 105                 110

Trp Gly Gln Gly Thr Gln Val Thr Val Ser Ser Ala Ala Ala Tyr Pro
        115                 120                 125

Tyr Asp Val Pro Asp Tyr Gly Ser His His His His His His
    130                 135                 140


<210> SEQ ID NO 96
<211> LENGTH: 142
<212> TYPE: PRT
<213> ORGANISM: Lama glama

<400> SEQUENCE: 96

Gln Val Gln Leu Gln Glu Ser Gly Gly Gly Ser Val Gln Thr Gly Gly
1               5                   10                  15

Ser Leu Arg Leu Ser Cys Ala Ala Ser Gly Arg Asp Phe Ser Thr Tyr
            20                  25                  30

Ser Met Gly Trp Phe Arg Gln Ala Pro Gly Lys Glu Arg Glu Ser Val
        35                  40                  45

Ala Thr Ile Ser Trp Ser Gly Gln Arg Thr Arg Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Pro Arg Thr Trp Gly Glu Phe Pro Pro Thr Gln Tyr Asp Ser
            100                 105                 110

Trp Gly Gln Gly Thr Gln Val Thr Val Ser Ser Ala Ala Ala Tyr Pro
        115                 120                 125

Tyr Asp Val Pro Asp Tyr Gly Ser His His His His His His
    130                 135                 140


<210> SEQ ID NO 97
<211> LENGTH: 141
<212> TYPE: PRT
<213> ORGANISM: Lama glama

<400> SEQUENCE: 97

Gln Val Gln Leu Gln Glu Ser Gly Gly Gly Leu Ala Gln Ala Gly Asn
1               5                   10                  15

Ser Leu Arg Ile Ser Cys Val Ala Ser Gly Asn Thr Phe Asp Thr Arg
            20                  25                  30

Ala Met Gly Trp Phe Arg Gln Ala Pro Gly Lys Glu Arg Glu Phe Val
        35                  40                  45

Ala Ala Ile Ser Arg Ser Ser Phe Asn Thr Tyr Tyr Ser Asp Ser Val
    50                  55                  60

Thr Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Lys Tyr Gly Met Lys Trp Arg Asp Gly Ala Asp Tyr Trp
            100                 105                 110

Gly Gln Gly Thr Gln Val Thr Val Ser Ser Ala Ala Ala Tyr Pro Tyr
        115                 120                 125
```

Asp Val Pro Asp Tyr Gly Ser His His His His His His
    130                 135                 140

<210> SEQ ID NO 98
<211> LENGTH: 141
<212> TYPE: PRT
<213> ORGANISM: Lama glama

<400> SEQUENCE: 98

Gln Val Gln Leu Gln Glu Ser Gly Gly Gly Leu Ala Gln Ala Gly Asn
1               5                   10                  15

Ser Leu Arg Ile Ser Cys Val Ala Ser Gly Asn Thr Phe Asp Thr Arg
            20                  25                  30

Ala Met Gly Trp Phe Arg Gln Ala Pro Gly Lys Glu Arg Glu Phe Val
        35                  40                  45

Ala Ala Ile Ser Arg Ser Ser Phe Asn Thr Tyr Tyr Ser Asp Ser Val
    50                  55                  60

Thr Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Val Ala Gly Lys Tyr Gly Met Lys Trp Arg Asp Gly Ala Asp Tyr Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140

<210> SEQ ID NO 99
<211> LENGTH: 141
<212> TYPE: PRT
<213> ORGANISM: Lama glama

<400> SEQUENCE: 99

Gln Val Gln Leu Gln Glu Ser Gly Gly Gly Leu Val Gln Ala Gly Glu
1               5                   10                  15

Ser Leu Arg Ile Ser Cys Val Ala Ser Gly Asn Thr Phe Asp Thr Arg
            20                  25                  30

Ala Met Gly Trp Phe Arg Gln Ala Pro Gly Lys Glu Arg Glu Phe Val
        35                  40                  45

Ala Ala Ile Ser Arg Ser Ser Phe Asn Thr Tyr Tyr Ser Asp Ser Val
    50                  55                  60

Thr Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Val Ala Gly Lys Tyr Gly Met Lys Trp Arg Asp Gly Ala Asp Tyr Trp
            100                 105                 110

Gly Gln Gly Thr Gln Val Thr Val Ser Ser Ala Ala Ala Tyr Pro Tyr
        115                 120                 125

Asp Val Pro Asp Tyr Gly Ser His His His His His His
    130                 135                 140

<210> SEQ ID NO 100
<211> LENGTH: 141
<212> TYPE: PRT
<213> ORGANISM: Lama glama

<400> SEQUENCE: 100

Gln Val Gln Leu Gln Glu Ser Gly Gly Gly Leu Ala Gln Glu Gly Gly
1 5 10 15

Ser Leu Arg Leu Ser Cys Val Ala Ser Gly Asn Thr Phe Asp Thr Arg
20 25 30

Ala Met Gly Trp Phe Arg Gln Ala Pro Gly Lys Glu Arg Glu Phe Val
35 40 45

Ala Ala Ile Ser Arg Ser Ser Phe Asn Thr Tyr Tyr Ser Asp Ser Val
50 55 60

Thr Gly Arg Phe Thr Ile Ser Arg Asp Asn Ala Lys Asn Met Val Tyr
65 70 75 80

Leu Gln Met Asn Ser Leu Lys Pro Glu Asp Thr Ala Val Tyr Tyr Cys
85 90 95

Ala Ala Gly Lys Tyr Gly Met Lys Trp Arg Asp Gly Ala Asp Tyr Trp
100 105 110

Gly Gln Gly Thr Gln Val Thr Val Ser Ser Ala Ala Ala Tyr Pro Tyr
115 120 125

Asp Val Pro Asp Tyr Gly Ser His His His His His His
130 135 140

<210> SEQ ID NO 101
<211> LENGTH: 141
<212> TYPE: PRT
<213> ORGANISM: Lama glama

<400> SEQUENCE: 101

Gln Val Gln Leu Gln Glu Ser Gly Gly Gly Leu Val Gln Thr Gly Gly
1 5 10 15

Ser Leu Arg Leu Ser Cys Ala Ala Ser Gly Asn Thr Phe Asp Thr Arg
20 25 30

Ala Met Gly Trp Phe Arg Gln Ala Pro Gly Lys Glu Arg Glu Phe Val
35 40 45

Ala Ala Ile Ser Arg Ser Ser Phe Asn Thr Tyr Tyr Ser Asp Ser Val
50 55 60

Thr Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Gly Lys Tyr Gly Met Lys Trp Arg Asp Gly Ala Asp Tyr Trp
100 105 110

Gly Gln Gly Thr Gln Val Thr Val Ser Ser Ala Ala Ala Tyr Pro Tyr
115 120 125

Asp Val Pro Asp Tyr Gly Ser His His His His His His
130 135 140

<210> SEQ ID NO 102
<211> LENGTH: 141
<212> TYPE: PRT
<213> ORGANISM: Lama glama

<400> SEQUENCE: 102

Gln Val Gln Leu Gln Glu Ser Gly Gly Gly Ser Val Gln Thr Gly Gly
1 5 10 15

Thr Leu Thr Leu Ser Cys Val Ala Ser Gly Asn Thr Phe Asp Thr Arg
20 25 30

Ala Met Gly Trp Phe Arg Gln Ala Pro Gly Glu Glu Arg Glu Phe Val
35 40 45

Ala Ala Ile Ser Arg Ser Ser Phe Asn Thr Tyr Tyr Ser Asp Ser Val
50 55 60

Thr Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Tyr Cys
85 90 95

Ala Ala Gly Lys Tyr Gly Met Lys Trp Arg Asp Gly Ala Asp Tyr Trp
100 105 110

Gly Gln Gly Thr Gln Val Thr Val Ser Ser Ala Ala Ala Tyr Pro Tyr
115 120 125

Asp Val Pro Asp Tyr Gly Ser His His His His His His
130 135 140

<210> SEQ ID NO 103
<211> LENGTH: 141
<212> TYPE: PRT
<213> ORGANISM: Lama glama

<400> SEQUENCE: 103

Gln Val Gln Leu Gln Glu Ser Gly Gly Gly Leu Val Gln Ala Glu Gly
1 5 10 15

Ser Leu Arg Leu Ser Cys Ala Ala Ser Gly Arg Thr Arg Asp Ala Asn
20 25 30

Ala Met Gly Trp Phe Arg Gln Ala Pro Gly Lys Glu Arg Glu Leu Val
35 40 45

Ala Ala Ile Ser Trp Ser Gly Ser Arg Thr Tyr Tyr Ala Asp Ser Val
50 55 60

Lys Gly Arg Phe Thr Ile Ser Arg Asp Asn Val Met His Thr Val Tyr
65 70 75 80

Leu Ser Met Asn Ser Leu Lys Pro Glu Asp Thr Ala Val Tyr Tyr Cys
85 90 95

Ala Ala Asp Arg Ser Ile Glu Val Gln Ile Ala Asp Tyr Asp Tyr Trp
100 105 110

Gly Arg Gly Thr Gln Val Thr Val Ser Ser Ala Ala Ala Tyr Pro Tyr
115 120 125

Asp Val Pro Asp Tyr Gly Ser His His His His His His
130 135 140

<210> SEQ ID NO 104
<211> LENGTH: 140
<212> TYPE: PRT
<213> ORGANISM: Lama glama

<400> SEQUENCE: 104

Gln Val Gln Leu Gln Glu Ser Gly Gly Gly Ser Val Gln Ala Gly Gly
1 5 10 15

Ser Leu Arg Leu Ser Cys Ala Ala Ser Gly Ser Thr Phe Ser Ile Lys
20 25 30

Ala Met Gly Trp Tyr Arg Gln Ala Pro Gly Lys Gln Arg Glu Leu Val
35 40 45

Ala Ala Phe Ile Ser Gly Arg Gly Ser Thr Lys Tyr Ala Asp Ser Val
50 55 60

Lys Gly Arg Phe Ala Ile Ser Arg Asp Asn Ala Lys Asn Thr Met Tyr
65 70 75 80

```
Leu Gln Met Asp Ser Leu Glu Pro Glu Asp Thr Ala Val Tyr Tyr Cys
                85                  90                  95

Tyr Ile Val Leu Pro Thr Gly Gly Gly Ser Ala Met Asp Tyr Trp Gly
            100                 105                 110

Glu Gly Thr Gln Val Thr Val Ser Ser Ala Ala Ala Tyr Pro Tyr Asp
        115                 120                 125

Val Pro Asp Tyr Gly Ser His His His His His His
    130                 135                 140
```

<210> SEQ ID NO 105
<211> LENGTH: 140
<212> TYPE: PRT
<213> ORGANISM: Lama glama

<400> SEQUENCE: 105

```
Gln Val Gln Leu Gln Glu Ser Gly Gly Gly Val Val Gln Ala Gly Gly
1               5                   10                  15

Ser Leu Arg Leu Ser Cys Ala Ala Ser Gly Ser Thr Phe Ser Ile Lys
            20                  25                  30

Ala Met Gly Trp Tyr Arg Gln Ala Pro Gly Lys Gln Arg Asp Leu Val
        35                  40                  45

Ala Gly Phe Ile Ser Gly Arg Gly Ser Ala Lys Tyr Ala Asp Ser Val
    50                  55                  60

Lys Gly Arg Phe Ala Ile Ser Arg Asp Asn Ala Lys Asn Thr Met Tyr
65                  70                  75                  80

Leu Gln Met Asp Ser Leu Lys Pro Glu Asp Thr Ala Val Tyr Tyr Cys
                85                  90                  95

Tyr Ile Val Leu Thr Thr Gly Gly Gly Ser Ala Met Asp Tyr Trp Gly
            100                 105                 110

Gln Gly Thr Gln Val Thr Val Ser Ser Ala Ala Ala Tyr Pro Tyr Asp
        115                 120                 125

Val Pro Asp Tyr Gly Ser His His His His His His
    130                 135                 140
```

<210> SEQ ID NO 106
<211> LENGTH: 10
<212> TYPE: PRT
<213> ORGANISM: Lama glama

<400> SEQUENCE: 106

```
Gly Arg Asp Phe Ala Thr Tyr Ser Met Ala
1               5                   10
```

<210> SEQ ID NO 107
<211> LENGTH: 10
<212> TYPE: PRT
<213> ORGANISM: Lama glama

<400> SEQUENCE: 107

```
Gly Arg Asp Phe Ala Thr Tyr Ser Met Thr
1               5                   10
```

<210> SEQ ID NO 108
<211> LENGTH: 10
<212> TYPE: PRT
<213> ORGANISM: Lama glama

<400> SEQUENCE: 108

Gly Arg Asp Phe Ser Thr Tyr Ser Met Gly
1 5 10

<210> SEQ ID NO 109
<211> LENGTH: 10
<212> TYPE: PRT
<213> ORGANISM: Lama glama

<400> SEQUENCE: 109

Gly Arg Thr Phe Asn Thr Tyr Ser Met Gly
1 5 10

<210> SEQ ID NO 110
<211> LENGTH: 10
<212> TYPE: PRT
<213> ORGANISM: Lama glama

<400> SEQUENCE: 110

Gly Arg Thr Phe Ser Thr Tyr Ser Met Gly
1 5 10

<210> SEQ ID NO 111
<211> LENGTH: 10
<212> TYPE: PRT
<213> ORGANISM: Lama glama

<400> SEQUENCE: 111

Gly Arg Asp Phe Ser Thr Tyr Ser Met Gly
1 5 10

<210> SEQ ID NO 112
<211> LENGTH: 10
<212> TYPE: PRT
<213> ORGANISM: Lama glama

<400> SEQUENCE: 112

Gly Asn Thr Phe Asp Thr Arg Ala Met Gly
1 5 10

<210> SEQ ID NO 113
<211> LENGTH: 10
<212> TYPE: PRT
<213> ORGANISM: Lama glama

<400> SEQUENCE: 113

Gly Arg Thr Arg Asp Ala Asn Ala Met Gly
1 5 10

<210> SEQ ID NO 114
<211> LENGTH: 10
<212> TYPE: PRT
<213> ORGANISM: Lama glama

<400> SEQUENCE: 114

Gly Ser Thr Phe Ser Ile Lys Ala Met Gly
1 5 10

<210> SEQ ID NO 115
<211> LENGTH: 17
<212> TYPE: PRT
<213> ORGANISM: Lama glama

<400> SEQUENCE: 115

Thr Ile Ser Trp Ser Gly Gln Arg Thr Arg Tyr Ala Asp Ser Val Lys
1 5 10 15

Gly

<210> SEQ ID NO 116
<211> LENGTH: 17
<212> TYPE: PRT
<213> ORGANISM: Lama glama

<400> SEQUENCE: 116

Ser Ile Ser Trp Ser Gly Gln Arg Ser Arg Tyr Ala Asp Ser Val Lys
1 5 10 15

Gly

<210> SEQ ID NO 117
<211> LENGTH: 17
<212> TYPE: PRT
<213> ORGANISM: Lama glama

<400> SEQUENCE: 117

Ile Ile Ser Trp Ser Gly Gln Arg Thr Arg Tyr Ala Asp Ser Val Lys
1 5 10 15

Gly

<210> SEQ ID NO 118
<211> LENGTH: 17
<212> TYPE: PRT
<213> ORGANISM: Lama glama

<400> SEQUENCE: 118

Ala Ile Ser Arg Ser Ser Phe Asn Thr Tyr Tyr Ser Asp Ser Val Thr
1 5 10 15

Gly

<210> SEQ ID NO 119
<211> LENGTH: 17
<212> TYPE: PRT
<213> ORGANISM: Lama glama

<400> SEQUENCE: 119

Ala Ile Ser Trp Ser Gly Ser Arg Thr Tyr Tyr Ala Asp Ser Val Lys
1 5 10 15

Gly

<210> SEQ ID NO 120
<211> LENGTH: 17
<212> TYPE: PRT
<213> ORGANISM: Lama glama

<400> SEQUENCE: 120

Ala Phe Ile Ser Gly Arg Gly Ser Thr Lys Tyr Ala Asp Ser Val Lys
1 5 10 15

Gly

<210> SEQ ID NO 121
<211> LENGTH: 17
<212> TYPE: PRT
<213> ORGANISM: Lama glama

<400> SEQUENCE: 121

Gly Phe Ile Ser Gly Arg Gly Ser Ala Lys Tyr Ala Asp Ser Val Lys
1 5 10 15

Gly

<210> SEQ ID NO 122
<211> LENGTH: 14
<212> TYPE: PRT
<213> ORGANISM: Lama glama

<400> SEQUENCE: 122

Pro Arg Thr Trp Gly Glu Phe Pro Pro Thr Gln Tyr Asp Ser
1 5 10

<210> SEQ ID NO 123
<211> LENGTH: 13
<212> TYPE: PRT
<213> ORGANISM: Lama glama

<400> SEQUENCE: 123

Gly Lys Tyr Gly Met Lys Trp Arg Asp Gly Ala Asp Tyr
1 5 10

<210> SEQ ID NO 124
<211> LENGTH: 13
<212> TYPE: PRT
<213> ORGANISM: Lama glama

<400> SEQUENCE: 124

Asp Arg Ser Ile Glu Val Gln Ile Ala Asp Tyr Asp Tyr
1 5 10

<210> SEQ ID NO 125
<211> LENGTH: 12
<212> TYPE: PRT
<213> ORGANISM: Lama glama

<400> SEQUENCE: 125

Val Leu Pro Thr Gly Gly Gly Ser Ala Met Asp Tyr
1 5 10

<210> SEQ ID NO 126
<211> LENGTH: 12
<212> TYPE: PRT
<213> ORGANISM: Lama glama

<400> SEQUENCE: 126

Val Leu Thr Thr Gly Gly Gly Ser Ala Met Asp Tyr
1 5 10

<210> SEQ ID NO 127
<211> LENGTH: 165
<212> TYPE: PRT
<213> ORGANISM: Artificial Sequence
<220> FEATURE:
<223> OTHER INFORMATION: IFN-alpha2a

<400> SEQUENCE: 127

Cys Asp Leu Pro Gln Thr His Ser Leu Gly Ser Arg Arg Thr Leu Met
1 5 10 15

Leu Leu Ala Gln Met Arg Lys Ile Ser Leu Phe Ser Cys Leu Lys Asp
20 25 30

```
Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 128
<211> LENGTH: 165
<212> TYPE: PRT
<213> ORGANISM: Artificial Sequence
<220> FEATURE:
<223> OTHER INFORMATION: IFN-alpha2b

<400> SEQUENCE: 128

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165


<210> SEQ ID NO 129
<211> LENGTH: 297
<212> TYPE: PRT
<213> ORGANISM: Homo sapiens
```

<400> SEQUENCE: 129

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 130
<211> LENGTH: 157
<212> TYPE: PRT
<213> ORGANISM: Homo sapiens

<400> SEQUENCE: 130

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

```
Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155


<210> SEQ ID NO 131
<211> LENGTH: 171
<212> TYPE: PRT
<213> ORGANISM: Homo sapiens

<400> SEQUENCE: 131

Leu Pro Gly Val Gly Leu Thr Pro Ser Ala Ala Gln Thr Ala Arg Gln
1               5                   10                  15

His Pro Lys Met His Leu Ala His Ser Asn Leu Lys Pro Ala Ala His
            20                  25                  30

Leu Ile Gly Asp Pro Ser Lys Gln Asn Ser Leu Leu Trp Arg Ala Asn
        35                  40                  45

Thr Asp Arg Ala Phe Leu Gln Asp Gly Phe Ser Leu Ser Asn Asn Ser
    50                  55                  60

Leu Leu Val Pro Thr Ser Gly Ile Tyr Phe Val Tyr Ser Gln Val Val
65                  70                  75                  80

Phe Ser Gly Lys Ala Tyr Ser Pro Lys Ala Thr Ser Ser Pro Leu Tyr
                85                  90                  95

Leu Ala His Glu Val Gln Leu Phe Ser Ser Gln Tyr Pro Phe His Val
            100                 105                 110

Pro Leu Leu Ser Ser Gln Lys Met Val Tyr Pro Gly Leu Gln Glu Pro
        115                 120                 125

Trp Leu His Ser Met Tyr His Gly Ala Ala Phe Gln Leu Thr Gln Gly
    130                 135                 140

Asp Gln Leu Ser Thr His Thr Asp Gly Ile Pro His Leu Val Leu Ser
145                 150                 155                 160

Pro Ser Thr Val Phe Phe Gly Ala Phe Ala Leu
                165                 170


<210> SEQ ID NO 132
<211> LENGTH: 281
<212> TYPE: PRT
<213> ORGANISM: Homo sapiens

<400> SEQUENCE: 132

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60
```

```
Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280


<210> SEQ ID NO 133
<211> LENGTH: 153
<212> TYPE: PRT
<213> ORGANISM: Homo sapiens

<400> SEQUENCE: 133

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140
```

Asp Phe Thr Met Gln Phe Val Ser Ser
145 150

<210> SEQ ID NO 134
<211> LENGTH: 133
<212> TYPE: PRT
<213> ORGANISM: Homo sapiens

<400> SEQUENCE: 134

Ala Pro Thr Ser Ser Ser Thr Lys Lys Thr Gln Leu Gln Leu Glu His
1 5 10 15

Leu Leu Leu Asp Leu Gln Met Ile Leu Asn Gly Ile Asn Asn Tyr Lys
20 25 30

Asn Pro Lys Leu Thr Arg Met Leu Thr Phe Lys Phe Tyr Met Pro Lys
35 40 45

Lys Ala Thr Glu Leu Lys His Leu Gln Cys Leu Glu Glu Glu Leu Lys
50 55 60

Pro Leu Glu Glu Val Leu Asn Leu Ala Gln Ser Lys Asn Phe His Leu
65 70 75 80

Arg Pro Arg Asp Leu Ile Ser Asn Ile Asn Val Ile Val Leu Glu Leu
85 90 95

Lys Gly Ser Glu Thr Thr Phe Met Cys Glu Tyr Ala Asp Glu Thr Ala
100 105 110

Thr Ile Val Glu Phe Leu Asn Arg Trp Ile Thr Phe Cys Gln Ser Ile
115 120 125

Ile Ser Thr Leu Thr
130

<210> SEQ ID NO 135
<211> LENGTH: 129
<212> TYPE: PRT
<213> ORGANISM: Homo sapiens

<400> SEQUENCE: 135

His Lys Cys Asp Ile Thr Leu Gln Glu Ile Ile Lys Thr Leu Asn Ser
1 5 10 15

Leu Thr Glu Gln Lys Thr Leu Cys Thr Glu Leu Thr Val Thr Asp Ile
20 25 30

Phe Ala Ala Ser Lys Asn Thr Thr Glu Lys Glu Thr Phe Cys Arg Ala
35 40 45

Ala Thr Val Leu Arg Gln Phe Tyr Ser His His Glu Lys Asp Thr Arg
50 55 60

Cys Leu Gly Ala Thr Ala Gln Gln Phe His Arg His Lys Gln Leu Ile
65 70 75 80

Arg Phe Leu Lys Arg Leu Asp Arg Asn Leu Trp Gly Leu Ala Gly Leu
85 90 95

Asn Ser Cys Pro Val Lys Glu Ala Asn Gln Ser Thr Leu Glu Asn Phe
100 105 110

Leu Glu Arg Leu Lys Thr Ile Met Arg Glu Lys Tyr Ser Lys Cys Ser
115 120 125

Ser

<210> SEQ ID NO 136
<211> LENGTH: 185
<212> TYPE: PRT
<213> ORGANISM: Homo sapiens

<400> SEQUENCE: 136

Ala Pro Val Pro Pro Gly Glu Asp Ser Lys Asp Val Ala Ala Pro His
1 5 10 15

Arg Gln Pro Leu Thr Ser Ser Glu Arg Ile Asp Lys Gln Ile Arg Tyr
20 25 30

Ile Leu Asp Gly Ile Ser Ala Leu Arg Lys Glu Thr Cys Asn Lys Ser
35 40 45

Asn Met Cys Glu Ser Ser Lys Glu Ala Leu Ala Glu Asn Asn Leu Asn
50 55 60

Leu Pro Lys Met Ala Glu Lys Asp Gly Cys Phe Gln Ser Gly Phe Asn
65 70 75 80

Glu Glu Thr Cys Leu Val Lys Ile Ile Thr Gly Leu Leu Glu Phe Glu
85 90 95

Val Tyr Leu Glu Tyr Leu Gln Asn Arg Phe Glu Ser Ser Glu Glu Gln
100 105 110

Ala Arg Ala Val Gln Met Ser Thr Lys Val Leu Ile Gln Phe Leu Gln
115 120 125

Lys Lys Ala Lys Asn Leu Asp Ala Ile Thr Thr Pro Asp Pro Thr Thr
130 135 140

Asn Ala Ser Leu Thr Thr Lys Leu Gln Ala Gln Asn Gln Trp Leu Gln
145 150 155 160

Asp Met Thr Thr His Leu Ile Leu Arg Ser Phe Lys Glu Phe Leu Gln
165 170 175

Ser Ser Leu Arg Ala Leu Arg Gln Met
180 185

<210> SEQ ID NO 137
<211> LENGTH: 114
<212> TYPE: PRT
<213> ORGANISM: Homo sapiens

<400> SEQUENCE: 137

Ser Pro Gly Pro Val Pro Pro Ser Thr Ala Leu Arg Glu Leu Ile Glu
1 5 10 15

Glu Leu Val Asn Ile Thr Gln Asn Gln Lys Ala Pro Leu Cys Asn Gly
20 25 30

Ser Met Val Trp Ser Ile Asn Leu Thr Ala Gly Met Tyr Cys Ala Ala
35 40 45

Leu Glu Ser Leu Ile Asn Val Ser Gly Cys Ser Ala Ile Glu Lys Thr
50 55 60

Gln Arg Met Leu Ser Gly Phe Cys Pro His Lys Val Ser Ala Gly Gln
65 70 75 80

Phe Ser Ser Leu His Val Arg Asp Thr Lys Ile Glu Val Ala Gln Phe
85 90 95

Val Lys Asp Leu Leu Leu His Leu Lys Lys Leu Phe Arg Glu Gly Arg
100 105 110

Phe Asn

<210> SEQ ID NO 138
<211> LENGTH: 194
<212> TYPE: PRT
<213> ORGANISM: Homo sapiens

<400> SEQUENCE: 138

Met Ala Ala Glu Pro Val Glu Asp Asn Cys Ile Asn Phe Val Ala Met
1 5 10 15

```
Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp Leu


<210> SEQ ID NO 139
<211> LENGTH: 270
<212> TYPE: PRT
<213> ORGANISM: Homo sapiens

<400> SEQUENCE: 139

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190
```

```
Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270


<210> SEQ ID NO 140
<211> LENGTH: 119
<212> TYPE: PRT
<213> ORGANISM: Homo sapiens

<400> SEQUENCE: 140

Glu Val Gln Leu Val Glu Ser Gly Gly Gly Leu Val Gln Ala Gly Lys
1               5                   10                  15

Ser Leu Arg Leu Ser Cys Ala Ala Ser Gly Ser Ile Phe Ser Ile His
            20                  25                  30

Ala Met Gly Trp Phe Arg Gln Ala Pro Gly Lys Glu Arg Glu Phe Val
        35                  40                  45

Ala Ala Ile Thr Trp Ser Gly Gly Ile Thr Tyr Tyr Glu Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Asp Arg Ala Glu Ser Ser Trp Tyr Asp Tyr Trp Gly Gln Gly
            100                 105                 110

Thr Gln Val Thr Val Ser Ser
        115


<210> SEQ ID NO 141
<211> LENGTH: 123
<212> TYPE: PRT
<213> ORGANISM: Homo sapiens

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Lys Cys Trp Phe Arg Gln Ala Pro Gly Lys Glu Arg Glu Trp Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Phe Cys
                85                  90                  95

Ala Ala Arg His Gly Gly Pro Leu Thr Val Glu Tyr Phe Phe Asp Tyr
            100                 105                 110

Trp Gly Gln Gly Thr Gln Val Thr Val Ser Ser
        115                 120
```

<210> SEQ ID NO 142
<211> LENGTH: 16
<212> TYPE: PRT
<213> ORGANISM: Artificial Sequence
<220> FEATURE:
<223> OTHER INFORMATION: Linker

<400> SEQUENCE: 142

Gly Gly Ser Gly Gly Ser Gly Gly Gly Gly Ser Gly Gly Gly Gly Ser
1 5 10 15

<210> SEQ ID NO 143
<211> LENGTH: 40
<212> TYPE: DNA
<213> ORGANISM: Artificial Sequence
<220> FEATURE:
<223> OTHER INFORMATION: primer

<400> SEQUENCE: 143
gataagatct caggcggatc cacaacaccc agaaattcag 40

<210> SEQ ID NO 144
<211> LENGTH: 42
<212> TYPE: DNA
<213> ORGANISM: Artificial Sequence
<220> FEATURE:
<223> OTHER INFORMATION: primer

<400> SEQUENCE: 144 ggtttttct ctagatcaag gagagctgtc attttctatt gg 42

<210> SEQ ID NO 145
<211> LENGTH: 20
<212> TYPE: DNA
<213> ORGANISM: Artificial Sequence
<220> FEATURE:
<223> OTHER INFORMATION: primer

<400> SEQUENCE: 145
ttatgcttcc ggctcgtatg 20

<210> SEQ ID NO 146
<211> LENGTH: 29
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: r can be a or g

<400> SEQUENCE: 146
gatgtgcagc tgcaggagtc tggrggagg 29

<210> SEQ ID NO 147
<211> LENGTH: 34
<212> TYPE: DNA
<213> ORGANISM: Artificial Sequence
<220> FEATURE:
<223> OTHER INFORMATION: primer

<400> SEQUENCE: 147
ctagtgcggc cgctgaggag acggtgacct gggt 34

<210> SEQ ID NO 148
<211> LENGTH: 22
<212> TYPE: DNA
<213> ORGANISM: Artificial Sequence
<220> FEATURE:
<223> OTHER INFORMATION: primer

<400> SEQUENCE: 148
tcacacagga aacagctatg ac 22

<210> SEQ ID NO 149
<211> LENGTH: 24
<212> TYPE: DNA
<213> ORGANISM: Artificial Sequence
<220> FEATURE:
<223> OTHER INFORMATION: primer

<400> SEQUENCE: 149
cgccagggtt ttcccagtca cgac 24

<210> SEQ ID NO 150
<211> LENGTH: 43
<212> TYPE: DNA
<213> ORGANISM: Artificial Sequence
<220> FEATURE:
<223> OTHER INFORMATION: primer

<400> SEQUENCE: 150
gataagatct caggcggatc cagtggacct ttcccagcag agc 43

<210> SEQ ID NO 151
<211> LENGTH: 41
<212> TYPE: DNA
<213> ORGANISM: Artificial Sequence
<220> FEATURE:
<223> OTHER INFORMATION: primer

<400> SEQUENCE: 151 ggtttttct ctagatcaag gagcgatctc attttccact g 41

<210> SEQ ID NO 152
<211> LENGTH: 5
<212> TYPE: PRT
<213> ORGANISM: Artificial Sequence
<220> FEATURE:
<223> OTHER INFORMATION: Linker

<400> SEQUENCE: 152

Gly Gly Gly Gly Ser
1 5

<210> SEQ ID NO 153
<211> LENGTH: 10
<212> TYPE: PRT
<213> ORGANISM: Artificial Sequence
<220> FEATURE:
<223> OTHER INFORMATION: Linker

<400> SEQUENCE: 153

Gly Gly Gly Gly Ser Gly Gly Gly Gly Ser
1 5 10

<210> SEQ ID NO 154
<211> LENGTH: 15
<212> TYPE: PRT
<213> ORGANISM: Artificial Sequence
<220> FEATURE:

<223> OTHER INFORMATION: linker

<400> SEQUENCE: 154

Gly Gly Gly Gly Ser Gly Gly Gly Gly Ser Gly Gly Gly Gly Ser
1 5 10 15

<210> SEQ ID NO 155
<211> LENGTH: 20
<212> TYPE: PRT
<213> ORGANISM: Artificial Sequence
<220> FEATURE:
<223> OTHER INFORMATION: linker

<400> SEQUENCE: 155

Gly Gly Gly Gly Ser Gly Gly Gly Gly Ser Gly Gly Gly Gly Ser Gly
1 5 10 15

Gly Gly Gly Ser
20

<210> SEQ ID NO 156
<211> LENGTH: 8
<212> TYPE: PRT
<213> ORGANISM: Artificial Sequence
<220> FEATURE:
<223> OTHER INFORMATION: linker

<400> SEQUENCE: 156

Gly Gly Gly Gly Gly Gly Gly Gly
1 5

<210> SEQ ID NO 157
<211> LENGTH: 6
<212> TYPE: PRT
<213> ORGANISM: Artificial Sequence
<220> FEATURE:
<223> OTHER INFORMATION: linker

<400> SEQUENCE: 157

Gly Gly Gly Gly Gly Gly
1 5

<210> SEQ ID NO 158
<211> LENGTH: 5
<212> TYPE: PRT
<213> ORGANISM: Artificial Sequence
<220> FEATURE:
<223> OTHER INFORMATION: linker

<400> SEQUENCE: 158

Glu Ala Ala Ala Lys
1 5

<210> SEQ ID NO 159
<211> LENGTH: 10
<212> TYPE: PRT
<213> ORGANISM: Artificial Sequence
<220> FEATURE:
<223> OTHER INFORMATION: linker

<400> SEQUENCE: 159

Glu Ala Ala Ala Lys Glu Ala Ala Ala Lys
1 5 10

<210> SEQ ID NO 160
<211> LENGTH: 15
<212> TYPE: PRT

<213> ORGANISM: Artificial Sequence
<220> FEATURE:
<223> OTHER INFORMATION: linker

<400> SEQUENCE: 160

Glu Ala Ala Ala Lys Glu Ala Ala Ala Lys Glu Ala Ala Ala Lys
1 5 10 15

<210> SEQ ID NO 161
<211> LENGTH: 12
<212> TYPE: PRT
<213> ORGANISM: Artificial Sequence
<220> FEATURE:
<223> OTHER INFORMATION: linker

<400> SEQUENCE: 161

Ala Glu Ala Ala Ala Lys Glu Ala Ala Ala Lys Ala
1 5 10

<210> SEQ ID NO 162
<211> LENGTH: 17
<212> TYPE: PRT
<213> ORGANISM: Artificial Sequence
<220> FEATURE:
<223> OTHER INFORMATION: linker

<400> SEQUENCE: 162

Ala Glu Ala Ala Ala Lys Glu Ala Ala Ala Lys Glu Ala Ala Ala Lys
1 5 10 15

Ala

<210> SEQ ID NO 163
<211> LENGTH: 22
<212> TYPE: PRT
<213> ORGANISM: Artificial Sequence
<220> FEATURE:
<223> OTHER INFORMATION: linker

<400> SEQUENCE: 163

Ala Glu Ala Ala Ala Lys Glu Ala Ala Ala Lys Glu Ala Ala Ala Lys
1 5 10 15

Glu Ala Ala Ala Lys Ala
20

<210> SEQ ID NO 164
<211> LENGTH: 27
<212> TYPE: PRT
<213> ORGANISM: Artificial Sequence
<220> FEATURE:
<223> OTHER INFORMATION: linker

<400> SEQUENCE: 164

Ala Glu Ala Ala Ala Lys Glu Ala Ala Ala Lys Glu Ala Ala Ala Lys
1 5 10 15

Glu Ala Ala Ala Lys Glu Ala Ala Ala Lys Ala
20 25

<210> SEQ ID NO 165
<211> LENGTH: 46
<212> TYPE: PRT
<213> ORGANISM: Artificial Sequence
<220> FEATURE:
<223> OTHER INFORMATION: linker

<400> SEQUENCE: 165

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
            20                  25                  30

Ala Ala Lys Glu Ala Ala Ala Lys Glu Ala Ala Ala Lys Ala
        35                  40                  45

<210> SEQ ID NO 166
<211> LENGTH: 5
<212> TYPE: PRT
<213> ORGANISM: Artificial Sequence
<220> FEATURE:
<223> OTHER INFORMATION: linker

<400> SEQUENCE: 166

Pro Ala Pro Ala Pro
1               5

<210> SEQ ID NO 167
<211> LENGTH: 18
<212> TYPE: PRT
<213> ORGANISM: Artificial Sequence
<220> FEATURE:
<223> OTHER INFORMATION: linker

<400> SEQUENCE: 167

Lys Glu Ser Gly Ser Val Ser Ser Glu Gln Leu Ala Gln Phe Arg Ser
1               5                   10                  15

Leu Asp

<210> SEQ ID NO 168
<211> LENGTH: 14
<212> TYPE: PRT
<213> ORGANISM: Artificial Sequence
<220> FEATURE:
<223> OTHER INFORMATION: linker

<400> SEQUENCE: 168

Glu Gly Lys Ser Ser Gly Ser Gly Ser Glu Ser Lys Ser Thr
1               5                   10

<210> SEQ ID NO 169
<211> LENGTH: 12
<212> TYPE: PRT
<213> ORGANISM: Artificial Sequence
<220> FEATURE:
<223> OTHER INFORMATION: linker

<400> SEQUENCE: 169

Gly Ser Ala Gly Ser Ala Ala Gly Ser Gly Glu Phe
1               5                   10

<210> SEQ ID NO 170
<211> LENGTH: 297
<212> TYPE: PRT
<213> ORGANISM: Artificial Sequence
<220> FEATURE:
<223> OTHER INFORMATION: Synthetic polymer.

<400> SEQUENCE: 170

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
20 25 30

Arg Met Ser Ser Leu Val Gly Pro Thr Gln Ser Phe Phe Met Arg Glu
35 40 45

Ser Lys Thr Leu Gly Ala Val Gln Ile Met Asn Gly Leu Phe His Ile
50 55 60

Ala Leu Gly Gly Leu Leu Met Ile Pro Ala Gly Ile Tyr Ala Pro Ile
65 70 75 80

Cys Val Thr Val Trp Tyr Pro Leu Trp Gly Gly Ile Met Tyr Ile Ile
85 90 95

Ser Gly Ser Leu Leu Ala Ala Thr Glu Lys Asn Ser Arg Lys Cys Leu
100 105 110

Val Lys Gly Lys Met Ile Met Asn Ser Leu Ser Leu Phe Ala Ala Ile
115 120 125

Ser Gly Met Ile Leu Ser Ile Met Asp Ile Leu Asn Ile Lys Ile Ser
130 135 140

His Phe Leu Lys Met Glu Ser Leu Asn Phe Ile Arg Ala His Thr Pro
145 150 155 160

Tyr Ile Asn Ile Tyr Asn Cys Glu Pro Ala Asn Pro Ser Glu Lys Asn
165 170 175

Ser Pro Ser Thr Gln Tyr Cys Tyr Ser Ile Gln Ser Leu Phe Leu Gly
180 185 190

Ile Leu Ser Val Met Leu Ile Phe Ala Phe Phe Gln Glu Leu Val Ile
195 200 205

Ala Gly Ile Val Glu Asn Glu Trp Lys Arg Thr Cys Ser Arg Pro Lys
210 215 220

Ser Asn Ile Val Leu Leu Ser Ala Glu Glu Lys Lys Glu Gln Thr Ile
225 230 235 240

Glu Ile Lys Glu Glu Val Val Gly Leu Thr Glu Thr Ser Ser Gln Pro
245 250 255

Lys Asn Glu Glu Asp Ile Glu Ile Ile Pro Ile Gln Glu Glu Glu Glu
260 265 270

Glu Glu Thr Glu Thr Asn Phe Pro Glu Pro Pro Gln Asp Gln Glu Ser
275 280 285

Ser Pro Ile Glu Asn Asp Ser Ser Pro
290 295

<210> SEQ ID NO 171
<211> LENGTH: 157
<212> TYPE: PRT
<213> ORGANISM: Artificial Sequence
<220> FEATURE:
<223> OTHER INFORMATION: Synthetic polymer.

<400> SEQUENCE: 171

Val Arg Ser Ser Ser Arg Thr Pro Ser Asp Lys Pro Val Ala His Val
1 5 10 15

Val Ala Asn Pro Gln Ala Glu Gly Gln Leu Gln Trp Leu Asn Arg Arg
20 25 30

Ala Asn Ala Leu Leu Ala Asn Gly Val Glu Leu Arg Asp Asn Gln Leu
35 40 45

Val Val Pro Ser Glu Gly Leu Tyr Leu Ile Tyr Ser Gln Val Leu Phe
50 55 60

Lys Gly Gln Gly Cys Pro Ser Thr His Val Leu Leu Thr His Thr Ile
65 70 75 80

```
Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155


<210> SEQ ID NO 172
<211> LENGTH: 171
<212> TYPE: PRT
<213> ORGANISM: Artificial Sequence
<220> FEATURE:
<223> OTHER INFORMATION: Synthetic polymer.

<400> SEQUENCE: 172

Leu Pro Gly Val Gly Leu Thr Pro Ser Ala Ala Gln Thr Ala Arg Gln
1               5                   10                  15

His Pro Lys Met His Leu Ala His Ser Asn Leu Lys Pro Ala Ala His
            20                  25                  30

Leu Ile Gly Asp Pro Ser Lys Gln Asn Ser Leu Leu Trp Arg Ala Asn
        35                  40                  45

Thr Asp Arg Ala Phe Leu Gln Asp Gly Phe Ser Leu Ser Asn Asn Ser
    50                  55                  60

Leu Leu Val Pro Thr Ser Gly Ile Tyr Phe Val Tyr Ser Gln Val Val
65                  70                  75                  80

Phe Ser Gly Lys Ala Tyr Ser Pro Lys Ala Thr Ser Ser Pro Leu Tyr
                85                  90                  95

Leu Ala His Glu Val Gln Leu Phe Ser Ser Gln Tyr Pro Phe His Val
            100                 105                 110

Pro Leu Leu Ser Ser Gln Lys Met Val Tyr Pro Gly Leu Gln Glu Pro
        115                 120                 125

Trp Leu His Ser Met Tyr His Gly Ala Ala Phe Gln Leu Thr Gln Gly
    130                 135                 140

Asp Gln Leu Ser Thr His Thr Asp Gly Ile Pro His Leu Val Leu Ser
145                 150                 155                 160

Pro Ser Thr Val Phe Phe Gly Ala Phe Ala Leu
                165                 170


<210> SEQ ID NO 173
<211> LENGTH: 281
<212> TYPE: PRT
<213> ORGANISM: Artificial Sequence
<220> FEATURE:
<223> OTHER INFORMATION: Synthetic polymer.

<400> SEQUENCE: 173

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60
```

```
Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280


<210> SEQ ID NO 174
<211> LENGTH: 153
<212> TYPE: PRT
<213> ORGANISM: Artificial Sequence
<220> FEATURE:
<223> OTHER INFORMATION: Synthetic polymer.

<400> SEQUENCE: 174

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140
```

Asp Phe Thr Met Gln Phe Val Ser Ser
145 150

<210> SEQ ID NO 175
<211> LENGTH: 133
<212> TYPE: PRT
<213> ORGANISM: Artificial Sequence
<220> FEATURE:
<223> OTHER INFORMATION: Synthetic polymer.

<400> SEQUENCE: 175

Ala Pro Thr Ser Ser Ser Thr Lys Lys Thr Gln Leu Gln Leu Glu His
1 5 10 15

Leu Leu Leu Asp Leu Gln Met Ile Leu Asn Gly Ile Asn Asn Tyr Lys
20 25 30

Asn Pro Lys Leu Thr Arg Met Leu Thr Phe Lys Phe Tyr Met Pro Lys
35 40 45

Lys Ala Thr Glu Leu Lys His Leu Gln Cys Leu Glu Glu Glu Leu Lys
50 55 60

Pro Leu Glu Glu Val Leu Asn Leu Ala Gln Ser Lys Asn Phe His Leu
65 70 75 80

Arg Pro Arg Asp Leu Ile Ser Asn Ile Asn Val Ile Val Leu Glu Leu
85 90 95

Lys Gly Ser Glu Thr Thr Phe Met Cys Glu Tyr Ala Asp Glu Thr Ala
100 105 110

Thr Ile Val Glu Phe Leu Asn Arg Trp Ile Thr Phe Cys Gln Ser Ile
115 120 125

Ile Ser Thr Leu Thr
130

<210> SEQ ID NO 176
<211> LENGTH: 129
<212> TYPE: PRT
<213> ORGANISM: Artificial Sequence
<220> FEATURE:
<223> OTHER INFORMATION: Synthetic polymer.

<400> SEQUENCE: 176

His Lys Cys Asp Ile Thr Leu Gln Glu Ile Ile Lys Thr Leu Asn Ser
1 5 10 15

Leu Thr Glu Gln Lys Thr Leu Cys Thr Glu Leu Thr Val Thr Asp Ile
20 25 30

Phe Ala Ala Ser Lys Asn Thr Thr Glu Lys Glu Thr Phe Cys Arg Ala
35 40 45

Ala Thr Val Leu Arg Gln Phe Tyr Ser His His Glu Lys Asp Thr Arg
50 55 60

Cys Leu Gly Ala Thr Ala Gln Gln Phe His Arg His Lys Gln Leu Ile
65 70 75 80

Arg Phe Leu Lys Arg Leu Asp Arg Asn Leu Trp Gly Leu Ala Gly Leu
85 90 95

Asn Ser Cys Pro Val Lys Glu Ala Asn Gln Ser Thr Leu Glu Asn Phe
100 105 110

Leu Glu Arg Leu Lys Thr Ile Met Arg Glu Lys Tyr Ser Lys Cys Ser
115 120 125

Ser

<210> SEQ ID NO 177

<211> LENGTH: 185
<212> TYPE: PRT
<213> ORGANISM: Artificial Sequence
<220> FEATURE:
<223> OTHER INFORMATION: Synthetic polymer.

<400> SEQUENCE: 177

```
Ala Pro Val Pro Pro Gly Glu Asp Ser Lys Asp Val Ala Ala Pro His
1               5                   10                  15

Arg Gln Pro Leu Thr Ser Ser Glu Arg Ile Asp Lys Gln Ile Arg Tyr
            20                  25                  30

Ile Leu Asp Gly Ile Ser Ala Leu Arg Lys Glu Thr Cys Asn Lys Ser
        35                  40                  45

Asn Met Cys Glu Ser Ser Lys Glu Ala Leu Ala Glu Asn Asn Leu Asn
    50                  55                  60

Leu Pro Lys Met Ala Glu Lys Asp Gly Cys Phe Gln Ser Gly Phe Asn
65                  70                  75                  80

Glu Glu Thr Cys Leu Val Lys Ile Ile Thr Gly Leu Leu Glu Phe Glu
                85                  90                  95

Val Tyr Leu Glu Tyr Leu Gln Asn Arg Phe Glu Ser Ser Glu Glu Gln
            100                 105                 110

Ala Arg Ala Val Gln Met Ser Thr Lys Val Leu Ile Gln Phe Leu Gln
        115                 120                 125

Lys Lys Ala Lys Asn Leu Asp Ala Ile Thr Thr Pro Asp Pro Thr Thr
    130                 135                 140

Asn Ala Ser Leu Thr Thr Lys Leu Gln Ala Gln Asn Gln Trp Leu Gln
145                 150                 155                 160

Asp Met Thr Thr His Leu Ile Leu Arg Ser Phe Lys Glu Phe Leu Gln
                165                 170                 175

Ser Ser Leu Arg Ala Leu Arg Gln Met
            180                 185
```

<210> SEQ ID NO 178
<211> LENGTH: 114
<212> TYPE: PRT
<213> ORGANISM: Artificial Sequence
<220> FEATURE:
<223> OTHER INFORMATION: Synthetic polymer.

<400> SEQUENCE: 178

```
Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Arg
            100                 105                 110

Phe Asn
```

<210> SEQ ID NO 179

<211> LENGTH: 194
<212> TYPE: PRT
<213> ORGANISM: Artificial Sequence
<220> FEATURE:
<223> OTHER INFORMATION: Synthetic polymer.

<400> SEQUENCE: 179

```
Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
    130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp Leu
```

<210> SEQ ID NO 180
<211> LENGTH: 270
<212> TYPE: PRT
<213> ORGANISM: Artificial Sequence
<220> FEATURE:
<223> OTHER INFORMATION: Synthetic polymer.

<400> SEQUENCE: 180

```
Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125
```

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270

<210> SEQ ID NO 181
<211> LENGTH: 119
<212> TYPE: PRT
<213> ORGANISM: Artificial Sequence
<220> FEATURE:
<223> OTHER INFORMATION: Synthetic polymer.

<400> SEQUENCE: 181

Glu Val Gln Leu Val Glu Ser Gly Gly Gly Leu Val Gln Ala Gly Lys
1               5                   10                  15

Ser Leu Arg Leu Ser Cys Ala Ala Ser Gly Ser Ile Phe Ser Ile His
            20                  25                  30

Ala Met Gly Trp Phe Arg Gln Ala Pro Gly Lys Glu Arg Glu Phe Val
        35                  40                  45

Ala Ala Ile Thr Trp Ser Gly Gly Ile Thr Tyr Tyr Glu Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Asp Arg Ala Glu Ser Ser Trp Tyr Asp Tyr Trp Gly Gln Gly
            100                 105                 110

Thr Gln Val Thr Val Ser Ser
        115

<210> SEQ ID NO 182
<211> LENGTH: 123
<212> TYPE: PRT
<213> ORGANISM: Artificial Sequence
<220> FEATURE:
<223> OTHER INFORMATION: Synthetic polymer.

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Lys Cys Trp Phe Arg Gln Ala Pro Gly Lys Glu Arg Glu Trp Val
35 40 45

Ser Cys Ile Ser Ser Ser Asp Gly Ser Thr Tyr Tyr Ala Asp Ser Val
50 55 60

Lys Gly Arg Phe Thr Ile Ser Arg Asp Asn Ala Lys Asn Thr Val Tyr
65 70 75 80

Leu Gln Met Asn Ser Leu Lys Pro Glu Asp Thr Ala Val Tyr Phe Cys
85 90 95

Ala Ala Arg His Gly Gly Pro Leu Thr Val Glu Tyr Phe Phe Asp Tyr
100 105 110

Trp Gly Gln Gly Thr Gln Val Thr Val Ser Ser
115 120

<210> SEQ ID NO 183
<211> LENGTH: 5
<212> TYPE: PRT
<213> ORGANISM: Artificial Sequence
<220> FEATURE:
<223> OTHER INFORMATION: Synthetic polymer.

<400> SEQUENCE: 183

Gly Gly Gly Gly Ser
1 5

<210> SEQ ID NO 184
<211> LENGTH: 6
<212> TYPE: PRT
<213> ORGANISM: Artificial Sequence
<220> FEATURE:
<223> OTHER INFORMATION: Synthetic polymer.

<400> SEQUENCE: 184

Gly Gly Gly Gly Ser Ser
1 5

<210> SEQ ID NO 185
<211> LENGTH: 7
<212> TYPE: PRT
<213> ORGANISM: Artificial Sequence
<220> FEATURE:
<223> OTHER INFORMATION: Synthetic polymer.

<400> SEQUENCE: 185

Gly Gly Gly Gly Ser Ser Ser
1 5

<210> SEQ ID NO 186
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 186

Gly Gly Gly Gly Ser Ser Ser Ser
1 5

<210> SEQ ID NO 187
<211> LENGTH: 9
<212> TYPE: PRT
<213> ORGANISM: Artificial Sequence
<220> FEATURE:
<223> OTHER INFORMATION: Synthetic polymer.

<400> SEQUENCE: 187

Gly Gly Gly Gly Ser Ser Ser Ser Ser
1 5

<210> SEQ ID NO 188
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 188

Gly Gly Gly Gly Ser Ser Ser Ser Ser Ser
1 5 10

<210> SEQ ID NO 189
<211> LENGTH: 11
<212> TYPE: PRT
<213> ORGANISM: Artificial Sequence
<220> FEATURE:
<223> OTHER INFORMATION: Synthetic polymer.

<400> SEQUENCE: 189

Gly Gly Gly Gly Ser Ser Ser Ser Ser Ser Ser
1 5 10

<210> SEQ ID NO 190
<211> LENGTH: 12
<212> TYPE: PRT
<213> ORGANISM: Artificial Sequence
<220> FEATURE:
<223> OTHER INFORMATION: Synthetic polymer.

<400> SEQUENCE: 190

Gly Gly Gly Gly Ser Ser Ser Ser Ser Ser Ser Ser
1 5 10

<210> SEQ ID NO 191
<211> LENGTH: 16
<212> TYPE: PRT
<213> ORGANISM: Artificial Sequence
<220> FEATURE:
<223> OTHER INFORMATION: Synthetic polymer.

<400> SEQUENCE: 191

Gly Gly Ser Gly Gly Ser Gly Gly Gly Gly Ser Gly Gly Gly Gly Ser
1 5 10 15

<210> SEQ ID NO 192
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 192

Gly Gly Gly Gly Ser Gly Gly Gly Gly Ser
1 5 10

<210> SEQ ID NO 193
<211> LENGTH: 15
<212> TYPE: PRT
<213> ORGANISM: Artificial Sequence
<220> FEATURE:
<223> OTHER INFORMATION: Synthetic polymer.

<400> SEQUENCE: 193

Gly Gly Gly Gly Ser Gly Gly Gly Gly Ser Gly Gly Gly Gly Ser
1 5 10 15

<210> SEQ ID NO 194
<211> LENGTH: 20
<212> TYPE: PRT
<213> ORGANISM: Artificial Sequence
<220> FEATURE:
<223> OTHER INFORMATION: Synthetic polymer.

<400> SEQUENCE: 194

Gly Gly Gly Gly Ser Gly Gly Gly Gly Ser Gly Gly Gly Gly Ser Gly
1 5 10 15

Gly Gly Gly Ser
20

<210> SEQ ID NO 195
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 195

Gly Gly Gly Gly Gly Gly Gly Gly
1 5

<210> SEQ ID NO 196
<211> LENGTH: 6
<212> TYPE: PRT
<213> ORGANISM: Artificial Sequence
<220> FEATURE:
<223> OTHER INFORMATION: Synthetic polymer.

<400> SEQUENCE: 196

Gly Gly Gly Gly Gly Gly
1 5

<210> SEQ ID NO 197
<211> LENGTH: 5
<212> TYPE: PRT
<213> ORGANISM: Artificial Sequence
<220> FEATURE:
<223> OTHER INFORMATION: Synthetic polymer.

<400> SEQUENCE: 197

Glu Ala Ala Ala Lys
1 5

<210> SEQ ID NO 198
<211> LENGTH: 10
<212> TYPE: PRT
<213> ORGANISM: Artificial Sequence
<220> FEATURE:
<223> OTHER INFORMATION: Synthetic polymer.

<400> SEQUENCE: 198

Glu Ala Ala Ala Lys Glu Ala Ala Ala Lys
1 5 10

<210> SEQ ID NO 199
<211> LENGTH: 15
<212> TYPE: PRT
<213> ORGANISM: Artificial Sequence
<220> FEATURE:
<223> OTHER INFORMATION: Synthetic polymer.

<400> SEQUENCE: 199

Glu Ala Ala Ala Lys Glu Ala Ala Ala Lys Glu Ala Ala Ala Lys
1 5 10 15

<210> SEQ ID NO 200
<211> LENGTH: 12
<212> TYPE: PRT
<213> ORGANISM: Artificial Sequence
<220> FEATURE:
<223> OTHER INFORMATION: Synthetic polymer.

<400> SEQUENCE: 200

Ala Glu Ala Ala Ala Lys Glu Ala Ala Ala Lys Ala
1 5 10

<210> SEQ ID NO 201
<211> LENGTH: 17
<212> TYPE: PRT
<213> ORGANISM: Artificial Sequence
<220> FEATURE:
<223> OTHER INFORMATION: Synthetic polymer.

<400> SEQUENCE: 201

Ala Glu Ala Ala Ala Lys Glu Ala Ala Ala Lys Glu Ala Ala Ala Lys
1 5 10 15

Ala

<210> SEQ ID NO 202
<211> LENGTH: 22
<212> TYPE: PRT
<213> ORGANISM: Artificial Sequence
<220> FEATURE:
<223> OTHER INFORMATION: Synthetic polymer.

<400> SEQUENCE: 202

Ala Glu Ala Ala Ala Lys Glu Ala Ala Ala Lys Glu Ala Ala Ala Lys
1 5 10 15

Glu Ala Ala Ala Lys Ala
20

<210> SEQ ID NO 203
<211> LENGTH: 27
<212> TYPE: PRT
<213> ORGANISM: Artificial Sequence
<220> FEATURE:
<223> OTHER INFORMATION: Synthetic polymer.

<400> SEQUENCE: 203

Ala Glu Ala Ala Ala Lys Glu Ala Ala Ala Lys Glu Ala Ala Ala Lys
1 5 10 15

Glu Ala Ala Ala Lys Glu Ala Ala Ala Lys Ala
20 25

<210> SEQ ID NO 204
<211> LENGTH: 46
<212> TYPE: PRT
<213> ORGANISM: Artificial Sequence
<220> FEATURE:
<223> OTHER INFORMATION: Synthetic polymer.

<400> SEQUENCE: 204

Ala Glu Ala Ala Ala Lys Glu Ala Ala Ala Lys Glu Ala Ala Ala Lys
1 5 10 15

Glu Ala Ala Ala Lys Ala Leu Glu Ala Glu Ala Ala Ala Lys Glu Ala
20 25 30

Ala Ala Lys Glu Ala Ala Ala Lys Glu Ala Ala Ala Lys Ala
35 40 45

<210> SEQ ID NO 205
<211> LENGTH: 5
<212> TYPE: PRT
<213> ORGANISM: Artificial Sequence
<220> FEATURE:
<223> OTHER INFORMATION: Synthetic polymer.

<400> SEQUENCE: 205

Pro Ala Pro Ala Pro
1 5

<210> SEQ ID NO 206
<211> LENGTH: 18
<212> TYPE: PRT
<213> ORGANISM: Artificial Sequence
<220> FEATURE:
<223> OTHER INFORMATION: Synthetic polymer.

<400> SEQUENCE: 206

Lys Glu Ser Gly Ser Val Ser Ser Glu Gln Leu Ala Gln Phe Arg Ser
1 5 10 15

Leu Asp

<210> SEQ ID NO 207
<211> LENGTH: 14
<212> TYPE: PRT
<213> ORGANISM: Artificial Sequence
<220> FEATURE:
<223> OTHER INFORMATION: Synthetic polymer.

<400> SEQUENCE: 207

Glu Gly Lys Ser Ser Gly Ser Gly Ser Glu Ser Lys Ser Thr
1 5 10

<210> SEQ ID NO 208
<211> LENGTH: 12
<212> TYPE: PRT
<213> ORGANISM: Artificial Sequence
<220> FEATURE:
<223> OTHER INFORMATION: Synthetic polymer.

<400> SEQUENCE: 208

Gly Ser Ala Gly Ser Ala Ala Gly Ser Gly Glu Phe
1 5 10

<210> SEQ ID NO 209
<211> LENGTH: 40
<212> TYPE: DNA
<213> ORGANISM: Artificial Sequence
<220> FEATURE:
<223> OTHER INFORMATION: Synthetic polymer.

<400> SEQUENCE: 209
gataagatct caggcggatc cacaacaccc agaaattcag 40

<210> SEQ ID NO 210
<211> LENGTH: 42
<212> TYPE: DNA
<213> ORGANISM: Artificial Sequence
<220> FEATURE:
<223> OTHER INFORMATION: Synthetic polymer.

<400> SEQUENCE: 210
ggttttttct ctagatcaag gagagctgtc attttctatt gg 42

<210> SEQ ID NO 211
<211> LENGTH: 20
<212> TYPE: DNA
<213> ORGANISM: Artificial Sequence
<220> FEATURE:
<223> OTHER INFORMATION: Synthetic polymer.

<400> SEQUENCE: 211
ttatgcttcc ggctcgtatg 20

<210> SEQ ID NO 212
<211> LENGTH: 29
<212> TYPE: DNA
<213> ORGANISM: Artificial Sequence
<220> FEATURE:
<223> OTHER INFORMATION: Synthetic polymer.

<400> SEQUENCE: 212
gatgtgcagc tgcaggagtc tggrggagg 29

<210> SEQ ID NO 213
<211> LENGTH: 34
<212> TYPE: DNA
<213> ORGANISM: Artificial Sequence
<220> FEATURE:
<223> OTHER INFORMATION: Synthetic polymer.

<400> SEQUENCE: 213
ctagtgcggc cgctgaggag acggtgacct gggt 34

<210> SEQ ID NO 214
<211> LENGTH: 22
<212> TYPE: DNA
<213> ORGANISM: Artificial Sequence
<220> FEATURE:
<223> OTHER INFORMATION: Synthetic polymer.

<400> SEQUENCE: 214
tcacacagga aacagctatg ac 22

<210> SEQ ID NO 215
<211> LENGTH: 24
<212> TYPE: DNA
<213> ORGANISM: Artificial Sequence
<220> FEATURE:
<223> OTHER INFORMATION: Synthetic polymer.

<400> SEQUENCE: 215
cgccagggtt ttcccagtca cgac 24

<210> SEQ ID NO 216
<211> LENGTH: 43
<212> TYPE: DNA
<213> ORGANISM: Artificial Sequence
<220> FEATURE:
<223> OTHER INFORMATION: Synthetic polymer.

<400> SEQUENCE: 216
gataagatct caggcggatc cagtggacct ttcccagcag agc 43

<210> SEQ ID NO 217
<211> LENGTH: 41
<212> TYPE: DNA
<213> ORGANISM: Artificial Sequence
<220> FEATURE:
<223> OTHER INFORMATION: Synthetic polymer.

<400> SEQUENCE: 217 ggtttttct ctagatcaag gagcgatctc attttccact g 41

<210> SEQ ID NO 218
<211> LENGTH: 20
<212> TYPE: DNA
<213> ORGANISM: Artificial Sequence
<220> FEATURE:
<223> OTHER INFORMATION: Synthetic polymer.

<400> SEQUENCE: 218
ttatgcttcc ggctcgtatg 20

<210> SEQ ID NO 219
<211> LENGTH: 29
<212> TYPE: DNA
<213> ORGANISM: Artificial Sequence
<220> FEATURE:
<223> OTHER INFORMATION: Synthetic polymer.
<220> FEATURE:
<221> NAME/KEY: R
<222> LOCATION: (24)..(24)
<223> OTHER INFORMATION: R stands for A or G.

<400> SEQUENCE: 219
gatgtgcagc tgcaggagtc tggrggagg 29

<210> SEQ ID NO 220
<211> LENGTH: 34
<212> TYPE: DNA
<213> ORGANISM: Artificial Sequence
<220> FEATURE:
<223> OTHER INFORMATION: Synthetic polymer.

<400> SEQUENCE: 220
ctagtgcggc cgctgaggag acggtgacct gggt 34

<210> SEQ ID NO 221
<211> LENGTH: 22
<212> TYPE: DNA
<213> ORGANISM: Artificial Sequence
<220> FEATURE:
<223> OTHER INFORMATION: Synthetic polymer.

<400> SEQUENCE: 221
tcacacagga aacagctatg ac 22

<210> SEQ ID NO 222
<211> LENGTH: 24
<212> TYPE: DNA
<213> ORGANISM: Artificial Sequence
<220> FEATURE:
<223> OTHER INFORMATION: Synthetic polymer.

-continued

<400> SEQUENCE: 222
cgccagggtt ttcccagtca cgac 24

CD20 BINDING SINGLE DOMAIN ANTIBODIES

PRIORITY

This application is a continuation application of U.S. Ser. No. 16/082,300 (now U.S. Pat. No. 11,248,057), filed Sep. 5, 2018, which is a National Stage application of PCT/EP2017/055312, filed Mar. 7, 2017, which claims the benefit of and priority to EP 16158962.7, filed Mar. 7, 2016, and EP 16166206.9, filed Apr. 20, 2016, the contents of which are hereby incorporated by reference in their entireties.

FIELD

The present invention relates, in part, to binding agents (e.g., antibodies, such as, without limitation, VHHs) which bind CD20 and their use as therapeutic agents.

SEQUENCE LISTING

The instant application contains a Sequence Listing which has been submitted in ASCII format via EFS-Web and is hereby incorporated by reference in its entirety. Said ASCII copy, created on Aug. 12, 2025, is named ORN-049C1_ST25.txt and is 144,274 bytes in size.

BACKGROUND

CD20 is a transmembrane protein expressed on the surface of B lymphocytes. It is expressed during the development of a B lymphocyte from the early pre-B stage until terminal differentiation into plasmocytes, a stage at which CD20 expression disappears. CD20 is also expressed on malignant B cells. In particular, CD20 is expressed on greater than 90% of B cell non-Hodgkin's lymphoma (NHL) cells and over 95% B-type Chronic Lymphocytic Leukemia (B-CLL) cells.

Antibodies directed against CD20 have been used for the treatment of B-cell derived leukemia and lymphomas. Specifically, rituximab (Rituxan) is a genetically engineered chimeric murine/human monoclonal antibody directed against CD20. Rituximab is currently approved for the treatment of relapsed or refractory follicular lymphoma. Reports indicate that weekly infusions with rituximab resulted in overall response rates of 48%. However, many patients do not respond to rituximab treatment. In addition, responding patients often develop resistance to rituximab and eventually relapse. Further still, rituximab appears to kill normal CD20-positive cells non-specifically, thereby resulting in significant toxicity and side effects.

Accordingly, there remains a need for therapeutically effective CD20 binding agents that can bind to CD20-expressing malignant cells with high specificity while causing minimal side effects.

SUMMARY

In various aspects, the present invention relates to CD20 binding agents having at least one targeting moiety that specifically binds to CD20. In an embodiment, the targeting moiety is a single domain antibody (VHH or Nanobody). In some embodiments, these CD20 binding agents bind to, but do not functionally modulate (e.g. partially or fully neutralize) CD20. In some embodiments, the CD20 binding agent binds to CD20 positive cells to result in death of the CD20 positive cells.

In various embodiments, the CD20 binding agent further comprises a signaling agent, e.g., without limitation, an interferon, an interleukin, and a tumor necrosis factor, that may be modified. In various embodiments, the CD20 binding agent comprises additional targeting moieties that bind to other targets (e.g. antigens, receptor) of interest. In an embodiment, the other targets (e.g. antigens, receptor) of interest are present on tumor cells. In another embodiment, the other targets (e.g. antigens, receptor) of interest are present on immune cells.

In various embodiments, the present CD20 binding agents find use in the treatment of various diseases or disorders involving cells that express CD20. In some embodiments, such diseases or disorders include cancer, infections, immune disorders, and other diseases and disorders. In various embodiments, the present invention encompasses various methods of treatment.

DETAILED DESCRIPTION

Figure 1:
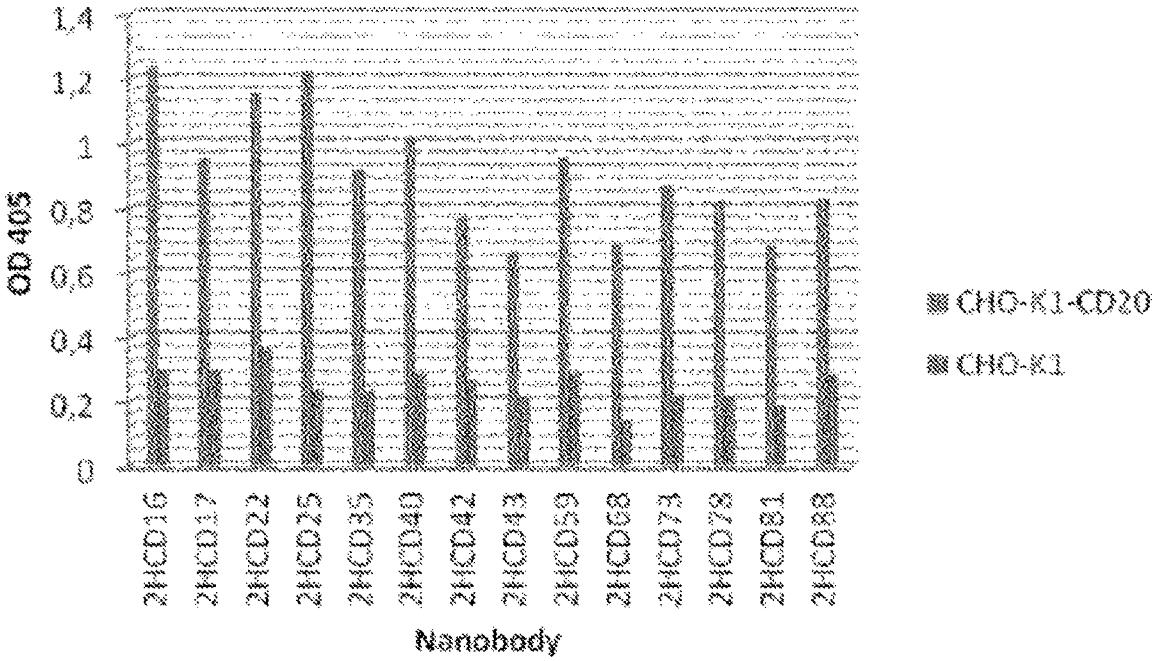
FIG. 1 depicts results from cell ELISA assays using periplasmic extracts of positive colonies. For each set of histograms, the first bar is CHO-K1-hCD20 and the second bar is CHO-K1. A clone is considered as specific, if it gives a signal on transfected cells which is at least 2-fold higher than the signal obtained with negative control parental cells. In addition, the relative strength of the signals may not reflect the relative quality of the Nanobodies since in these experiments the crude periplasmic extracts are used and the differences in ELISA signals may be related to factors such as the amount of VHH used, etc. rather than to their quality such as affinity, actual yield, etc.
Figure 1:
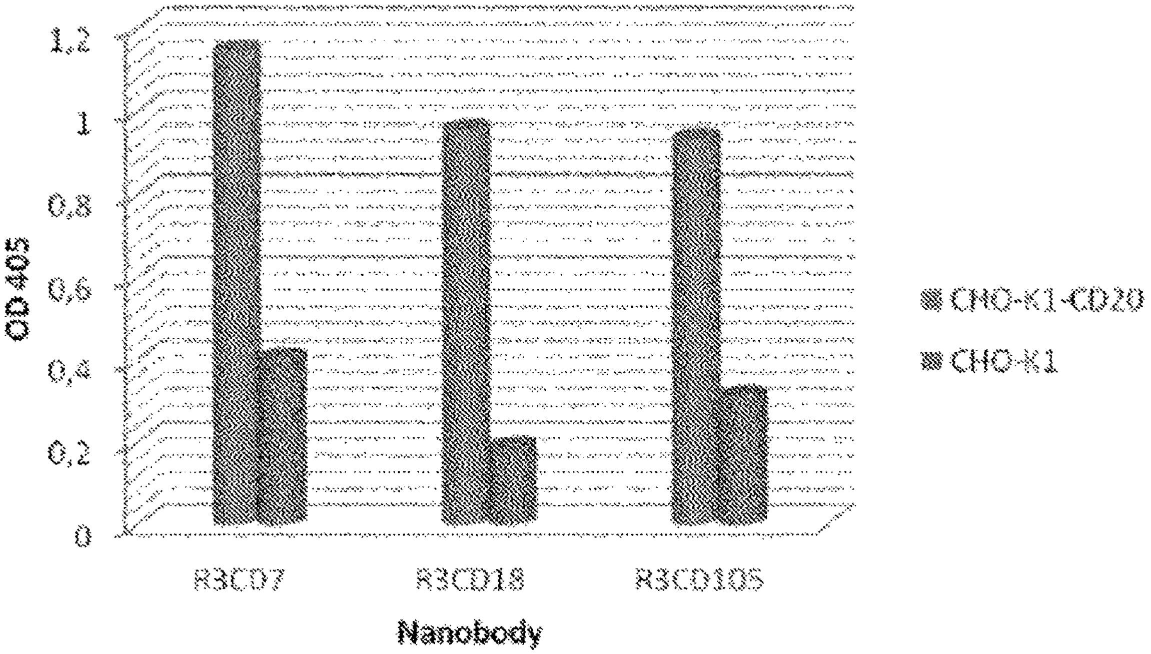

The present application is based, in part, on the discovery of agents (e.g. antibodies such as, by way of non-limiting example, VHHs or Nanobodies) that recognize and bind to CD20. In various embodiments, these CD20 binding agents bind to, but do not functionally modulate CD20. In various embodiments, these CD20 binding agents may bind and directly or indirectly recruit immune cells to sites in need of therapeutic action (e.g. a tumor or tumor microenvironment). In various embodiments, the CD20 binding agent binds to CD20 positive cells and result in the death of such cells. The present application provides pharmaceutical compositions comprising the CD20 binding agents and their use in the treatment of various diseases. In various embodiments, the CD20 binding agent is part of chimeric protein with a modified signaling agent as described herein.

CD20 Binding Agents

In various embodiments, the present CD20 binding agent is a protein-based agent capable of specific binding to CD20. In various embodiments, the present CD20 binding agent is a protein-based agent capable of specific binding to CD20 without neutralization of CD20. CD20 is a nonglycosylated member of the membrane-spanning 4-A (MS4A) family. It functions as a B cell specific differentiation antigen in both mouse and human (Stashenko et al., 1980; Oettgen et al., 1983; Ishibashi et al., 2001). In particular, human CD20 cDNA encodes a transmembrane protein consisting of four hydrophobic membrane-spanning domains, two extracellular loops and intracellular N- and C-terminal regions (Einfield et al., 1988).

In various embodiments, the CD20 binding agent of the application comprises a targeting moiety having an antigen recognition domain that recognizes an epitope present on CD20. In an embodiment, the antigen-recognition domain recognizes one or more linear epitopes present on CD20. As used herein, a linear epitope refers to any continuous sequence of amino acids present on CD20. In another embodiment, the antigen-recognition domain recognizes one or more conformational epitopes present on CD20. As used herein, a conformation epitope refers to one or more sections of amino acids (which may be discontinuous) which form a three-dimensional surface with features and/or shapes and/or tertiary structures capable of being recognized by an antigen recognition domain.

In various embodiments, the CD20 binding agent of the present application may bind to the full-length and/or mature forms and/or isoforms and/or splice variants and/or fragments and/or any other naturally occurring or synthetic analogs, variants, or mutants of CD20 (e.g., human CD20). In various embodiments, the CD20 binding agent of the application may bind to any forms of CD20 (e.g., human CD20), including monomeric, dimeric, trimeric, tetrameric, heterodimeric, multimeric and associated forms. In an embodiment, the CD20 binding agent binds to the monomeric form of CD20. In another embodiment, the CD20 binding agent binds to a dimeric form of CD20. In another embodiment, the CD20 binding agent binds to a tetrameric form of CD20. In a further embodiment, the CD20 binding agent binds to phosphorylated form of CD20, which may be either monomeric, dimeric, or tetrameric.

In an embodiment, the present CD20 binding agent comprises a targeting moiety with an antigen recognition domain that recognizes one or more epitopes present on human CD20. In an embodiment, the human CD20 comprises the amino acid sequence of:

```
MTTPRNSVNGTFPAEPMKGPIAMQSGPKPLFRRMSSLVG

PTQSFFMRESKTLGAVQIMNGLFHIALGGLLMIPAGIYA

PICVTVWYPLWGGIMYIISGSLLAATEKNSRKCLVKGKM

IMNSLSLFAAISGMILSIMDILNIKISHFLKMESLNFIR

AHTPYINIYNCEPANPSEKNSPSTQYCYSIQSLFLGILS

VMLIFAFFQELVIAGIVENEWKRTCSRPKSNIVLLSAEE

KKEQTIEIKEEWGLTETSSQPKNEEDIEIIPIQEEEEEE

TETNFPEPPQDQESSPIENDSSP
```

In various embodiments, the present CD20 binding agent comprises a targeting moiety capable of specific binding. In various embodiments, the CD20 binding agent comprises a targeting moiety having an antigen recognition domain such as an antibody or derivatives thereof. In an embodiment, the CD20 binding agent comprises a targeting moiety which is an antibody. In various embodiments, the antibody is a full-length multimeric protein that includes two heavy chains and two light chains. Each heavy chain includes one variable region (e.g., $V_H$) and at least three constant regions (e.g., $CH_1$, $CH_2$ and $CH_3$), and each light chain includes one variable region ($V_L$) and one constant region ($C_L$). The variable regions determine the specificity of the antibody. Each variable region comprises three hypervariable regions also known as complementarity determining regions (CDRs) flanked by four relatively conserved framework regions (FRs). The three CDRs, referred to as CDR1, CDR2, and CDR3, contribute to the antibody binding specificity. In some embodiments, the antibody is a chimeric antibody. In some embodiments, the antibody is a humanized antibody.

In some embodiments, the CD20 binding agent comprises a targeting moiety which is an antibody derivative or format. In some embodiments, the present CD20 binding agent comprises a targeting moiety which is a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; an Affimer, a Transbody; an Anticalin; an AdNectin; an Affilin; a Microbody; a peptide aptamer; an alterases; a plastic antibodies; a phylomer; a stradobodies; a maxibodies; an evibody; a fynomer, an armadillo repeat protein, a Kunitz domain, an avimer, an atrimer, a probody, an immunobody, a triomab, a troybody; a pepbody; a vaccibody, a UniBody; a DuoBody, a Fv, a Fab, a Fab', a $F(ab')_2$, a peptide mimetic molecule, or a synthetic molecule, as described in US Patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

In some embodiments, the CD20 binding agent comprises a targeting moiety which is a single-domain antibody, such as a VHH. The VHH may be derived from, for example, an organism that produces VHH antibody such as a camelid, a shark, or the VHH may be a designed VHH. VHHs are antibody-derived therapeutic proteins that contain the unique structural and functional properties of naturally-occurring heavy-chain antibodies. VHH technology is based on fully functional antibodies from camelids that lack light chains. These heavy-chain antibodies contain a single variable domain ($V_HH$) and two constant domains (CH2 and CH3). VHHs are commercially available under the trademark of NANOBODIES. In an embodiment, the CD20 binding agent comprises a Nanobody. In some embodiments, the single domain antibody as described herein is an immunoglobulin single variable domain or ISVD.

In some embodiments, the CD20 binding agent comprises a targeting moiety which is a VHH comprising a single amino acid chain having four "framework regions" or FRs and three "complementary determining regions" or CDRs. As used herein, "framework region" or "FR" refers to a region in the variable domain which is located between the CDRs. As used herein, "complementary determining region" or "CDR" refers to variable regions in VHHs that contains the amino acid sequences capable of specifically binding to antigenic targets.

In various embodiments, the CD20 binding agent comprises a VHH having a variable domain comprising at least one CDR1, CDR2, and/or CDR3 sequences.

In some embodiments, the CDR1 sequence is selected from:

(SEQ ID NO: 35)
GRTFSRQSMG;

(SEQ ID NO: 36)
GRTFSGQSMG;

(SEQ ID NO: 37)
GRTFSSYAMG;

(SEQ ID NO: 38)
GRTFSSYNMG;

(SEQ ID NO: 39)
GRTFSNYNMG;

(SEQ ID NO: 40)
GRTFSNSNMG;

(SEQ ID NO: 41)
GRSFSSVNMG;

(SEQ ID NO: 42)
GRTFSMG;

(SEQ ID NO: 43)
GRTVGSYSMG;

(SEQ ID NO: 44)
RFTLDYYAIG;

(SEQ ID NO: 45)
GFTLDYYAIG;

(SEQ ID NO: 106)
GRDFATYSMA;

(SEQ ID NO: 107)
GRDFATYSMT;

(SEQ ID NO: 108)
GRDFSTYSMG;

(SEQ ID NO: 109)
GRTFNTYSMG;

(SEQ ID NO: 110)
GRTFSTYSMG;

(SEQ ID NO: 111)
GRDFSTYSMG;

(SEQ ID NO: 112)
GNTFDTRAMG;

(SEQ ID NO: 113)
GRTRDANAMG;
or (SEQ ID NO: 114)
GSTFSIKAMG.

In some embodiments, the CDR2 sequence is selected from:

(SEQ ID NO: 46)
VITWSGGSPYYADSVRG;

(SEQ ID NO: 47)
VITWSGGSPYYADSVKG;

(SEQ ID NO: 48)
VISWSGGSPYYADSVKG;

(SEQ ID NO: 49)
AIDWSGGSPYYAASVRG;

-continued (SEQ ID NO: 50)
VIDWSGGSPYYTDSVRG;

(SEQ ID NO: 51)
AITYSGGSPYYASSVRG;

(SEQ ID NO: 52)
AVIWSGASPYYADSVKG;

(SEQ ID NO: 53)
AVTINSGASPYYADSVKG;

(SEQ ID NO: 54)
AVTRSGASPYYADSVKG;

(SEQ ID NO: 55)
CISSSGGSTNYADSVKG;

(SEQ ID NO: 115)
TISINSGQRTRYADSVKG;

(SEQ ID NO: 116)
SISWSGQRSRYADSVKG;

(SEQ ID NO: 117)
IISINSGQRTRYADSVKG;

(SEQ ID NO: 118)
AISRSSFNTYYSDSVTG;

(SEQ ID NO: 119)
AISINSGSRTYYADSVKG;

(SEQ ID NO: 120)
AFISGRGSTKYADSVKG;
or (SEQ ID NO: 121)
GFISGRGSAKYADSVKG.

In some embodiments, the CDR3 sequence is selected from:

(SEQ ID NO: 56)
PVSYGSQWLADY;

(SEQ ID NO: 57)
PVSYGSSWLADY;

(SEQ ID NO: 58)
PLSYGSTWLADY;

(SEQ ID NO: 59)
GVSFGSRWLSDY;

(SEQ ID NO: 60)
GVSYGSRWLGDY;

(SEQ ID NO: 61)
NPTYGSDWNAEN;

(SEQ ID NO: 62)
NPTYSGGWHAEY;

(SEQ ID NO: 63)
ERTWVSNYYCSGDGDGYDYD;

(SEQ ID NO: 122)
PRTWGEFPPPTQYDS;

(SEQ ID NO: 123)
GKYGMKVVRDGADY;

(SEQ ID NO: 124)
DRSIEVQIADYDY;

(SEQ ID NO: 125)
VLPTGGGSAMDY;

-continued or (SEQ ID NO: 126)
VLTTGGGSAMDY.

In various embodiments, the CD20 binding agent comprises a CDR1 comprising the amino acid sequence of SEQ ID NO:35, a CDR2 comprising the amino acid sequence of SEQ ID NO:46, and a CDR3 comprising the amino acid sequence of SEQ ID NO:56.

In various embodiments, the CD20 binding agent comprises a CDR1 comprising the amino acid sequence of SEQ ID NO:35, a CDR2 comprising the amino acid sequence of SEQ ID NO:47, and a CDR3 comprising the amino acid sequence of SEQ ID NO:56.

In various embodiments, the CD20 binding agent comprises a CDR1 comprising the amino acid sequence of SEQ ID NO:36, a CDR2 comprising the amino acid sequence of SEQ ID NO:46, and a CDR3 comprising the amino acid sequence of SEQ ID NO:56.

In various embodiments, the CD20 binding agent comprises a CDR1 comprising the amino acid sequence of SEQ ID NO:37, a CDR2 comprising the amino acid sequence of SEQ ID NO:46, and a CDR3 comprising the amino acid sequence of SEQ ID NO:56.

In various embodiments, the CD20 binding agent comprises a CDR1 comprising the amino acid sequence of SEQ ID NO:38, a CDR2 comprising the amino acid sequence of SEQ ID NO:48, and a CDR3 comprising the amino acid sequence of SEQ ID NO:57.

In various embodiments, the CD20 binding agent comprises a CDR1 comprising the amino acid sequence of SEQ ID NO:39, a CDR2 comprising the amino acid sequence of SEQ ID NO:49, and a CDR3 comprising the amino acid sequence of SEQ ID NO:58.

In various embodiments, the CD20 binding agent comprises a CDR1 comprising the amino acid sequence of SEQ ID NO:40, a CDR2 comprising the amino acid sequence of SEQ ID NO:50, and a CDR3 comprising the amino acid sequence of SEQ ID NO:59.

In various embodiments, the CD20 binding agent comprises a CDR1 comprising the amino acid sequence of SEQ ID NO:41, a CDR2 comprising the amino acid sequence of SEQ ID NO:50, and a CDR3 comprising the amino acid sequence of SEQ ID NO:60.

In various embodiments, the CD20 binding agent comprises a CDR1 comprising the amino acid sequence of SEQ ID NO:42, a CDR2 comprising the amino acid sequence of SEQ ID NO:51, and a CDR3 comprising the amino acid sequence of SEQ ID NO:61.

In various embodiments, the CD20 binding agent comprises a CDR1 comprising the amino acid sequence of SEQ ID NO:43, a CDR2 comprising the amino acid sequence of SEQ ID NO:52, and a CDR3 comprising the amino acid sequence of SEQ ID NO:62.

In various embodiments, the CD20 binding agent comprises a CDR1 comprising the amino acid sequence of SEQ ID NO:43, a CDR2 comprising the amino acid sequence of SEQ ID NO:53, and a CDR3 comprising the amino acid sequence of SEQ ID NO:62.

In various embodiments, the CD20 binding agent comprises a CDR1 comprising the amino acid sequence of SEQ ID NO:43, a CDR2 comprising the amino acid sequence of SEQ ID NO:54, and a CDR3 comprising the amino acid sequence of SEQ ID NO:62.

In various embodiments, the CD20 binding agent comprises a CDR1 comprising the amino acid sequence of SEQ ID NO:44, a CDR2 comprising the amino acid sequence of SEQ ID NO:53, and a CDR3 comprising the amino acid sequence of SEQ ID NO:62.

In various embodiments, the CD20 binding agent comprises a CDR1 comprising the amino acid sequence of SEQ ID NO:45, a CDR2 comprising the amino acid sequence of SEQ ID NO:55, and a CDR3 comprising the amino acid sequence of SEQ ID NO:63.

In various embodiments, the CD20 binding agent comprises a CDR1 comprising the amino acid sequence of SEQ ID NO:106, a CDR2 comprising the amino acid sequence of SEQ ID NO:115, and a CDR3 comprising the amino acid sequence of SEQ ID NO:122.

In various embodiments, the CD20 binding agent comprises a CDR1 comprising the amino acid sequence of SEQ ID NO:107, a CDR2 comprising the amino acid sequence of SEQ ID NO:115, and a CDR3 comprising the amino acid sequence of SEQ ID NO:122.

In various embodiments, the CD20 binding agent comprises a CDR1 comprising the amino acid sequence of SEQ ID NO:108, a CDR2 comprising the amino acid sequence of SEQ ID NO:115, and a CDR3 comprising the amino acid sequence of SEQ ID NO:122.

In various embodiments, the CD20 binding agent comprises a CDR1 comprising the amino acid sequence of SEQ ID NO:109, a CDR2 comprising the amino acid sequence of SEQ ID NO:116, and a CDR3 comprising the amino acid sequence of SEQ ID NO:122.

In various embodiments, the CD20 binding agent comprises a CDR1 comprising the amino acid sequence of SEQ ID NO:110, a CDR2 comprising the amino acid sequence of SEQ ID NO:117, and a CDR3 comprising the amino acid sequence of SEQ ID NO:122.

In various embodiments, the CD20 binding agent comprises a CDR1 comprising the amino acid sequence of SEQ ID NO:111, a CDR2 comprising the amino acid sequence of SEQ ID NO:115, and a CDR3 comprising the amino acid sequence of SEQ ID NO:122.

In various embodiments, the CD20 binding agent comprises a CDR1 comprising the amino acid sequence of SEQ ID NO:112, a CDR2 comprising the amino acid sequence of SEQ ID NO:118, and a CDR3 comprising the amino acid sequence of SEQ ID NO:123.

In various embodiments, the CD20 binding agent comprises a CDR1 comprising the amino acid sequence of SEQ ID NO:113, a CDR2 comprising the amino acid sequence of SEQ ID NO:119, and a CDR3 comprising the amino acid sequence of SEQ ID NO:124.

In various embodiments, the CD20 binding agent comprises a CDR1 comprising the amino acid sequence of SEQ ID NO:114, a CDR2 comprising the amino acid sequence of SEQ ID NO:120, and a CDR3 comprising the amino acid sequence of SEQ ID NO:125.

In various embodiments, the CD20 binding agent comprises a CDR1 comprising the amino acid sequence of SEQ ID NO:114, a CDR2 comprising the amino acid sequence of SEQ ID NO:121, and a CDR3 comprising the amino acid sequence of SEQ ID NO:126.

In various embodiments, the CD20 binding agent comprises an amino acid sequence selected from the following sequences:

2HCD16:

(SEQ ID NO: 18)
QVQLQESGGGLVQAGGSLRLSCAASGRTFSRQSMG

WFRQAPGKEREFVAVITWSGGSPYYADSVRGRFTI

SRDNAKNTVYLQMNSLKPEDTAVYYCAAPVSYGSQ

WLADYWGQGTQVTVSSAAAYPYDVPDYGSHHHHHH

-continued

2HCD22:

(SEQ ID NO: 19)

QVQLQESGGGLVQAGDSLRLSCAASGRTFSRQSMG
WFRQAPGKEREFVAVITWSGGSPYYADSVKGRFTI
SRDNAKNTVYLQMNSLKPEDTAVYYCAAPVSYGSQ
WLADYWGQGTQVTVSSAAAYPYDVPDYGSHHHHHH

2HCD35:

(SEQ ID NO: 20)

QVQLQESGGGLVQAGGSLRLSCAASGRTFSGQSMG
WFRQAPGKEREFVAVITWSGGSPYYADSVRGRFTI
SRDNAKNTVHLQMNSLKPEDTAVYYCAAPVSYGSQ
WLADYWGQGTQVTVSSAAAYPYDVPDYGSHHHHHH

2HCD42:

(SEQ ID NO: 21)

QVQLQESGGGLVQAGGSLRLSCAASGRTFSSYAMG
WFRQAPGKEREFVAVITWSGGSPYYADSVRGRFTI
SRDNAKNTVYLQMNSLKPEDTAVYYCAAPVSYGSQ
WLADYWGQGTQVTVSSAAAYPYDVPDYGSHHHHHH

2HCD73:

(SEQ ID NO: 22)

QVQLQESGGGLVQAGGSLRLSCAASGRTFSRQSMG
WFRQAPGEEREFVAVITWSGGSPYYADSVRGRFTI
SRDNAKNTVYLQMNSLKPEDTAVYYCAAPVSYGSQ
WLADYWGQGTQVTVSSAAAYPYDVPDYGSHHHHHH

2HCD81:

(SEQ ID NO: 23)

QVQLQESGGGLVQAGGSLRLSCAASGRTFSSYNMG
WFRQAPGKEREFVAVISWSGGSPYYADSVKGRFTI
SRDNAKNTVYLQMNSLKPEDTAVYYCAAPVSYGSS
WLADYWGQGTQVTVSSAAAYPYDVPDYGSHHHHHH

R3CD105:

(SEQ ID NO: 24)

QVQLQESGGGLVQAGGSLRLSCAASGRTFSNYNMG
WFRQAPGKEREFVAAIDWSGGSPYYAASVRGRFTI
SRDNAENTVYLQMNSLKPEDTAVYYCAAPLSYGST
WLADYWGQGTQVTVSSAAAYPYDVPDYGSHHHHHH

R3CD18:

(SEQ ID NO: 25)

QVQLQESGGGLVQAGGSLRLSCAASGRTFSNSNMG
WFRQAPGKEREFVAVIDWSGGSPYYTDSVRGRFTI
SRDNAKNTVYLQMNRLKPEDTAVYYCAGGVSFGSR
WLSDYWGQGTQVTVSSAAAYPYDVPDYGSHHHHHH

R3CD7:

(SEQ ID NO: 26)

QVQLQESGGGLVQAGGSLRLSCAASGRSFSSVNMG
WFRQAPGKEREFVAVIDWSGGSPYYTDSVRGRFTI
SRDNSKNTVYLQMNSLKPEDTAVYYCAAGVSYGSR
WLGDYWGQGTQVTVSSAAAYPYDVPDYGSHHHHHH

-continued

2HCD25:

(SEQ ID NO: 27)

QVQLQESGGGLAQAGGSLRLSCAASGRTFSMGWFR
QAPGKEREFVAAITYSGGSPYYASSVRGRFTISRD
NAKNTVYLQMNSLKPEDTAVYYCAANPTYGSDWNA
ENWGQGTQVTVSSAAAYPYDVPDYGSHHHHHH

2HCD78:

(SEQ ID NO: 28)

QVQLQESGGGLVQPGGSLRLSCAASGRTFSMGWFR
QAPGKEREFVAAITYSGGSPYYASSVRGRFTISRD
NAKNTVYLQMNSLKPEDTAVYYCAANPTYGSDWNA
ENWGQGTQVTVSSAAAYPYDVPDYGSHHHHHH

2HCD17:

(SEQ ID NO: 29)

QVQLQESGGGLVQAGGSLRLSCAASGRTVGSYSMG
WFRQAPGKEREFVAAVIWSGASPYYADSVKGRFTI
SRDNAKNTVYLQMNSLKPEDTAVYYCAANPTYSGG
WHAEYWGQGTQVTVSSAAAYPYDVPDYGSHHHHHH

2HCD40:

(SEQ ID NO: 30)

QVQLQESGGGLVQAGGSLRLSCAASGRTVGSYSMG
WFRQAPGKEREFVAAVTWSGASPYYADSVKGRFTI
SRDNAKNTVYLQMNSLKPEDTAVYYCAANPTYSGG
WHAEYWGQGTQVTVSSAAAYPYDVPDYGSHHHHHH

2HCD88:

(SEQ ID NO: 31)

QVQLQESGGGLVQAGDSLRLSCAASGRTVGSYSMG
VVFRQAPGKEREFVAAVTWSGASPYYADSVKGRFT
ISRDNAKNIVYLQMNSLKPEDTAVYYCAANPTYSG
GWHAEYWGQGTQVIVSSAAAYPYDVPDYGSHHHHH
H

2HCD59:

(SEQ ID NO: 32)

QVQLQESGGGSEQPGGSLRLSCAASGRTVGSYSMG
WFRQAPGKEREFVAAVTRSGASPYYADSVKGRFTI
SRDNAKNTVYLQMNSLKPEDTAVYYCAANPTYSGG
WHAEYVVGQGTQVTVSSAAAYPYDVPDYGSHHHHH
H

2HCD68:

(SEQ ID NO: 33)

QVQLQESGGGLVQPGGSLRLSCAASRFTLDYYAIG
WFRQAPGKEREFVAAVTWSGASPYYADSVKGRFTI
SRDNAKNTVYLQMNSLKPEDTAVYYCAANPTYSGG
WHAEYWGQGTQVTVSSAAAYPYDVPDYGSHHHHHH

2HCD43:

(SEQ ID NO: 34)

QVQLQESGGGLVQPGGSLRLSCTASGFTLDYYAIG
WLRQAPGKEREGVSCISSSGGSTNYADSVKGRFTI
SRDNAKNTVYLLMNSLKPEDTAVYYCAAERTVVVS

-continued

NYYCSGDGDGYDYDYWGQGTQVTVSSAAAYPYDVP
DYGSHHHHHH

2MC57:
(SEQ ID NO: 85)
QVQLQESGGGLVQAGGSLRLSCAASGRDFATYSMA
WFRQAPGKERESVATISWSGQRTRYADSVKGRFTI
SRDNAKNTVYLQMNSLKPEDTAVYYCAMPRTWGEF
PPTQYDSWGQGTQVTVSSAAAYPYDVPDYGSHHHH
HH

R2MUC70:
(SEQ ID NO: 86)
QVQLQESGGGLVQAGGSLRLSCAASGRDFATYSMA
WFRQAPGKERESVATISWSGQRTRYADSVKGRFTI
SRDNAKNTVYLQMNSLKPEDTAVYYCAAPRTWGEF
PPTQYDSWGQGTQVTVSSAAAYPYDVPDYGSHHHH
HH

R3MUC17:
(SEQ ID NO: 87)
QVQLQESGGGLVPAGGSLRLSCAASGRDFATYSMA
WFRQAPGKERESVATISWSGQRTRYADSVKGRFTI
SRDNAKNTVYLQMNSLKPEDTAVYYCAAPRTWGEF
PPTQYDSWGQGTQVTVSSAAAYPYDVPDYGSHHHH
HH

R3MUC56:
(SEQ ID NO: 88)
QVQLQESGGGLVQAGDSLRLSCAASGRDFATYSMA
WFRQAPGKERESVATISWSGQRTRYADSVKGRFTI
SRDNAKNTVYLQMNSLKPEDTAVYYCAAPRTWGEF
PPTQYDSWGQGTQVTVSSAAAYPYDVPDYGSHHHH
HH

R3MUC57:
(SEQ ID NO: 89)
QVQLQESGGGLVQAGGSLRLSCAASGRDFATYSMA
WFRQAPGEERESVATISWSGQRTRYADSVKGRFTI
SRDNAKNTVYLQMNSLKPEDTAVYYCAAPRTWGEF
PPTQYDSWGQGTQVTVSSAAAYPYDVPDYGSHHHH
HH

R3MUC58:
(SEQ ID NO: 90)
QVQLQESGGGLVQPGGSLRLSCAASGRDFATYSMA
WFRQAPGKERESVATISWSGQRTRYADSVKGRFTI
SRDNAKNTVYLQMNSLKPEDTAVYYCAAPRTWGEF
PPTQYDSWGQGTQVTVSSAAAYPYDVPDYGSHHHH
HH

-continued

R2MUC85:
(SEQ ID NO: 91)
QVQLQESGGGLVQPGGSLRLSCATSGRDFATYSMA
WFRQAPGKERESVATISWSGQRTRYADSVKGRFTI
SRDNAKNTVYLQMNSLKPEDTAVYYCAAPRTWGEF
PPTQYDSWGQGTQVTVSSAAAYPYDVPDYGSHHHH
HH

R3MUC66:
(SEQ ID NO: 92)
QVQLQESGGGLVQAGGSLRLSCAASGRDFATYSMT
WFRQAPGKERESVATISWSGQRTRYADSVKGRFTI
SRDNAKNTVYLQMNSLRPEDTAVYYCAAPRTWGEF
PPTQYDSWGQGTQVTVSSAAAYPYDVPDYGSHHHH
HH

R2MUC21:
(SEQ ID NO: 93)
QVQLQESGGGLVQAGDSLRLSCAASGRDFSTYSMG
WFRQAPGKERESVATISWSGQRTRYADSVKGRFTI
SRDNAKNTVYLQMNSLKPEDTAVYYCAAPRTWGEF
PPTQYDSWGQGTQVTVSSAAAYPYDVPDYGSHHHH
HH

2MC52:
(SEQ ID NO: 94)
QVQLQESGGGLVQAGGSLRLSCVASGRTFNTYSMG
WFRQAPGKEREFVASISWSGQRSRYADSVKGRFTI
SRDNAKNTVYLQMNSLKPEDTAVYYCASPRTWGEF
PPTQYDSWGQGTQVTVSSAAAYPYDVPDYGSHHHH
HH

R3MUC22:
(SEQ ID NO: 95)
QVQLQESGGGLVQAGGSLRLSCAASGRTFSTYSMG
WFRQAPGKEREFVAIISWSGQRTRYADSVKGRFTI
SRDNAKNTVYLQMNSLKPEDTAVYYCAAPRTWGEF
PPTQYDSWGQGTQVTVSSAAAYPYDVPDYGSHHHH
HH

R3MUC75:
(SEQ ID NO: 96)
QVQLQESGGGSVQTGGSLRLSCAASGRDFSTYSMG
WFRQAPGKERESVATISWSGQRTRYADSVKGRFTI
SRDNAKNTVYLQMNSLKPEDTAVYYCAAPRTWGEF
PPTQYDSWGQGTQVTVSSAAAYPYDVPDYGSHHHH
HH

2MC39:
(SEQ ID NO: 97)
QVQLQESGGGLAQAGNSLRISCVASGNTFDTRAMG
WFRQAPGKEREFVAAISRSSFNTYYSDSVTGRFTI

-continued

SRDNAKNTVYLQMNSLKPEDTAVYYCAAGKYGMKW

RDGADYWGQGTQVTVSSAAAYPYDVPDYGSHHHHH

H

2MC51:

(SEQ ID NO: 98)

QVQLQESGGGLAQAGNSLRISCVASGNTFDTRAMG

WFRQAPGKEREFVAAISRSSFNTYYSDSVTGRFTI

SRDNAKNTVYLQMNSLKPEDTAVYYCVAGKYGMKW

RDGADYWGQGTQVTVSSAAAYPYDVPDYGSHHHHH

H

2MC38:

(SEQ ID NO: 99)

QVQLQESGGGLVQAGESLRISCVASGNTFDTRAMG

WFRQAPGKEREFVAAISRSSFNTYYSDSVTGRFTI

SRDNAKNTVYLQMNSLKPEDTAVYYCVAGKYGMKW

RDGADYWGQGTQVTVSSAAAYPYDVPDYGSHHHHH

H

2MC82:

(SEQ ID NO: 100)

QVQLQESGGGLAQEGGSLRLSCVASGNTFDTRAMG

WFRQAPGKEREFVAAISRSSFNTYYSDSVTGRFTI

SRDNAKNMVYLQMNSLKPEDTAVYYCAAGKYGMKW

RDGADYWGQGTQVTVSSAAAYPYDVPDYGSHHHHH

H

2MC20:

(SEQ ID NO: 101)

QVQLQESGGGLVQTGGSLRLSCAASGNTFDTRAMG

WFRQAPGKEREFVAAISRSSFNTYYSDSVTGRFTI

SRDNAKNTVYLQMNSLKPEDTAVYYCAAGKYGMKW

RDGADYWGQGTQVTVSSAAAYPYDVPDYGSHHHHH

H

2MC42:

(SEQ ID NO: 102)

QVQLQESGGGSVQTGGTLTLSCVASGNTFDTRAMG

WFRQAPGEEREFVAAISRSSFNTYYSDSVTGRFTI

SRDNAKNTVYLQMNSLKPEDTAVYYCAAGKYGMKW

RDGADYWGQGTQVTVSSAAAYPYDVPDYGSHHHHH

H

R2MUC36:

(SEQ ID NO: 103)

QVQLQESGGGLVQAEGSLRLSCAASGRTRDANAMG

WFRQAPGKERELVAAISWSGSRTYYADSVKGRFTI

SRDNVMHTVYLSMNSLKPEDTAVYYCAADRSIEVQ

IADYDYWGRGTQVTVSSAAAYPYDVPDYGSHHHHH

H

-continued

R3MCD137:

(SEQ ID NO: 104)

QVQLQESGGGSVQAGGSLRLSCAASGSTFSIKAMG

WYRQAPGKQRELVAAFISGRGSTKYADSVKGRFAI

SRDNAKNTMYLQMDSLEPEDTAVYYCYIVLPTGGG

SAMDYWGEGTQVTVSSAAAYPYDVPDYGSHHHHHH

R3MCD22:

(SEQ ID NO: 105)

QVQLQESGGGVVQAGGSLRLSCAASGSTFSIKAMG

WYRQAPGKQRDLVAGFISGRGSAKYADSVKGRFAI

SRDNAKNTMYLQMDSLKPEDTAVYYCYIVLTTGGG

SAMDYWGQGTQVTVSSAAAYPYDVPDYGSHHHHHH

In various embodiments, the present application contemplates the use of any natural or synthetic analogs, mutants, variants, alleles, homologs and orthologs (herein collectively referred to as "analogs") of the CD20 binding agent of the application as described herein. In various embodiments, the amino acid sequence of the CD20 binding agent further includes an amino acid analog, an amino acid derivative, or other non-classical amino acids.

In various embodiments, the CD20 binding agent comprises a targeting moiety comprising a sequence that is at least 60% identical to any one of SEQ ID NOs: 18-34 or 85-105. In various embodiments, the CD20 binding agent comprises a targeting moiety comprising a sequence that is at least 60% identical to any one of SEQ ID NOs: 18-34 or 85-105 minus the linker sequence, the HA tag and/or the $HIS_6$ tag. For example, the CD20 binding agent may comprise a targeting moiety comprising a sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to SEQ ID NOs: 2-87 (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity to any one of SEQ ID NOs: 18-34 or 85-105).

In various embodiments, the CD20 binding agent comprises a targeting moiety comprising an amino acid sequence having one or more amino acid mutations with respect to SEQ ID NOs: 18-34 or 85-105. In various embodiments, the CD20 binding agent comprises a targeting moiety comprising an amino acid sequence having one, or two, or three, or four, or five, or six, or seen, or eight, or nine, or ten, or fifteen, or twenty amino acid mutations with respect to SEQ ID NOs: 18-34 or 85-105. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

In various embodiments, the amino acid mutation may be in the CDRs of the targeting moiety (e.g., the CDR1, CDR2 or CDR3 regions). In another embodiment, amino acid alteration may be in the framework regions (FRs) of the targeting moiety (e.g., the FR1, FR2, FR3, or FR4 regions).

Modification of the amino acid sequences may be achieved using any known technique in the art e.g., site-directed mutagenesis or PCR based mutagenesis. Such techniques are described, for example, in Sambrook et al., Molecular Cloning: A Laboratory Manual, Cold Spring Harbor Press, Plainview, N.Y., 1989 and Ausubel et al., Current Protocols in Molecular Biology, John Wiley & Sons, New York, N.Y., 1989.

In various embodiments, the mutations do not substantially reduce the present CD20 binding agent's capability to specifically bind to CD20. In various embodiments, the mutations do not substantially reduce the present CD20 binding agent's capability to specifically bind to CD20 without neutralizing CD20.

In various embodiments, the binding affinity of the CD20 binding agent of the application for the full-length and/or mature forms and/or isoforms and/or splice variants and/or fragments and/or monomeric and/or dimeric and/or tetrameric forms and/or any other naturally occurring or synthetic analogs, variants, or mutants (including monomeric and/or dimeric and/or tetrameric forms) of human CD20 may be described by the equilibrium dissociation constant ($K_D$). In various embodiments, the CD20 binding agent comprises a targeting moiety that binds to the full-length and/or mature forms and/or isoforms and/or splice variants and/or fragments and/or any other naturally occurring or synthetic analogs, variants, or mutants (including monomeric and/or dimeric and/or tetrameric forms) of human CD20 with a $K_D$ of less than about 1 uM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, or about 5 nM, or about 4.5 nM, or about 1 nM.

In various embodiments, the CD20 binding agent comprises a targeting moiety that binds but does not functionally modulate the antigen of interest, i.e., CD20. For instance, in various embodiments, the targeting moiety of the CD20 binding agent simply targets the antigen but does not substantially functionally modulate (e.g. substantially inhibit, reduce or neutralize) a biological effect that the antigen has. In various embodiments, the targeting moiety of the CD20 binding agent binds an epitope that is physically separate from an antigen site that is important for its biological activity (e.g. an antigen's active site).

Such binding without significant function modulation finds use in various embodiments of the present application. In various embodiments, the present CD20 binding agent binds to CD20 positive cells and induces the death of such cells. In some embodiments, the CD20 binding agent induces cell death as mediated by one or more of apoptosis or direct cell death, complement-dependent cytotoxicity (CDC), antibody-dependent cellular cytotoxicity (ADCC), and/or or antibody-dependent cellular phagocytosis (ADCP). In some embodiments, the present CD20 binding agent induces translocation of CD20 into large lipid micro-domains or 'lipid rafts' within the plasma membrane upon binding. This clustering process enhances the activation of complement and exerts strong complement-dependent cytotoxicity (CDC). In other embodiments, the present CD20 binding agent induces direct cell death. In alternative embodiments, the therapeutic efficacy of the CD20 binding agent is not dependent on B cell depletion.

In various embodiments, the present CD20 binding agent may be used to directly or indirectly recruit active immune cells to a site of need via an effector antigen. For example, in various embodiments, the present CD20 binding agent may be used to directly or indirectly recruit an immune cell to a cancer or tumor cell in a method of reducing or eliminating a cancer or tumor (e.g. the CD20 binding agent may comprise a targeting moiety having an anti-CD20 antigen recognition domain and a targeting moiety having a recognition domain (e.g. antigen recognition domain) directed against Clec9A, which is an antigen expressed on dendritic cells). In these embodiments, CD20 signaling is an important piece of the cancer reducing or eliminating effect. In various embodiments, the present CD20 binding agent may recruit a T cell, a B cell, a dendritic cell, a macrophage, and a natural killer (NK) cell.

Therapeutic Agents Comprising the Present CD20 Binding Agents

Chimeras and Fusions with Signaling Agents

In various embodiments, the CD20 binding agent of the application is part of a chimera or fusion with one or more signaling agents. Accordingly, the present application provides for chimeric or fusion proteins that include, for example, a targeting moiety against CD20 and one or more signaling agents.

In various embodiments, the signaling agent is modified to have reduced affinity or activity for one or more of its receptors, which allows for attenuation of activity (inclusive of agonism or antagonism) and/or prevents non-specific signaling or undesirable sequestration of the chimeric or fusion protein. In various embodiments, the signaling agent is antagonistic in its wild type form and bears one or more mutations that attenuate its antagonistic activity. In various embodiments, the signaling agent is antagonistic due to one or more mutations, e.g. an agonistic signaling agent is converted to an antagonistic signaling agent and, such a converted signaling agent, optionally, also bears one or more mutations that attenuate its antagonistic activity (e.g. as described in WO 2015/007520, the entire contents of which are hereby incorporated by reference).

Accordingly, in various embodiments, the signaling agent is a modified (e.g. mutant) form of the signaling agent having one or more mutations. In various embodiments, the modifications (e.g. mutations) allow for the modified signaling agent to have one or more of attenuated activity such as one or more of reduced binding affinity, reduced endogenous activity, and reduced specific bioactivity relative to unmodified or unmutated, i.e. the wild type form of the signaling agent (e.g. comparing the same signaling agent in a wild type form versus a modified or mutant form). In some embodiments, the mutations which attenuate or reduce binding or affinity include those mutations which substantially reduce or ablate binding or activity. In some embodiments, the mutations which attenuate or reduce binding or affinity are different than those mutations which substantially reduce or ablate binding or activity. Consequentially, in various embodiments, the mutations allow for the signaling agent to have improved safety, e.g. reduced systemic toxicity, reduced side effects, and reduced off-target effects relative to unmutated, i.e. wild type, signaling agent (e.g. comparing the same signaling agent in a wild type form versus a modified (e.g. mutant) form).

As described herein, the agent may have improved safety due to one of more modifications, e.g. mutations. In various embodiments, improved safety means that the present chimeric protein provides lower toxicity (e.g. systemic toxicity and/or tissue/organ-associated toxicities); and/or lessened or substantially eliminated side effects; and/or increased tolerability, lessened or substantially eliminated adverse events; and/or reduced or substantially eliminated off-target effects; and/or an increased therapeutic window.

In various embodiments, the signaling agent is modified to have one or more mutations that reduce its binding affinity or activity for one or more of its receptors. In some embodiments, the signaling agent is modified to have one or more mutations that substantially reduce or ablate binding affinity or activity for the receptors. In some embodiments, the activity provided by the wild type signaling agent is agonism at the receptor (e.g. activation of a cellular effect at a site of therapy). For example, the wild type signaling agent may activate its receptor. In such embodiments, the mutations result in the modified signaling agent to have reduced or ablated activating activity at the receptor. For example, the mutations may result in the modified signaling agent to deliver a reduced activating signal to a target cell or the activating signal could be ablated. In some embodiments, the activity provided by the wild type signaling agent is antagonism at the receptor (e.g. blocking or dampening of a cellular effect at a site of therapy). For example, the wild type signaling agent may antagonize or inhibit the receptor. In these embodiments, the mutations result in the modified signaling agent to have a reduced or ablated antagonizing activity at the receptor. For example, the mutations may result in the modified signaling agent to deliver a reduced inhibitory signal to a target cell or the inhibitory signal could be ablated. In various embodiments, the signaling agent is antagonistic due to one or more mutations, e.g. an agonistic signaling agent is converted to an antagonistic signaling agent (e.g. as described in WO 2015/007520, the entire contents of which are hereby incorporated by reference) and, such a converted signaling agent, optionally, also bears one or more mutations that reduce its binding affinity or activity for one or more of its receptors or that substantially reduce or ablate binding affinity or activity for one or more of its receptors.

In some embodiments, the reduced affinity or activity at the receptor is restorable by attachment with one or more of the targeting moieties as described herein (e.g., a targeting moiety against CD20 or any other targeting moiety described herein). In other embodiments, the reduced affinity or activity at the receptor is not substantially restorable by the activity of one or more of the targeting moieties.

In various embodiments, the chimeric proteins of the present application reduce off-target effects because their signaling agents have mutations that weaken or ablate binding affinity or activity at a receptor. In various embodiments, this reduction in side effects is observed relative with, for example, the wild type signaling agents. In various embodiments, the signaling agent is active on target cells because the targeting moiety(ies) compensates for the missing/insufficient binding (e.g., without limitation and/or avidity) required for substantial activation. In various embodiments, the modified signaling agent is substantially inactive en route to the site of therapeutic activity and has its effect substantially on specifically targeted cell types which greatly reduces undesired side effects.

In some embodiments, the signaling agent may include one or more mutations that attenuate or reduce binding or affinity for one receptor (i.e., a therapeutic receptor) and one or more mutations that substantially reduce or ablate binding or activity at a second receptor. In such embodiments, these mutations may be at the same or at different positions (i.e., the same mutation or multiple mutations). In some embodiments, the mutation(s) that reduce binding and/or activity at one receptor is different than the mutation(s) that substantially reduce or ablate at another receptor. In some embodiments, the mutation(s) that reduce binding and/or activity at one receptor is the same as the mutation(s) that substantially reduce or ablate at another receptor. In some embodiments, the present chimeric proteins have a modified signaling agent that has both mutations that attenuate binding and/or activity at a therapeutic receptor and therefore allow for a more controlled, on-target therapeutic effect (e.g. relative wild type signaling agent) and mutations that substantially reduce or ablate binding and/or activity at another receptor and therefore reduce side effects (e.g. relative to wild type signaling agent).

In some embodiments, the substantial reduction or ablation of binding or activity is not substantially restorable with a targeting moiety (e.g., a targeting moiety against CD20 or any other targeting moiety described herein). In some embodiments, the substantial reduction or ablation of binding or activity is restorable with a targeting moiety. In various embodiments, substantially reducing or ablating binding or activity at a second receptor also may prevent deleterious effects that are mediated by the other receptor.

Alternatively, or in addition, substantially reducing or ablating binding or activity at the other receptor causes the therapeutic effect to improve as there is a reduced or eliminated sequestration of the therapeutic chimeric proteins away from the site of therapeutic action. For instance, in some embodiments, this obviates the need of high doses of the present chimeric proteins that compensate for loss at the other receptor. Such ability to reduce dose further provides a lower likelihood of side effects.

In various embodiments, the modified signaling agent comprises one or more mutations that cause the signaling agent to have reduced, substantially reduced, or ablated affinity, e.g. binding (e.g. $K_D$) and/or activation (for instance, when the modified signaling agent is an agonist of its receptor, measurable as, for example, $K_A$ and/or $EC_{50}$) and/or inhibition (for instance, when the modified signaling agent is an antagonist of its receptor, measurable as, for example, $K_I$ and/or $IC_{50}$), for one or more of its receptors. In various embodiments, the reduced affinity at the agent's receptor allows for attenuation of activity (inclusive of agonism or antagonism). In such embodiments, the modified signaling agent has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity for the receptor relative to the wild type signaling agent. In some embodiments, the binding affinity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower relative to the wild type signaling agent.

In embodiments wherein the chimeric protein has mutations that reduce binding at one receptor and substantially reduce or ablate binding at a second receptor, the attenuation or reduction in binding affinity of a modified signaling agent for one receptor is less than the substantial reduction or ablation in affinity for the other receptor. In some embodiments, the attenuation or reduction in binding affinity of a modified signaling agent for one receptor is less than the substantial reduction or ablation in affinity for the other receptor by about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, or about 95%. In various embodiments, substantial reduction or ablation refers to a greater reduction in binding affinity and/or activity than attenuation or reduction.

In various embodiments, the modified signaling agent comprises one or more mutations that reduce the endogenous activity of the signaling agent to about 75%, or about 70%, or about 60%, or about 50%, or about 40%, or about 30%, or about 25%, or about 20%, or about 10%, or about 5%, or about 3%, or about 1%, e.g., relative to the wild type signaling agent.

In some embodiments, the modified signaling agent comprises one or more mutations that cause the signaling agent to have reduced affinity for its receptor that is lower than the binding affinity of the targeting moiety(ies) for its (their) receptor(s). In some embodiments, this binding affinity differential is between signaling agent/receptor and targeting moiety/receptor on the same cell. In some embodiments, this binding affinity differential allows for the signaling agent, e.g. mutated signaling agent, to have localized, on-target effects and to minimize off-target effects that underlie side effects that are observed with wild type signaling agent. In some embodiments, this binding affinity is at least about 2-fold, or at least about 5-fold, or at least about 10-fold, or at least about 15-fold lower, or at least about 25-fold, or at least about 50-fold lower, or at least about 100-fold, or at least about 150-fold.

Receptor binding activity may be measured using methods known in the art. For example, affinity and/or binding activity may be assessed by Scatchard plot analysis and computer-fitting of binding data (e.g. Scatchard, 1949) or by reflectometric interference spectroscopy under flow through conditions, as described by Brecht et al. (1993), the entire contents of all of which are hereby incorporated by reference.

In various embodiments, the signaling agent is an immune-modulating agent, e.g. one or more of an interleukin, interferon, and tumor necrosis factor.

In some embodiments, the signaling agent is an interleukin or a modified interleukin, including for example IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; IL-36 or a fragment, variant, analogue, or family-member thereof. Interleukins are a group of multi-functional cytokines synthesized by lymphocytes, monocytes, and macrophages. Known functions include stimulating proliferation of immune cells (e.g., T helper cells, B cells, eosinophils, and lymphocytes), chemotaxis of neutrophils and T lymphocytes, and/or inhibition of interferons. Interleukin activity can be determined using assays known in the art: Matthews et al., in *Lymphokines and Interferens: A Practical Approach*, Clemens et al., eds, IRL Press, Washington, D.C. 1987, pp. 221-225; and Orencole & Dinarello (1989) Cytokine 1, 14-20.

In some embodiments, the signaling agent is an interferon or a modified version of an interferon such as interferon types I, II, and III. Illustrative interferons, including for example, interferon-α-1, 2, 4, 5, 6, 7, 8, 10, 13, 14, 16, 17, and 21, interferon-β and interferon-γ, interferon κ, interferon ε, interferon τ, and interferon $\overline{\omega}$.

In some embodiments, the signaling agent is a tumor necrosis factor (TNF) or a modified version of a tumor necrosis factor (TNF) or a protein in the TNF family, including but not limited to, TNF-α, TNF-β, LT-β, CD40L, CD27L, CD30L, FASL, 4-1BBL, OX40L, and TRAIL.

The amino acid sequences of the wild type signaling agents described herein are well known in the art. Accordingly, in various embodiments the modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known wild type amino acid sequences of the signaling agents described herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments the modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with any amino acid sequences of the signaling agents described herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments, the modified signaling agent comprises an amino acid sequence having one or more amino acid mutations. In some embodiments, the one or more amino acid mutations may be independently selected from substitutions, insertions, deletions, and truncations. In some embodiments, the amino acid mutations are amino acid substitutions, and may include conservative and/or non-conservative substitutions, as described elsewhere herein.

In various embodiments, the substitutions may also include non-classical amino acids as described elsewhere herein.

As described herein, the modified signaling agents bear mutations that affect affinity and/or activity at one or more receptors. The receptors of any signaling agents, as described herein, are known in the art.

Illustrative mutations which provide reduced affinity and/or activity (e.g. agonistic) at a receptor are found in WO 2013/107791 (e.g. with regard to interferons), WO 2015/007542 (e.g. with regard to interleukins), and WO 2015/007903 (e.g. with regard to TNF), the entire contents of each of which are hereby incorporated by reference. Illustrative mutations which provide reduced affinity and/or activity (e.g. antagonistic) at a receptor are found in WO 2015/007520, the entire contents of which are hereby incorporated by reference.

In an embodiment, the modified signaling agent is interferon α. In such embodiments, the modified IFN-α agent has reduced affinity and/or activity for the IFN-α/β receptor (IFNAR), i.e., IFNAR1 and/or IFNAR2 chains. In some embodiments, the modified IFN-α agent has substantially reduced or ablated affinity and/or activity for the IFN-α/β receptor (IFNAR), i.e., IFNAR1 and/or IFNAR2 chains.

Mutant forms of interferon α are known to the person skilled in the art. In an illustrative embodiment, the modified signaling agent is the allelic form IFN-α2a having the amino acid sequence of:

```
IFN-α2a:
                                        (SEQ ID NO: 127)
CDLPQTHSLGSRRTLMLLAQMRKISLFSCLKDRHDFGFPQEE

FGNQFQKAETIPVLHEMIQQIFNLFSTKDSSAAWDETLLDKF

YTELYQQLNDLEACVIQGVGVTETPLMKEDSILAVRKYFQRI

TLYLKEKKYSPCAWEVVRAEIMRSFSLSTNLQESLRSKE.
```

In an illustrative embodiment, the modified signaling agent is the allelic form IFN-α2b having the amino acid sequence of (which differs from IFN-α2a at amino acid position 23):

```
IFN-α2b:
                                        (SEQ ID NO: 128)
CDLPQTHSLGSRRTLMLLAQMRRISLFSCLKDRHD

FGFPQEEFGNQFQKAETIPVLHEMIQQIFNLFSTK

DSSAAWDETLLDKFYTELYQQLNDLEACVIQGVGV

TETPLMKEDSILAVRKYFQRITLYLKEKKYSPCAW

EVVRAEIMRSFSLSTNLQESLRSKE.
```

In some embodiments, said IFN-α2 mutant (IFN-α2a or IFN-α2b) is mutated atone or more amino acids at positions 144-154, such as amino acid positions 148, 149 and/or 153. In some embodiments, the IFN-α2 mutant comprises one or more mutations selected from L153A, R149A, and M148A. Such mutants are described, for example, in WO2013/107791 and Piehler et al., (2000) J. Biol. Chem, 275:40425-33, the entire contents of all of which are hereby incorporated by reference.

In some embodiments, the IFN-α2 mutants have reduced affinity and/or activity for IFNAR1. In some embodiments, the IFN-α2 mutant comprises one or more mutations selected from F64A, N65A, T69A, L80A, Y85A, and Y89A, as described in WO2010/030671, the entire contents of which is hereby incorporated by reference.

In some embodiments, the IFN-α2 mutant comprises one or more mutations selected from K133A, R144A, R149A, and L153A as described in WO2008/124086, the entire contents of which is hereby incorporated by reference.

In some embodiments, the IFN-α2 mutant comprises one or more mutations selected from R120E and R120E/K121E, as described in WO2015/007520 and WO2010/030671, the entire contents of which are hereby incorporated by reference. In such embodiments, said IFN-α2 mutant antagonizes wildtype IFN-α2 activity. In such embodiments, said mutant IFN-α2 has reduced affinity and/or activity for IFNAR1 while affinity and/or activity of IFNR2 is retained.

In some embodiments, the IFN-α2 mutant comprises (1) one or more mutations selected from R120E and R120E/K121E, which, without wishing to be bound by theory, create an antagonistic effect and (2) one or more mutations selected from K133A, R144A, R149A, and L153A, which, without wishing to be bound by theory, allow for an attenuated effect at, for example, IFNAR2.

In an embodiment, the modified signaling agent is interferon β. In such embodiments, the modified interferon β agent has reduced affinity and/or activity for the IFN-α/β receptor (IFNAR), i.e., IFNAR1 and/or IFNAR2 chains. In some embodiments, the modified interferon β agent has substantially reduced or ablated affinity and/or activity for the IFN-α/β receptor (IFNAR), i.e., IFNAR1 and/or IFNAR2 chains.

In an embodiment, the modified signaling agent is interferon γ. In such embodiments, the modified interferon γ agent has reduced affinity and/or activity for the interferon-gamma receptor (IFNGR), i.e., IFNGR1 and IFNGR2 chains. In some embodiments, the modified interferon γ agent has substantially reduced or ablated affinity and/or activity for the interferon-gamma receptor (IFNGR), i.e., IFNGR1 and/or IFNGR2 chains.

In an embodiment, the modified signaling agent is TNF-α. TNF is a pleiotropic cytokine with many diverse functions, including regulation of cell growth, differentiation, apoptosis, tumorigenesis, viral replication, autoimmunity, immune cell functions and trafficking, inflammation, and septic shock. It binds to two distinct membrane receptors on target cells: TNFR1 (p55) and TNFR2 (p75). TNFR1 exhibits a very broad expression pattern whereas TNFR2 is expressed preferentially on certain populations of lymphocytes, Tregs, endothelial cells, certain neurons, microglia, cardiac myocytes and mesenchymal stem cells. Very distinct biological pathways are activated in response to receptor activation, although there is also some overlap. As a general rule, without wishing to be bound by theory, TNFR1 signaling is associated with induction of apoptosis (cell death) and TNFR2 signaling is associated with activation of cell survival signals (e.g. activation of NFkB pathway). Administration of TNF is systemically toxic, and this is largely due to TNFR1 engagement. However, it should be noted that activation of TNFR2 is also associated with a broad range of activities and, as with TNFR1, in the context of developing TNF based therapeutics, control over TNF targeting and activity is important.

In some embodiments, the modified signaling agent has reduced affinity and/or activity for TNFR1 and/or TNFR2. In some embodiments, the modified signaling agent has substantially reduced or ablated affinity and/or activity for TNFR1 and/or TNFR2. TNFR1 is expressed in most tissues, and is involved in cell death signaling while, by contrast, TNFR2 is involved in cell survival signaling. Accordingly in embodiments directed to methods of treating cancer, the modified signaling agent has reduced affinity and/or activity for TNFR1 and/or substantially reduced or ablated affinity and/or activity for TNFR2. In these embodiments, the chimeric proteins may be targeted to a cell for which apoptosis is desired, e.g. a tumor cell or a tumor vasculature endothelial cell. In embodiments directed to methods of promoting cell survival, for example, in neurogenesis for the treatment of neurodegenerative disorders, the modified signaling agent has reduced affinity and/or activity for TNFR2 and/or substantially reduced or ablated affinity and/or activity for TNFR1. Stated another way, the present chimeric proteins, in some embodiments, comprise modified TNF-α agent that allows of favoring either death or survival signals.

In some embodiments, the chimeric protein has a modified TNF having reduced affinity and/or activity for TNFR1 and/or substantially reduced or ablated affinity and/or activity for TNFR2. Such a chimera, in some embodiments, is a more potent inducer of apoptosis as compared to a wild type TNF and/or a chimera bearing only mutation(s) causing reduced affinity and/or activity for TNFR1. Such a chimera, in some embodiments, finds use in inducing tumor cell death or a tumor vasculature endothelial cell death (e.g. in the treatment of cancers). Also, in some embodiments, these chimeras avoid or reduce activation of $T_{reg}$ cells via TNFR2, for example, thus further supporting TNFR1-mediated antitumor activity in vivo.

In some embodiments, the chimeric protein has a modified TNF having reduced affinity and/or activity for TNFR2 and/or substantially reduced or ablated affinity and/or activity for TNFR1. Such a chimera, in some embodiments, is a more potent activator of cell survival in some cell types, which may be a specific therapeutic objective in various disease settings, including without limitation, stimulation of neurogenesis. In some embodiments, the chimera is targeted to auto-reactive T cells. In some embodiments, the chimera promotes $T_{reg}$ cell activation and indirect suppression of cytotoxic T cells.

In some embodiments, the chimera causes the death of auto-reactive T cells, e.g. by activation of TNFR2 and/or avoidance TNFR1 (e.g. a modified TNF having reduced affinity and/or activity for TNFR2 and/or substantially reduced or ablated affinity and/or activity for TNFR1). Without wishing to be bound by theory these auto-reactive T cells, have their apoptosis/survival signals altered e.g. by NFkB pathway activity/signaling alterations.

In some embodiments, a TNFR-2 based chimera has additional therapeutic applications in diseases, including various heart disease, de-myelinating and neurodegenerative disorders, and infectious disease, among others.

In an embodiment, the wild type TNF-α has the amino acid sequence of:

```
TNF-α
VRSSSRTPSDKPVAHVVANPQAEGQLQWLNRRANA

LLANGVELRDNQLVVPSEGLYLIYSQVLFKGQGCP

STHVLLTHTISRIAVSYQTKVNLLSAIKSPCQRET

PEGAEAKPWYEPIYLGGVFQLEKGDRLSAEINRPD

YLDFAESGQVYFGIIAL.
```

In such embodiments, the modified TNF-α agent has mutations at one or more amino acid positions 29, 31, 32, 84, 85, 86, 87, 88, 89, 145, 146 and 147 which produces a modified TNF-α with reduced receptor binding affinity. See, for example, U.S. Pat. No. 7,993,636, the entire contents of which are hereby incorporated by reference.

In some embodiments, the modified TNF-α agent has mutations at one or more amino acid positions R32, N34, Q67, H73, L75, T77, S86, Y87, V91, I97, T105, P106, A109, P113, Y115, E127, N137, D143, and A145, as described, for example, in WO/2015/007903, the entire contents of which is hereby incorporated by reference (numbering according to the human TNF sequence, Genbank accession number BAG70306, version BAG70306.1 GI: 197692685). In some embodiments, the modified TNF-α agent has substitution mutations selected from R32G, N34G, Q67G, H73G, L75G, L75A, L75S, T77A, S86G, Y87Q, Y87L, Y87A, Y87F, V91G, V91A, 197A, 197Q, 197S, T105G, P106G, A109Y, P113G, Y115G, Y115A, E127G, N137G, D143N, A145G and A145T.

In some embodiments, the modified TNF-α agent has one or more mutations selected from N39Y, S147Y, and Y87H, as described in WO2008/124086, the entire contents of which is hereby incorporated by reference.

In an embodiment, the modified signaling agent is TNF-β. TNF-β can form a homotrimer or a heterotrimer with LT-β (LT-α1β2). In some embodiments, the modified signaling agent has substantially reduced or ablated affinity and/or activity for TNFR1 and/or TNFR2 and/or herpes virus entry mediator (HEVM) and/or LT-βR.

In an embodiment, the wild type TNF-β has the amino acid sequence of:

```
TNF-beta
LPGVGLTPSAAQTARQHPKMHLAHSNLKPAAHLIG

DPSKQNSLLWRANTDRAFLQDGFSLSNNSLLVPTS

GIYFVYSQVVFSGKAYSPKATSSPLYLAHEVQLFS

SQYPFHVPLLSSQKMVYPGLQEPWLHSMYHGAAFQ

LTQGDQLSTHTDGIPH        LVLSPSTVFFGAFAL.
```

In such embodiments, the modified TNF-β agent may comprise mutations at one or more amino acids at positions 106-113, which produce a modified TNF-β with reduced receptor binding affinity to TNFR2. In an embodiment, the modified signaling agent has one or more substitution mutations at amino acid positions 106-113. In illustrative embodiments, the substitution mutations are selected from Q107E, Q107D, S106E, S106D, Q107R, Q107N, Q107E/S106E, Q107E/S106D, Q107D/S106E, and Q107D/S106D. In another embodiment, the modified signaling agent has an insertion of about 1 to about 3 amino acids at positions 106-113.

In some embodiments, the modified agent is a TNF family member (e.g. TNF-alpha, TNF-beta) which can be a single chain trimeric version as described in WO 2015/007903, the entire contents of which are incorporated by reference. In some embodiments, the modified agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR1. In these embodiments, the modified agent is a TNF family member (e.g. TNF-alpha, TNF-beta) which also, optionally, has substantially reduced or ablated affinity and/or activity for TNFR2. In some embodiments, the modified agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR2. In these embodiments, the modified agent is a TNF family member (e.g. TNF-alpha, TNF-beta) which also, optionally, has substantially reduced or ablated affinity and/or activity for TNFR1. The constructs of such embodiments find use in, for example, methods of dampening TNF response in a cell specific manner. In some embodiments, the antagonistic TNF family member (e.g. TNF-alpha, TNF-beta) is a single chain trimeric version as described in WO 2015/007903.

In an embodiment, the modified signaling agent is TRAIL. In some embodiments, the modified TRAIL agent has reduced affinity and/or activity for DR4 (TRAIL-RI) and/or DR5 (TRAIL-RII) and/or DcR1 and/or DcR2. In some embodiments, the modified TRAIL agent has substantially reduced or ablated affinity and/or activity for DR4 (TRAIL-RI) and/or DR5 (TRAIL-RII) and/or DcR1 and/or DcR2.

In an embodiment, the wild type TRAIL has the amino acid sequence of:

```
TRAIL
MAMMEVQGGPSLGQTCVLIVIFTVLLQSLCVAVTY

VYFTNELKQMQDKYSKSGIACFLKEDDSYWDPNDE

ESMNSPCWQVKWQLRQLVRKMILRTSEETISTVQE

KQQNISPLVRERGPQRVAAHITGTRGRSNTLSSPN

SKNEKALGRKINSWESSRSGHSFLSNLHLRNGELV

IHEKGFYYIYSQTYFRFQEEIKENTKNDKQMVQYI

YKYTSYPDPILLMKSARNSCWSKDAEYGLYSIYQG

GIFELKENDRIFVSVTNEHLIDMDHEASFFGAFLV

G.
```

In such embodiments, the modified TRAIL agent may comprise a mutation at amino acid positions T127-R132, E144-R149, E155-H161, Y189-Y209, T214-1220, K224-A226, W231, E236-L239, E249-K251, T261-H264 and H270-E271 (Numbering based on the human sequence, Genbank accession number NP_003801, version 10 NP_003801.1, GI: 4507593; see above).

In an embodiment, the modified signaling agent is an interleukin. In an embodiment, the modified signaling agent is IL-1. In an embodiment, the modified signaling agent is IL-1α or IL-1β. In some embodiments, the modified signaling agent has reduced affinity and/or activity for IL-1R1 and/or IL-1RAcP. In some embodiments, the modified signaling agent has substantially reduced or ablated affinity and/or activity for IL-1R1 and/or IL-1RAcP. In some embodiments, the modified signaling agent has reduced affinity and/or activity for IL-1R2. In some embodiments, the modified signaling agent has substantially reduced or ablated affinity and/or activity for IL-1R2. For instance, in some embodiments, the present modified IL-1 agents avoid interaction at IL-1R2 and therefore substantially reduce its function as a decoy and/or sink for therapeutic agents.

In an embodiment, the wild type IL-1pβ has the amino acid sequence of:

```
IL-1 beta (mature form, wild type)
APVRSLNCTLRDSQQKSLVMSGPYELKALHLQGQD

MEQQWFSMSFVQGEESNDKIPVALGLKEKNLYLSC

VLKDDKPTLQLESVDPKNYPKKKMEKRFVFNKIEI

NNKLEFESAQFPNWYISTSQAENMPVFLGGTKGGQ

DITDFTMQFVSS.
```

IL1 is a proinflammatory cytokine and an important immune system regulator. It is a potent activator of CD4 T cell responses, increases proportion of Th17 cells and expansion of IFNγ and IL-4 producing cells. IL-1 is also a potent regulator of $CD8^+$ T cells, enhancing antigen-specific $CD8^+$ T cell expansion, differentiation, migration to periphery and memory. IL-1 receptors comprise IL-1R1 and IL-1R2. Binding to and signaling through the IL-1R1 constitutes the mechanism whereby IL-1 mediates many of its biological (and pathological) activities. IL1-R2 can function as a decoy receptor, thereby reducing IL-1 availability for interaction and signaling through the IL-1R1.

In some embodiments, the modified IL-1 has reduced affinity and/or activity (e.g. agonistic activity) for IL-1R1. In some embodiments, the modified IL-1 has substantially reduced or ablated affinity and/or activity for IL-1R2. In such embodiments, there is restorable IL-1/IL-1R1 signaling and prevention of loss of therapeutic chimeras at IL-R2 and therefore a reduction in dose of IL-1 that is required (e.g. relative to wild type or a chimera bearing only an attenuation mutation for IL-R1). Such constructs find use in, for example, methods of treating cancer, including, for example, stimulating the immune system to mount an anti-cancer response.

In some embodiments, the modified IL-1 has reduced affinity and/or activity (e.g. antagonistic activity, e.g. natural antagonistic activity or antagonistic activity that is the result of one or more mutations, see, e.g., WO 2015/007520, the entire contents of which are hereby incorporated by reference) for IL-1R1. In some embodiments, the modified IL-1 has substantially reduced or ablated affinity and/or activity for IL-1R2. In such embodiments, there is the IL-1/IL-1R1 signaling is not restorable and prevention of loss of therapeutic chimeras at IL-R2 and therefore a reduction in dose of IL-1 that is required (e.g. relative to wild type or a chimera bearing only an attenuation mutation for IL-R1).

In such embodiments, the modified signaling agent has a deletion of amino acids 52-54 which produces a modified IL-1β with reduced binding affinity for type IIL-1R and reduced biological activity. See, for example, WO 1994/000491, the entire contents of which are hereby incorporated by reference. In some embodiments, the modified IL-1β has one or more substitution mutations selected from A117G/P118G, R120X, L122A, T125G/L126G, R127G, Q130X, Q131G, K132A, S137G/Q138Y, L145G, H146X, L145A/L147A, Q148X, Q148G/Q150G, Q150G/D151A, M152G, F162A, F162A/Q164E, F166A, Q164E/E167K, N169G/D170G, 1172A, V174A, K208E, K209X, K209A/K210A, K219X, E221X, E221 S/N224A, N224S/K225S, E244K, N245Q (where X can be any change in amino acid, e.g., a non-conservative change), which exhibit reduced binding to IL-1R, as described, for example, in WO2015/007542 and WO/2015/007536, the entire contents of which is hereby incorporated by reference (numbering base on the human IL-1 β sequence, Genbank accession number NP_000567, version NP-000567.1, GI: 10835145). In some embodiments, the modified IL-1p may have one or more mutations selected from R120A, R120G, Q130A, Q130W, H146A, H146G, H146E, H146N, H146R, Q148E, Q148G, Q148L, K209A, K209D, K219S, K219Q, E221S and E221K.

In an embodiment, the modified signaling agent is IL-2. In such an embodiment, the modified signaling agent has reduced affinity and/or activity for IL-2Rα and/or IL-2Rβ and/or IL-2Rγ. In some embodiments, the modified signaling agent has reduced affinity and/or activity for IL-2Rβ and/or IL-2Rγ. In some embodiments, the modified signaling agent has substantially reduced or ablated affinity and/or activity for IL-2Rα. Such embodiments may be relevant for treatment of cancer, for instance when the modified IL-2 is agonistic at IL-2Rβ and/or IL-2Rγ. For instance, the present constructs may favor attenuated activation of $CD8^+$ T cells (which can provide an anti-tumor effect), which have IL2 receptors β and γ and disfavor $T_{regs}$ (which can provide an immune suppressive, pro-tumor effect), which have IL2 receptors α, β, and γ. Further, in some embodiments, the preferences for IL-2Rβ and/or IL-2Rγ over IL-2Rα avoid IL-2 side effects such as pulmonary edema. Also, IL-2-based chimeras are useful for the treatment of diseases, for instance when the modified IL-2 is antagonistic (e.g. natural antagonistic activity or antagonistic activity that is the result of one or more mutations, see, e.g., WO 2015/007520, the entire contents of which are hereby incorporated by reference) at IL-2Rβ and/or IL-2Rγ. For instance, the present constructs may favor attenuated suppression of $CD8^+$ T cells (and therefore dampen the immune response), which have IL2 receptors β and γ and disfavor $T_{regs}$ which have IL2 receptors α, β, and γ. Alternatively, in some embodiments, the chimeras bearing IL-2 favor the activation of $T_{regs}$, and therefore immune suppression, and activation of disfavor of $CD8^+$ T cells. For instance, these constructs find use in the treatment of diseases or diseases that would benefit from immune suppression.

In some embodiments, the chimeric protein has targeting moieties as described herein directed to $CD8^+$ T cells as well as a modified IL-2 agent having reduced affinity and/or activity for IL-2Rβ and/or IL-2Rγ and/or substantially reduced or ablated affinity and/or activity for IL-2Rα. In some embodiments, these constructs provide targeted $CD8^+$ T cell activity and are generally inactive (or have substantially reduced activity) towards $T_{reg}$ cells. In some embodiments, such constructs have enhanced immune stimulatory effect compared to wild type IL-2 (e.g., without wishing to be bound by theory, by not stimulating Tregs), whilst eliminating or reducing the systemic toxicity associated with IL-2.

In an embodiment, the wild type IL-2 has the amino acid sequence of:

```
IL-2 (mature form, wild type)
APTSSSTKKTQLQLEHLLLDLQMILNGINNYKNPK

LTRMLTFKFYMPKKATELKHLQCLEEELKPLEEVL

NLAQSKNFHLRPRDLISNINVIVLELKGSETTFMC

EYADETATIVEFLNRVVITFCQSIISTLT.
```

In such embodiments, the modified IL-2 agent has one or more mutations at amino acids L72 (L72G, L72A, L72S, L72T, L72Q, L72E, L72N, L72D, L72R, or L72K), F42 (F42A, F42G, F42S, F42T, F42Q, F42E, F42N, F42D, F42R, or F42K) and Y45 (Y45A, Y45G, Y45S, Y45T, Y45Q, Y45E, Y45N, Y45D, Y45R or Y45K). Without wishing to be bound by theory, it is believed that these modified IL-2 agents have reduced affinity for the high-affinity IL-2 receptor and preserves affinity to the intermediate-affinity IL-2 receptor, as compared to the wild-type IL-2. See, for example, US Patent Publication No. 2012/0244112, the entire contents of which are hereby incorporated by reference.

In an embodiment, the modified signaling agent is IL-3. In some embodiments, the modified signaling agent has reduced affinity and/or activity for the IL-3 receptor, which is a heterodimer with a unique alpha chain paired with the common beta (beta c or CD131) subunit. In some embodiments, the modified signaling agent has substantially reduced or ablated affinity and/or activity for the IL-3 receptor, which is a heterodimer with a unique alpha chain paired with the common beta (beta c or CD131) subunit.

In an embodiment, the modified signaling agent is IL-4. In such an embodiment, the modified signaling agent has reduced affinity and/or activity for type 1 and/or type 2 IL-4 receptors. In such an embodiment, the modified signaling agent has substantially reduced or ablated affinity and/or activity for type 1 and/or type 2 IL-4 receptors. Type 1 IL-4 receptors are composed of the IL-4Rα subunit with a common γ chain and specifically bind IL-4. Type 2 IL-4 receptors include an IL-4Rα subunit bound to a different subunit known as IL-13Rα1. In some embodiments, the modified signaling agent has substantially reduced or ablated affinity and/or activity the type 2 IL-4 receptors.

In an embodiment, the wild type IL-4 has the amino acid sequence of:

```
IL-4 (mature form, wild type)
HKCDITLQEIIKTLNSLTEQKTLCTELTVTDIFAA

SKNITTEKETFCRAATVLRQFYSHHEKDTRCLGAT

AQQFHRHKQURFLKRLDRNLWGLAGLNSCPVKEAN

QSTLENFLERLKTIMREKYSKCSS.
```

In such embodiments, the modified IL-4 agent has one or more mutations at amino acids R121 (R121A, R121D, R121E, R121F, R121H, R121I, R121K, R121N, R121P, R121T, R121W), E122 (E122F), Y124 (Y124A, Y124Q, Y124R, Y124S, Y124T) and S125 (S125A). Without wishing to be bound by theory, it is believed that these modified IL-4 agents maintain the activity mediated by the type I receptor, but significantly reduces the biological activity mediated by the other receptors. See, for example, U.S. Pat. No. 6,433,157, the entire contents of which are hereby incorporated by reference.

In an embodiment, the modified signaling agent is IL-6. IL-6 signals through a cell-surface type I cytokine receptor complex including the ligand-binding IL-6R chain (CD126), and the signal-transducing component gp130. IL-6 may also bind to a soluble form of IL-6R (sIL-6R), which is the extracellular portion of IL-6R. The sIL-6R/IL-6 complex may be involved in neurites outgrowth and survival of neurons and, hence, may be important in nerve regeneration through remyelination. Accordingly, in some embodiments, the modified signaling agent has reduced affinity and/or activity for IL-6R/gp130 and/or sIL-6R. In some embodiments, the modified signaling agent has substantially reduced or ablated affinity and/or activity for IL-6R/gp130 and/or sIL-6R.

In an embodiment, the wild type IL-6 has the amino acid sequence of:

```
IL-6 (mature form, wild type)
APVPPGEDSKDVAAPHRQPLTSSERIDKQIRYILD

GISALRKETCNKSNMCESSKEALAENNLNLPKMAE

KDGCFQSGFNEETCLVKIITGLLEFEVYLEYLQNR

FESSEEQARAVQMSTKVLIQFLQKKAKNLDAITTP

DPTTNASLTTKLQAQNQVVLQDMTTHLILRSFKEF

LQSSLRALRQM.
```

In such embodiments, the modified signaling agent has one or more mutations at amino acids 58, 160, 163, 171 or 177. Without wishing to be bound by theory, it is believed that these modified IL-6 agents exhibit reduced binding affinity to IL-6Ralpha and reduced biological activity. See, for example, WO 97/10338, the entire contents of which are hereby incorporated by reference.

In an embodiment, the modified signaling agent is IL-10. In such an embodiment, the modified signaling agent has reduced affinity and/or activity for IL-10 receptor-1 and IL-10 receptor-2. In some embodiments, the modified signaling agent has substantially reduced affinity and/or activity for IL-10 receptor-1 and IL-10 receptor-2 In an embodiment, the modified signaling agent is IL-11. In such an embodiment, the modified signaling agent has reduced affinity and/or activity for IL-11Ra and/or IL-11Rp and/or gp130. In such an embodiment, the modified signaling agent has ablated or substantially reduced affinity and/or activity for IL-11Ra and/or IL-11Rp and/or gp130.

In an embodiment, the modified signaling agent is IL-12. In such an embodiment, the modified signaling agent has reduced affinity and/or activity for IL-12Rβ1 and/or IL-12Rβ2. In such an embodiment, the modified signaling agent has substantially reduced or ablated affinity and/or activity for IL-12Rβ1 and/or IL-12Rβ2.

In an embodiment, the modified signaling agent is IL-13. In such an embodiment, the modified signaling agent has reduced affinity and/or activity for the IL-4 receptor (IL-4Rα) and IL-13Rα1. In some embodiments, the modified signaling agent has substantially reduced or ablated affinity and/or activity for IL-4 receptor (IL-4Rα) or IL-13Rα1.

In an embodiment, the wild type IL-13 has the amino acid sequence of:

```
IL-13 (mature form, wild type)
SPGPVPPSTALRELIEELVNITQNQKAPLCNGSMV

WSINLTAGMYCAALESLINVSGCSAIEKTQRMLSG

FCPHKVSAGQFSSLHVRDTKIEVAQFVKDLLLHLK

KLFREGRFN.
```

In such embodiments, the modified IL-13 agent has one or more mutations at amino acids 13, 16, 17, 66, 69, 99, 102, 104, 105, 106, 107, 108, 109, 112, 113 and 114. Without wishing to be bound by theory, it is believed that these modified IL-13 agents exhibit reduced biological activity. See, for example, WO 2002/018422, the entire contents of which are hereby incorporated by reference.

In an embodiment, the modified signaling agent is IL-18. In some embodiments, the modified signaling agent has reduced affinity and/or activity for IL-18Rα and/or IL-18Rβ. In some embodiments, the modified signaling agent has substantially reduced or ablated affinity and/or activity for IL-18Rα and/or IL-18Rβ. In some embodiments, the modified signaling agent has substantially reduced or ablated affinity and/or activity for IL-18Rα type II, which is an isoform of IL-18Rα that lacks the TIR domain required for signaling.

In an embodiment, the wild type IL-18 has the amino acid sequence of:

```
IL-18 (wild type)
MAAEPVEDNCINFVAMKFIDNTLYFIAEDDENLES

DYFGKLESKLSVIRNLNDQVLFIDQGNRPLFEDMT

DSDCRDNAPRTIFIISMYKDSQPRGMAVTISVKCE

KISTLSCENKIISFKEMNPPDNIKDTKSDIIFFQR
```

-continued

SVPGHDNKMQFESSSYEGYFLACEKERDLFKLILK

KEDELGDRSIMFTVQNEDL.

In such embodiments, the modified IL-18 agent may comprise one or more mutations in amino acids or amino acid regions selected from Y37-K44, R49-Q54, D59-R63, E67-C74, R80, M87-A97, N 127-K129, Q139-M149, K165-K171, R183 and Q190-N191, as described in WO/2015/007542, the entire contents of which are hereby incorporated by reference (numbering based on the human IL-18 sequence, Genbank accession number AAV38697, version AAV38697.1, GI: 54696650).

In an embodiment, the modified signaling agent is IL-33. In such an embodiment, the modified signaling agent has reduced affinity and/or activity for the ST-2 receptor and IL-1RAcP. In some embodiments, the modified signaling agent has substantially reduced or ablated affinity and/or activity for the ST-2 receptor and IL-1RAcP.

In an embodiment, the wild type IL-33 has the amino acid sequence of:

MKPKMKYSTNKISTAKWKNTASKALCFKLGKSQQK

AKEVCPMYFMKLRSGLMIKKEACYFRRETTKRPSL

KTGRKHKRHLVLAACQQQSTVECFAFGISGVQKYT

RALHDSSITGISPITEYLASLSTYNDQSITFALED

ESYEIYVEDLKKDEKKDKVLLSYYESQHPSNESGD

GVDGKMLMVTLSPTKDFWLHANNKEHSVELHKCEK

PLPDQAFFVLHNMHSNCVSFECKTDPGVFIGVKDN

HLALIKVDSSENLCTENILFKLSET.

In such embodiments, the modified IL-33 agent may comprise one or more mutations in amino acids or amino acid regions selected from I113-Y122, S127-E139, E144-D157, Y163-M183, E200, Q215, L220-C227 and T260-E269, as described in WO/2015/007542, the entire contents of which are hereby incorporated by reference (numbering based on the human sequence, Genbank accession number NP_254274, version NP_254274.1, GI:15559209).

In one embodiment, the present chimeric protein has (i) a targeting moiety against CD20 and (ii) a targeting moiety which is directed against a tumor cell, along with any of the modified or mutant signaling agents described herein. In an embodiment, the present chimeric protein has a targeting moiety directed against CD20 and a second targeting moiety directed against PD-L1 or PD-L2 on tumor cells.

Multi-Specific Chimeras and Fusions with Signaling Agents

In various embodiments, the CD20 binding agent of the application is part of a chimera or fusion with one or more signaling agents as described herein and/or one or more additional targeting moieties. Accordingly, the present application provides for chimeric or fusion proteins that include one or more signaling agents and a targeting moiety against CD20 and/or one or more additional targeting moieties.

In various embodiments, the chimeric proteins of the present application have targeting moieties which target two different cells (e.g. to make a synapse) or the same cell (e.g. to get a more concentrated signaling agent effect).

In various embodiments, the CD20 binding agent of the application is multispecific, i.e., the CD20 binding agent comprises two or more targeting moieties having recognition domains (e.g. antigen recognition domains) that recognize and bind two or more targets (e.g. antigens, or receptors, or epitopes). In such embodiments, the CD20 binding agent of the application may comprises two more targeting moieties having recognition domains that recognize and bind two or more epitopes on the same antigen or on different antigens or on different receptors. In various embodiments, such multi-specific CD20 binding agents exhibit advantageous properties such as increased avidity and/or improved selectivity. In an embodiment, the CD20 binding agent of the application comprises two targeting moieties and is bispecific, i.e., binds and recognizes two epitopes on the same antigen or on different antigens or different receptors.

In various embodiments, the multispecific CD20 binding agent of the application comprises two or more targeting moieties with each targeting moiety being an antibody or an antibody derivative as described herein. In an embodiment, the multispecific CD20 binding agent of the application comprises at least one VHH comprising an antigen recognition domain against CD20 and one antibody or antibody derivative comprising a recognition domain against a tumor antigen or an immune cell.

In various embodiments, the present multispecific CD20 binding agents have two or more targeting moieties that target different antigens or receptors, and one targeting moiety may be attenuated for its antigen or receptor, e.g. the targeting moiety binds its antigen or receptor with a low affinity or avidity (including, for example, at an affinity or avidity that is less than the affinity or avidity the other targeting moiety has for its for its antigen or receptor, for instance the difference between the binding affinities may be about 10-fold, or 25-fold, or 50-fold, or 100-fold, or 300-fold, or 500-fold, or 1000-fold, or 5000-fold; for instance the lower affinity or avidity targeting moiety may bind its antigen or receptor at a $K_D$ in the mid- to high-nM or low- to mid-NM range while the higher affinity or avidity targeting moiety may bind its antigen or receptor at a $K_D$ in the mid- to high-pM or low- to mid-nM range). For instance, in some embodiments, the present multispecific CD20 binding agent comprises an attenuated targeting moiety that is directed against a promiscuous antigen or receptor, which may improve targeting to a cell of interest (e.g. via the other targeting moiety) and prevent effects across multiple types of cells, including those not being targeted for therapy (e.g. by binding promiscuous antigen or receptor at a higher affinity than what is provided in these embodiments).

The multispecific CD20 binding agent of the application may be constructed using methods known in the art, see for example, U.S. Pat. No. 9,067,991, U.S. Patent Publication No. 20110262348 and WO 2004/041862, the entire contents of which are hereby incorporated by reference. In an illustrative embodiment, the multispecific CD20 binding agent of the application comprising two or more targeting moieties may be constructed by chemical crosslinking, for example, by reacting amino acid residues with an organic derivatizing agent as described by Blattler et al., Biochemistry 24,1517-1524 and EP294703, the entire contents of which are hereby incorporated by reference. In another illustrative embodiment, the multispecific CD20 binding agent comprising two or more targeting moieties is constructed by genetic fusion, i.e., constructing a single polypeptide which includes the polypeptides of the individual targeting moieties. For example, a single polypeptide construct may be formed which encodes a first VHH with an antigen recognition domain against CD20 and a second antibody or antibody derivative with a recognition domain against a tumor antigen. A method for producing bivalent or multivalent VHH polypeptide constructs is disclosed in PCT patent application WO 96/34103, the entire contents of which is hereby incorporated by reference. In a further illustrative embodiment, the multispecific CD20 binding agent of the application may be constructed by using linkers. For example, the carboxy-terminus of a first VHH with an antigen recognition domain against CD20 may be linked to the amino-terminus of a second antibody or antibody derivative with a recognition domain against a tumor antigen (or vice versa). Illustrative linkers that may be used are described herein. In some embodiments, the components of the multispecific CD20 binding agent of the application are directly linked to each other without the use of linkers.

In various embodiments, the multi-specific CD20 binding agent of the application recognizes and binds to CD20 and one or more antigens found on one or more immune cells, which can include, without limitation, megakaryocytes, thrombocytes, erythrocytes, mast cells, basophils, neutrophils, eosinophils, monocytes, macrophages, natural killer cells, T lymphocytes (e.g., cytotoxic T lymphocytes, T helper cells, natural killer T cells), B lymphocytes, plasma cells, dendritic cells, or subsets thereof. In some embodiments, the CD20 binding agent specifically binds to an antigen of interest and effectively directly or indirectly recruits one of more immune cells. In exemplary embodiments, the present CD20 binding agents may directly or indirectly recruit an immune cell, e.g. a dendritic cell, to a site of action (such as, by way of non-limiting example, the tumor microenvironment).

In various embodiments, the multi-specific CD20 binding agent of the application recognizes and binds to CD20 and one or more antigens found on cancer or tumor cells. In these embodiments, the present CD20 binding agents may have enhanced selectivity to CD20 positive cancer or tumor cells by binding to two or more antigens on the cancer or tumor cells (i.e., CD20 and another cancer or tumor antigen).

In some embodiments, the present CD20 binding agents are capable of, or find use in methods involving, shifting the balance of immune cells in favor of immune attack of a tumor. For instance, the present CD20 binding agents can shift the ratio of immune cells at a site of clinical importance in favor of cells that can kill and/or suppress a tumor (e.g. T cells, cytotoxic T lymphocytes, T helper cells, natural killer (NK) cells, natural killer T (NKT) cells, anti-tumor macrophages (e.g. M1 macrophages), B cells, and dendritic cells and in opposition to cells that protect tumors (e.g. myeloid-derived suppressor cells (MDSCs), regulatory T cells (Tregs); tumor associated neutrophils (TANs), M2 macrophages, tumor associated macrophages (TAMs), or subsets thereof). In some embodiments, the present CD20 binding agent is capable of increasing a ratio of effector T cells to regulatory T cells.

In some embodiments, the multi-specific CD20 binding agent of the application comprises a targeting moiety having a recognition domain that specifically binds to a target (e.g. antigen or receptor) associated with cancer or tumor cells. In some embodiments, the targeting moiety directly or indirectly recruits tumor cells. For instance, in some embodiments, the recruitment of the tumor cell is to one or more effector cell (e.g. an immune cell as described herein) that can kill and/or suppress the tumor cell.

Tumor cells, or cancer cells refer to an uncontrolled growth of cells or tissues and/or an abnormal increased in cell survival and/or inhibition of apoptosis which interferes with the normal functioning of bodily organs and systems. For example, tumor cells include benign and malignant cancers, polyps, hyperplasia, as well as dormant tumors or micrometastases. Illustrative tumor cells include, but are not limited to cells of: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

Tumor cells, or cancer cells also include, but are not limited to, carcinomas, e.g. various subtypes, including, for example, adenocarcinoma, basal cell carcinoma, squamous cell carcinoma, and transitional cell carcinoma), sarcomas (including, for example, bone and soft tissue), leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g. gliomas (e.g. astrocytoma, oligodendroglioma, and ependymoma), meningioma, pituitary adenoma, and neuromas, and spinal cord tumors (e.g. meningiomas and neurofibroma).

In specific embodiments, the cancer or tumor cells refer to leukemia or lymphoma cells such as cells of: B cell lymphoma, non-Hodgkin's lymphoma (NHL), lymphocyte predominant subtype of Hodgkin's lymphoma, precursor B cell lymphoblastic leukemia/lymphoma, mature B cell neoplasm, B cell chronic lymphocytic leukemia (CLL), small lymphocytic lymphoma (SLL), B cell prolymphocytic leukemia, lymphoplasmacytic lymphoma, mantle cell lymphoma (MCL), follicular lymphoma (FL) including low-grade, intermediate-grade and high-grade FL, cutaneous follicle center lymphoma, marginal zone B cell lymphoma, MALT type marginal zone B cell lymphoma, nodal marginal zone B cell lymphoma, splenic type marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, multiple myeloma, and anaplastic large-cell lymphoma (ALCL)

Illustrative tumor antigens include, but are not limited to, MART-1/Melan-A, gp100, Dipeptidyl peptidase IV (DPPIV), adenosine deaminase-binding protein (ADAbp), cyclophilin b, Colorectal associated antigen (CRC)-0017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pmel117, PRAME, NY-ESO-1, cdc27, adenomatous polyposis *coli* protein (APC), fodrin, Connexin 37, Ig-idiotype, p15, gp75, GM2 and GD2 gangliosides, viral products such as human papilloma virus proteins, Smad family of tumor antigens, Imp-1, NA, EBV-encoded nuclear antigen (EBNA)-1, brain glycogen phosphorylase, SSX-1, SSX-2 (HOM-MEL-40), SSX-1, SSX-4, SSX-5, SCP-1 CT-7, c-erbB-2, CD19, CD20, CD22, CD30, CD33, CD37, CD56, CD70, CD74, CD138, AGS16, MUC1, GPNMB, Ep-CAM, PD-L1, PD-L2, and PMSA. In various embodiments, the CD20 binding agent comprises a targeting moiety that binds one or more of these tumor antigens.

In some embodiments, the present multi-specific CD20 binding agent recognizes and binds to CD20 as well as an antigen on a tumor cell. In some embodiments, the multi-specific CD20 binding agent directly or indirectly recruits immune cells to the tumor cell or tumor microenvironment.

In some embodiments, the multi-specific CD20 binding agent of the application comprises a targeting moiety having a recognition domain that specifically binds to a target (e.g. an antigen or receptor) associated with T cells. In some embodiments, the targeting moiety directly or indirectly recruits T cells. In an embodiment, the antigen recognition domains specifically bind to effector T cells. In some embodiments, the antigen recognition domain directly or indirectly recruits effector T cells, e.g., in some embodiments, to a therapeutic site (e.g. a locus with one or more disease cell or cell to be modulated for a therapeutic effect). Illustrative effector T cells include cytotoxic T cells (e.g. αβ TCR, $CD3^+$, $CD8^+$, $CD45RO^+$); $CD4^+$ effector T cells (e.g. αβ TCR, $CD3^+$, $CD4^+$, $CCR7^+$, CD62Lhi, IL-7R/$CD127^+$); $CD8^+$ effector T cells (e.g. αβ TCR, $CD3^+$, $CD8^+$, $CCR7^+$, CD62Lhi, IL-7R/$CD127^+$); effector memory T cells (e.g. CD62Llow, $CD44^+$, TCR, $CD3^+$, IL-7R/$CD127^+$, IL-$15R^+$, CCR7low); central memory T cells (e.g. $CCR7^+$, $CD62L^+$, $CD27^+$; or CCR7hi, $CD44^+$, CD62Lhi, TCR, $CD3^+$, IL-7R/$CD127^+$, IL-$15R^+$); $CD62L^+$ effector T cells; $CD8^+$ effector memory T cells (TEM) including early effector memory T cells ($CD27^+$ $CD62L^-$) and late effector memory T cells ($CD27^-$ $CD62L^-$) (TemE and TemL, respectively); CD127($^+$)CD25(low/−) effector T cells; CD127($^-$)CD25($^-$) effector T cells; $CD8^+$ stem cell memory effector cells (TSCM) (e.g. CD44(low)CD62L(high)CD122(high)sca($^+$)); TH1 effector T-cells (e.g. $CXCR3^+$, $CXCR6^+$ and $CCR5^+$; or αβ TCR, $CD3^+$, $CD4^+$, IL-$12R^+$, IFNγ$R^+$, $CXCR3^+$), TH2 effector T cells (e.g. $CCR3^+$, $CCR4^+$ and $CCR8^+$; or αβ TCR, $CD3^+$, $CD4^+$, IL-$4R^+$, IL-$33R^+$, $CCR4^+$, IL-$17RB^+$, $CRTH2^+$); TH9 effector T cells (e.g. αβ TCR, $CD3^+$, $CD4^+$); TH17 effector T cells (e.g. αβ TCR, $CD3^+$, $CD4^+$, IL-$23R^+$, $CCR6^+$, IL-$1R^+$); $CD4^+CD45RO^+CCR7^+$ effector T cells, $ICOS^+$ effector T cells; $CD4^+CD45RO^+$CCR7($^-$) effector T cells; and effector T cells secreting IL-2, IL-4 and/or IFN-γ.

Illustrative T cell antigens of interest include, for example (and inclusive of the extracellular domains, where applicable): CD8, CD3, SLAMF4, IL-2Rα, 4-1BB/TNFRSF9, IL-2 Rβ, ALCAM, B7-1, IL-4R, B7-H3, BLAME/SLAMFS, CEACAM1, IL-6R, CCR3, IL-7 Rα, CCR4, CXCRI/IL-SRA, CCR5, CCR6, IL-10Rα, CCR7, IL-10 Rβ, CCRS, IL-12Rβ1, CCR9, IL-12Rβ2, CD2, IL-13Rα1, IL-13, CD3, CD4, ILT2/CDS5j, ILT3/CDS5k, ILT4/CDS5d, ILT5/CDS5a, lutegrin α 4/CD49d, CDS, Integrin α E/CD103, CD6, Integrin α M/CD 11b, CDS, Integrin α X/CD11c, Integrin β 2/CDIS, KIR/CD15S, CD27/TNFRSF7, KIR2DL1, CD2S, KIR2DL3, CD30/TNFRSFS, KIR2DL4/CD15Sd, CD31/PECAM-1, KIR2DS4, CD40 Ligand/TNFSF5, LAG-3, CD43, LAIR1, CD45, LAIR2, CDS3, Leukotriene B4-R1, CDS4/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2Rγ, Osteopontin, CRACC/SLAMF7, PD-1, CRTAM, PSGL-1, CTLA-4, RANK/TNFRSF11A, CX3CR1, CX3CL1, L-Selectin, CXCR3, SIRPβ1, CXCR4, SLAM, CXCR6, TCCR/WSX-1, DNAM-1, Thymopoietin, EMMPRIN/CD147, TIM-1, EphB6, TIM-2, Fas/TNFRSF6, TIM-3, Fas Ligand/TNFSF6, TIM-4, Fcγ RIII/CD16, TIM-6, TNFR1/TNFRSF1A, Granulysin, TNF RIII/TNFRSF1B, TRAIL RI/TNFRSFIOA, ICAM-1/CD54, TRAIL R2/TNFRSF10B, ICAM-2/CD102, TRAILR3/TNFRSF10C, IFN-γR1, TRAILR4/TNFRSF10D, IFN-γ R2, TSLP, IL-1 R1 and TSLP R. In various embodiments, the CD20 binding agent comprises a targeting moiety that binds one or more of these illustrative T cell antigens.

By way of non-limiting example, in various embodiments, the present chimeric protein has a targeting moiety directed against a checkpoint marker expressed on a T cell, e.g. one or more of PD-1, CD28, CTLA4, ICOS, BTLA, KIR, LAG3, CD137, OX40, CD27, CD40L, TIM3, and A2aR.

In some embodiments, the multi-specific CD20 binding agent of the application comprises a targeting moiety having a recognition domain that specifically binds to a target (e.g. an antigen or receptor) associated with B cells. In some embodiments, the targeting moiety directly or indirectly recruits B cells, e.g., in some embodiments, to a therapeutic site (e.g. a locus with one or more disease cell or cell to be modulated for a therapeutic effect). Illustrative B cell antigens of interest include, for example, CD10, CD19, CD20, CD21, CD22, CD23, CD24, CD37, CD38, CD39, CD40, CD72, CD73, CD74, CDw75, CDw76, CD77, CD78, CD79a/b, CD80, CD81, CD82, CD83, CD84, CD85, CD86, CD89, CD98, CD126, CD127, CDw130, CD138 and CDw150. In various embodiments, the CD20 binding agent comprises a targeting moiety that binds one or more of these illustrative B cell antigens.

In some embodiments, the multi-specific CD20 binding agent of the application comprises a targeting moiety having a recognition domain that specifically binds to a target (e.g. an antigen or receptor) associated with Natural Killer cells. In some embodiments, the targeting moiety directly or indirectly recruits Natural Killer cells, e.g., in some embodiments, to a therapeutic site (e.g. a locus with one or more disease cell or cell to be modulated for a therapeutic effect).

Illustrative Natural Killer cell antigens of interest include, for example TIGIT, 2B4/SLAMF4, KIR2DS4, CD155/PVR, KIR3DL1, CD94, LMIR1/CD300A, CD69, LMIR2/CD300c, CRACC/SLAMF7, LMIR3/CD300LF, Kir1alpha, DNAM-1, LMIR5/CD300LB, Fc-epsilon RII, LMIR6/CD300LE, Fc-γ RI/CD64, MICA, Fc-γ RIIB/CD32b, MICB, Fc-γ RIIC/CD32c, MULT-1, Fc-γ RIIA/CD32a, Nectin-2/CD112, Fc-γ RIII/CD16, NKG2A, FcRH1/IRTA5, NKG2C, FcRH2/IRTA4, NKG2D, FcRH4/IRTA1, NKp30, FcRH5/IRTA2, NKp44, Fc-Receptor-like 3/CD16-2, NKp46/NCR1, NKp80/KLRF1, NTB-A/SLAMF6, Rae-1, Rae-1 α, Rae-1 β, Rae-1 delta, H60, Rae-1 epsilon, ILT2/CD85j, Rae-1 γ, ILT3/CD85k, TREM-1, ILT4/CD85d, TREM-2, ILT5/CD85a, TREM-3, KIR/CD158, TREML1/TLT-1, KIR2DL1, ULBP-1, KIR2DL3, ULBP-2, KIR2DL4/CD158d and ULBP-3. In various embodiments, the CD20 binding agent comprises a targeting moiety that binds one or more of these illustrative NK cell antigens.

In some embodiments, the multi-specific CD20 binding agent of the application comprises a targeting moiety having a recognition domain that specifically binds to a target (e.g. an antigen or receptor) associated with macrophages/monocytes. In some embodiments, the targeting moiety directly or indirectly directly or indirectly recruits macrophages/monocytes, e.g., in some embodiments, to a therapeutic site (e.g. a locus with one or more disease cell or cell to be modulated for a therapeutic effect). Illustrative macrophages/monocyte antigens of interest include, for example SIRP1a, B7-1/CD80, ILT4/CD85d, B7-H1, ILT5/CD85a, Common β Chain, Integrin α 4/CD49d, BLAME/SLAMF8, Integrin α X/CDIIc, CCL6/C10, Integrin β 2/CD18, CD155/PVR, Integrin β 3/CD61, CD31/PECAM-1, Latexin, CD36/SR-B3, Leukotriene B4 R1, CD40/TNFRSF5, LIMPIIISR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/SLAMF9, MARCO, CRACC/SLAMF7, MD-1, ECF-L, MD-2, EMMPRIN/CD147, MGL2, Endoglin/CD105, Osteoactivin/GPNMB, Fc-γ RI/CD64, Osteopontin, Fc-γ RIIB/CD32b, PD-L2, Fc-γ RIIC/CD32c, Siglec-3/CD33, Fc-γ RIIA/CD32a, SIGNR1/CD209, Fc-γ RIII/CD16, SLAM, GM-CSF R α, TCCR/WSX-1, ICAM-2/CD102, TLR3, IFN-γ RI, TLR4, IFN-gamma R2, TREM-1, IL-I RII, TREM-2, ILT2/CD85j, TREM-3, ILT3/CD85k, TREML1/TLT-1, 2B4/SLAMF 4, IL-10R α, ALCAM, IL-10R β, AminopeptidaseN/ANPEP, ILT2/CD85j, Common β Chain, ILT3/CD85k, Clq R1/CD93, ILT4/CD85d, CCR1, ILT5/CD85a, CCR2, CD206, Integrin α 4/CD49d, CCR5, Integrin α M/CDII b, CCR8, Integrin α X/CDIIc, CD155/PVR, Integrin β 2/CD18, CD14, Integrin β 3/CD61, CD36/SR-B3, LAIR1, CD43, LAIR2, CD45, Leukotriene B4-R1, CD68, LIMPIIISR-B2, CD84/SLAMF5, LMIR1/CD300A, CD97, LMIR2/CD300c, CD163, LMIR3/CD300LF, Coagulation Factor Ill/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD147, MMR, Endoglin/CD105, NCAM-L1, Fc-γ RI/CD64, PSGL-1, Fc-γ RIIICD16, RP105, G-CSF R, L-Selectin, GM-CSF Rα, Siglec-3/CD33, HVEM/TNFRSF14, SLAM, ICAM-1/CD54, TCCR/WSX-1, ICAM-2/CD102, TREM-1, IL-6R, TREM-2, CXCRI/IL-8 RA, TREM-3 and TREMLI/TLT-1. In various embodiments, the CD20 binding agent comprises a targeting moiety that binds one or more of these illustrative macrophage/monocyte antigens.

In some embodiments, the multi-specific CD20 binding agent of the application comprises a targeting moiety having a recognition domain that specifically binds to a target (e.g. an antigen or receptor) associated with dendritic cells. In some embodiments, the targeting moiety directly or indirectly recruits dendritic cells, e.g., in some embodiments, to a therapeutic site (e.g. a locus with one or more disease cell or cell to be modulated for a therapeutic effect). Illustrative dendritic cell antigens of interest include, for example, Clec9A, XCR1, RANK, CD36/SRB3, LOX-1/SR-E1, CD68, MARCO, CD163, SR-A1/MSR, CD5L, SREC-1, CL-PI/COLEC12, SREC-II, LIMPIIISRB2, RP105, TLR4, TLR1, TLR5, TLR2, TLR6, TLR3, TLR9, 4-IBB Ligand/TNFSF9, IL-12/IL-23p40, 4-Amino-1,8-naphthalimide, ILT2/CD85j, CCL21/6Ckine, ILT3/CD85k, 8-oxo-dG, ILT4/CD85d, 8D6A, ILT5/CD85a, A2B5, lutegrin α 4/CD49d, Aag, Integrin β 2/CD18, AMICA, Langerin, B7-2/CD86, Leukotriene B4 RI, B7-H3, LMIR1/CD300A, BLAME/SLAMF8, LMIR2/CD300c, Clq R1/CD93, LMIR3/CD300LF, CCR6, LMIR5/CD300LB CCR7, LMIR6/CD300LE, CD40/TNFRSF5, MAG/Siglec-4-a, CD43, MCAM, CD45, MD-1, CD68, MD-2, CD83, MDL-1/CLEC5A, CD84/SLAMF5, MMR, CD97, NCAMLI, CD2F-10/SLAMF9, Osteoactivin GPNMB, Chern 23, PD-L2, CLEC-1, RP105, CLEC-2, CLEC-8, Siglec-2/CD22, CRACC/SLAMF7, Siglec-3/CD33, DC-SIGN, DCE205, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD148, SIGNR4, DLEC, SLAM, EMMPRIN/CD147, TCCR/WSX-1, Fc-γ R1/CD64, TLR3, Fc-γ RIIB/CD32b, TREM-1, Fc-γ RIIC/CD32c, TREM-2, Fc-γ RIIA/CD32a, TREM-3, Fc-γ RIII/CD16, TREML1/TLT-1, ICAM-2/CD102 and Vanilloid R1. In various embodiments, the CD20 binding agent comprises a targeting moiety that binds one or more of these illustrative DC antigens. In some embodiments, the CD20 binding agent comprises a targeting moiety that binds to Clec9A, and such a CD20 binding agent finds uses, for example, in the treatment of multiple sclerosis.

In some embodiments, the multi-specific CD20 binding agent of the application comprises a targeting moiety having a recognition domain that specifically binds to a target (e.g. an antigen or receptor) associated with immune cells selected from, but not limited to, megakaryocytes, thrombocytes, erythrocytes, mast cells, basophils, neutrophils, eosinophils, or subsets thereof. In some embodiments, the antigen recognition domains directly or indirectly recruit megakaryocytes, thrombocytes, erythrocytes, mast cells, basophils, neutrophils, eosinophils, or subsets thereof, e.g., in some embodiments, to a therapeutic site (e.g. a locus with one or more disease cell or cell to be modulated for a therapeutic effect).

In some embodiments, the multi-specific CD20 binding agent of the application comprises a targeting moiety having a recognition domain that specifically binds to a target (e.g. an antigen or receptor) associated with megakaryocytes and/or thrombocytes. Illustrative megakaryocyte and/or thrombocyte antigens of interest include, for example, GP IIb/IIIa, GPIb, vWF, PF4, and TSP. In various embodiments, the CD20 binding agent comprises a targeting moiety that binds one or more of these illustrative megakaryocyte and/or thrombocyte antigens.

In some embodiments, the multi-specific CD20 binding agent of the application comprises a targeting moiety having a recognition domain that specifically binds to a target (e.g. an antigen or receptor) associated with erythrocytes. Illustrative erythrocyte antigens of interest include, for example, CD34, CD36, CD38, CD41a (platelet glycoprotein IIb/IIIa), CD41b (GPIIb), CD71 (transferrin receptor), CD105, glycophorin A, glycophorin C, c-kit, HLA-DR, H2 (MHC-II), and Rhesus antigens. In various embodiments, the CD20 binding agent comprises a targeting moiety that binds one or more of these illustrative erythrocyte antigens.

In some embodiments, the multi-specific CD20 binding agent of the application comprises a targeting moiety having a recognition domain that specifically binds to a target (e.g. an antigen or receptor) associated with mast cells. Illustrative mast cells antigens of interest include, for example, SCFR/CD117, $Fc_{\epsilon}RI$, CD2, CD25, CD35, CD88, CD203c, C5R1, CMAI, FCERIA, FCER2, TPSABI. In various embodiments, the CD20 binding agent comprises a targeting moiety that binds one or more of these mast cell antigens.

In some embodiments, the multi-specific CD20 binding agent of the application comprises a targeting moiety having a recognition domain that specifically binds to a target (e.g. an antigen or receptor) associated with basophils. Illustrative basophils antigens of interest include, for example, $Fc_{\epsilon}RI$, CD203c, CD123, CD13, CD107a, CD107b, and CD164. In various embodiments, the CD20 binding agent comprises a targeting moiety that binds one or more of these basophil antigens.

In some embodiments, the multi-specific CD20 binding agent of the application comprises a targeting moiety having a recognition domain that specifically binds to a target (e.g. an antigen or receptor) associated with neutrophils. Illustrative neutrophils antigens of interest include, for example, 7D5, CD10/CALLA, CD13, CD16 (FcRIII), CD18 proteins (LFA-1, CR3, and p150, 95), CD45, CD67, and CD177. In various embodiments, the CD20 binding agent comprises a targeting moiety that binds one or more of these neutrophil antigens.

In some embodiments, the multi-specific CD20 binding agent of the application comprises a targeting moiety having a recognition domain that specifically binds to a target (e.g. an antigen or receptor) associated with eosinophils. Illustrative eosinophils antigens of interest include, for example, CD35, CD44 and CD69. In various embodiments, the CD20 binding agent comprises a targeting moiety that binds one or more of these eosinophil antigens.

In various embodiments, the multi-specific CD20 binding agent of the application comprises a targeting moiety having a recognition domain that specifically binds to an appropriate antigen or cell surface marker known by the skilled artisan. In some embodiments, the antigen or cell surface marker is a tissue-specific marker. Illustrative tissue-specific markers include, but are not limited to, endothelial cell surface markers such as ACE, CD14, CD34, CDH5, ENG, ICAM2, MCAM, NOS3, PECAMI, PROCR, SELE, SELP, TEK, THBD, VCAMI, VWF; smooth muscle cell surface markers such as ACTA2, MYHIO, MYHI 1, MYH9, MYOCD; fibroblast (stromal) cell surface markers such as ALCAM, CD34, COLIAI, COL1A2, COL3A1, FAP, PH-4; epithelial cell surface markers such as CDID, K6IRS2, KRTIO, KRT13, KRT17, KRT18, KRT19, KRT4, KRT5, KRT8, MUCI, TACSTDI; neovasculature markers such as CD13, TFNA, Alpha-v beta-3 (aVβ3), E-selectin; and adipocyte surface markers such as ADIPOQ, FABP4, and RETN. In various embodiments, the CD20 binding agent comprises a targeting moiety that binds one or more of these antigens. In various embodiments, a targeting moiety of the chimeric protein binds one or more of cells having these antigens.

In various embodiments, the multi-specific CD20 binding agent of the application has one or more targeting moieties directed against a checkpoint marker, e.g. one or more of PD-1/PD-L1 or PD-L2, CD28/CD80 or CD86, CTLA4/CD80 or CD86, ICOS/ICOSL or B7RP1, BTLA/HVEM, KIR, LAG3, CD137/CD137L, OX40/OX40L, CD27, CD40L, TIM3/Gal9, and A2aR.

By way of non-limiting example, in various embodiments, the present chimeric protein comprises a targeting moiety directed against (i) a checkpoint marker expressed on a T cell, e.g. one or more of PD-1, PD-L1, PD-L2, CD28, CTLA4, ICOS, BTLA, KIR, LAG3, CD137, OX40, Cd27, CD40L, TIM3, and A2aR and (ii) a targeting moiety is directed against a cancer or tumor cell (e.g., CD20 on a cancer or tumor cell), along with any of the modified (e.g. mutant) signaling agents described herein.

By way of non-limiting example, in various embodiments, the present chimeric protein has a targeting moiety directed against PD-1:

EVQLVESGGGLVQAGKSLRLSCAASGSIFSIHAMG
WFRQAPGKEREFVAAITWSGGITYYEDSVKGRFTI
SRDNAKNTVYLQMNSLKPEDTAIYYCAADRAESSW
YDYWGQGTQVTVSS, or a sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to the above sequence (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity to the above sequence.

By way of further non-limiting example, in various embodiments, the present chimeric protein has a targeting moiety directed against PD-L1:

EVQLVESGGGLVQPGGSLRLSCAASGFTLDYYAKC
WFRQAPGKEREWVSCISSSDGSTYYADSVKGRFTI
SRDNAKNTVYLQMNSLKPEDTAVYFCAARHGGPLT
VEYFFDYWGQGTQVTVSS, or a sequence that is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to the above sequence (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity to the above sequence.

Linkers and Functional Groups

In various embodiments, the CD20 binding agent may include one or more functional groups, residues, or moieties. In various embodiments, the one or more functional groups, residues, or moieties are attached or genetically fused to any of the signaling agents or targeting moieties described herein. In some embodiments, such functional groups, residues or moieties confer one or more desired properties or functionalities to the CD20 binding agent of the application. Examples of such functional groups and of techniques for introducing them into the CD20 binding agent are known in the art, for example, see Remington's Pharmaceutical Sciences, 16th ed., Mack Publishing Co., Easton, Pa. (1980).

In some embodiments, the functional groups, residues, or moieties comprise a suitable pharmacologically acceptable polymer, such as poly(ethyleneglycol) (PEG) or derivatives thereof (such as methoxypoly(ethyleneglycol) or mPEG). In some embodiments, attachment of the PEG moiety increases the half-life and/or reduces the immunogenicity of the CD20 binding protein. Generally, any suitable form of pegylation can be used, such as the pegylation used in the art for antibodies and antibody fragments (including but not limited to single domain antibodies such as VHHs); see, for example, Chapman, *Nat. Biotechnol.*, 54, 531-545 (2002); by Veronese and Harris, *Adv. Drug Deliv. Rev.* 54, 453-456 (2003), by Harris and Chess, *Nat. Rev. Drug. Discov.*, 2, (2003) and in WO04060965, the entire contents of which are hereby incorporated by reference. Various reagents for pegylation of proteins are also commercially available, for example, from Nektar Therapeutics, USA. In some embodiments, site-directed pegylation is used, in particular via a cysteine-residue (see, for example, Yang et al., Protein Engineering, 16, 10, 761-770 (2003), the entire contents of which is hereby incorporated by reference). For example, for this purpose, PEG may be attached to a cysteine residue that naturally occurs in the CD20 binding agent of the application. In some embodiments, the CD20 binding agent of the application is modified so as to suitably introduce one or more cysteine residues for attachment of PEG, or an amino acid sequence comprising one or more cysteine residues for attachment of PEG may be fused to the amino- and/or carboxy-terminus of the CD20 binding agent, using techniques known in the art.

In some embodiments, the functional groups, residues, or moieties comprise N-linked or O-linked glycosylation. In some embodiments, the N-linked or O-linked glycosylation is introduced as part of a co-translational and/or post-translational modification.

In some embodiments, the functional groups, residues, or moieties comprise one or more detectable labels or other signal-generating groups or moieties. Suitable labels and techniques for attaching, using and detecting them are known in the art and, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels include moieties that can be detected using NMR or ESR spectroscopy. Such labeled VHHs and polypeptides of the application may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label.

In some embodiments, the functional groups, residues, or moieties comprise a tag that is attached or genetically fused to the CD20 binding agent. In some embodiments, the CD20 binding agent may include a single tag or multiple tags. The tag for example is a peptide, sugar, or DNA molecule that does not inhibit or prevent binding of the CD20 binding agent to CD20 or any other antigen of interest such as tumor antigens. In various embodiments, the tag is at least about: three to five amino acids long, five to eight amino acids long, eight to twelve amino acids long, twelve to fifteen amino acids long, or fifteen to twenty amino acids long. Illustrative tags are described for example, in U.S. Patent Publication No. US2013/0058962. In some embodiment, the tag is an affinity tag such as glutathione-S-transferase (GST) and histidine (His) tag. In an embodiment, the CD20 binding agent comprises a His tag. In an embodiment, the CD20 binding agent comprises an HA tag.

In some embodiments, the functional groups, residues, or moieties comprise a chelating group, for example, to chelate one of the metals or metallic cations. Suitable chelating groups, for example, include, without limitation, diethylenetriaminepentaacetic acid (DTPA) or ethylenediaminetetraacetic acid (EDTA).

In some embodiments, the functional groups, residues, or moieties comprise a functional group that is one part of a specific binding pair, such as the biotin-(strept)avidin binding pair. Such a functional group may be used to link the CD20 binding agent of the application to another protein, polypeptide or chemical compound that is bound to the other half of the binding pair, i.e., through formation of the binding pair. For example, a CD20 binding agent of the application may be conjugated to biotin, and linked to another protein, polypeptide, compound or carrier conjugated to avidin or streptavidin. For example, such a conjugated CD20 binding agent may be used as a reporter, for example, in a diagnostic system where a detectable signal-producing agent is conjugated to avidin or streptavidin. Such binding pairs may, for example, also be used to bind the CD20 binding agent to a carrier, including carriers suitable for pharmaceutical purposes. One non-limiting example are the liposomal formulations described by Cao and Suresh, *Journal of Drug Targeting,* 8, 4, 257 (2000). Such binding pairs may also be used to link a therapeutically active agent to the CD20 binding agent of the application.

In some embodiments, the present CD20 binding agent optionally comprises one or more linkers. In some embodiments, the CD20 binding agent includes a linker that connects each binding region and/or targeting moieties. . In some embodiments, the CD20 binding agent includes a linker that connects each signaling agent and targeting moiety (or, if more than one targeting moiety, a signaling agent to one of the targeting moieties). In some embodiments, the linker may be utilized to link various functional groups, residues, or moieties as described herein to the CD20 binding agent. In some embodiments, the linker is a single amino acid or a plurality of amino acids that does not affect or reduce the stability, orientation, binding, neutralization, and/or clearance characteristics of the binding regions and the binding protein. In various embodiments, the linker is selected from a peptide, a protein, a sugar, or a nucleic acid.

In some embodiments, the present CD20 binding agent comprises a linker connecting the targeting moiety and the signaling agent. In some embodiments, the present chimeric protein comprises a linker within the signaling agent (e.g. in the case of single chain TNF, which can comprise two linkers to yield a trimer).

The application contemplates the use of a variety of linker sequences. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present CD20 binding agent.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is a polypeptide.

In some embodiments, the linker is greater than about 100 amino acids long. For example, the linker may be greater than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In some embodiments, the linker length allows for efficient binding of a targeting moiety and the signaling agent to their receptors. For instance, in some embodiments, the linker length allows for efficient binding of one of the targeting moieties and the signaling agent to receptors on the same cell as well as the efficient binding of the other targeting moiety to another cell. Illustrative pairs of cells are provided elsewhere herein.

In some embodiments the linker length is at least equal to the minimum distance between the binding sites of one of the targeting moieties and the signaling agent to receptors on the same cell. In some embodiments the linker length is at least twice, or three times, or four times, or five times, or ten times, or twenty times, or 25 times, or 50 times, or one hundred times, or more the minimum distance between the binding sites of one of the targeting moieties and the signaling agent to receptors on the same cell.

In some embodiments, a linker connects the two targeting moieties to each other and this linker has a short length and a linker connects a targeting moiety and a signaling agent this linker is longer than the linker connecting the two targeting moieties. For example, the difference in amino acid length between the linker connecting the two targeting moieties and the linker connecting a targeting moiety and a signaling agent may be about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids. In some embodiments, the linker is flexible. In another embodiment, the linker is rigid.

In an embodiment, the linker is AAA.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). For example, in some embodiments, the linker is $(Gly_4Ser)_n$, where n is from about 1 to about 8, e.g. 1, 2, 3, 4, 5, 6, 7, or 8 (SEQ ID NO: 183 to SEQ ID NO: 190). In an embodiment, the linker sequence is GGSGGSGGGGSGGGGS (SEQ ID NO: 191). Additional illustrative linkers include, but are not limited to, linkers having the sequence LE, GGGGS (SEQ ID NO: 183), $(GGGGS)_n$ (n=1-4) (SEQ ID NO: 183, SEQ ID NO: 192 to 194), $(Gly)_8$ (SEQ ID NO: 195), $(Gly)_6$ (SEQ ID NO: 196), $(EAAAK)_n$ (n=1-3) (SEQ ID NO: 197 to 199), $A(EAAAK)_4$ A (n=2-5) (SEQ ID NO: 200 to 203), AEAAAKEAAAKA (SEQ ID NO: 200), $A(EAAAK)_4ALEA(EAAAK)_4A$ (SEQ ID NO: 204), PAPAP (SEQ ID NO: 205), KESGSVSSE-QLAQFRSLD (SEQ ID NO: 206), EGKSSGSGSESKST (SEQ ID NO: 207), GSAGSAAGSGEF (SEQ ID NO: 208), and $(XP)_n$, with X designating any amino acid, e.g., Ala, Lys, or Glu. In various embodiments, the linker is GGS.

In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

According to crystallographic studies, the immunoglobulin hinge region can be further subdivided functionally into three regions: the upper hinge region, the core region, and the lower hinge region. See Shin et al., 1992 *Immunological Reviews* 130:87. The upper hinge region includes amino acids from the carboxyl end of $C_{H1}$ to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. Id. The core hinge region of wild-type human IgG1 contains the sequence Cys-Pro-Pro-Cys (SEQ ID NO: 223) which, when dimerized by disulfide bond formation, results in a cyclic octapeptide believed to act as a pivot, thus conferring flexibility. In various embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In various embodiments, the linker of the present application comprises one or more glycosylation sites. In various embodiments, the linker is a hinge-CH2-CH3 domain of a human IgG4 antibody.

If desired, the present CD20 binding agent can be linked to an antibody Fc region, comprising one or both of $C_H2$ and $C_H3$ domains, and optionally a hinge region. For example, vectors encoding the present CD20 binding agents linked as a single nucleotide sequence to an Fc region can be used to prepare such polypeptides.

In some embodiments, the linker is a synthetic linker such as PEG.

In various embodiments, the linker may be functional. For example, without limitation, the linker may function to improve the folding and/or stability, improve the expression, improve the pharmacokinetics, and/or improve the bioactivity of the present CD20 binding agent. In another example, the linker may function to target the CD20 binding agent to a particular cell type or location.

Modifications and Production of CD20 Binding Agents

In various embodiments, the CD20 binding agent comprises a targeting moiety that is a VHH. In various embodiments, the VHH is not limited to a specific biological source or to a specific method of preparation. For example, the VHH can generally be obtained: (1) by isolating the $V_H$H domain of a naturally occurring heavy chain antibody; (2) by expression of a nucleotide sequence encoding a naturally occurring $V_H$H domain; (3) by "humanization" of a naturally occurring $V_H$H domain or by expression of a nucleic acid encoding a such humanized $V_H$H domain; (4) by "camelization" of a naturally occurring VH domain from any animal species, such as from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known in the art; (7) by preparing a nucleic acid encoding a VHH using techniques for nucleic acid synthesis known in the art, followed by expression of the nucleic acid thus obtained; and/or (8) by any combination of one or more of the foregoing.

In an embodiment, the CD20 binding agent comprises a VHH that corresponds to the $V_H$H domains of naturally occurring heavy chain antibodies directed against human CD20. In some embodiments, such $V_H$H sequences can generally be generated or obtained by suitably immunizing a species of Camelid with a CD20 molecule, (i.e., so as to raise an immune response and/or heavy chain antibodies directed against CD20), by obtaining a suitable biological sample from the Camelid (such as a blood sample, or any sample of B-cells), and by generating $V_H$H sequences directed against CD20, starting from the sample, using any suitable known techniques. In some embodiments, naturally occurring $V_H$H domains against CD20 can be obtained from naive libraries of Camelid $V_H$H sequences, for example, by screening such a library using CD20 or at least one part, fragment, antigenic determinant or epitope thereof using one or more screening techniques known in the art. Such libraries and techniques are, for example, described in WO9937681, WO0190190, WO03025020 and WO03035694, the entire contents of which are hereby incorporated by reference. In some embodiments, improved synthetic or semi-synthetic libraries derived from naive $V_H$H libraries may be used, such as $V_H$H libraries obtained from naive $V_H$H libraries by techniques such as random mutagenesis and/or CDR shuffling, as for example, described in WO0043507, the entire contents of which are hereby incorporated by reference. In some embodiments, another technique for obtaining $V_H$H sequences directed against a CD20 involves suitably immunizing a transgenic mammal that is capable of expressing heavy chain antibodies (i.e., so as to raise an immune response and/or heavy chain antibodies directed against CD20), obtaining a suitable biological sample from the transgenic mammal (such as a blood sample, or any sample of B-cells), and then generating $V_H$H sequences directed against CD20 starting from the sample, using any suitable known techniques. For example, for this purpose, the heavy chain antibody-expressing mice and the further methods and techniques described in WO02085945 and in WO04049794 (the entire contents of which are hereby incorporated by reference) can be used.

In an embodiment, the CD20 binding agent comprises a VHH that has been "humanized" i.e., by replacing one or more amino acid residues in the amino acid sequence of the naturally occurring $V_HH$ sequence (and in particular in the framework sequences) by one or more of the amino acid residues that occur at the corresponding position(s) in a VH domain from a conventional 4-chain antibody from a human being. This can be performed using humanization techniques known in the art. In some embodiments, possible humanizing substitutions or combinations of humanizing substitutions may be determined by methods known in the art, for example, by a comparison between the sequence of a VHH and the sequence of a naturally occurring human VH domain. In some embodiments, the humanizing substitutions are chosen such that the resulting humanized VHHs still retain advantageous functional properties. Generally, as a result of humanization, the VHHs of the application may become more "human-like," while still retaining favorable properties such as a reduced immunogenicity, compared to the corresponding naturally occurring $V_HH$ domains. In various embodiments, the humanized VHHs of the application can be obtained in any suitable manner known in the art and thus are not strictly limited to polypeptides that have been obtained using a polypeptide that comprises a naturally occurring $V_HH$ domain as a starting material.

In an embodiment, the CD20 binding agent comprises a VHH that has been "camelized," i.e., by replacing one or more amino acid residues in the amino acid sequence of a naturally occurring VH domain from a conventional 4-chain antibody by one or more of the amino acid residues that occur at the corresponding position(s) in a $V_HH$ domain of a heavy chain antibody of a camelid. In some embodiments, such "camelizing" substitutions are inserted at amino acid positions that form and/or are present at the VH-VL interface, and/or at the so-called Camelidae hallmark residues (see, for example, WO9404678, the entire contents of which are hereby incorporated by reference). In some embodiments, the VH sequence that is used as a starting material or starting point for generating or designing the camelized VHH is a VH sequence from a mammal, for example, the VH sequence of a human being, such as a VH3 sequence. In various embodiments, the camelized VHHs can be obtained in any suitable manner known in the art (i.e., as indicated under points (1)-(8) above) and thus are not strictly limited to polypeptides that have been obtained using a polypeptide that comprises a naturally occurring VH domain as a starting material.

In various embodiments, both "humanization" and "camelization" can be performed by providing a nucleotide sequence that encodes a naturally occurring $V_HH$ domain or VH domain, respectively, and then changing, in a manner known in the art, one or more codons in the nucleotide sequence in such a way that the new nucleotide sequence encodes a "humanized" or "camelized" VHH, respectively. This nucleic acid can then be expressed in a manner known in the art, so as to provide the desired VHH of the application. Alternatively, based on the amino acid sequence of a naturally occurring $V_HH$ domain or VH domain, respectively, the amino acid sequence of the desired humanized or camelized VHH of the application, respectively, can be designed and then synthesized de novo using techniques for peptide synthesis known in the art. Also, based on the amino acid sequence or nucleotide sequence of a naturally occurring $V_HH$ domain or VH domain, respectively, a nucleotide sequence encoding the desired humanized or camelized VHH, respectively, can be designed and then synthesized de novo using techniques for nucleic acid synthesis known in the art, after which the nucleic acid thus obtained can be expressed in a manner known in the art, so as to provide the desired VHH of the application. Other suitable methods and techniques for obtaining the VHHs of the application and/or nucleic acids encoding the same, starting from naturally occurring VH sequences or $V_HH$ sequences, are known in the art, and may, for example, comprise combining one or more parts of one or more naturally occurring VH sequences (such as one or more FR sequences and/or CDR sequences), one or more parts of one or more naturally occurring $V_HH$ sequences (such as one or more FR sequences or CDR sequences), and/or one or more synthetic or semi-synthetic sequences, in a suitable manner, so as to provide a VHH of the application or a nucleotide sequence or nucleic acid encoding the same.

Methods for producing the CD20 binding agents of the application are described herein. For example, DNA sequences encoding the CD20 binding agents of the application can be chemically synthesized using methods known in the art. Synthetic DNA sequences can be ligated to other appropriate nucleotide sequences, including, e.g., expression control sequences, to produce gene expression constructs encoding the desired CD20 binding agents. Accordingly, in various embodiments, the present application provides for isolated nucleic acids comprising a nucleotide sequence encoding the CD20 binding agent of the application.

Nucleic acids encoding the CD20 binding agent of the application can be incorporated (ligated) into expression vectors, which can be introduced into host cells through transfection, transformation, or transduction techniques. For example, nucleic acids encoding the CD20 binding agent of the application can be introduced into host cells by retroviral transduction. Illustrative host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the CD20 binding agent of the application. Accordingly, in various embodiments, the present application provides expression vectors comprising nucleic acids that encode the CD20 binding agent of the application. In various embodiments, the present application additional provides host cells comprising such expression vectors.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. In another example, if the engineered gene is to be expressed in eukaryotic host cells, e.g., CHO cells, it is first inserted into an expression vector containing for example, a suitable eukaryotic promoter, a secretion signal, enhancers, and various introns. The gene construct can be introduced into the host cells using transfection, transformation, or transduction techniques.

The CD20 binding agent of the application can be produced by growing a host cell transfected with an expression vector encoding the CD20 binding agent under conditions that permit expression of the protein. Following expression, the protein can be harvested and purified using techniques well known in the art, e.g., affinity tags such as glutathione-S-transferase (GST) and histidine (His) tags or by chromatography. In an embodiment, the CD20 binding agent comprises a His tag. In an embodiment, the CD20 binding agent comprises a His tag and a proteolytic site to allow cleavage of the His tag.

Accordingly, in various embodiments, the present application provides for a nucleic acid encoding a CD20 binding agent of the present application. In various embodiments, the present application provides for a host cell comprising a nucleic acid encoding a CD20 binding agent of the present application.

Pharmaceutically Acceptable Salts and Excipients

The CD20 binding agents described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science,* 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term “pharmaceutically acceptable salt” also refers to a salt of the compositions of the present application having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions described herein are in the form of a pharmaceutically acceptable salt.

Pharmaceutical Compositions and Formulations

In various embodiments, the present application pertains to pharmaceutical compositions comprising the CD20 binding agents described herein and a pharmaceutically acceptable carrier or excipient. Any pharmaceutical compositions described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

In various embodiments, pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents. Other examples of suitable pharmaceutical excipients are described in *Remington's Pharmaceutical Sciences* 1447-1676 (Alfonso R. Gennaro eds., 19th ed. 1995), incorporated herein by reference.

The present application includes the described pharmaceutical compositions (and/or additional therapeutic agents) in various formulations. Any inventive pharmaceutical composition (and/or additional therapeutic agents) described herein can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, desiccated powder, or any other form suitable for use. In one embodiment, the composition is in the form of a capsule. In another embodiment, the composition is in the form of a tablet. In yet another embodiment, the pharmaceutical composition is formulated in the form of a soft-gel capsule. In a further embodiment, the pharmaceutical composition is formulated in the form of a gelatin capsule. In yet another embodiment, the pharmaceutical composition is formulated as a liquid.

Where necessary, the inventive pharmaceutical compositions (and/or additional agents) can also include a solubilizing agent. Also, the agents can be delivered with a suitable vehicle or delivery device as known in the art. Combination therapies outlined herein can be co-delivered in a single delivery vehicle or delivery device.

The formulations comprising the inventive pharmaceutical compositions (and/or additional agents) of the present application may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, any pharmaceutical compositions (and/or additional agents) described herein is formulated in accordance with routine procedures as a composition adapted for a mode of administration described herein.

Routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically. Administration can be local or systemic. In some embodiments, the administering is effected orally. In another embodiment, the administration is by parenteral injection. The mode of administration can be left to the discretion of the practitioner, and depends in-part upon the site of the medical condition. In most instances, administration results in the release of any agent described herein into the bloodstream.

In one embodiment, the CD20 binding agent described herein is formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving any CD20 binding agents described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

The compositions provided herein, alone or in combination with other suitable components, can be made into aerosol formulations (i.e., "nebulized") to be administered via inhalation. Aerosol formulations can be placed into pressurized acceptable propellants, such as dichlorodifluoromethane, propane, nitrogen, and the like.

Any inventive pharmaceutical compositions (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598, 123; 4,008,719; 5,674,533; 5,059,595; 5,591,767; 5,120, 548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropyl cellulose, hydropropylmethyl cellulose, polyvinylpyrrolidone, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The application thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, a controlled-release system can be placed in proximity of the target area to be treated, thus requiring only a fraction of the systemic dose (see, e.g., Goodson, in *Medical Applications of Controlled Release, supra*, vol. 2, pp. 115-138 (1984)). Other controlled-release systems discussed in the review by Langer, 1990, Science 249:1527-1533) may be used.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

Administration and Dosage

It will be appreciated that the actual dose of the CD20 binding agent to be administered according to the present application will vary according to the particular dosage form, and the mode of administration. Many factors that may modify the action of the CD20 binding agent (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

In some embodiments, a suitable dosage of the CD20 binding agent is in a range of about 0.01 mg/kg to about 10 g/kg of body weight of the subject, about 0.01 mg/kg to about 1 g/kg of body weight of the subject, about 0.01 mg/kg to about 100 mg/kg of body weight of the subject, about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 100 mg/kg body weight, about 1 g/kg of body weight, about 10 g/kg of body weight, inclusive of all values and ranges there between.

Individual doses of the CD20 binding agent can be administered in unit dosage forms containing, for example, from about 0.01 mg to about 100 g, from about 0.01 mg to about 75 g, from about 0.01 mg to about 50 g, from about 0.01 mg to about 25 g, about 0.01 mg to about 10 g, about 0.01 mg to about 7.5 g, about 0.01 mg to about 5 g, about 0.01 mg to about 2.5 g, about 0.01 mg to about 1 g, about 0.01 mg to about 100 mg, from about 0.1 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg active ingredient, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg per unit dosage form, or from about 5 mg to about 80 mg per unit dosage form. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 500 mg, about 1 g, about 2.5 g, about 5 g, about 10 g, about 25 g, about 50 g, about 75 g, about 100 g, inclusive of all values and ranges therebetween.

In one embodiment, the CD20 binding agent is administered at an amount of from about 0.01 mg to about 100 g daily, from about 0.01 mg to about 75 g daily, from about 0.01 mg to about 50 g daily, from about 0.01 mg to about 25 g daily, from about 0.01 mg to about 10 g daily, from about 0.01 mg to about 7.5 g daily, from about 0.01 mg to about 5 g daily, from about 0.01 mg to about 2.5 g daily, from about 0.01 mg to about 1 g daily, from about 0.01 mg to about 100 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the CD20 binding agent is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 500 mg, about 1 g, about 2.5 g, about 5 g, about 7.5 g, about 10 g, about 25 g, about 50 g, about 75 g, about 100 g, inclusive of all values and ranges therebetween.

In accordance with certain embodiments of the application, the pharmaceutical composition comprising the CD20 binding agent may be administered, for example, more than once daily (e.g., about two times, about three times, about four times, about five times, about six times, about seven times, about eight times, about nine times, or about ten times daily), about once per day, about every other day, about every third day, about once a week, about once every two weeks, about once every month, about once every two months, about once every three months, about once every six months, or about once every year.

Combination Therapy and Additional Therapeutic Agents

In various embodiments, the pharmaceutical composition of the present application is co-administered in conjunction with additional therapeutic agent(s). Co-administration can be simultaneous or sequential.

In one embodiment, the additional therapeutic agent and the CD20 binding agent of the present application are administered to a subject simultaneously. The term "simultaneously" as used herein, means that the additional therapeutic agent and the CD20 binding agent are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the CD20 binding agent can be by simultaneous administration of a single formulation (e.g., a formulation comprising the additional therapeutic agent and the CD20 binding agent) or of separate formulations (e.g., a first formulation including the additional therapeutic agent and a second formulation including the CD20 binding agent).

Co-administration does not require the therapeutic agents to be administered simultaneously, if the timing of their administration is such that the pharmacological activities of the additional therapeutic agent and the CD20 binding agent overlap in time, thereby exerting a combined therapeutic effect. For example, the additional therapeutic agent and the CD20 binding agent can be administered sequentially. The term "sequentially" as used herein means that the additional therapeutic agent and the CD20 binding agent are administered with a time separation of more than about 60 minutes. For example, the time between the sequential administration of the additional therapeutic agent and the CD20 binding agent can be more than about 60 minutes, more than about 2 hours, more than about 5 hours, more than about 10 hours, more than about 1 day, more than about 2 days, more than about 3 days, more than about 1 week, or more than about 2 weeks, or more than about one month apart. The optimal administration times will depend on the rates of metabolism, excretion, and/or the pharmacodynamic activity of the additional therapeutic agent and the CD20 binding agent being administered. Either the additional therapeutic agent or the CD20 binding agent cell may be administered first.

Co-administration also does not require the therapeutic agents to be administered to the subject by the same route of administration. Rather, each therapeutic agent can be administered by any appropriate route, for example, parenterally or non-parenterally.

In some embodiments, the CD20 binding agent described herein acts synergistically when co-administered with another therapeutic agent. In such embodiments, the CD20 binding agent and the additional therapeutic agent may be administered at doses that are lower than the doses employed when the agents are used in the context of monotherapy.

In some embodiments, the present application pertains to chemotherapeutic agents as additional therapeutic agents. For example, without limitation, such combination of the present CD20 binding agents and chemotherapeutic agent find use in the treatment of cancers, as described elsewhere herein. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; def of amine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of photodynamic therapy.

In some embodiments, the present application relates to combination therapies using the CD20 binding agent and a chemotherapeutic agent. In some embodiments, the present application relates to administration of the CD20 binding agent to a patient undergoing treatment with a chemotherapeutic agent. In some embodiments, the chemotherapeutic agent is a DNA-intercalating agent such as, without limitation, doxorubicin, cisplatin, daunorubicin, and epirubicin. In an embodiment, the DNA-intercalating agent is doxorubicin.

In illustrative embodiments, the CD20 binding agent acts synergistically when co-administered with doxorubicin. In an illustrative embodiment, the CD20 binding agent acts synergistically when co-administered with doxorubicin for use in treating tumor or cancer. For example, co-administration of the CD20 binding agent and doxorubicin may act synergistically to reduce or eliminate the tumor or cancer, or slow the growth and/or progression and/or metastasis of the tumor or cancer. In illustrative embodiments, the combination of the CD20 binding agent and doxorubicin may exhibit improved safety profiles when compared to the agents used alone in the context of monotherapy. In illustrative embodiments, the CD20 binding agent and doxorubicin may be administered at doses that are lower than the doses employed when the agents are used in the context of monotherapy. In some embodiments, the CD20 binding agent comprises a mutated interferon such as a mutated IFNα. In illustrative embodiments, the mutated IFNα comprises one or more mutations at positions 148, 149, and 153 with reference to SEQ ID NO:127 or SEQ ID NO:128, such as the substitutions M148A, R149A, and L153A.

In some embodiments, the present application relates to combination therapy with one or more immune-modulating agents, for example, without limitation, agents that modulate immune checkpoint. In various embodiments, the immune-modulating agent targets one or more of PD-1, PD-L1, and PD-L2. In various embodiments, the immune-modulating agent is PD-1 inhibitor. In various embodiments, the immune-modulating agent is an antibody specific for one or more of PD-1, PD-L1, and PD-L2. For instance, in some embodiments, the immune-modulating agent is an antibody such as, by way of non-limitation, nivolumab, (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), MPDL3280A (ROCHE). In some embodiments, the immune-modulating agent targets one or more of CD137 or CD137L. In various embodiments, the immune-modulating agent is an antibody specific for one or more of CD137 or CD137L. For instance, in some embodiments, the immune-modulating agent is an antibody such as, by way of non-limitation, urelumab (also known as BMS-663513 and anti-4-1BB antibody). In some embodiments, the present chimeric protein is combined with urelumab (optionally with one or more of nivolumab, lirilumab, and urelumab) for the treatment of solid tumors and/or B-cell non-Hodgkins lymphoma and/or head and neck cancer and/or multiple myeloma. In some embodiments, the immune-modulating agent is an agent that targets one or more of CTLA-4, AP2M1, CD80, CD86, SHP-2, and PPP2R5A. In various embodiments, the immune-modulating agent is an antibody specific for one or more of CTLA-4, AP2M1, CD80, CD86, SHP-2, and PPP2R5A. For instance, in some embodiments, the immune-modulating agent is an antibody such as, by way of non-limitation, ipilimumab (MDX-010, MDX-101, Yervoy, BMS) and/or tremelimumab (Pfizer). In some embodiments, the present chimeric protein is combined with ipilimumab (optionally with bavituximab) for the treatment of one or more of melanoma, prostate cancer, and lung cancer. In various embodiments, the immune-modulating agent targets CD20. In various embodiments, the immune-modulating agent is an antibody specific CD20. For instance, in some embodiments, the immune-modulating agent is an antibody such as, by way of non-limitation, Ofatumumab (GENMAB), obinutuzumab (GAZYVA), AME-133v (APPLIED MOLECULAR EVOLUTION), Ocrelizumab (GENENTECH), TRU-015 (TRUBION/EMERGENT), veltuzumab (IMMU-106). In an embodiment, the immune modulating agent is an antibody that targets OX40.

In some embodiments, the present application relates to combination therapy using the CD20 binding agent and a checkpoint inhibitor. In some embodiments, the present application relates to administration of the CD20 binding agent to a patient undergoing treatment with a checkpoint inhibitor. In some embodiments, the checkpoint inhibitor is an agent that targets one or more of PD-1, PD-L1, PD-L2, and CTLA-4. In some embodiment, the checkpoint inhibitor is one or more of nivolumab, (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), MPDL3280A (ROCHE), ipilimumab (MDX-010, MDX-101, Yervoy, BMS) and tremelimumab (Pfizer). In an embodiment, the checkpoint inhibitor is an antibody against PD-L1.

In illustrative embodiments, the CD20 binding agent acts synergistically when co-administered with the anti-PD-L1 camelid VHH. In an illustrative embodiment, the CD20 binding agent acts synergistically when co-administered with the anti-PD-L1 camelid VHH for use in treating tumor or cancer. For example, co-administration of the CD20 binding agent and the anti-PD-L1 camelid VHH may act synergistically to reduce or eliminate the tumor or cancer, or slow the growth and/or progression and/or metastasis of the tumor or cancer. In some embodiments, the combination of the CD20 binding agent and the anti-PD-L1 camelid VHH may exhibit improved safety profiles when compared to the agents used alone in the context of monotherapy. In some embodiments, the CD20 binding agent and the anti-PD-L1 camelid VHH may be administered at doses that are lower than the doses employed when the agents are used in the context of monotherapy. In some embodiments, the CD20 binding agent comprises a mutated interferon such as a mutated IFNα. In illustrative embodiments, the mutated IFNα comprises one or more mutations at positions 148, 149, and 153 with reference to SEQ ID NO:127 or SEQ ID NO:128, such as the substitutions M148A, R149A, and L153A.

In some embodiments, the present application relates to administration of the CD20 binding agent combined with depletion of Treg cells.

In some embodiments, the present application relates to combination therapy with one or more chimeric agents described in WO 2013/10779, WO 2015/007536, WO 2015/007520, WO 2015/007542, and WO 2015/007903, the entire contents of which are hereby incorporated by reference in their entireties.

In some embodiments, inclusive of, without limitation, infectious disease applications, the present application pertains to anti-infectives as additional therapeutic agents. In some embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In some embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In some embodiments, inclusive, without limitation, of autoimmune applications, the additional therapeutic agent is an immunosuppressive agent. In some embodiments, the immunosuppressive agent is an anti-inflammatory agent such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present application include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used in the present application, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In some embodiments, the immunosuppressive agent may be cytostatics such as alkylating agents, antimetabolites (e.g., azathioprine, methotrexate), cytotoxic antibiotics, antibodies (e.g., basiliximab, daclizumab, and muromonab), anti-immunophilins (e.g., cyclosporine, tacrolimus, sirolimus), interferons, opioids, tumor necrosis factor (TNF), TNF binding proteins, mycophenolates, and small biological agents (e.g., fingolimod, myriocin). Additional anti-inflammatory agents are described, for example, in U.S. Pat. No. 4,537,776, the entire contents of which is incorporated by reference herein.

In some embodiments, the present application relates to combination therapies using the CD20 binding agent and an immunosuppressive agent. In some embodiments, the present application relates to administration of the CD20 binding agent to a patient undergoing treatment with an immunosuppressive agent. In an embodiment, the immunosuppressive agent is TNF.

In illustrative embodiments, the CD20 binding agent acts synergistically when co-administered with TNF. In an illustrative embodiment, the CD20 binding agent acts synergistically when co-administered with TNF for use in treating tumor or cancer. For example, co-administration of the CD20 binding agent and TNF may act synergistically to reduce or eliminate the tumor or cancer, or slow the growth and/or progression and/or metastasis of the tumor or cancer. In some embodiments, the combination of the CD20 binding agent and TNF may exhibit improved safety profiles when compared to the agents used alone in the context of monotherapy. In some embodiments, the CD20 binding agent and TNF may be administered at doses that are lower than the doses employed when the agents are used in the context of monotherapy. In some embodiments, the CD20 binding agent comprises a mutated interferon such as a mutated IFNα. In illustrative embodiments, the mutated IFNα comprises one or more mutations at positions 148, 149, and 153 with reference to SEQ ID NO:127 or SEQ ID NO:128, such as the substitutions M148A, R149A, and L153A.

In some embodiments, the CD20 binding agent described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc.

In still other embodiments, the CD20 binding agent described herein further comprise a cytotoxic agent, comprising, in illustrative embodiments, a toxin, a chemotherapeutic agent, and an agent that causes apoptosis or cell death. Such agents may be conjugated to a composition described herein.

The CD20 binding agent described herein may thus be modified post-translationally to add effector moieties such as chemical linkers, detectable moieties such as for example fluorescent dyes, enzymes, substrates, bioluminescent materials, and chemiluminescent moieties, or functional moieties such as for example streptavidin, avidin, biotin, a cytotoxin and cytotoxic agents.

Illustrative cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the *vinca* alkaloids, vincristine and vinblastine. Other cytotoxic agents include paclitaxel (taxol), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, *vinca* alkaloids (e.g., vinblastine, vincristine, vindesine and vinorelbine), mustines, tyrosine kinase inhibitors, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux, Avastin, Pertuzumab, anti-CD20 antibodies, Rituxan, ocrelizumab, ofatumumab, DXL625, HERCEPTIN®, or any combination thereof. Toxic enzymes from plants and bacteria such as ricin, diphtheria toxin and *Pseudomonas* toxin may be conjugated to the therapeutic agents (e.g. antibodies) to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)). Other cytotoxic agents include cytotoxic ribonucleases as described by Goldenberg in U.S. Pat. No. 6,653,104.

Illustrative detectable moieties further include, but are not limited to, horseradish peroxidase, acetylcholinesterase, alkaline phosphatase, beta-galactosidase and luciferase. Further illustrative fluorescent materials include, but are not limited to, rhodamine, fluorescein, fluorescein isothiocyanate, umbelliferone, dichlorotriazinylamine, phycoerythrin and dansyl chloride. Further illustrative chemiluminescent moieties include, but are not limited to, luminol. Further illustrative bioluminescent materials include, but are not limited to, luciferin and aequorin.

Methods of Treatment

Methods and compositions described herein have application to treating various diseases and disorders involving CD20 positive cells. In various embodiments, the diseases and disorders include, but are not limited to cancer, infections, immune disorders, inflammatory diseases or conditions, autoimmune diseases, and neurological disorders.

Further, any of the present agents may be for use in the treating, or the manufacture of a medicament for treating, various diseases and disorders involving CD20 positive cells, including, but not limited to cancer, infections, immune disorders, inflammatory diseases or conditions, autoimmune diseases, and neurological disorders.

In some embodiments, the CD20 binding agents of the present application are used for treatment of diseases wherein depletion of CD20+ cells is therapeutically beneficial, such as Waldenstrom's macroglobulianemia, multiple myeloma, plasma cell dyscrasias, chronic lymphocytic leukemia, treatment of transplant, hairy cell leukemia, ITP, Epstein Barr virus lymphomas after stem cell transplant, and kidney transplant. In other embodiments, the CD20 binding agents of the present application are used for the treatment of a disease selected from B cell lymphomas, leukemias, myelomas, autoimmune disease, transplant, graft-vs-host disease, infectious diseases involving B cells, lymphoproliferation diseases, and treatment of any disease or condition wherein suppression of B cell activity and/or humoral immunity is desirably suppressed. In certain embodiments, the CD20 binding agents of the present application are used for the treatment of a disease selected from the group consisting of B cell lymphomas, leukemia, myeloma, transplant, graft-vs-host disease, autoimmune disease, lymphoproliferation conditions, and other treatment diseases and conditions wherein the inhibition of humoral immunity, B cell function, and/or proliferation, is therapeutically beneficial. In further embodiments, the CD20 binding molecules of the present application are used for the treatment of B-ALL, Hairy cell leukemia, Multiple myeloma, Richter Syndrome, Acquired Factor VIII inhibitors, Antiphospholipid syndrome, Autoimmune hemolytic anemia, Autoimmune thrombocytopenia, Bullous pemphigoid, Cold hemagglutinin disease, Evan's Syndrome, Goodpasture's syndrome, Idiopathic membranous nephropathy, Idiopathic thrombocytopenic purpura, IgM associated polyneuropathy, Kaposi sarcoma-associated herpesvirus (KSHV)-related multicentric Castleman disease (MCD), Myasthenia gravis, Pemphigus vulgaris, Primary biliary cirrhosis, Pure red cell aplasia, Rheumatoid arthritis, Sjogren's Syndrome, Systemic immune complex vasculitis, Systemic lupus erythematosus, Type II mixed cryoglobulinemia, Wegener's granulomatosis, Allograft rejection, Post-transplant lymphoproliferative disease, or Purging of stem cells for bone marrow transplantation.

In some embodiments, the present application relates to the treatment of, or a patient having cancer. As used herein, cancer refers to any uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject. For example, cancers can include benign and malignant cancers, polyps, hyperplasia, as well as dormant tumors or micrometastases.

Illustrative cancers that may be treated include, but are not limited to, basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

In some embodiments, the cancer is leukemia or lymphoma. Illustrative leukemias or lymphomas include, but are not limited to, a leukemia or lymphoma selected from B cell lymphoma, non-Hodgkin's lymphoma (NHL) including low grade and intermediate grade non-Hodgkin's lymphomas (NHLs), relapsed Hodgkin's disease, resistant Hodgkin's disease high grade, lymphocyte predominant subtype of Hodgkin's lymphoma, precursor B cell lymphoblastic leukemia/lymphoma, mature B cell neoplasm, B cell chronic lymphocytic leukemia (CLL), small lymphocytic lymphoma (SLL), B cell prolymphocytic leukemia, lymphoplasmacytic lymphoma, mantle cell lymphoma (MCL), follicular lymphoma (FL) including low-grade, intermediate-grade and high-grade FL, cutaneous follicle center lymphoma, marginal zone B cell lymphoma, MALT type marginal zone B cell lymphoma, nodal marginal zone B cell lymphoma, splenic type marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, multiple myeloma, and anaplastic large-cell lymphoma (ALCL).

In various embodiments, the present compositions are used to treat or prevent one or more immune disorders such as inflammatory diseases or conditions, such as inflammation, acute inflammation, chronic inflammation, respiratory disease, atherosclerosis, restenosis, asthma, allergic rhinitis, atopic dermatitis, septic shock, rheumatoid arthritis, inflammatory bowel disease, inflammatory pelvic disease, pain, ocular inflammatory disease, celiac disease, Leigh Syndrome, Glycerol Kinase Deficiency, Familial eosinophilia (FE), autosomal recessive spastic ataxia, laryngeal inflammatory disease; Tuberculosis, Chronic cholecystitis, Bronchiectasis, Silicosis and other pneumoconioses.

In some embodiments, illustrative immune disorders include, but are not limited to, rheumatoid arthritis (RA), juvenile rheumatoid arthritis, systemic lupus erythematosus (SLE), vasculitis, Wegener's disease, inflammatory bowel disease, idiopathic thrombocytopenic purpura (ITP), thrombotic thrombocytopenic purpura (TTP), autoimmune thrombocytopenia, multiple sclerosis (MS), chronic inflammatory demyelinating polyneuropathy, psoriasis, IgA nephropathy, IgM polyneuropathies, myasthenia gravis, diabetes mellitus, Reynaud's syndrome, Crohn's disease, ulcerative colitis, gastritis, Hashimoto's thyroiditis, ankylosing spondylitis, hepatitis C-associated cryoglobulinemic vasculitis, chronic focal encephalitis, hemophilia A, membranoproliferative glomerulonephritis, adult and juvenile dermatomyositis, adult polymyositis, chronic urticaria, primary biliary cirrhosis, neuromyelitis optica, Graves' dysthyroid disease, bullous skin disorders, bullous pemphigoid, pemphigus, Churg-Strauss syndrome, asthma, psoriatic arthritis, dermatitis, respiratory distress syndrome, meningitis, encephalitits, anti-NMDA receptor encephalitis, uveitis, eczema, atherosclerosis, leukocyte adhesion deficiency, juvenile onset diabetes, Reiter's disease, Behcet's disease, hemolytic anemia, atopic dermatitis, Wegener's granulomatosis, Omenn's syndrome, chronic renal failure, acute infectious mononucleosis, HIV and herpes-associated disease, systemic sclerosis, Sjorgen's syndrome and glomerulonephritis, dermatomyositis, ANCA vasculitis, aplastic anemia, autoimmune anemia, autoimmune hemolytic anemia (AIHA), pure red cell aplasia, Evan's syndrome, factor VIII deficiency, hemophilia A, autoimmune neutropenia, Castleman's syndrome, Goodpasture's syndrome, solid organ transplant rejection, graft versus host disease (GVHD), autoimmune hepatitis, lymphoid interstitial pneumonitis (HIV), bronchiolitis obliterans (non-transplant), Guillain-Barre Syndrome, large vessel vasculitis, giant cell (Takayasu's) arteritis, medium vessel vasculitis, Kawasaki's Disease, polyarteritis nodosa, Devic's disease, autoimmune pancreatitis, Opsoclonus Myoclonus Syndrome (OMS), IgG4-related disease, scleroderma, and chronic fatigue syndrome.

In some embodiments, the CD20 binding agent of the application may be utilized to treat vasculitides and other vessel disorders, such as microscopic polyangiitis, Churg-Strauss syndrome, and other ANCA-associated vasculitides, polyarteritis nodosa, essential cryoglobulinaemic vasculitis, cutaneous leukocytoclastic angiitis, Kawasaki disease, Takayasu arteritis, giant cell arthritis, Henoch-Schönlein purpura, primary or isolated cerebral angiitis, erythema nodosum, thrombangiitis obliterans, thrombotic thrombocytopenic purpura (including hemolytic uremic syndrome), and secondary vasculitides, including cutaneous leukocytoclastic vasculitis (e.g., secondary to hepatitis B, hepatitis C, Waldenström's macroglobulinemia, B-cell neoplasias, rheumatoid arthritis, Sjögren's syndrome, or systemic lupus erythematosus); further examples are erythema nodosum, allergic vasculitis, panniculitis, Weber-Christian disease, purpura hyperglobulinaemica, and Buerger's disease.

In some embodiments, the CD20 binding agent of the application may be utilized to treat skin disorders, such as contact dermatitis, linear IgA dermatosis, vitiligo, pyoderma gangrenosum, epidermolysis bullosa acquisita, pemphigus vulgaris (including cicatricial pemphigoid and bullous pemphigoid), alopecia greata (including alopecia universalis and alopecia totalis), dermatitis herpetiformis, erythema multiforme, and chronic autoimmune urticaria (including angioneurotic edema and urticarial vasculitis).

In some embodiments, the CD20 binding agent of the application may be utilized to treat immune-mediated cytopenias, such as autoimmune neutropenia, and pure red cell aplasia.

In some embodiments, the CD20 binding agent of the application may be utilized to treat connective tissue disorders, such as CNS lupus, discoid lupus erythematosus, CREST syndrome, mixed connective tissue disease, polymyositis/dermatomyositis, inclusion body myositis, secondary amyloidosis, cryoglobulinemia type I and type II, fibromyalgia, phospholipid antibody syndrome, secondary hemophilia, relapsing polychondritis, sarcoidosis, stiff man syndrome, and rheumatic fever; a further example is eosinophil fasciitis.

In some embodiments, the CD20 binding agent of the application may be utilized to treat arthritides, such as ankylosing spondylitis, juvenile chronic arthritis, adult Still's disease, and SAPHO syndrome; further examples are sacroileitis, reactive arthritis, Still's disease, and gout.

In some embodiments, the CD20 binding agent of the application may be utilized to treat hematologic disorders, such as aplastic anemia, primary hemolytic anemia (including cold agglutinin syndrome), hemolytic anemia secondary to CLL or systemic lupus erythematosus; POEMS syndrome, pernicious anemia, and Waldemström's purpura hyperglobulinaemica; further examples are agranulocytosis, autoimmune neutropenia, Franklin's disease, Seligmann's disease, μ-chain disease, paraneoplastic syndrome secondary to thymoma and lymphomas, and factor VIII inhibitor formation.

In some embodiments, the CD20 binding agent of the application may be utilized to treat endocrinopathies, such as polyendocrinopathy, and Addison's disease; further examples are autoimmune hypoglycemia, autoimmune hypothyroidism, autoimmune insulin syndrome, de Quervain's thyroiditis, and insulin receptor antibody-mediated insulin resistance.

In some embodiments, the CD20 binding agent of the application may be utilized to treat hepato-gastrointestinal disorders, such as celiac disease, Whipple's disease, primary biliary cirrhosis, chronic active hepatitis, and primary sclerosing cholangiitis; a further example is autoimmune gastritis.

In some embodiments, the CD20 binding agent of the application may be utilized to treat nephropathies, such as rapid progressive glomerulonephritis, post-streptococcal nephritis, Goodpasture's syndrome, membranous glomerulonephritis, and cryoglobulinemic nephritis; a further example is minimal change disease.

In some embodiments, the present application relates to the treatment of, or a patient having a neurological disorder. Illustrative neurological disorders include, but are not limited to, multiple sclerosis (MS; including, without limitation benign multiple sclerosis, relapsing-remitting multiple sclerosis (RRMS), secondary progressive multiple sclerosis (SPMS), progressive relapsing multiple sclerosis (PRMS), and primary progressive multiple sclerosis (PPMS)), Alzheimer's disease (including, without limitation, Early-onset Alzheimer's, Late-onset Alzheimer's, and Familial Alzheimer's disease (FAD), Parkinson's disease and parkinsonism (including, without limitation, Idiopathic Parkinson's disease, Vascular parkinsonism, Drug-induced parkinsonism, Dementia with Lewy bodies, Inherited Parkinson's, Juvenile Parkinson's), Huntington's disease, Amyotrophic lateral sclerosis (ALS, including, without limitation, Sporadic ALS, Familial ALS, Western Pacific ALS, Juvenile ALS, Hiramaya Disease), autoimmune neuropathies, mononeuritis multiplex, Lambert-Eaton's myasthenic syndrome, Sydenham's chorea, tabes dorsalis, and Guillain-Barré's syndrome; further examples are myelopathy/tropical spastic paraparesis, myasthenia gravis, acute inflammatory demyelinating polyneuropathy, and chronic inflammatory demyelinating polyneuropathy.

In some embodiments, the CD20 binding agent of the application may be utilized to treat cardiac and pulmonary disorders, such as fibrosing alveolitis, bronchiolitis obliterans, allergic aspergillosis, cystic fibrosis, Löffler's syndrome, myocarditis, and pericarditis; further examples are hypersensitivity pneumonitis, and paraneoplastic syndrome secondary to lung cancer.

In some embodiments, the CD20 binding agent of the application may be utilized to treat allergic disorders, such as bronchial asthma and hyper-IgE syndrome; a further example is amaurosis *fugax*.

In some embodiments, the CD20 binding agent of the application may be utilized to treat ophthalmologic disorders, such as idiopathic chorioretinitis.

In some embodiments, the CD20 binding agent of the application may be utilized to treat transplantation-derived disorders, such as allograft and xenograft rejection, and graft-versus-host disease. In some embodiments, the CD20 binding agent of the application may be utilized following transplantation.

In some embodiments, the present application relates to the treatment of, or a patient having a microbial infection and/or chronic infection (for example, infection of B cells). Illustrative infections include, but are not limited to, HIV/AIDS, tuberculosis, osteomyelitis, hepatitis B, hepatitis C, Epstein-Barr virus or parvovirus, T cell leukemia virus, bacterial overgrowth syndrome, fungal or parasitic infections.

Kits

The present application also provides kits for the administration of any CD20 binding agent described herein (e.g. with or without additional therapeutic agents). The kit is an assemblage of materials or components, including at least one of the inventive pharmaceutical compositions described herein. Thus, in some embodiments, the kit contains at least one of the pharmaceutical compositions described herein.

The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to effect a desired therapeutic outcome, such as to treat cancer. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner stored in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label which indicates the contents and/or purpose of the kit and/or its components.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "effective amount," when used in connection with medical uses is an amount that is effective for providing a measurable treatment, prevention, or reduction in the rate of pathogenesis of a disease of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

EXAMPLES

Example 1. Construction and Evaluation of VHHs Specific for Human CD20

Cloning of the Human CD20 Gene

Human CD20 was amplified from the Orfeome v5.1 collection (ID 11051) with forward primer 5'-GATAAGATCTCAGGCGGATCCACAACACCCAGAAATTCAG (O-7954) (SEQ ID NO: 209) and reverse primer 5'-GGTTTTTTCTCTAGATCAAGGAGAGCTGTCATTTTCTATTGG (O-7956) (SEQ ID NO: 210). The amplified product was cut with BglII and XbaI and ligated into the mammalian expression vector pMet7. The plasmid was used for transient transfection of Hek293T cells and for the generation of CHO-K1 clones stably expressing human CD20.

Isolation of Antigen-Specific VHHs

A VHH library was constructed and subjected to 3 consecutive rounds of panning (in solution), performed on stably transfected CHO-K1 cells expressing human CD20. A parallel panning was performed on parental (non-transfected CHO-K1) cells to serve as negative control for the calculation of CD20-specific phage enrichment. The enrichment for antigen-specific phages was assessed after each round of panning by comparing the number of phagemid particles eluted from transfected cells with the number of phagemid particles eluted from parental cells. These experiments suggested that the phage population was enriched (for antigen-specific phages) about 2-, 8- and 4-fold after 1st, 2nd and 3rd rounds of panning, respectively. In total, about 95 colonies from 2nd round of panning were randomly selected and their crude periplasmic extracts (including soluble VHHs) were analyzed by cell ELISA for specific binding to transfected CHO-K1, as compared to parental cells. Out of 95 colonies, 62 colonies scored positive in this assay. Based on sequence data, the 62 positive colonies represented 14 different VHHs (FIG. 1, top panel).

A VHH library was constructed and subjected to 3 consecutive rounds of panning (in solution), performed on stably transfected CHO-K1 cells expressing human CD20 as described above. Here, the phage population was enriched (for antigen-specific phages) about 7-fold after 3rd round of panning. No enrichment was observed after 1st and 2nd rounds of panning. About 142 colonies, randomly picked from 3rd round, were tested by cell ELISA as above and 8 colonies scored positive. Based on sequence data, the 8 positive colonies represented 3 different VHHs (FIG. 1, bottom panel). The 3 different VHHs belong to the same group. The group identified here is the same as one of the groups identified previously.

The table below provides a description of 17 clones representing 17 different anti-human CD20 VHH genes. *E. coli* TG1 harboring recombinant phagemid pMECS containing anti-human CD20 VHH sequences were stored at −80° C. The vector pMECS codes for ampicillin resistance.

| *E. coli* strain + Vector | VHH (Nb) | NSF Reference No. (Glycerol stock) |
|---|---|---|
| TG1, pMECS | R3CD 7 | 1418 |
| TG1, pMECS | R3CD 18 | 1419 |
| TG1, pMECS | R3CD 105 | 1420 |
| TG1, pMECS | 2HCD 16 | 1421 |
| TG1, pMECS | 2HCD 17 | 1422 |
| TG1, pMECS | 2HCD 22 | 1423 |
| TG1, pMECS | 2HCD 25 | 1424 |
| TG1, pMECS | 2HCD 35 | 1425 |
| TG1, pMECS | 2HCD 40 | 1426 |
| TG1, pMECS | 2HCD 42 | 1427 |
| TG1, pMECS | 2HCD 43 | 1428 |
| TG1, pMECS | 2HCD 59 | 1429 |
| TG1, pMECS | 2HCD 68 | 1430 |
| TG1, pMECS | 2HCD 73 | 1431 |
| TG1, pMECS | 2HCD 78 | 1432 |
| TG1, pMECS | 2HCD 81 | 1433 |
| TG1, pMECS | 2HCD 88 | 1434 |

Figure 2:
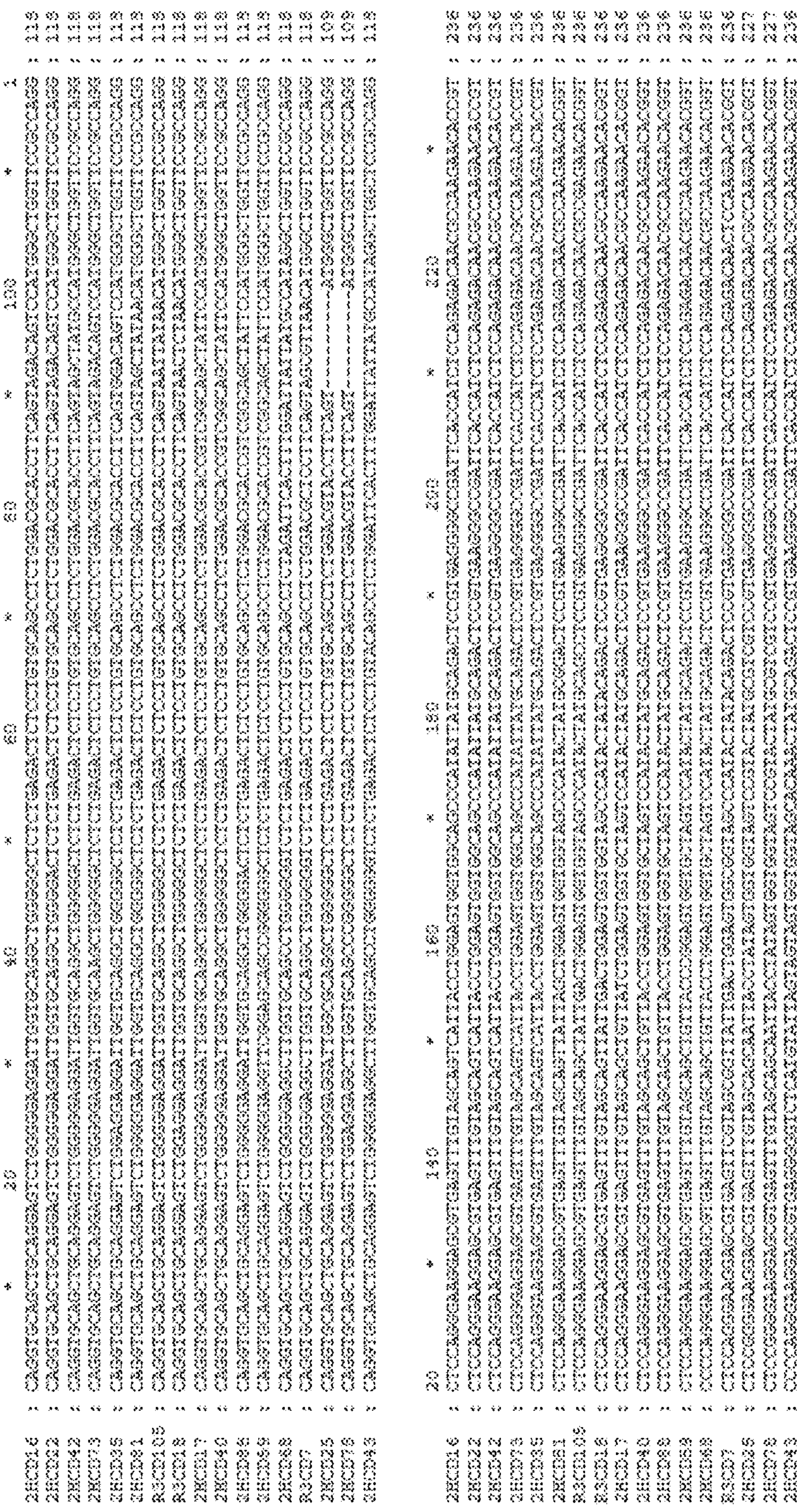
FIG. 2 shows the nucleotide sequences of 17 different VHHs specific for human CD20. VHHs are: 2HCD16, 2HCD17, 2HCD22, 2HCD25, 2HCD35, 2HCD40, 2HCD42, 2HCD43, 2HCD59, 2HCD68, 2HCD73, 2HCD78, 2HCD81, 2HCD88, R3CD7, R3CD18, R3CD105. Gaps were introduced in order to align sequences.
Figure 3:
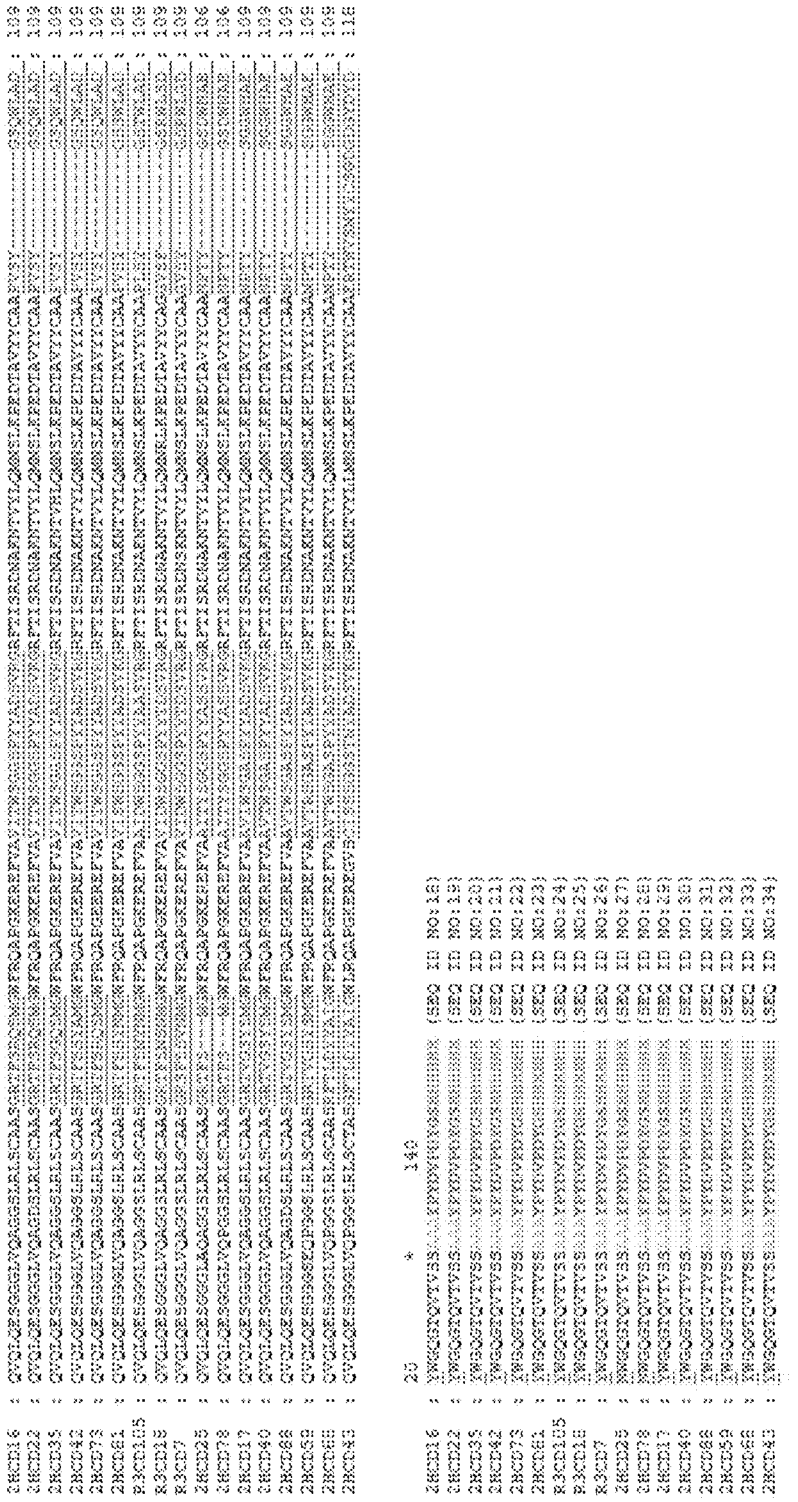
FIG. 3 shows the amino acid sequences of 17 different VHHs specific for human CD20. VHHs are: 2HCD16, 2HCD17, 2HCD22, 2HCD25, 2HCD35, 2HCD40, 2HCD42, 2HCD43, 2HCD59, 2HCD68, 2HCD73, 2HCD78, 2HCD81, 2HCD88, R3CD7, R3CD18, R3CD105. Complementarity determining regions (CDR1, CDR2 and CDR3) are underlined and defined according to Kabat. The peptide AAA sequence is a linker connecting the VHH sequence to HA tag (shown in bold) and His6 tag (carboxy terminus). Gaps were introduced in order to align sequences.

In summary, 17 different VHHs belonging to 4 different groups were identified as indicated in the table below. The nucleotide and amino acid sequences of the 17 anti-human CD20 VHHs are shown in FIGS. 2 and 3, respectively.

| Group | Member(s) |
|---|---|
| 1 | 2HCD16, 2HCD22, 2HCD35, 2HCD42, 2HCD73, 2HCD81, R3CD7, R3CD18, R3CD105 |
| 2 | 2HCD25, 2HCD78 |
| 3 | 2HCD17, 2HCD40, 2HCD59, 2HCD68, 2HCD88 |
| 4 | 2HCD43 |

Transformation of Non-Suppressor Strain (e.g. WK6) with Recombinant pMECS

The VHH gene cloned in pMECS vector contained PelB signal sequence at the N-terminus and HA tag and His6 tag at the C-terminus (PelB leader-VHH-HA-His6). The PelB leader sequence directs the VHH to the periplasmic space of the *E. coli* and the HA and His6 tags can be used for the purification and detection of VHH (e.g. in ELISA, Western Blot, etc.).

In pMECS vector, the His6 tag was followed by an amber stop codon (TAG) and this amber stop codon was followed by gene III of M13 phage. In suppressor *E. coli* strains (e.g. TG1), the amber stop codon was read as glutamine and therefore the VHH was expressed as fusion protein with protein III of the phage which allowed the display of VHH on the phage coat for panning. In non-suppressor *E. coli* strains (e. g., WK6), the amber stop codon was read as stop codon and therefore the resulting VHH was not fused to protein III.

In order to express and purify VHHs cloned in pMECS vector, pMECS containing the gene of the VHH of interest was prepared and transformed into a non-suppressor strain (e.g., WK6). The VHH of the resulting clone was sequenced using MP057 primer (5'-TTATGCTTCCGGCTCGTATG-3') (SEQ ID NO:211) to verify the identity of the clone. Antigen binding capacity was retested by ELISA or any other appropriate assay. The non-suppressor strain (e.g., WK6) containing the recombinant pMECS vector with the VHH gene was then used for the expression and purification of VHH as described herein.

Recloning VHH Genes from pMECS to pHEN6c Vector

In pMECS vector, the His6 tag is cleaved off upon storage of VHH (even for short periods of time and even at −20° C.). As such, the VHH gene was subcloned from pMECS into pHEN6c vector in cases where the His6 tag was used for detection, etc.

The VHH gene was amplied by PCR using *E. coli* containing recombinant pMECS harbouring the VHH gene as template and primers A6E and PMCF. Primers A6E and PMCF are framework1 and framework4 primers, respectively. The primer sequences were as follows:

```
Primer A6E
(5' GAT GTG CAG CTG CAG GAG TCT GGR GGA GG 3').

Primer PMCF
(5' CTA GTG CGG CCG CTG AGG AGA CGG TGA CCT

GGG T 3').

Universal reverse primer
(5' TCA CAC AGG AAA CAG CTA TGA C 3').

Universal forward primer
(5 CGC CAG GGT TTT CCC AGT CAC GAC 3').
*R (in bold) stands for A or G. PstI, NotI and
BstEII (Eco91I) sites are underlined.
```

The amplification protocol included about 30 cycles of PCR, each cycle consisting of 30 seconds at 94° C., 30 seconds at 55° C. and 45 seconds at 72° C., followed by 10 minutes extension at 72° C. at the end of PCR). A fragment of about 400 bp was amplified.

The PCR product was purified (e.g. by Qiaquick PCR purification kit from Qiagen) and digested overnight with PstI. The purified PCR product was digested with BstEII overnight (or with Eco91I from Fermentas). The temperature used for digestion varied. For example, digestion with BstEII was done at 50° C. or 60° C. depending on the supplier of the enzyme.

For ligation, the pHEN6c vector was digested with PstI for 3 hours, purified as described above, and then digested with BstEII for 2 to 3 hours. Alternatively, digestion was carried out using Eco91I from Fermentas. The digested vector was ran on 1% agarose gel, with the vector band excised out of the gel and purified (e.g. by Qiaquick gel extraction kit from Qiagen). The PCR fragment was subsequently ligated to the vector.

Electrocompetent WK6 cells were transformed with the ligation reaction, and transformants were selected using LB/agar/ampicillin (100 μg/ml)/glucose (1-2%) plates. Positive clones were screened by PCR using universal reverse and universal forward primers. A fragment of about 550 bp was amplified, if the insert is present. To verify the identity of the clones, at least 2 clones per each VHH were sequenced using universal reverse primers. Antigen binding capacity was retested by ELISA or any other appropriate assay.

Following the above protocol, the VHH gene cloned in pHEN6c vector was generated which contained PelB signal sequence at the N-terminus and $His_6$-tail at the C-terminus. The PelB leader sequence directed the VHH to the periplasmic space of the *E. coli* and the His-tag was used for the purification and detection of VHH (e.g. in ELISA, Western Blot, etc.).

Expression and purification of the VHHs were carried out. Specifically, on day 1, 10-20 ml of LB+ampicillin (100 μg/ml)+glucose (1%) were inoculated with a freshly transformed WK6 colony. This pre-culture was incubated at 37° C. overnight with shaking at 200-250 rpm. On day 2, a TB medium was used for expressing the VHHs. The TB medium included, per liter: 2.3 g $KH_2PO_4$, 16.4 g $K_2HPO_4 \cdot 3H_2O$, 12 g Tryptone (Duchefa Biochemie), 24 g Yeast (Duchefa Biochemie), and 4 ml 100% glycerol (Duchefa Biochemie).

A baffled shaker flask of 1 liter was filled with 330 ml TB and autoclaved. $KH_2PO_4$ and $K_2HPO_4 \cdot 3H_2O$ were not autoclaved. Instead, $KH_2PO_4$ and $K_2HPO_4 \cdot 3H_2O$ were prepared, filter sterilized, and then added to the rest of the medium that was already autoclaved. About 1 ml of the pre-culture was added to 330 ml of TB supplemented with 100 μg/ml Ampicillin, 2 mM $MgCl_2$ and 0.1% glucose and subsequently grew at 37° C. with shaking (200-250 rpm) until an $OD_{600}$ of 0.6-0.9 was reached. IPTG (final concentration of 1 mM) was added to induce VHH expression. The culture was incubated at 28° C. with shaking overnight (about 16-18 hours). The $OD_{600}$ after overnight induction was usually between 25 and 30. At least 1 liter of culture (3 bottles) per clone was prepared with an average yield of between 1 and 15 mg/l.

Extraction of the VHHs from the periplasm of *E. coli* was carried out on day 3. The solutions used included: TES: 0.2 M Tris pH 8.0, 0.5 mM EDTA, 0.5 M sucrose, and TES/4: TES diluted 4 times in water.

The overnight induced cultures were centrifuged for 8 minutes at 8000 rpm. The cell pellets from 1 liter culture were resuspended in 12 ml TES by pipetting up and down and shaken for 1 hour on ice. Per each 12 ml TES used, about 18 ml TES/4 were added and incubated on ice for an additional hour with shaking followed by centrifugation for 30 minutes at 8000 rpm at 4° C. The supernatant which contained proteins extracted from the periplasmic space was transferred to fresh falcon tubes.

The VHHs were subsequently purified by IMAC which utilized the following solution: HIS-select (SIGMA), PBS, and 50 mM NaAcetate pH 4.6.

His-select was equilibrated with PBS. Specifically, per periplasmic extract derived from 1 liter culture, 1 ml of Resin (about 2 ml His-select solution) was added to a 50 ml falcon tube. PBS was also added to final volume of 50 ml and mixed. Centrifugation was carried out at 2000 rpm for 2 minutes, and the supernatant was discarded. The resin was washed with PBS twice as described above. The periplasmic extract was added to the resin, incubated for 30 minutes to 1 hour at room temperature with gentle shaking. The samples were loaded on PD-10 columns with a filter at the bottom (GE healthcare, cat. No. 17-0435-01) and washed with 50 to 100 ml PBS (50-100 ml PBS per 1 ml resin used). Elution was carried out for 3 times, each time with 1 ml PBS/0.5 M imidazole per 1 ml resin used (for efficient elution, the beads could be resuspended and left overnight at 4° C. with the bottom of the column closed). Dialysis was performed overnight at 4° C. against PBS (cutoff 3500 daltons) to remove imidazole. For efficient dialysis, the dialysis buffer (PBS) was changed 2-3 times. Alternatively, instead of elution with imidazole, the bound VHHs could be eluted with 10 ml 50 mM Na-acetate pH 4.6. If 50 mM Na-acetate pH 4.6 was used to elute VHHs, the eluted VHHs was immediately neutralized with 1 M Tris pH 8.0, and no dialysis was required.

The amount of protein was estimated by $OD_{280}$ measurement of eluted sample. Extinction coefficient of each clone was determined by protParam tool under primary structure analysis at the Expasy proteomics server. Further purification of VHHs could be achieved by different methods. For example, the samples could be concentrated (Vivaspin 5000 MW cutoff, Vivascience) by centrifuging at 2000 rpm at 4° C. until an appropriate volume for loading on a Superdex 75 16/60 was obtained (max. 4 ml). The concentrated sample was loaded on a Superdex 75 16/60 column equilibrated with PBS. Peak fractions were pooled, and $OD_{280}$ measurements were performed for quantification. In general, VHHs eluted after 85-95 minutes when run at 1 ml/min. Aliquots of concentrated VHH samples were stored at −20° C. at a concentration of about 1 mg/ml.

Example 2. Construction and Evaluation of VHHs Specific for Mouse CD20

Cloning of the Mouse CD20 Gene

Mouse CD20 was purchased from Imagenes cat #IRAVP968C1280D and amplified with forward primer 5'-gataagatctcaGGCG-GATCCAGTGGACCTTTCCCAGCAGAGC (O-7962) (SEQ ID NO: 216) and reverse primer 5'-GGTTTTTTCTCTAGATCAAGGAGCGATCTCAT-TTTCCACTG (O-7964) (SEQ ID NO: 217). The amplified product was cut with BglII and XbaI and ligated into the mammalian expression vector pMet7. The plasmid was used for transient transfection of Hek293T cells and for the generation of CHO-K1 clones stably expressing mouse CD20.

Isolation of Antigen-Specific VHHs

A VHH library was constructed from peripheral blood lymphocytes (PBLs). Specifically, total RNA from PBLs was used as template for first strand cDNA synthesis with oligo(dT) primer. Using this cDNA, the VHH encoding sequences were amplified by PCR, digested with PstI and NotI, and cloned into the PstI and NotI sites of the phagemid vector pMECS. A VHH library of about $10^7$ independent transformants was obtained. About 90% of transformants harbored the vector with the right insert size.

Similarly, a VHH library with a size of about $10^8$ independent transformants was obtained from peripheral blood lymphocytes (PBLs). About 65% of transformants harbored the vector with the right insert size.

Figure 4:
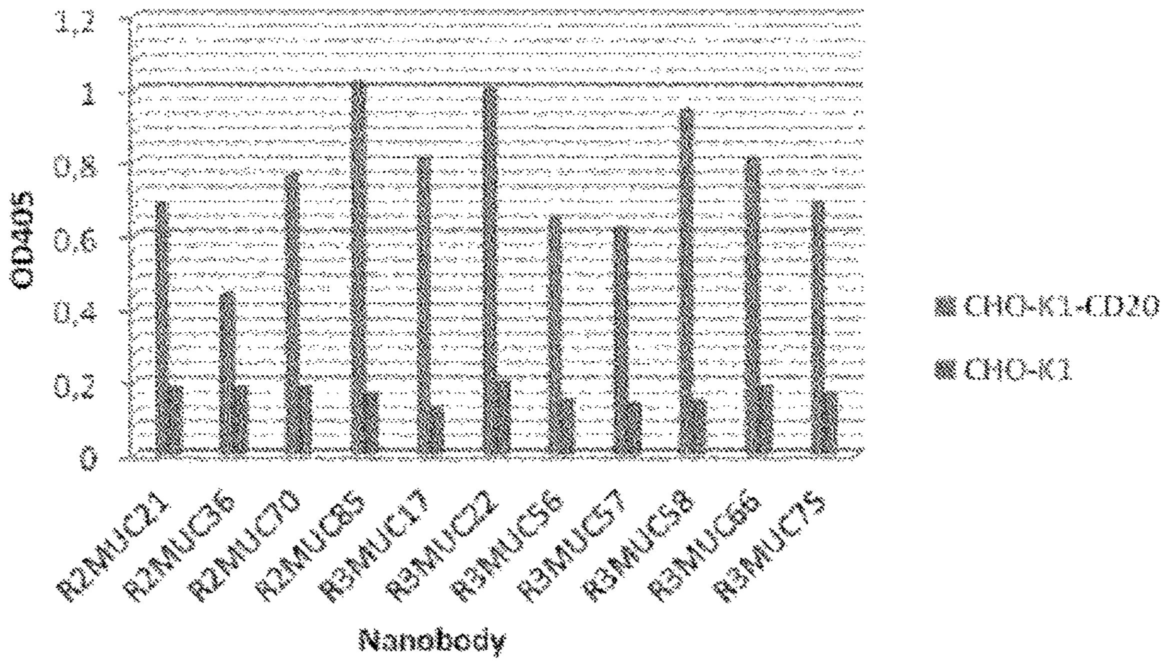
FIG. 4 depicts results from cell ELISA assays using periplasmic extracts of positive colonies. For each set of histograms, the first bar is CHO-K1-mCD20 and the second bar is CHO-K1. A clone is considered as specific, if it gives a signal on transfected cells which is at least 2-fold higher than the signal obtained with negative control parental cell. In addition, the relative strength of the signals may not reflect the relative quality of the VHHs since in these experiments the crude periplasmic extracts are used and the differences in ELISA signals may be related to factors such as the amount of VHH used, etc. rather than to their quality such as affinity, actual yield, etc. Nanobody as used in this figure is equivalent to camelid VHH.
Figure 4:
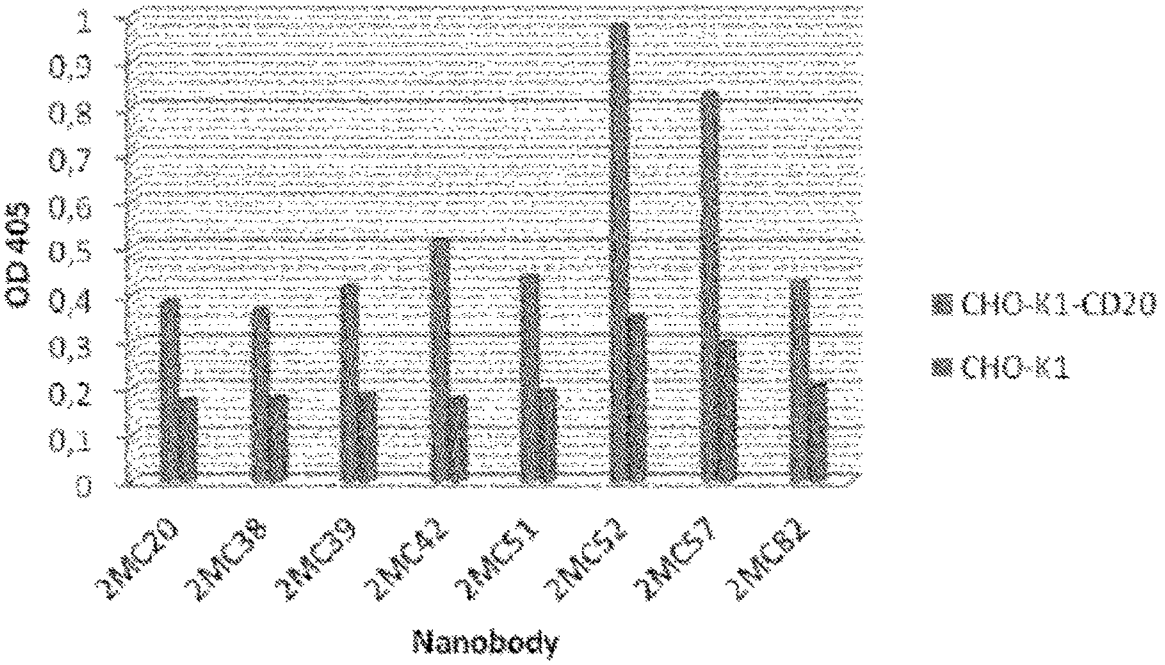

The library was subjected to 3 consecutive rounds of panning (in solution), performed on stably transfected CHO-K1 cells expressing mouse CD20. A parallel panning was performed on parental (non-transfected CHO-K1) cells to serve as negative control for the calculation of CD20-specific phage enrichment. The enrichment for antigen-specific phages was assessed after each round of panning by comparing the number of phagemid particles eluted from transfected cells with the number of phagemid particles eluted from parental cells. These experiments suggested that the phage population was enriched (for antigen-specific phages) about 2-, 2- and $10^3$-fold after 1st, 2nd and 3rd rounds of panning, respectively. In total, 285 colonies (95 from each round of panning) were randomly selected and their crude periplasmic extracts (including soluble VHHs) were analyzed by cell ELISA for specific binding to transfected CHO-K1, as compared to parental cells. Out of 285 colonies, 124 colonies (0, 40 and 84 from 1st, 2nd & 3rd rounds, respectively) scored positive in this assay. Based on sequence data, the 124 positive colonies represented 11 different VHHs (FIG. 4, top panel). The 11 different VHHs belong to 2 different groups.

The library was subjected to 2 consecutive rounds of panning (in solution), performed on stably transfected CHO-K1 cells expressing mouse CD20 as described above. Here, the phage population was enriched (for antigen-specific phages) about 2- and 45-fold after 1st and 2nd rounds of panning, respectively. Here, 190 colonies, randomly picked from 2nd round, were tested by cell ELISA as above and 10 colonies scored positive. Based on sequence data, the 10 positive colonies represented 8 different VHHs (FIG. 4, bottom panel). The 8 different VHHs belong to 2 different groups. One of the groups identified here is the same group as one of those identified above.

Figure 5:
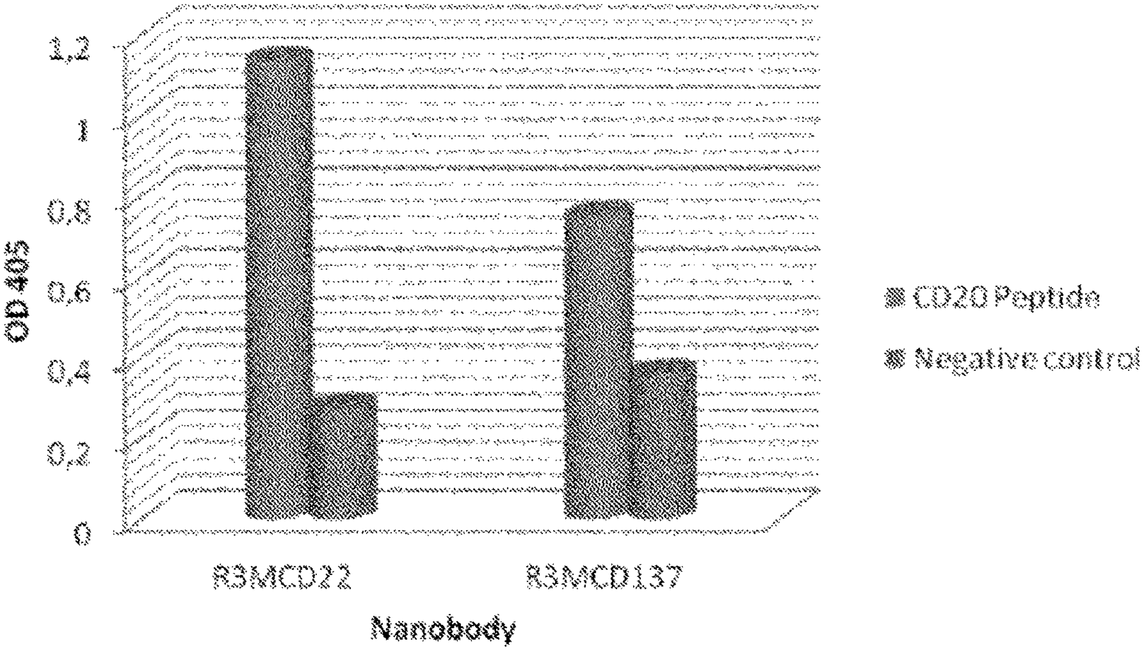
FIG. 5 depicts results from cell ELISA assays using periplasmic extracts of positive colonies screened on biotinylated mouse CD20 peptide. For each set of histograms, the first bar is CHO-K1-mCD20 and the second bar is CHO-K1. A clone is considered as specific, if it gives a signal on transfected cells which is at least 2-fold higher than the signal obtained with negative control parental cell. In addition, the relative strength of the signals may not reflect the relative quality of the VHHs since in these experiments the crude periplasmic extracts are used and the differences in ELISA signals may be related to factors such as the amount of VHH used, etc rather than to their quality such as affinity, actual yield, etc. Nanobody as used in this figure is equivalent to camelid VHH.

The library was subjected to 4 consecutive rounds of panning, performed on solid-phase coated biotinylated mouse CD20 peptide (3 μg/well). The coating of the peptide onto the well was mediated by streptavidin. The enrichment for antigen-specific phages was assessed after each round of panning by comparing the number of phagemid particles eluted from (streptavidin-mediated) antigen-coated blocked wells with the number of phagemid particles eluted from wells coated with streptavidin and then blocked with blocking buffer. These experiments suggested that the phage population was slightly enriched for antigen-specific phages only after 3rd round of panning. 190 colonies, randomly picked from 3rd panning round on peptide, were analyzed by ELISA for specific binding to biotinylated mouse CD20 peptide (ELISA using crude periplasmic extracts including soluble VHHs). Out of 190 colonies, 5 colonies scored positive in this assay. Based on sequence data, the 5 positive colonies represented 2 different VHHs (FIG. 5). The 2 different VHHs belong to the same group, which is a different group, as compared with all groups identified above by cell panning/cell ELISA.

The Table below provides a description of the 21 clones representing 21 different anti-mouse CD20 VHH genes. *E. coli* TG1 harboring recombinant phagemid pMECS containing anti-mouse CD20 VHH sequences was generated and stored at −80° C. The vector pMECS codes for ampicillin resistance.

| *E. coli* strain + Vector | VHH (Nb) | NSF Reference No. (Glycerol stock) |
|---|---|---|
| TG1, pMECS | R2MUC 21 | 1397 |
| TG1, pMECS | R2MUC 36 | 1398 |
| TG1, pMECS | R2MUC 70 | 1399 |
| TG1, pMECS | R2MUC 85 | 1400 |
| TG1, pMECS | R3MUC 17 | 1401 |
| TG1, pMECS | R3MUC 22 | 1402 |
| TG1, pMECS | R3MUC 56 | 1403 |
| TG1, pMECS | R3MUC 57 | 1404 |
| TG1, pMECS | R3MUC 58 | 1405 |
| TG1, pMECS | R3MUC 66 | 1406 |
| TG1, pMECS | R3MUC 75 | 1407 |
| TG1, pMECS | 2MC 20 | 1408 |
| TG1, pMECS | 2MC 38 | 1409 |
| TG1, pMECS | 2MC 39 | 1410 |
| TG1, pMECS | 2MC 42 | 1411 |
| TG1, pMECS | 2MC 51 | 1412 |
| TG1, pMECS | 2MC 52 | 1413 |
| TG1, pMECS | 2MC 57 | 1414 |

-continued

| *E. coli* strain + Vector | VHH (Nb) | NSF Reference No. (Glycerol stock) |
|---|---|---|
| TG1, pMECS | 2MC 82 | 1415 |
| TG1, pMECS | R3MCD 22 | 1416 |
| TG1, pMECS | R3MCD 137 | 1417 |

Figure 6:
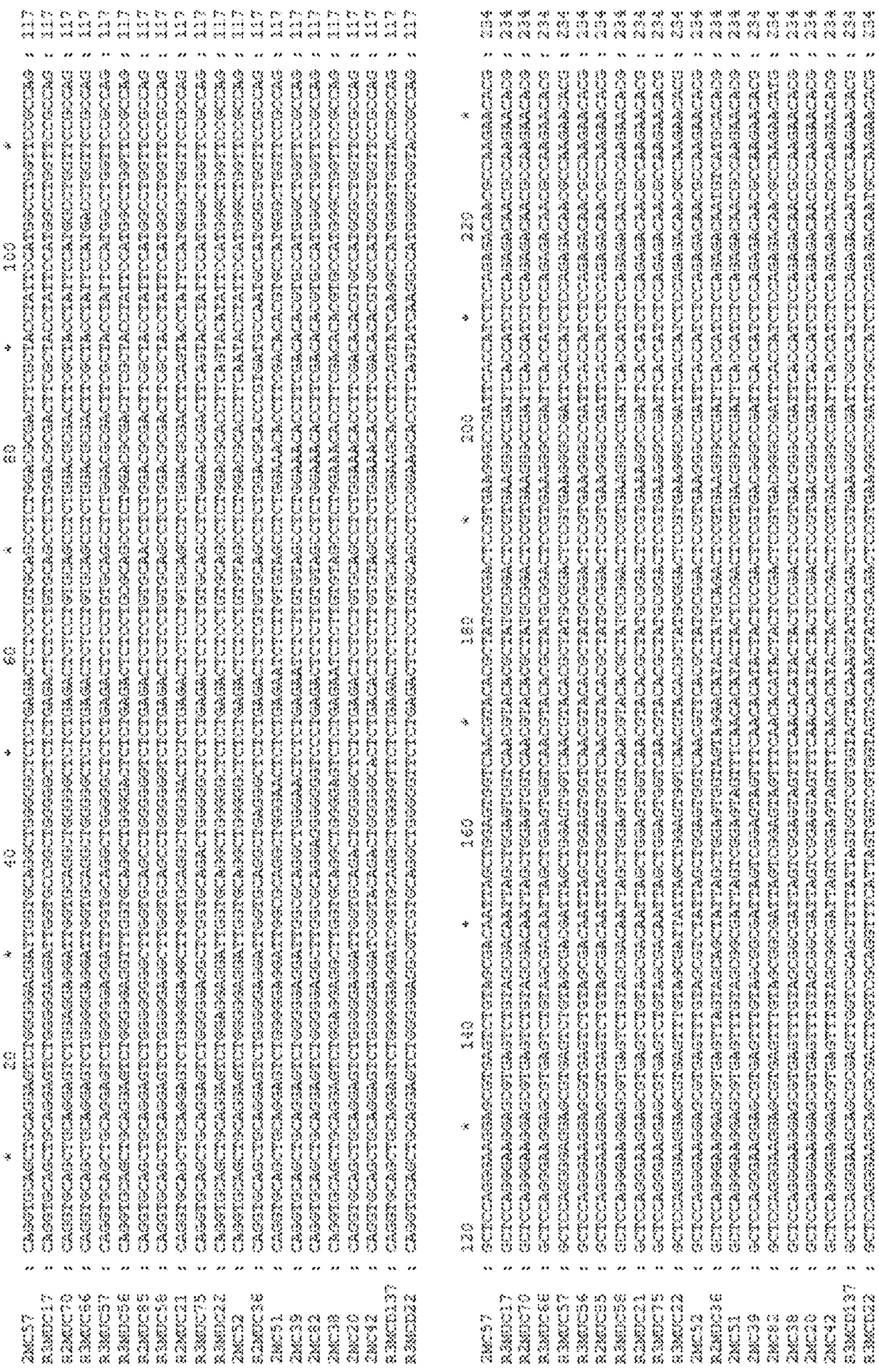
FIG. 6 shows the nucleotide sequences of 21 different VHHs specific for mouse CD20. VHHs are: R2MUC21, R2MUC36, R2MUC70, R2MUC85, R3MUC17, R3MUC22, R3MUC56, R3MUC57, R3MUC58, R3MUC66, R3MUC75, 2MC20, 2MC38, 2MC39, 2MC42, 2MC51, 2MC52, 2MC57, 2MC82, R3MCD22, R3MCD137. Gaps were introduced in order to align sequences.
Figure 7:
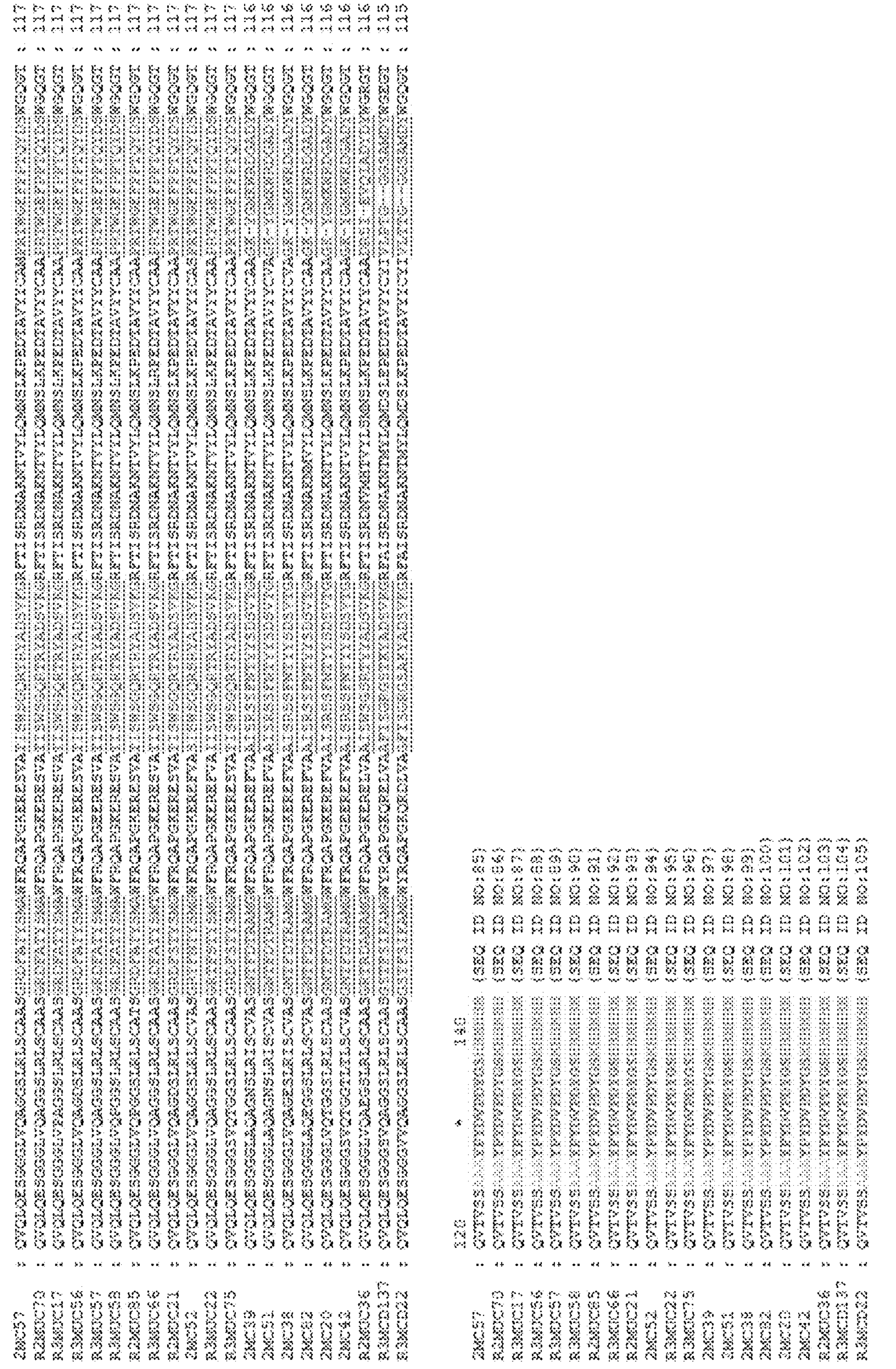
FIG. 7 shows the amino acid sequences of 21 different VHHs specific for mouse CD20. VHHs are: R2MUC21, R2MUC36, R2MUC70, R2MUC85, R3MUC17, R3MUC22, R3MUC56, R3MUC57, R3MUC58, R3MUC66, R3MUC75, 2MC20, 2MC38, 2MC39, 2MC42, 2MC51, 2MC52, 2MC57, 2MC82, R3MCD22, R3MCD137. Complementarity determining regions (CDR1, CDR2 and CDR3) are underlined and defined according to Kabat. The peptide AAA sequence is a linker connecting the VHH sequence to HA tag (shown in bold) and His6 tag (carboxy terminus). Gaps were introduced in order to align sequences.

In summary, 21 different VHHs belonging to 4 different groups were identified as indicated in the table below. The nucleotide and amino acid sequences of the 21 anti-mouse CD20 VHHs are shown in FIGS. 6 and 7, respectively.

| Group | Member(s) |
|---|---|
| 1 | 2MC52, 2MC57, R2MUC21, R2MUC70, R2MUC85, R3MUC17, R3MUC22, R3MUC56, R3MUC57, R3MUC58, R3MUC66, R3MUC75 |
| 2 | 2MC20, 2MC38, 2MC39, 2MC42, 2MC51, 2MC82 |
| 3 | R2MUC36 |
| 4 | R3MCD22, R3MCD137 |

Transformation of Non-Suppressor Strain (e.g. WK6) with Recombinant pMECS

The VHH gene cloned in pMECS vector contained PelB signal sequence at the N-terminus and HA tag and His6 tag at the C-terminus (PelB leader-VHH-HA-His6). The PelB leader sequence directed the VHH to the periplasmic space of the *E. coli* and the HA and His6 tags was used for the purification and detection of VHH (e.g. in ELISA, Western Blot, etc.).

In pMECS vector, the His6 tag was followed by an amber stop codon (TAG) and this amber stop codon was followed by gene III of M13 phage. In suppressor *E. coli* strains (e.g. TG1), the amber stop codon was read as glutamine and therefore the VHH was expressed as fusion protein with protein III of the phage which allowed the display of VHH on the phage coat for panning. In non-suppressor *E. coli* strains (e. g., WK6), the amber stop codon was read as stop codon and therefore the resulting VHH was not fused to protein III.

In order to express and purify VHHs cloned in pMECS vector, the pMECS containing the gene of the VHH of interest was prepared and transformed into a non-suppressor strain (e.g., WK6). The VHH of the resulting clone was sequenced using MP057 primer (5'-TTATGCTTCCGGCTCGTATG-3') (SEQ ID NO:218) to verify the identity of the clone. Antigen binding capacity was retested by ELISA or any other appropriate assay. The non-suppressor strain (e.g., WK6) containing the recombinant pMECS vector with the VHH gene was used for the expression and purification of VHH as described herein.

Recloning VHH Genes from pMECS to pHEN6c Vector

In the pMECS vector, the His6 tag was cleaved off upon storage of VHH (even for short periods of time and even at −20° C.). It was therefore better to subclone the VHH gene from pMECS into pHEN6c vector, if the His6 tag is to be used for detection, etc.

Specifically, the VHH gene was amplified using *E. coli* containing recombinant pMECS harboring the VHH gene as template and primers A6E and PMCF. Primers A6E and PMCF are framework1 and framework4 primers, respectively. The primer sequences were as follows:

```
Primer A6E
(5' GAT GTG CAG CTG CAG GAG TCT GGR GGA GG 3').

Primer PMCF
(5' CTA GTG CGG CCG CTG AGG AGA CGG TGA CCT

GGG T 3').

Universal reverse primer
(5' TCA CAC AGG AAA CAG CTA TGA C 3').

Universal forward primer
(5 CGC CAG GGT TTT CCC AGT CAC GAC 3').
*R (in bold) stands for A or G. PstI, NotI and
BstEII (Eco91I) sites are underlined.
```

The amplification protocol included about 30 cycles of PCR, each cycle included 30 seconds at 94° C., 30 seconds at 55° C. and 45 seconds at 72° C., followed by 10 minutes extension at 72° C. at the end of PCR. A fragment of about 400 bp was amplified.

The PCR product was purified (e.g. by Qiaquick PCR purification kit from Qiagen) and digested overnight with PstI. The purified PCR product was digested with BstEII overnight (or with Eco91I from Fermentas). The temperature used for digestion varied. For example, digestion with BstEII was done at 50° C. or 60° C. depending on the supplier of the enzyme.

For ligation, the PCR product was purified. The pHEN6c vector was digested with PstI for 3 hours, purified as described above, and then digested with BstEII for 2 to 3 hours. Alternatively, digestion was carried out using Eco91I from Fermentas. The digested vector was ran on 1% agarose gel, with the vector band excised out of the gel and purified (e.g. by Qiaquick gel extraction kit from Qiagen). The PCR fragment was subsequently ligated to the vector.

Electrocompetent WK6 cells were transformed with the ligation reaction, and transformants were selected using LB/agar/ampicillin (100 μg/ml)/glucose (1-2%) plates. Positive clones were screened by PCR using universal reverse and universal forward primers. A fragment of about 550 bp was amplified, if the insert is present. To verify the identity of the clones, at least 2 clones per each VHH were sequenced using universal reverse primers. Antigen binding capacity was retested by ELISA or any other appropriate assay.

Following the above protocol, the VHH gene cloned in pHEN6c vector contained PelB signal sequence at the N-terminus and His6-tail at the C-terminus. The PelB leader sequence directed the VHH to the periplasmic space of the *E. coli* and the His-tag was used for the purification and detection of VHH (e.g. in ELISA, Western Blot, etc.).

Expression and purification of the VHHs were carried out. Specifically, on day 1, 10-20 ml of LB+ampicillin (100 μg/ml)+glucose (1%) were inoculated with a freshly transformed WK6 colony. This pre-culture was incubated at 37° C. overnight with shaking at 200-250 rpm. On day 2, a TB medium was used for expressing the VHHs. The TB medium included, per liter: 2.3 g $KH_2PO_4$, 16.4 g $K_2HPO_4 \cdot 3H_2O$, 12 g Tryptone (Duchefa Biochemie), 24 g Yeast (Duchefa Biochemie), and 4 ml 100% glycerol (Duchefa Biochemie)

A baffled shaker flask of 1 liter was filled with 330 ml TB and autoclaved. $KH_2PO_4$ and $K_2HPO_4 \cdot 3H_2O$ were not autoclaved. Instead, $KH_2PO_4$ and $K_2HPO_4 \cdot 3H_2O$ were prepared, filter sterilized, and then added to the rest of the medium that was already autoclaved. About 1 ml of the pre-culture was added to 330 ml of TB supplemented with 100 μg/ml Ampicillin, 2 mM $MgCl_2$ and 0.1% glucose and subsequently grew at 37° C. with shaking (200-250 rpm) until an $OD_{600}$ of 0.6-0.9 was reached. IPTG (final concentration of 1 mM) was added to induce VHH expression. The culture was incubated at 28° C. with shaking overnight (about 16-18 hours). The $OD_{600}$ after overnight induction was usually between 25 and 30. At least 1 liter of culture (3 bottles) per clone was prepared with an average yield of between 1 and 15 mg/l.

Extraction of the VHHs from the periplasm of *E. coli* was carried out on day 3. The solutions used included: TES: 0.2 M Tris pH 8.0, 0.5 mM EDTA, 0.5 M sucrose, and TES/4: TES diluted 4 times in water.

The overnight induced cultures were centrifuged for 8 minutes at 8000 rpm. The cell pellets from 1 liter culture were resuspended in 12 ml TES by pipetting up and down and shaken for 1 hour on ice. Per each 12 ml TES used, about 18 ml TES/4 were added and incubated on ice for an additional hour with shaking followed by centrifugation for 30 minutes at 8000 rpm at 4° C. The supernatant which contained proteins extracted from the periplasmic space was transferred to fresh falcon tubes.

The VHHs were subsequently purified by IMAC which utilized the following solution: HIS-select (SIGMA), PBS, and 50 mM NaAcetate pH 4.6.

His-select was equilibrated with PBS. Specifically, per periplasmic extract derived from 1 liter culture, 1 ml of Resin (about 2 ml His-select solution) was added to a 50 ml falcon tube. PBS was also added to final volume of 50 ml and mixed. Centrifugation was carried out at 2000 rpm for 2 minutes, and the supernatant was discarded. The resin was washed with PBS twice as described above. The periplasmic extract was added to the resin, incubated for 30 minutes to 1 hour at room temperature with gentle shaking. The samples were loaded on PD-10 columns with a filter at the bottom (GE healthcare, cat. No. 17-0435-01) and washed with 50 to 100 ml PBS (50-100 ml PBS per 1 ml resin used). Elution was carried out for 3 times, each time with 1 ml PBS/0.5 M imidazole per 1 ml resin used (for efficient elution, the beads were suspended and left overnight at 4° C. with the bottom of the column closed). Dialysis was performed overnight at 4° C. against PBS (cutoff 3500 daltons) to remove imidazole. For efficient dialysis, the dialysis buffer (PBS) was changed 2-3 times. Alternatively, instead of elution with imidazole, the bound VHHs could be eluted with 10 ml 50 mM Na-acetate pH 4.6. If 50 mM Na-acetate pH 4.6 was used to elute VHHs, the eluted VHHs was immediately neutralized with 1 M Tris pH 8.0, and no dialysis was required.

The amount of protein can be estimated at this point by OD280 measurement of eluted sample. Extinction coefficient of each clone can be determined by protParam tool under primary structure analysis at the Expasy proteomics server. Further purification of VHHs can be achieved by different methods. Below, you will find one of these methods.

The amount of protein was estimated by $OD_{280}$ measurement of eluted sample. Extinction coefficient of each clone was determined by protParam tool under primary structure analysis at the Expasy proteomics server. Further purification of VHHs could be achieved by different methods. For example, the samples could be concentrated (Vivaspin 5000 MW cutoff, Vivascience) by centrifuging at 2000 rpm at 4° C. until an appropriate volume for loading on a Superdex 75 16/60 was obtained (max. 4 ml). The concentrated sample was loaded on a Superdex 75 16/60 column equilibrated with PBS. Peak fractions were pooled, and $OD_{280}$ measurements were performed for quantification. In general, VHHs eluted after 85-95 minutes when run at 1 ml/min. Aliquots of concentrated VHH samples were stored at −20° C. at a concentration of about 1 mg/ml.

Example 3. Functional Evaluation of VHHs Specific for Human and/or Mouse CD20

Specific Binding of the VHHs Demonstrated by FACS

Figure 8:
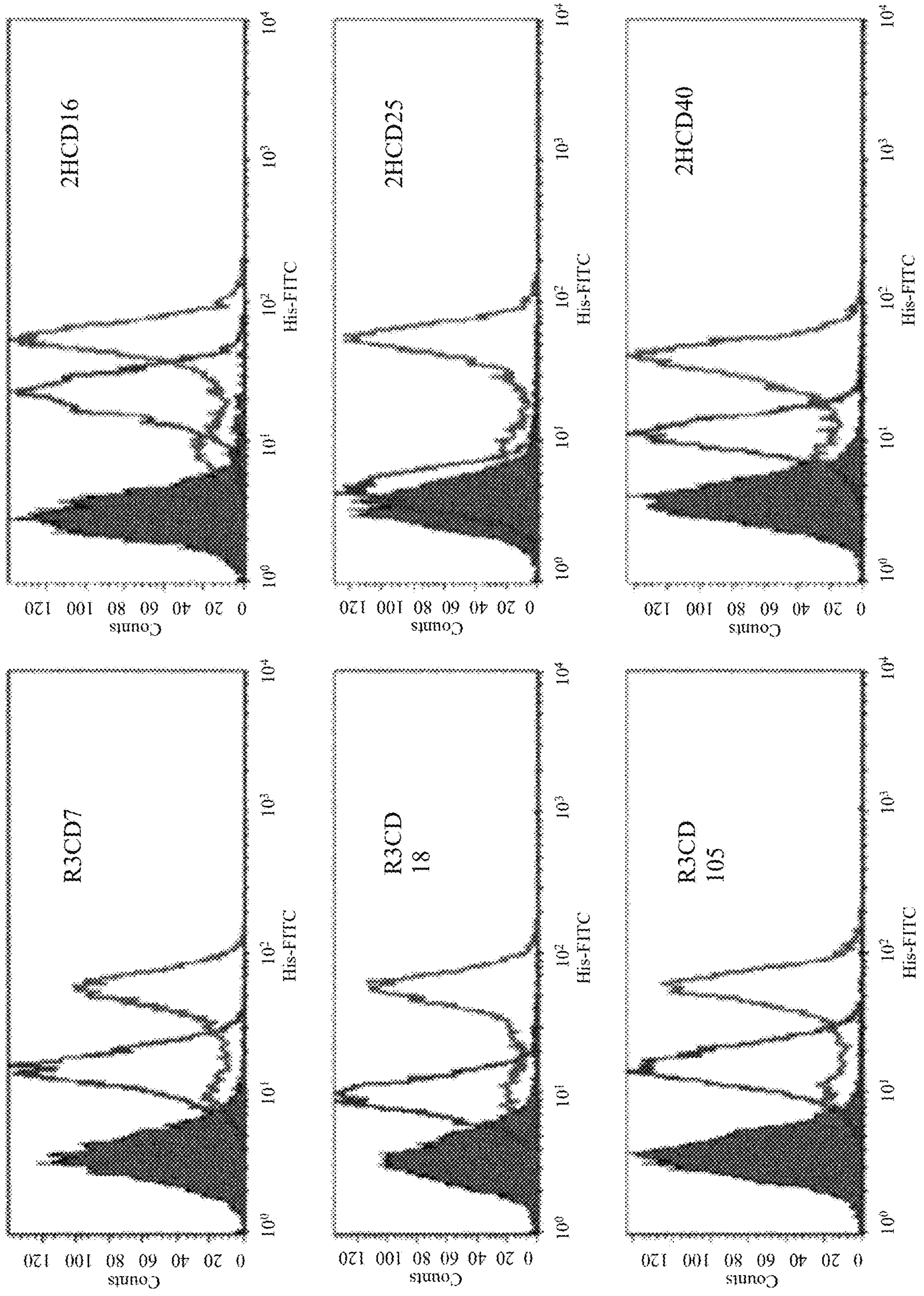
FIG. 8 shows binding data for selected anti human CD20 VHHs. The left peak represents parental CHO-K1, not transfected; the middle peak represents CHO-K1 expressing mouse CD20; and the right peak represents CHO-K1 expressing human CD20.
Figure 9:
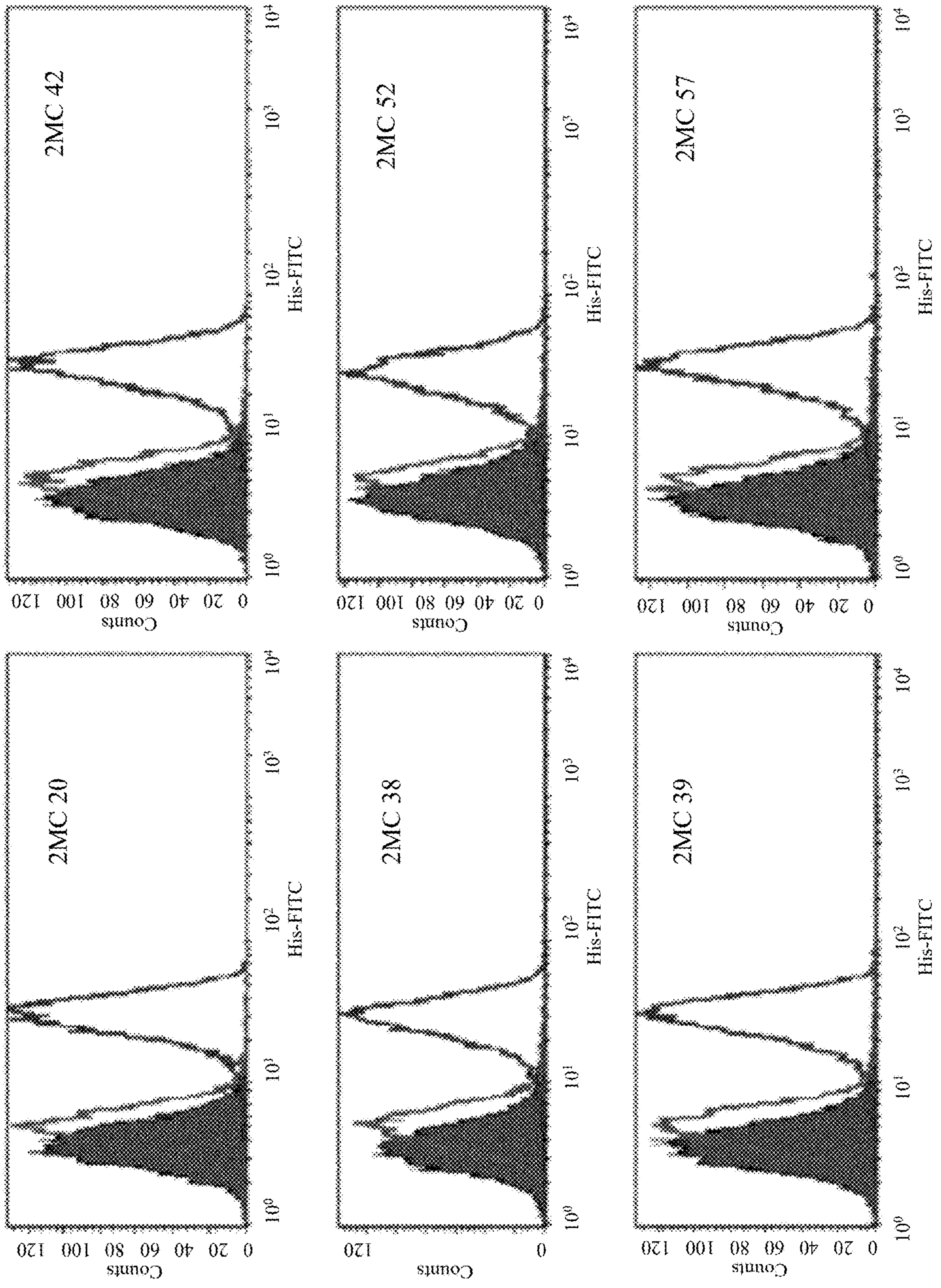
FIG. 9 shows binding data for selected anti mouse CD20 VHHs. The left peak represents parental CHO-K1, not transfected; the middle peak represents CHO-K1 expressing human CD20; and the right peak represents CHO-K1 expressing mouse CD20.

To determine the binding activities of the VHHs specific for human or mouse CD20, FACS analysis was carried out. Specifically, CHO-K1 cells and CHO-K1 cells stably expressing human or mouse CD20 were incubated with 5 μg/ml of the VHHs produced in accordance with the application. A monoclonal FITC labelled anti-his antibody (Genscript #A01620) was applied as secondary stain. FACS analysis was done on a FacsCalibur flow cytometer (Becton Dickinson). As shown in FIG. 8, all of the VHHs against human CD20 demonstrated specific binding to human CD20. Similarly, all of the VHHs against mouse CD20 also demonstrated specific binding to mouse CD20 (FIG. 9).

Example 4. Functional Analysis of Chimeric Proteins Comprising the CD20 VHH

Figure 10:
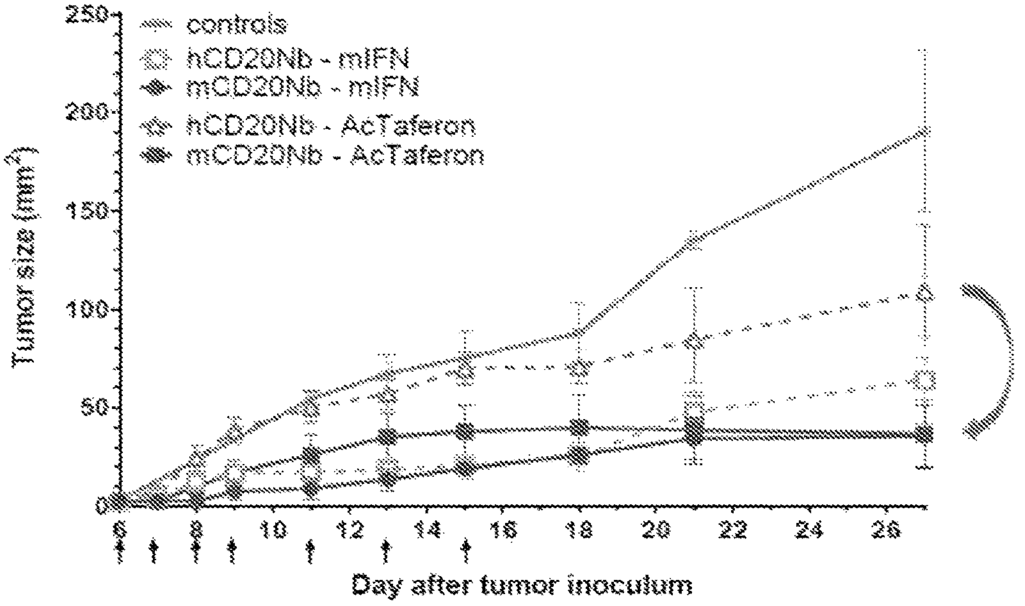
FIG. 10 shows the in vivo anti-tumor potential of chimeric CD20 VHHs in an A20 lymphoma model. The hCD20Nb refers to the 2HCD25 VHH against human CD20, and the mCD20 Nb refers to the 2MC57 VHH against mouse CD20. mIFN refers to wildtype mouse IFN. AcTAferon refers to the mutant Q124R interferon. Nb is the abbreviation of Nanobody and is used herein as equivalent to VHH.

Targeting In Vivo Interferon Activity Using Chimeric CD20 VHHs Using an A20 Lymphoma Model Mice were inoculated subcutaneously with A20 cells (a CD20+, and IFN sensitive mouse lymphoma cell line) to induce tumors. To determine the in vivo anti-tumor effects of chimeric CD20 VHHs, the mice were given perilesional (=s.c. at the edge of the tumor) treatments with the 2MC57 VHH (anti-mouse CD20) fused to wildtype IFN or the mutant IFNα2-Q124R (i.e., AcTaferon). The mice were also injected with the 2HCD25 VHH (anti-human CD20) fused to wildtype IFN or the mutant IFNα2-Q124R. As shown in FIG. 10, all CD20 VHHs significantly reduced tumor size with the chimeric 2MC57 VHHs being the most potent.

Figure 11:
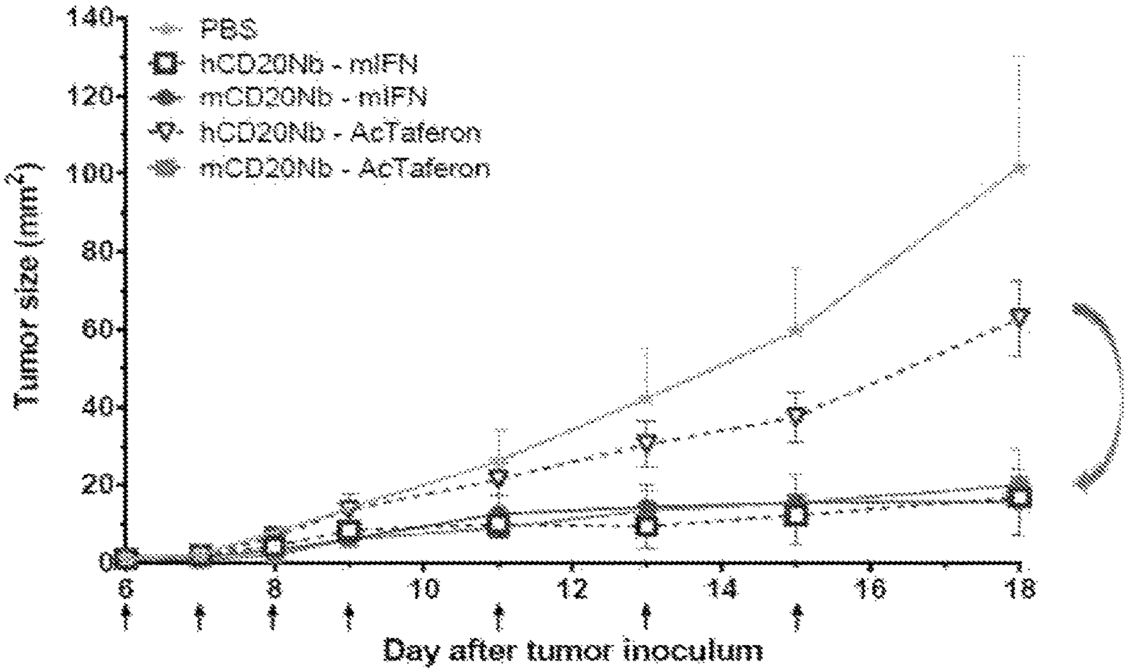
FIG. 11 shows the in vivo anti-tumor potential of chimeric CD20 VHHs in a B16 melanoma model. The hCD20Nb refers to the 2HCD25 VHH against human CD20, and the mCD20 Nb refers to the 2MC57 VHH against mouse CD20. mIFN refers to wildtype mouse IFN. AcTAferon refers to the mutant Q124R interferon. Nb is the abbreviation of Nanobody and is used herein as equivalent to VHH.

Targeting In Vivo Interferon Activity Using Chimeric CD20 VHHs Using a B16 Melanoma Model Mice were inoculated subcutaneously with B16-mCD20 cells (a mouse melanoma cell line that stably expresses mouse CD20) to induce tumors. To determine the in vivo anti-tumor effects of chimeric CD20 VHHs, mice were given perilesional (=s.c. at the edge of the tumor) treatments with the 2MC57 VHH (anti-mouse CD20) fused to wildtype IFN or the mutant IFNα2-Q124R (i.e., AcTaferon). The mice were given also injected with the 2HCD25 VHH (anti-human CD20) fused to wildtype IFN or the mutant IFNα2-Q124R. Control mice were treated with PBS. Tumor growth was monitored. As shown in FIG. 11, the mCD20 VHHs significantly reduced tumor size.

Figure 12:
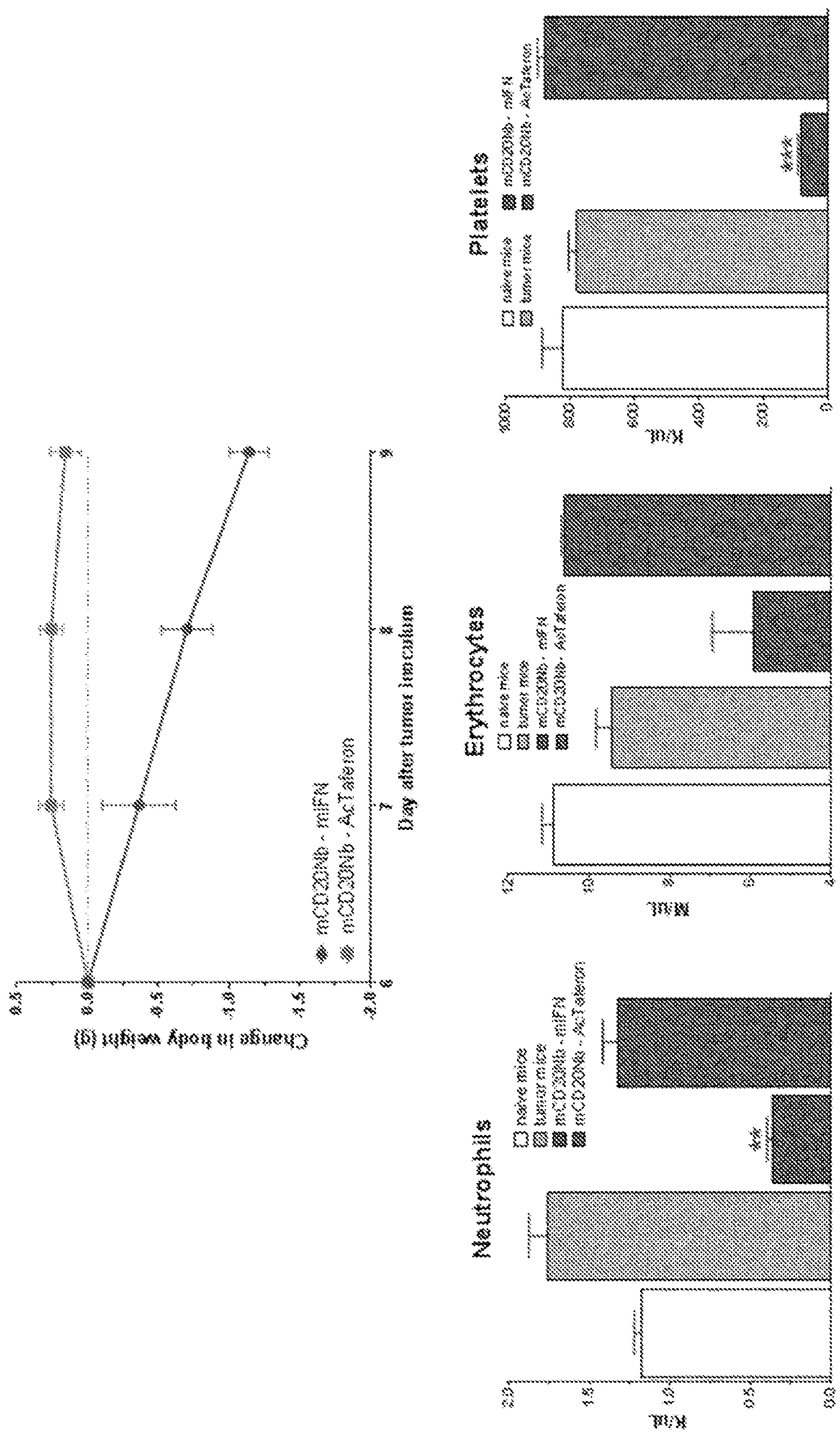
FIG. 12 shows that the anti-tumor efficacy of chimeric CD20 VHHs in a B16 melanoma model as shown in FIG. 11 does not cause concomitant life-threatening side effects. Nb is the abbreviation of Nanobody and is used herein as equivalent to VHH.
Figure 13:
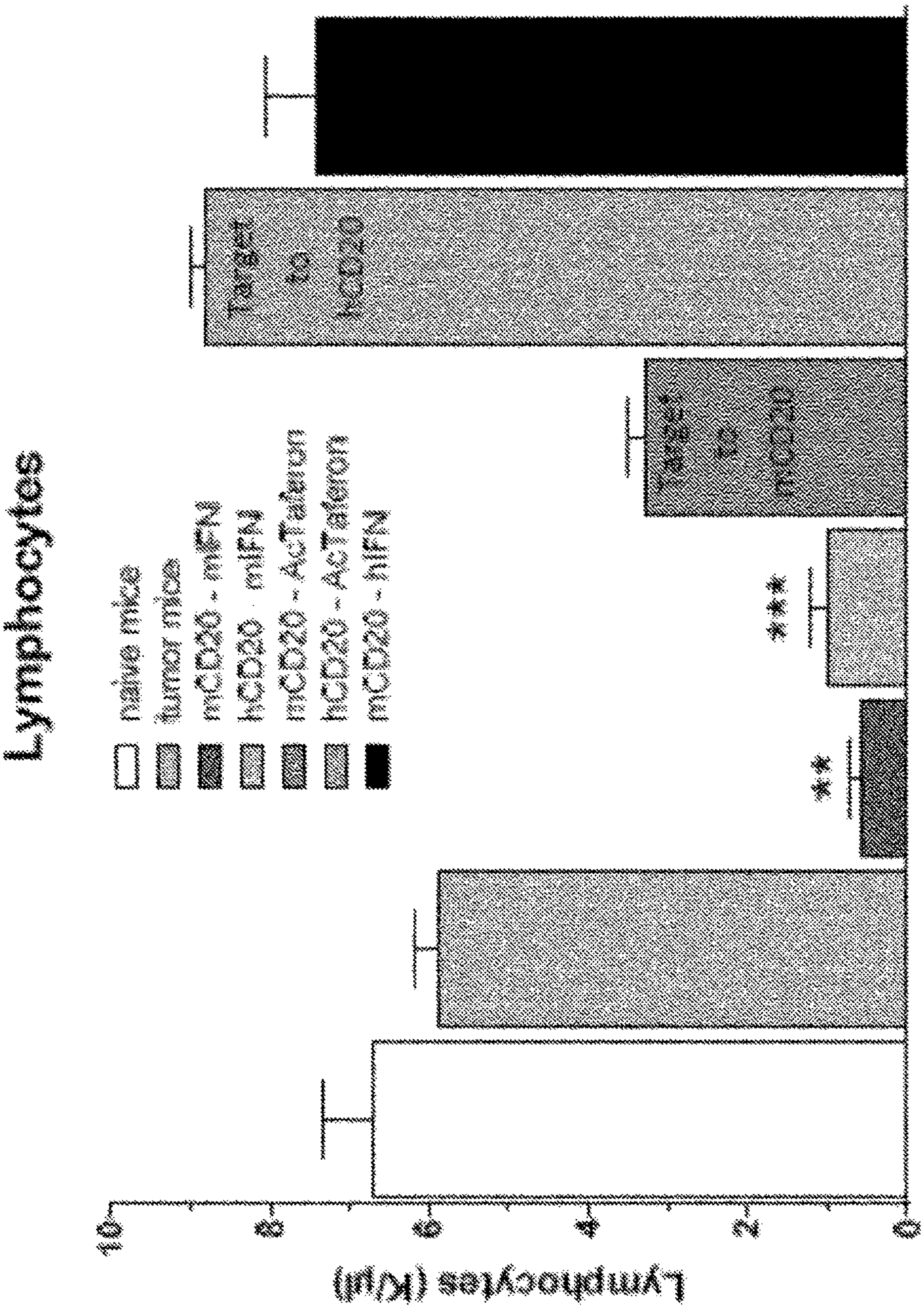
FIG. 13 shows that chimeric CD20 VHHs induce partial B cell depletion.
Figure 13:
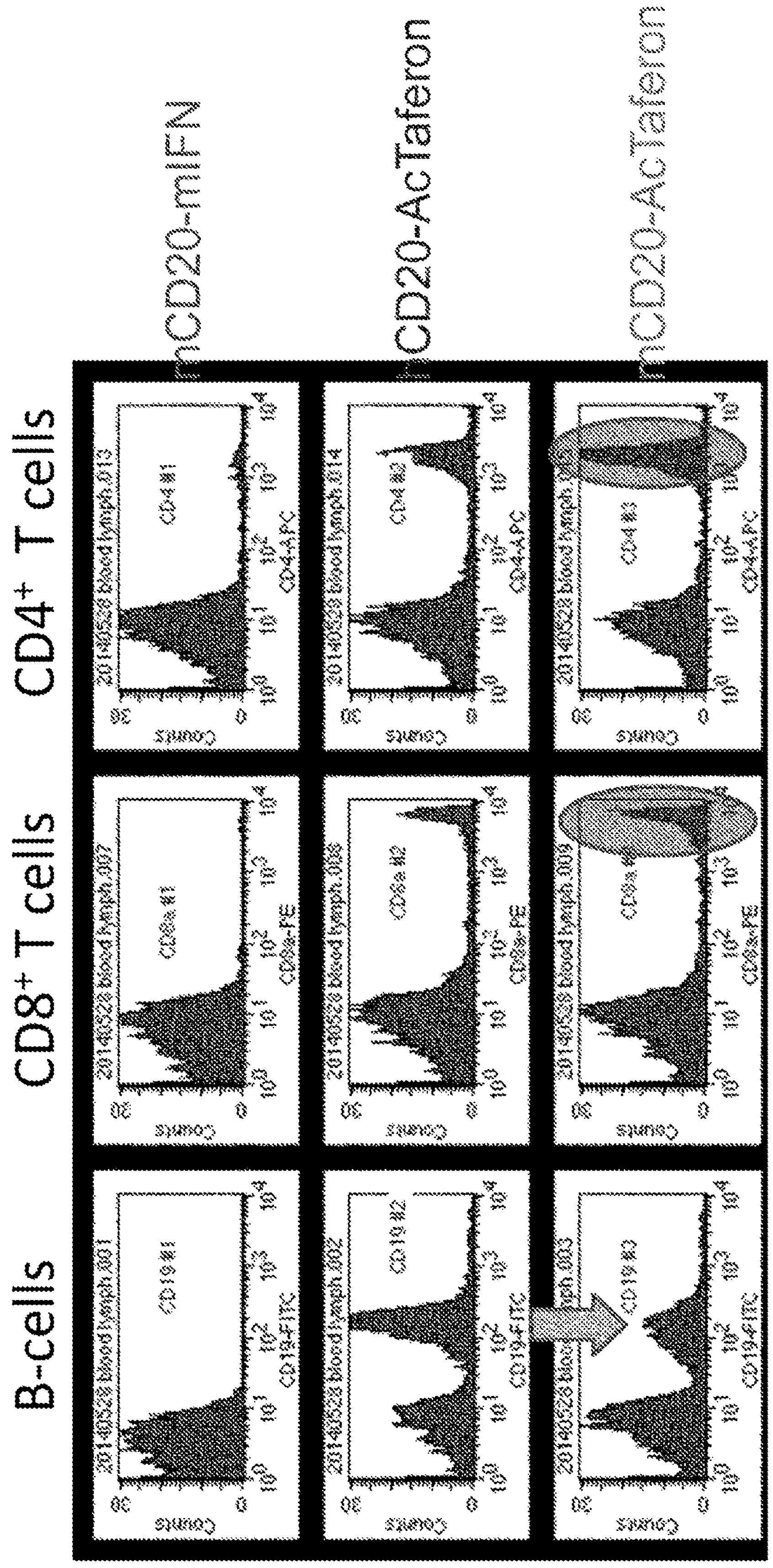

FIG. 12 shows that the chimeric 2MC57 VHH fused to the mutant IFNα2-Q124R (i.e., AcTaferon) targeted B16-mCD20 melanoma cells without life-threatening side effects. Specifically, mice treated with the chimeric 2MC57 VHH fused to the mutant IFNα2-Q124R maintained body weight and normal complete blood cell count including neutrophils, erythrocytes and platelets with no signs of hematological toxicity. In addition, administration of the chimeric 2MC57 VHH fused to the mutant IFNα2-Q124R resulted in partial B cell depletion (FIG. 13).

Figure 14:
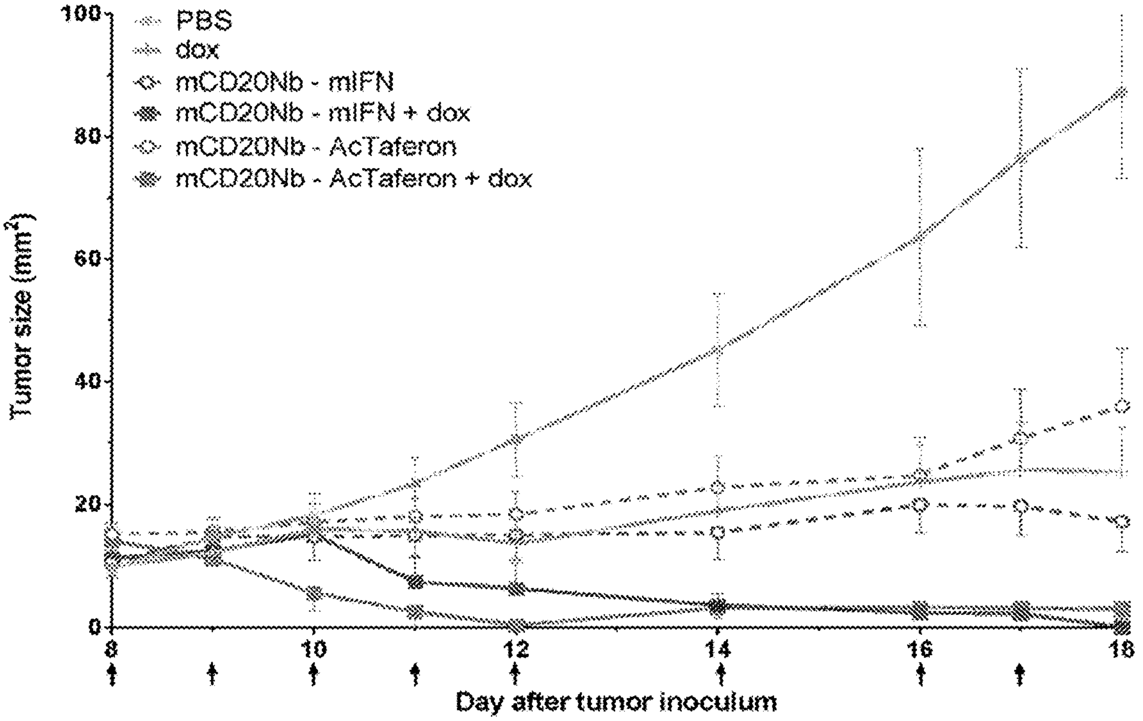
FIG. 14 shows the anti-tumor potential of chimeric CD20 VHHs in combination with doxorubicin (dox). Nb is the abbreviation of Nanobody and is used herein as equivalent to VHH.

Combination Therapy Using Chimeric CD20 VHHs and Doxorubicin in a B16 Melanoma Model The anti-tumor effects of a combination therapy using doxorubicin and chimeric 2MC57 VHHs were tested. Mice were inoculated subcutaneously with B16-mCD20 cells (a mouse melanoma cell line that stably expresses mouse CD20) to induce tumors. The mice were subsequently given perilesional (=s.c. at the edge of the tumor) treatments with 2MC57 VHH (anti-mouse CD20) fused to wildtype IFN or the mutant IFNα2-Q124R (i.e., AcTaferon) with or without doxorubicin. Doxorubicin was administered at 3 mg/kg of body weight every 2 days. As shown in FIG. 14, combining 2MC57 VHHs with doxorubicin significantly reduced tumor size compared with treatment using the 2MC57 VHHs without doxorubicin.

Figure 15:
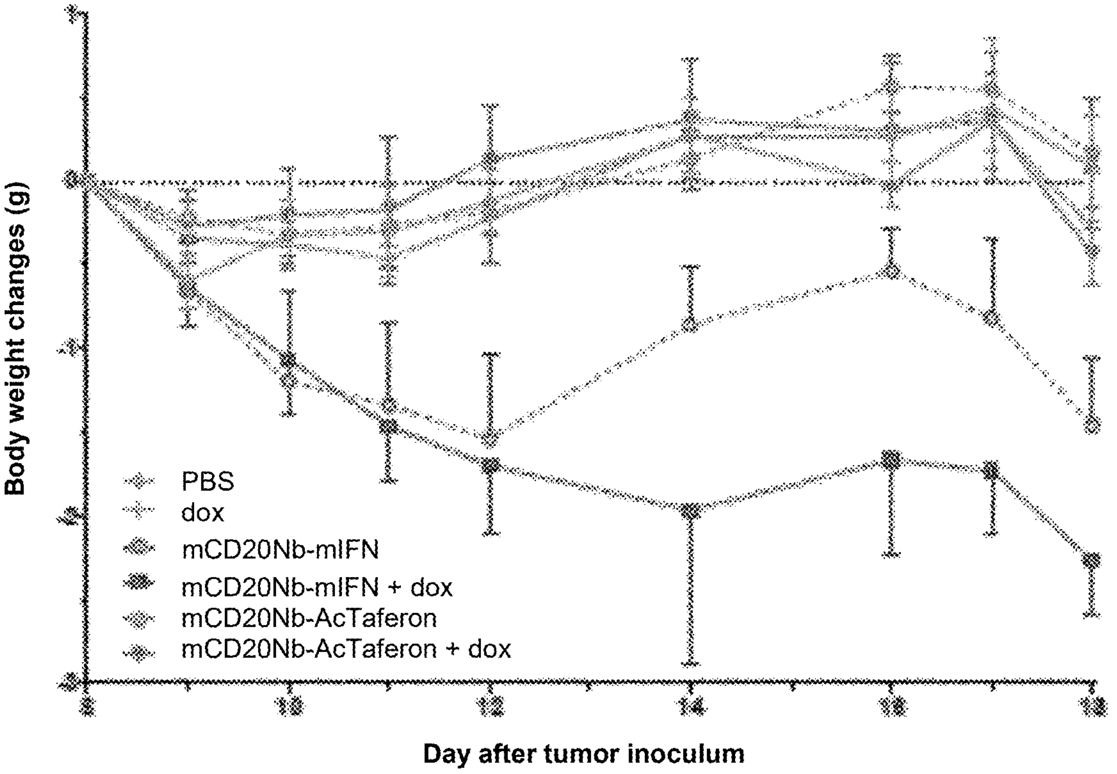
FIG. 15 shows that the anti-tumor potential of chimeric CD20 VHHs in combination with doxorubicin as shown in FIG. 14 does not cause concomitant life-threatening side effects.
Figure 15:
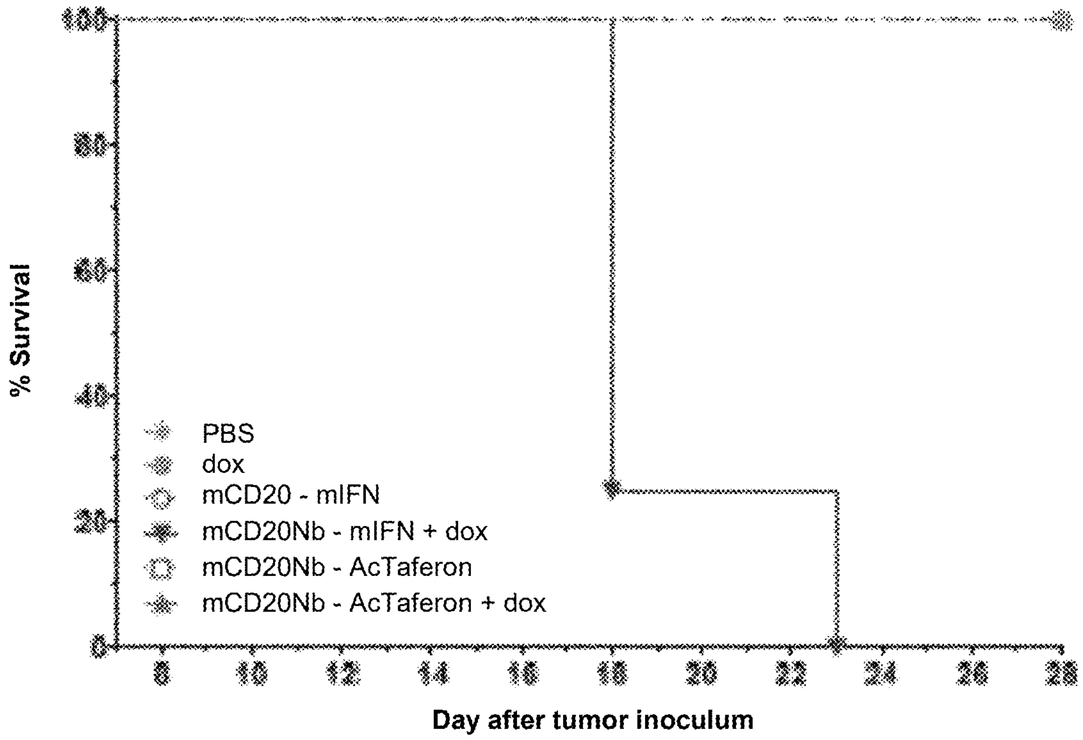
Figure 15:
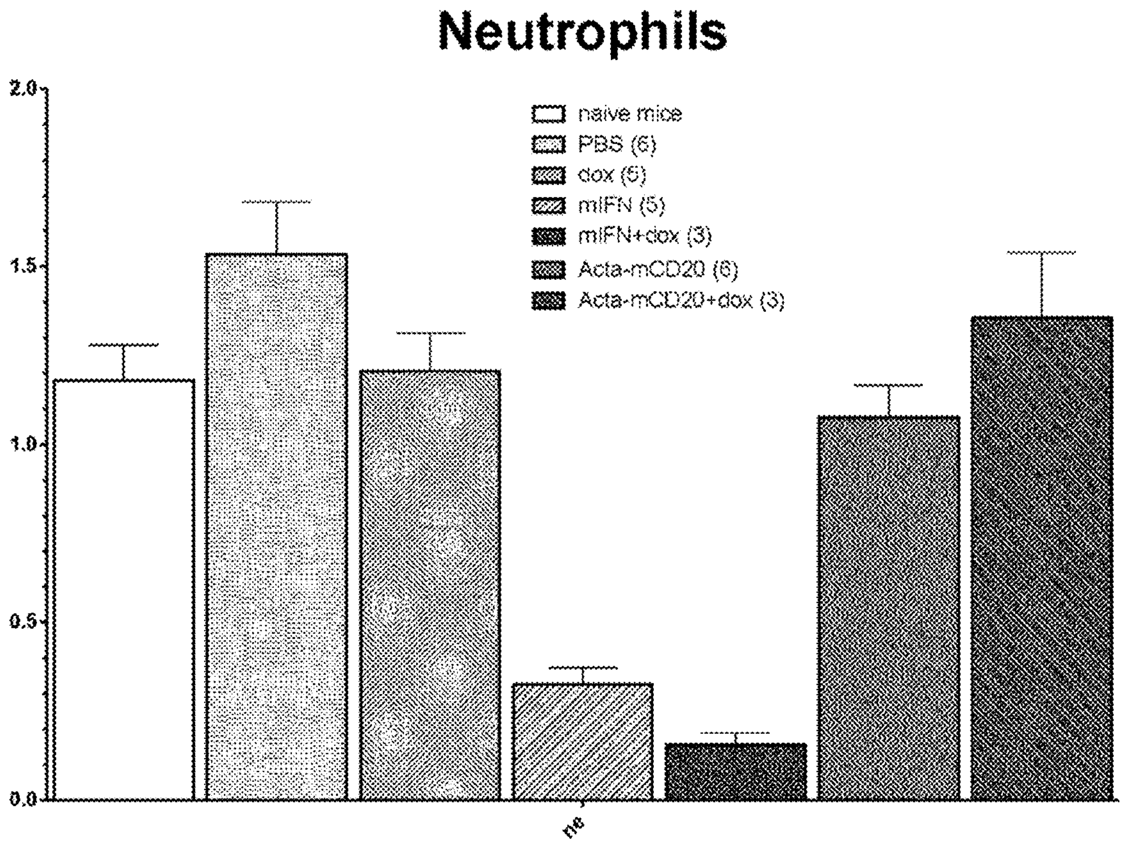
Figure 15:
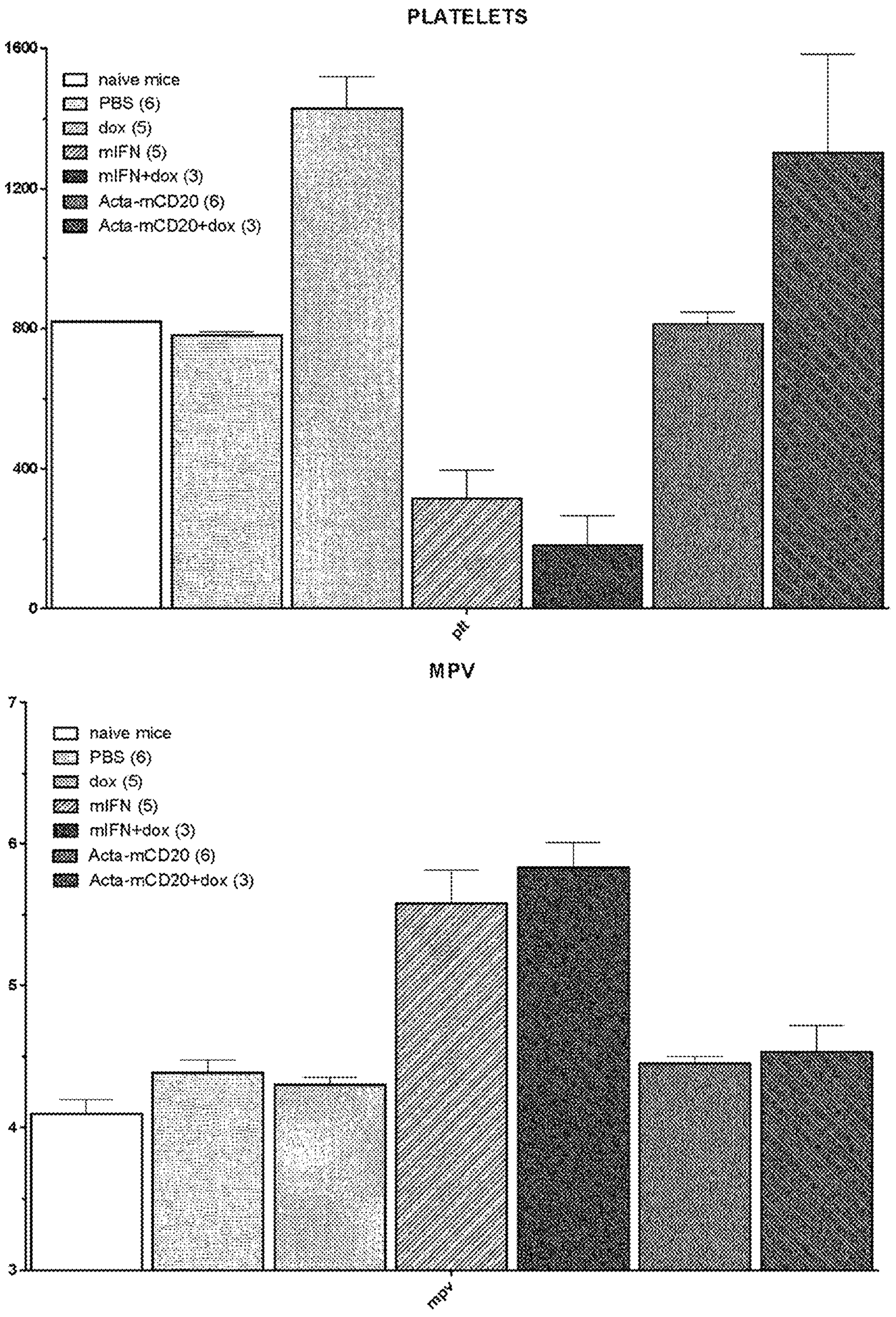

The combination of doxorubicin with the 2MC57 VHH fused to the mutant IFNα2-Q124R appeared to be particularly safe and effective. Specifically, combination treatment with doxorubicin worsened the morbidity and mortality associated with administration of wildtype IFN, but did not cause any side effects when used in combination with the 2MC57 VHH fused to the mutant IFNα2-Q124R as assessed by evolution of body weight, % survival and measurement of several blood parameters (FIG. 15).

Figure 16:
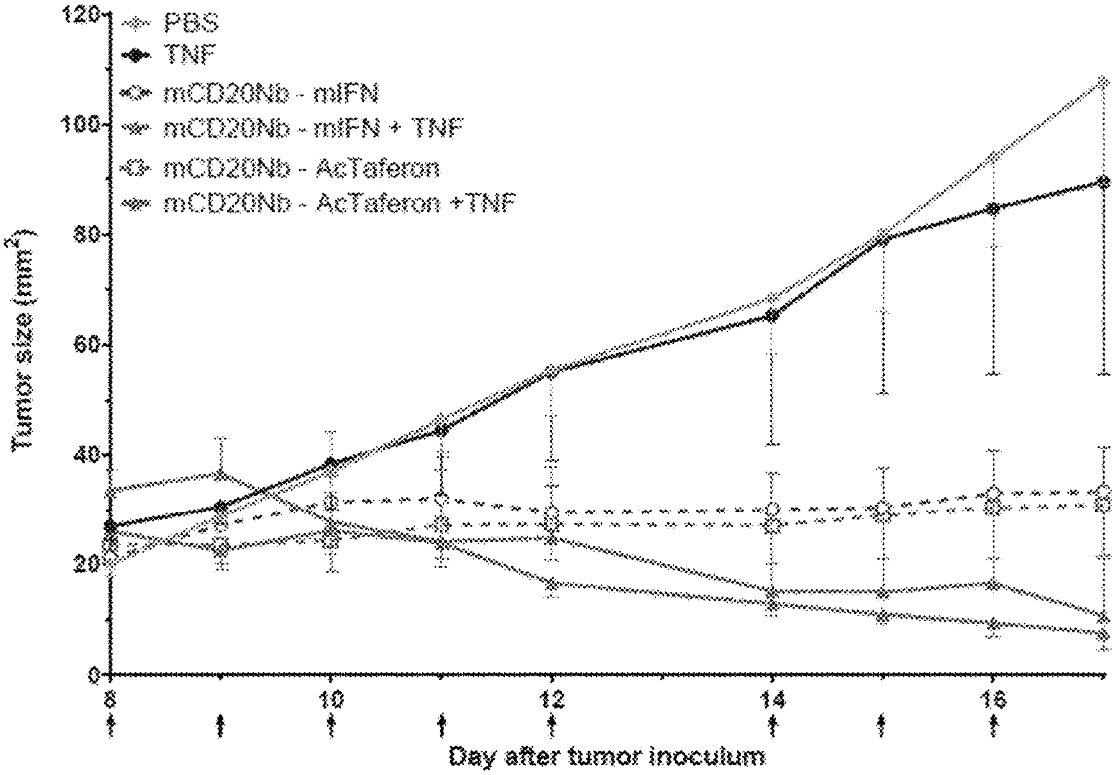
FIG. 16 shows the anti-tumor potential of chimeric CD20 VHHs in combination with tumor necrosis factor. Nb is the abbreviation of Nanobody and is used herein as equivalent to VHH.

Combination therapy using chimeric CD20 VHHs and Tumor Necrosis Factor in a B16 melanoma model The anti-tumor effects of a combination therapy using Tumor Necrosis Factor (TNF) and chimeric 2MC57 VHHs were tested. Mice were inoculated subcutaneously with B16-mCD20 cells (a mouse melanoma cell line that stably expresses mouse CD20) to induce tumors. The mice were subsequently given perilesional (=s.c. at the edge of the tumor) treatments with 2MC57 VHH (anti-mouse CD20) fused to wildtype IFN or the mutant IFNα2-Q124R (i.e., AcTaferon) with or without TNF. TNF was administered at 0.6 ug every 2 days. As shown in FIG. 16, combining 2MC57 VHHs with TNF significantly reduced tumor size compared with treatment using the 2MC57 VHHs without TNF.

Figure 17:
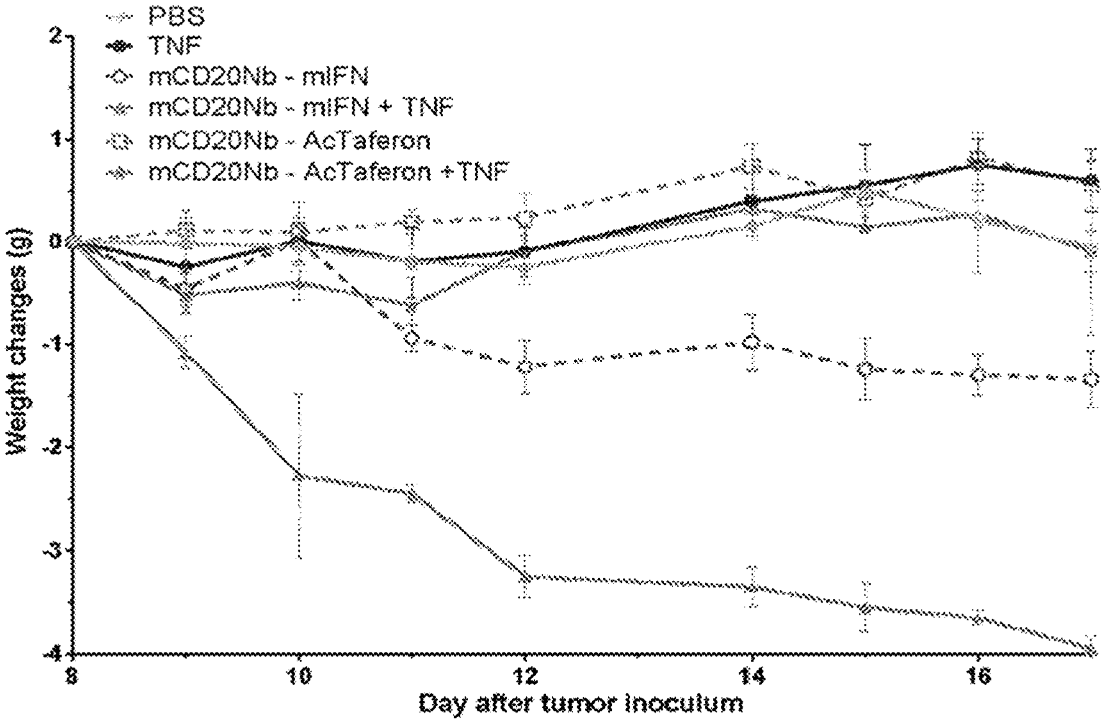
FIG. 17 shows that the anti-tumor potential of chimeric CD20 VHHs in combination with tumor necrosis factor as shown in FIG. 16 does not cause concomitant life-threatening side effects. Nb is the abbreviation of Nanobody and is used herein as equivalent to VHH.
Figure 17:
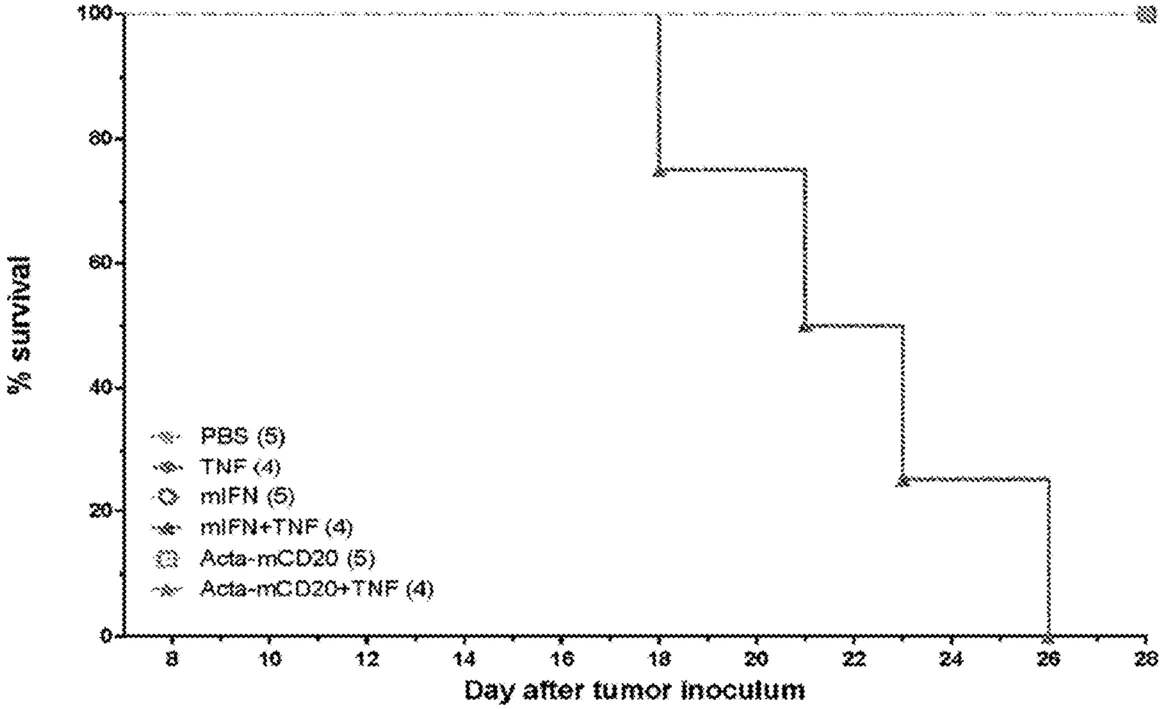
Figure 17:
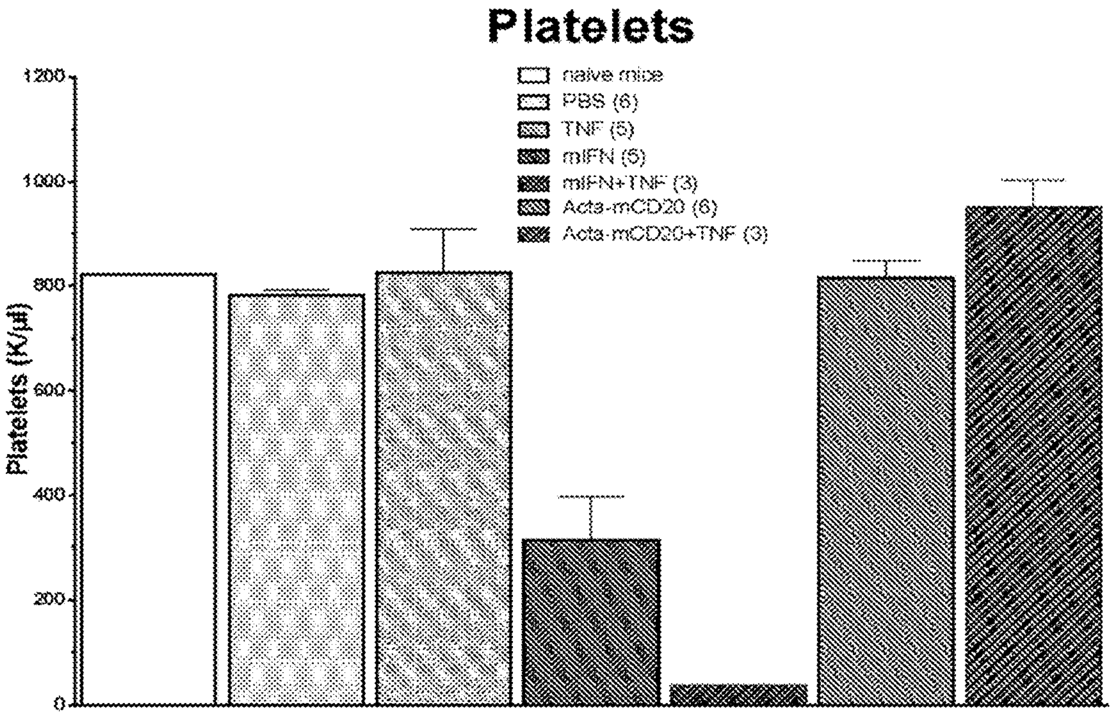
Figure 17:
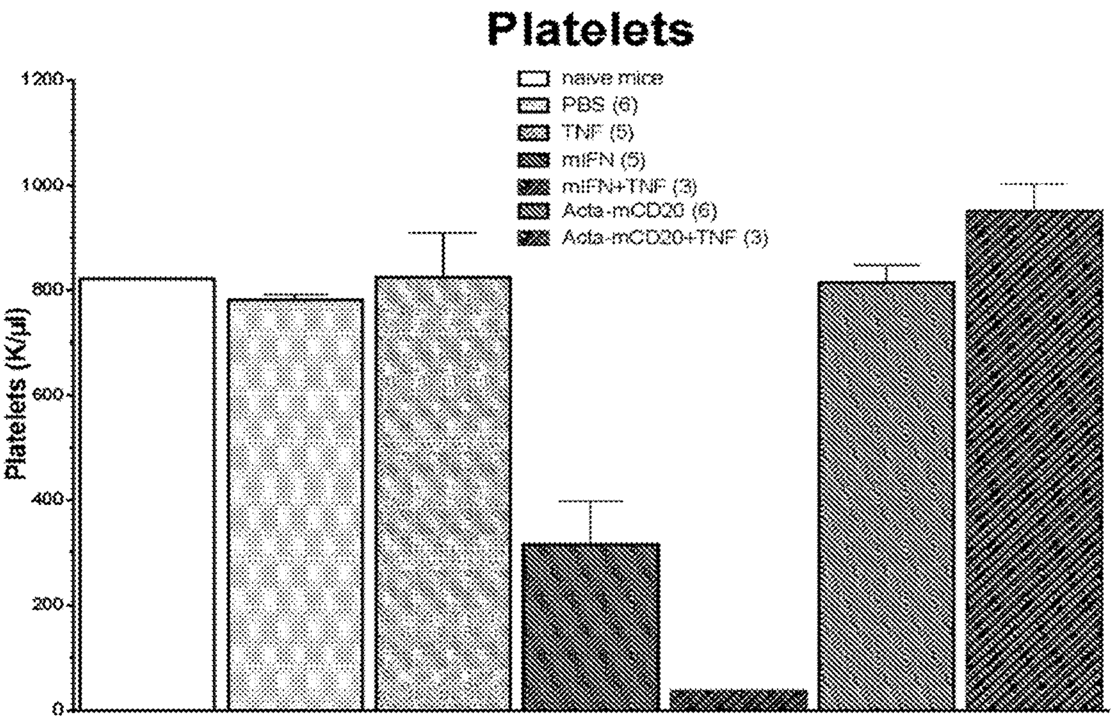

The combination of TNF with the 2MC57 VHH fused to the mutant IFNα2-Q124R appeared to be particularly safe and effective. Specifically, combination treatment with TNF worsened the thrombocytopenia and/or anemia as well as the mortality associated with administration of wildtype IFN, but did not cause any side effects when used in combination with the 2MC57 VHH fused to the mutant IFNα2-Q124R as assessed by evolution of body weight, % survival and measurement of several blood parameters (FIG. 17).

Figure 18:
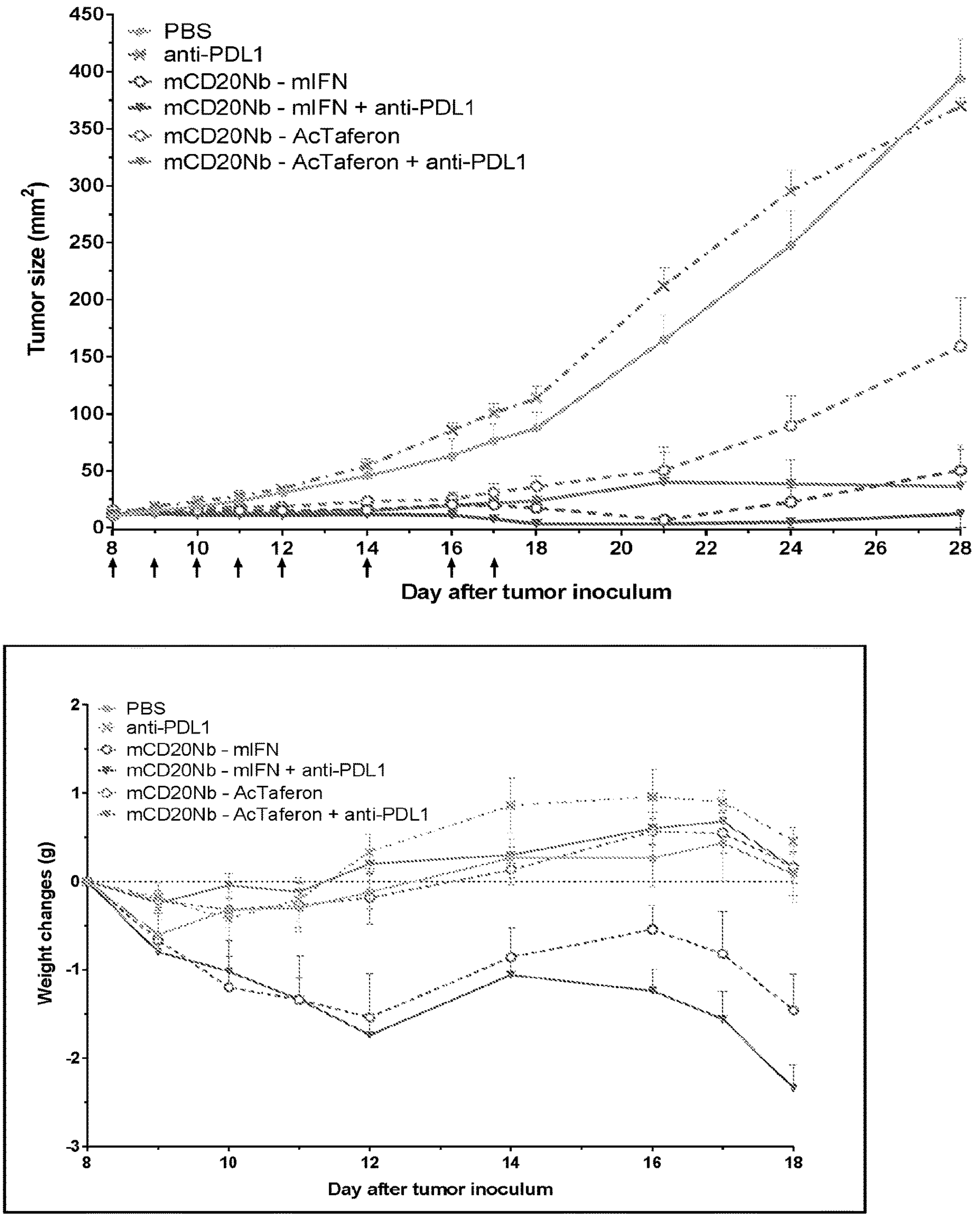
FIG. 18 shows the anti-tumor potential of chimeric CD20 VHHs in combination with anti-PD-L1 camelid VHH. Nb is the abbreviation of Nanobody and is used herein as equivalent to VHH.
Figure 19:
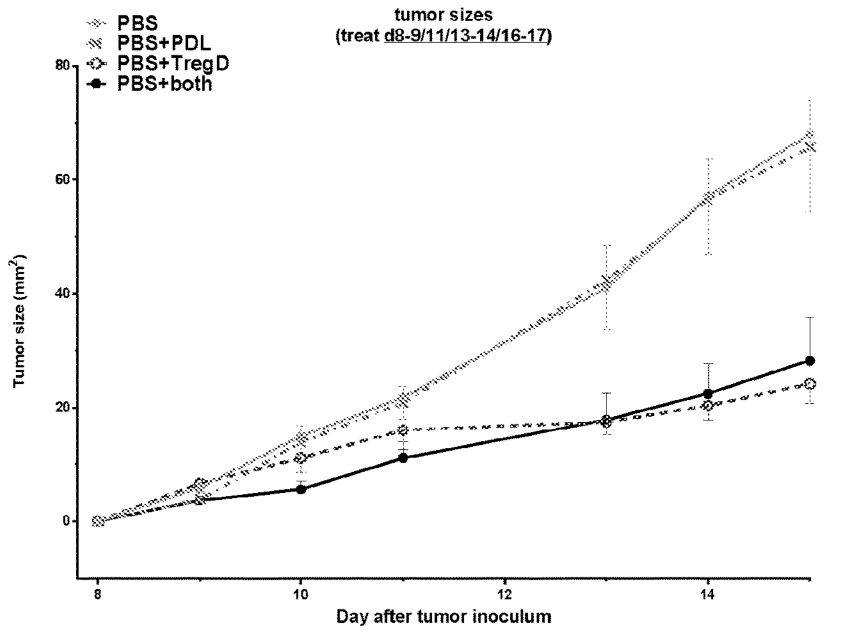
FIG. 19 shows the anti-tumor potential of chimeric CD20 VHHs in combination with anti-PD-L1 camelid VHH and Treg cell depletion.
Figure 19:
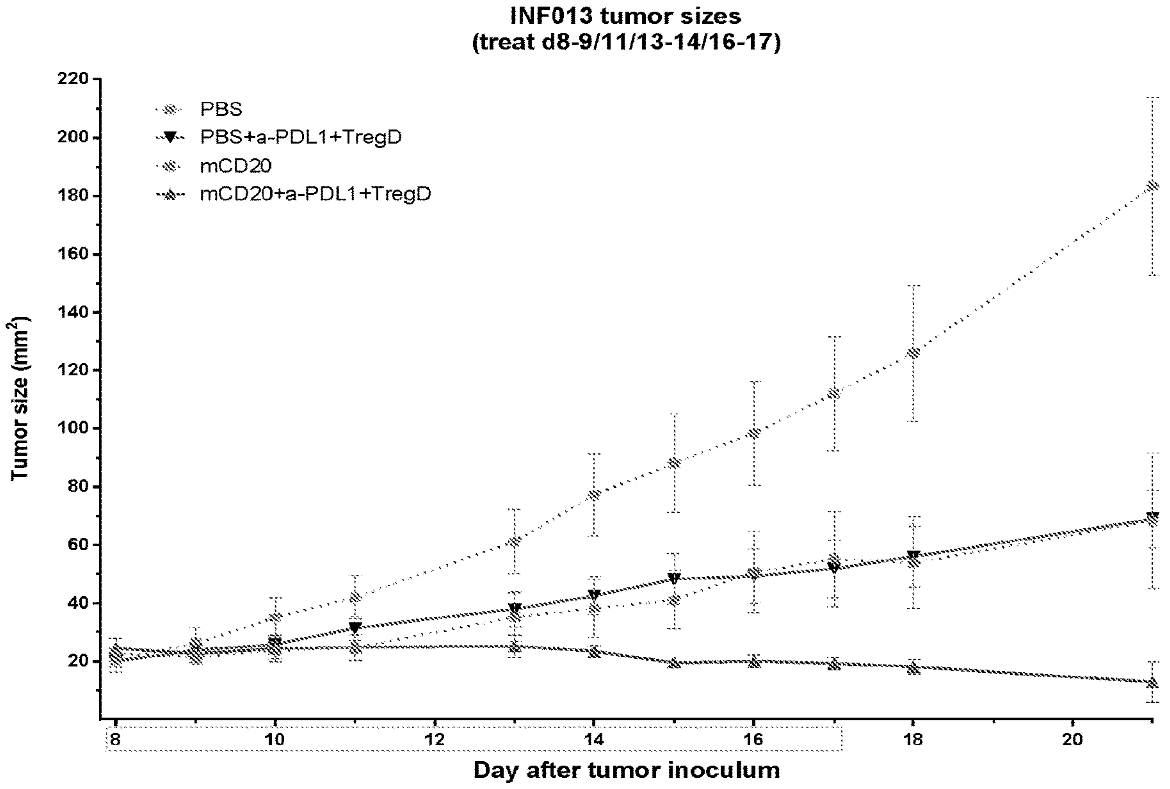
Figure 24:
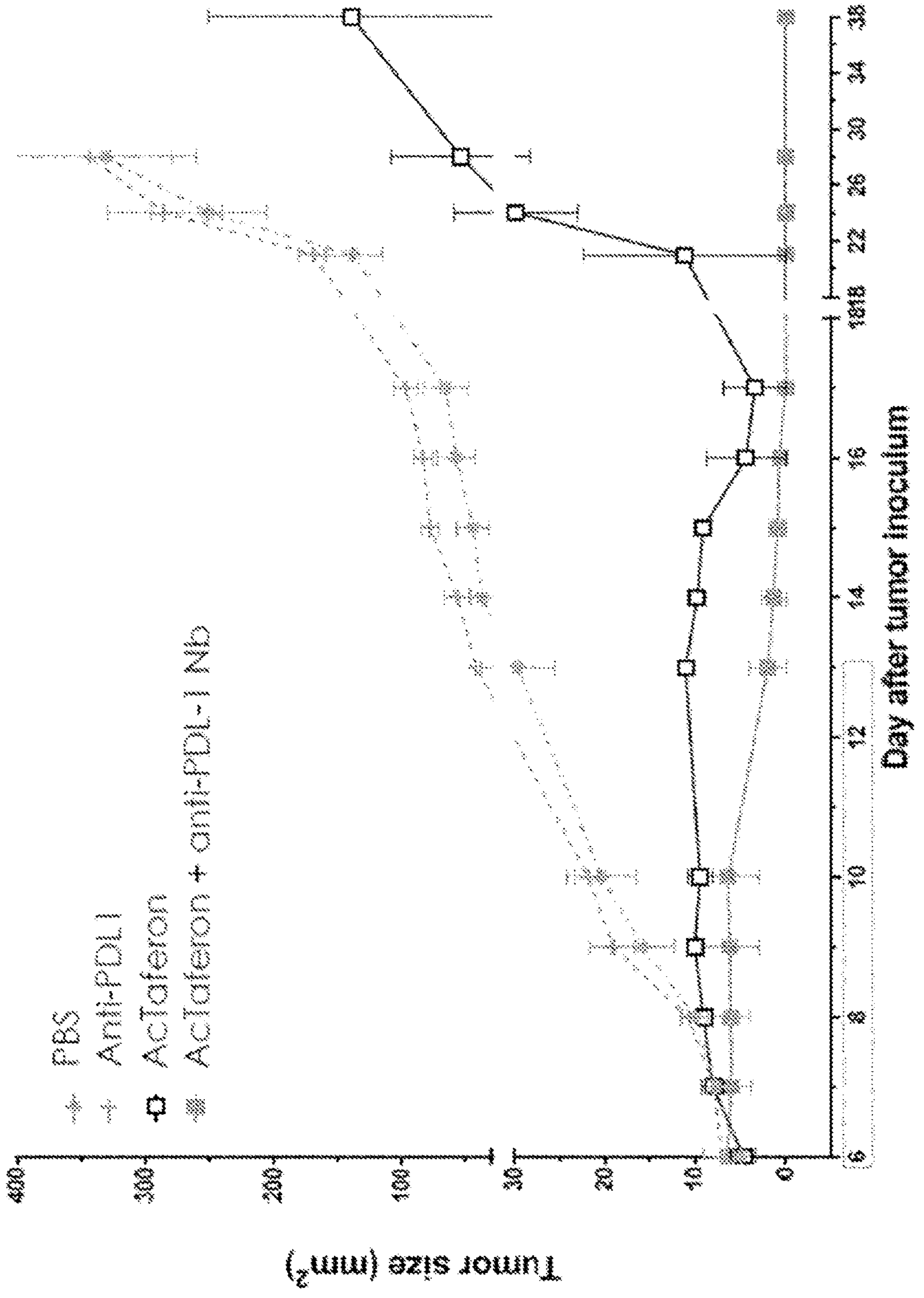
FIG. 24 shows the anti-tumor effect of chimeric CD20 VHHs fused to IFNα2 in combination with anti-PD-L1 camelid VHHs. The experiments were conducted as described in Example 4. Panel A supplements the data shown in FIG. 18, by demonstrating that combination treatment using a chimeric CD20 VHH (i.e., AcTaferon: 2MC57 VHH fused to the mutant IFNα2-Q124R) and an anti-PD-L1 camelid VHH exhibited potent anti-tumor activity with no tumor recurrence by day 38 (or 23 days post-dosing). Panel B shows that the combination treatment was well tolerated with no significant weight loss compared to treatment with wildtype IFN. Nb is the abbreviation of Nanobody and is used herein as equivalent to VHH.
Figure 24:
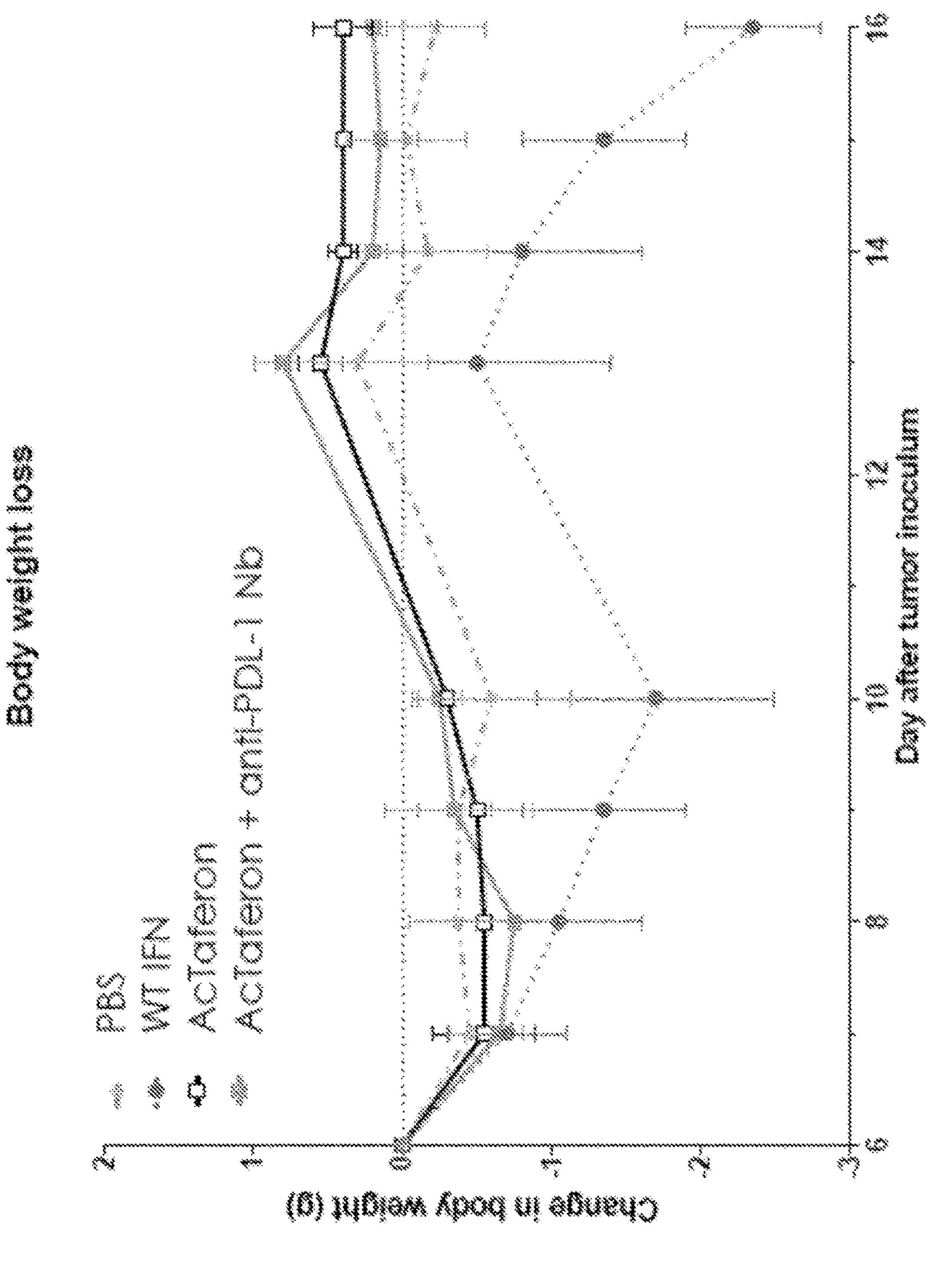

Combination Therapy Using Chimeric CD20 VHHs and Anti-PD-L1 Camelid VHH in a B16 Melanoma Model The anti-tumor effects of a combination therapy using an anti-PD-L1 camelid VHH and chimeric 2MC57 VHHs were tested. Mice were inoculated subcutaneously with B16-mCD20 cells (a mouse melanoma cell line that stably expresses mouse CD20) to induce tumors. The mice were subsequently given perilesional (=s.c. at the edge of the tumor) treatments with 2MC57 VHH (anti-mouse CD20) fused to wildtype IFN or the mutant IFNα2-Q124R (i.e., AcTaferon) with or without an anti-PD-L1 camelid VHH. The anti-PD-L1 camelid VHH was administered at 120 ug every 2 days. As shown in FIG. 18, the anti-PD-L1 camelid VHH provided a prolonged stasis effect for the 2MC57 VHH fused to the mutant IFNα2-Q124R. In addition, the combination of anti-PD-L1 camelid VHH and the 2MC57 VHH fused to the mutant IFNα2-Q124R did not cause significant weight loss (FIG. 18). As shown in FIG. 24, panel A, combination treatment using the 2MC57 VHH fused to the mutant IFNα2-Q124R (i.e., AcTaferon) and anti-PD-L1 camelid VHH elicited potent anti-tumor effects with no tumor recurrence by day 38 compared to treatment with either agent alone. FIG. 24, panel B, further demonstrates that the combination treatment was well tolerated and induced no significant weight loss compared to treatment with wildtype IFN alone. Altogether these data suggests a synergistic effect for combination therapy using chimeric 2MC57 VHHs and anti-PD-L1 antibodies. The anti-tumor effects of an anti-PD-L1 camelid VHH and chimeric 2MC57 VHH combined with Treg depletion were tested in the B16-mCD20 melanoma model. As shown in FIG. 19, the triple combination of administering the 2MC57 VHH fused to the mutant IFNα2-Q124R, anti-PD-L1 camelid VHH, and Treg depletion further reduced tumor size.

Systemic Administration of Chimeric CD20 VHHs in a B16 Melanoma Model

Figure 20:
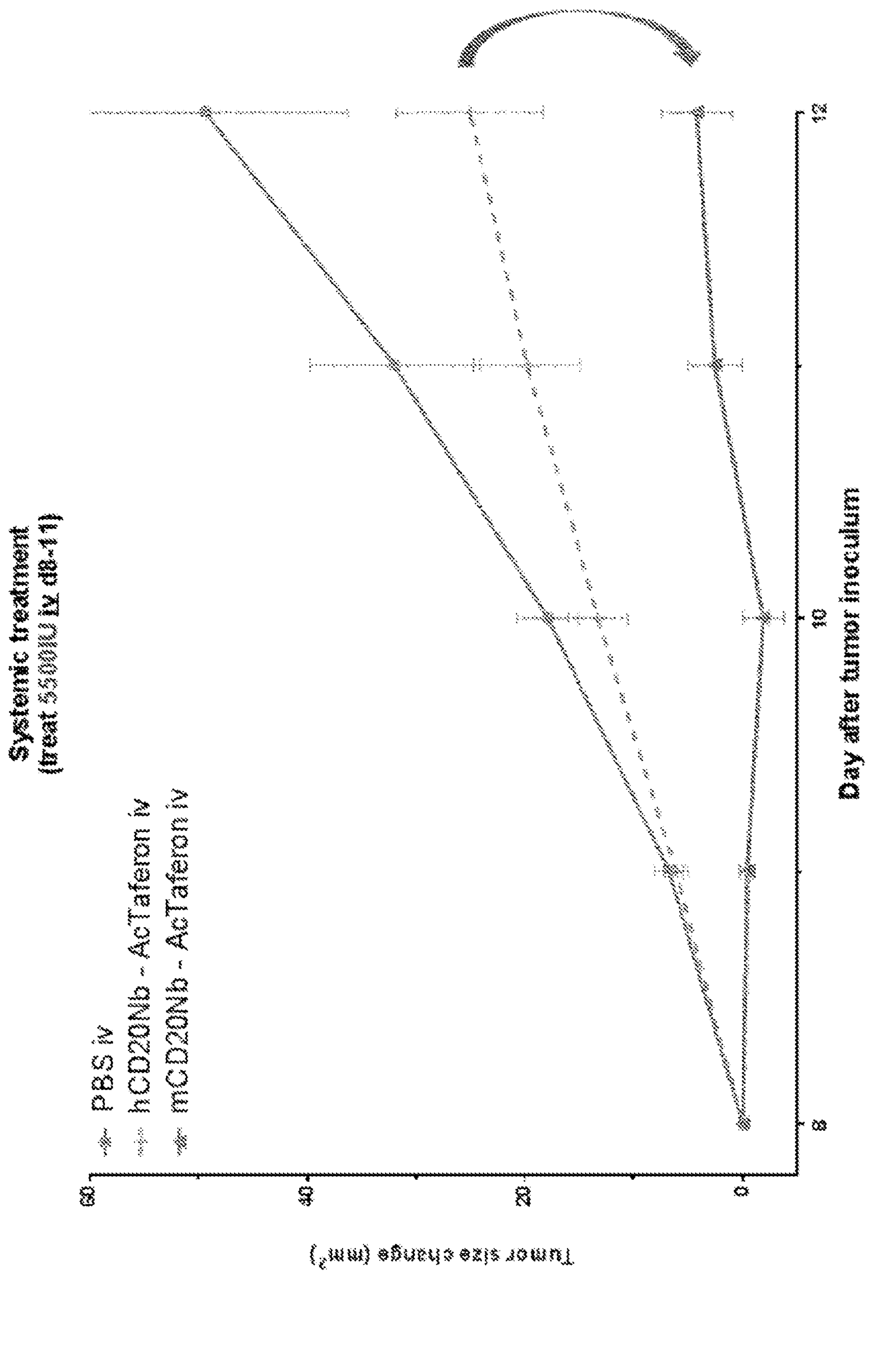
FIG. 20 shows the anti-tumor potential of systemically administered chimeric CD20 VHHs in a B16 melanoma model. Nb is the abbreviation of Nanobody and is used herein as equivalent to VHH.

The efficacy of systemically administered chimeric CD20 VHHs was tested in the B16-mCD20 melanoma model. Specifically, mice were given intravenous injections of the 2MC57 VHH (anti-mouse CD20) fused to the mutant IFNα2-Q124R (i.e., AcTaferon) or the 2HCD25 VHH (anti-human CD20) fused to the mutant IFNα2-Q124R. The chimeric VHHs were i.v. injected at a dose of 5,500 IU at days 8-11 after tumor inoculum. As shown in FIG. 20, systemic administration of the chimeric antibodies resulted in significant reduction in tumor growth with the chimeric 2MC57 VHH being more potent.

Role of B Cell Depletion in the Anti-Tumor Effect of Chimeric CD20 VHHs

Figure 21:
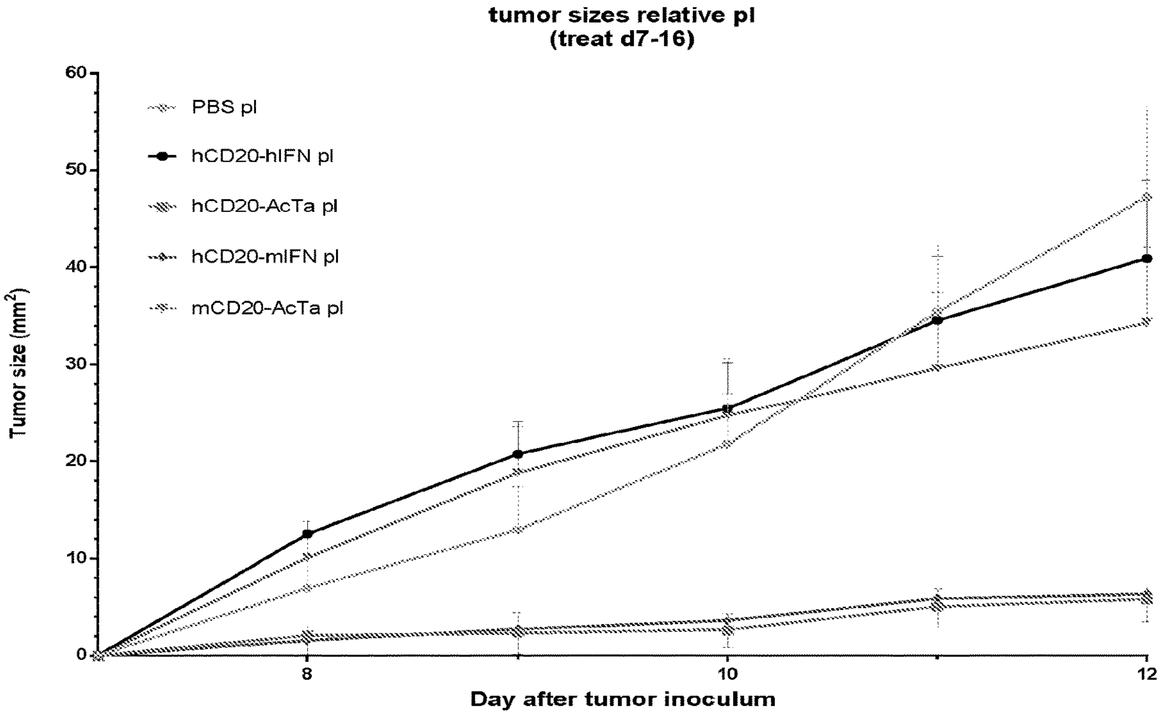
FIG. 21 shows that the anti-tumor effect of chimeric CD20 VHHs fused to a mutant interferon (i.e., hCD20-AcTa) does not require B cell depletion.
Figure 21:
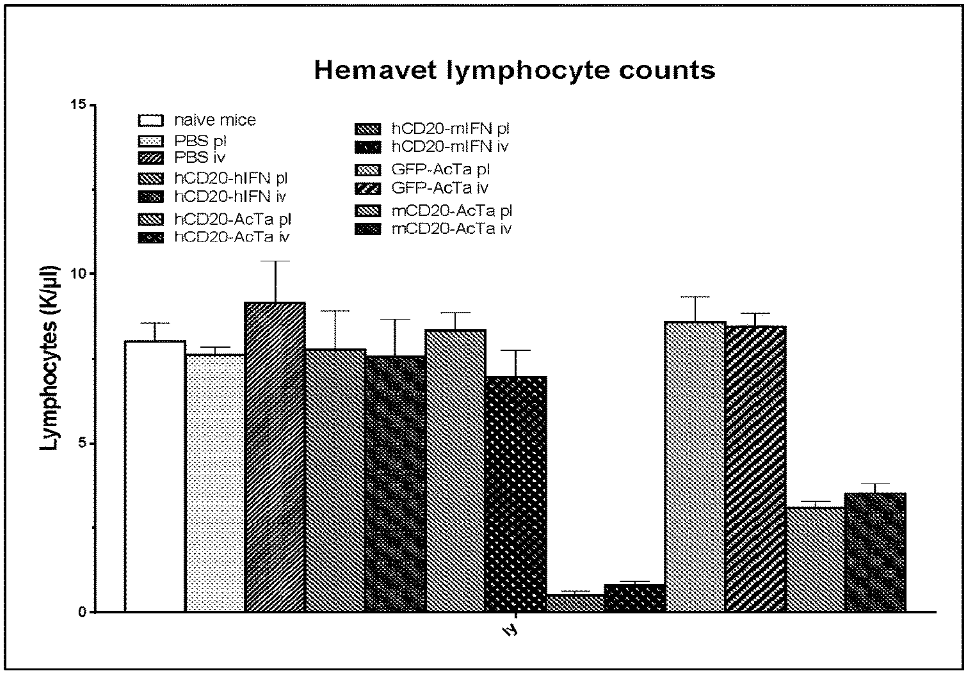

Mice were transplanted with B16-hCD20 cells (a mouse melanoma cell line that stably expresses human CD20) to induce tumors. To determine the in vivo anti-tumor effects of chimeric CD20 VHHs, mice were given perilesional (=s.c. at the edge of the tumor) treatments with 2HCD25 VHH (anti-human CD20) fused to wildtype human IFN, mouse IFN, or the mutant IFNα2-Q124R (i.e., AcTaferon). The mice were also given the 2MC57 VHH (anti-mouse CD20) fused to mutant IFNα2-Q124R. Tumor growth was monitored. As shown in FIG. 21, the chimeric 2HCD25 VHH fused to either mouse IFN or the mutant IFNα2-Q124R resulted in significant tumor reduction. However, as shown in the inset, the chimeric 2HCD25 VHH fused to the mutant IFNα2-Q124R did not appear to reduce lymphocyte numbers suggesting that B cell depletion was not required for the anti-tumor effects of the chimeric 2HCD25 VHH fused to the mutant IFNα2-Q124R.

Figure 22:
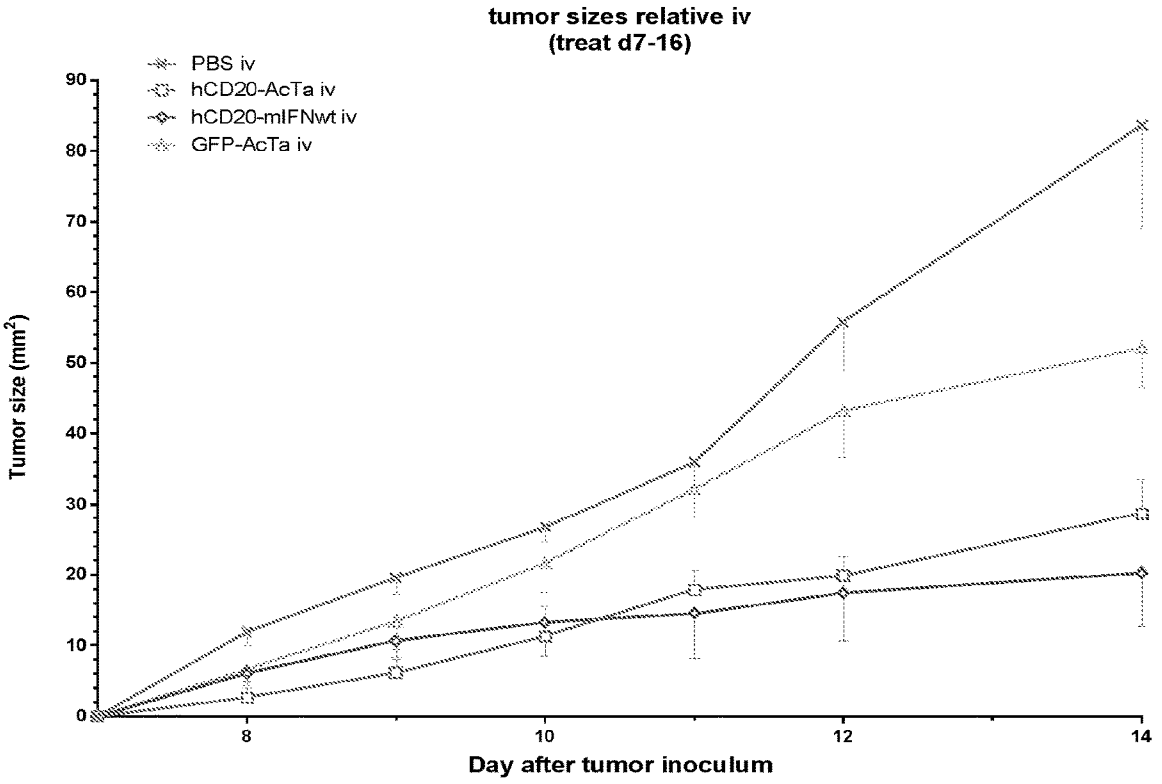
FIG. 22 shows that the anti-tumor effect of chimeric CD20 VHHs fused to a mutant interferon (i.e., hCD20-AcTa) does not require B cell depletion.

Similar study was performed with the mice being treated with the chimeric CD20 antibodies systemically by i.v. Consistent with the previous results, the chimeric 2HCD25 VHH fused to either mouse IFN or the mutant IFNα2-Q124R resulted in significant tumor reduction (FIG. 22). Given that the chimeric 2HCD25 VHH fused to the mutant IFNα2-Q124R did not appear to reduce lymphocyte numbers (FIG. 21), this result suggested that B cell depletion was not required for the anti-tumor effects of the chimeric 2HCD25 VHH fused to the mutant IFNα2-Q124R.

Efficacy of Chimeric CD20 VHHs in a Mouse Model of Multiple Sclerosis

Figure 23:
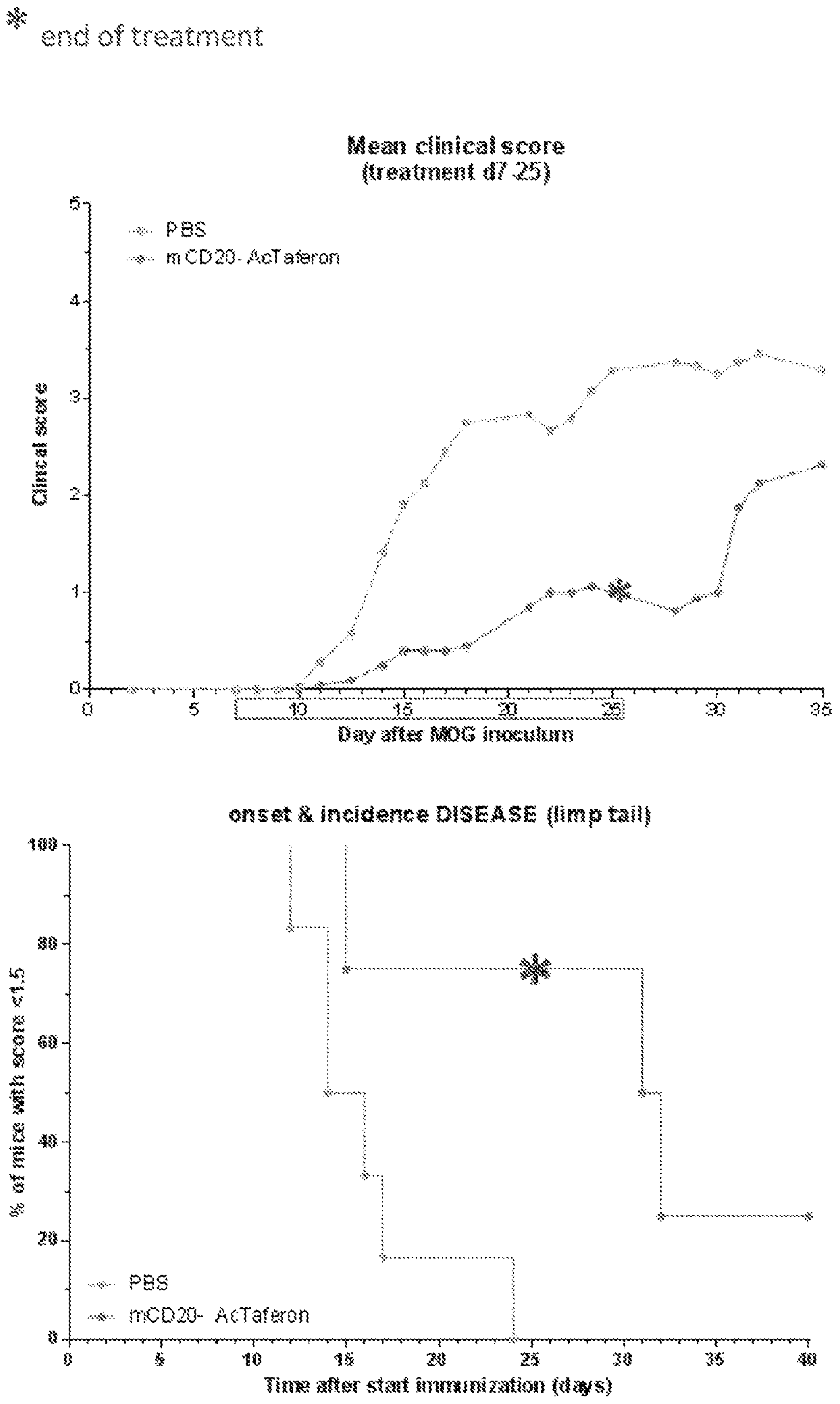
FIG. 23 shows the efficacy of chimeric CD20 VHHs using an experimental autoimmune encephalomyelitis (EAE) model.
Figure 23:
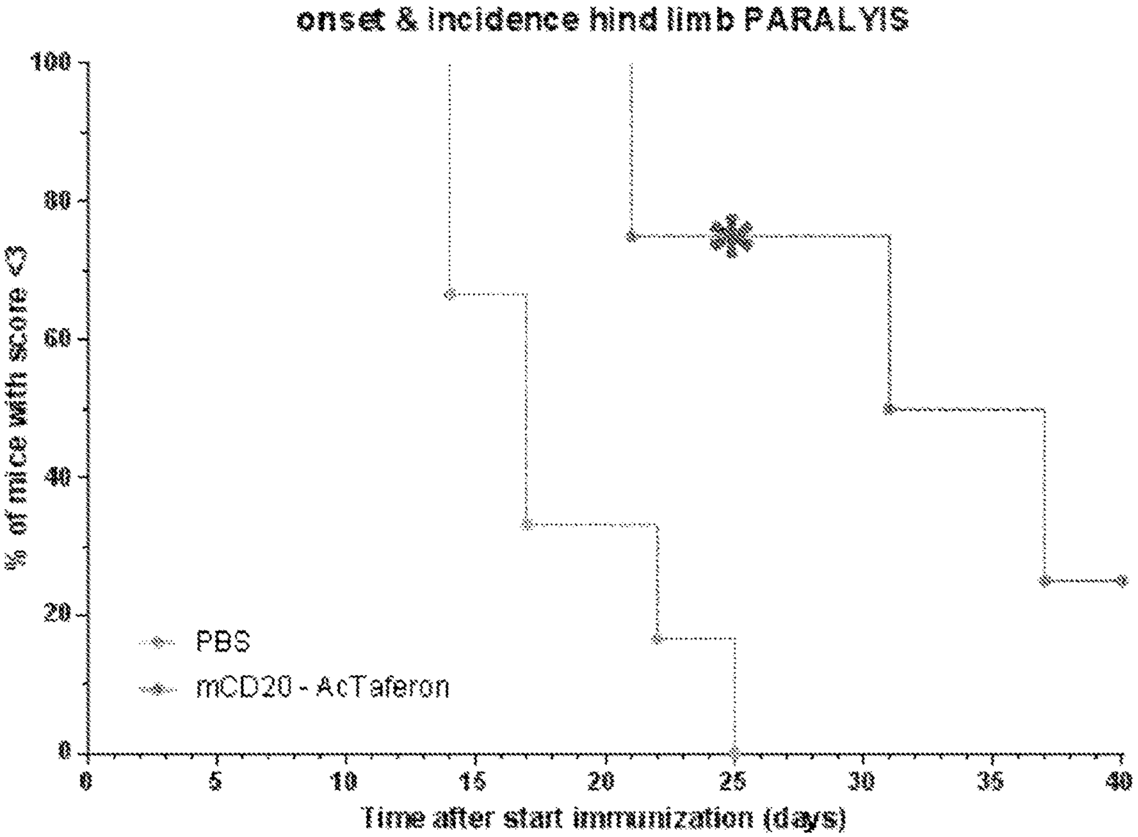

The efficacy of the chimeric CD20 VHHs in treating multiple sclerosis was tested using an established mouse experimental autoimmune encephalomyelitis (EAE) model. Specifically, the mice were administered peptides corresponding to the immunodominant epitopes of MOG ($MOG_{92-106}$) to induce inflammation of the brain and central nervous system (CNS) demyelination. The mice were also given the 2MC57 VHH (anti-mouse CD20) fused to the mutant IFNα2-Q124R from days 7-25 by i.p injection after administration of the MOG peptides. As shown in FIG. 23, the 2MC57 VHH (anti-mouse CD20) fused to the mutant IFNα2-Q124R significantly improved clinical scores and delayed the onset and incidence of the disease and symptoms such as paralysis. Together these results suggested that the chimeric CD20 VHHs of the application may have therapeutic efficacy in treating multiple sclerosis as well as other CNS demyelinating diseases in humans.

EQUIVALENTS

While the application has been described in connection with specific embodiments thereof, it will be understood that it is capable of further modifications and this application is intended to cover any variations, uses, or adaptations of the application following, in general, the principles of the application and including such departures from the present disclosure as come within known or customary practice within the art to which the application pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present application is not entitled to antedate such publication by virtue of prior application.

As used herein, all headings are simply for organization and are not intended to limit the disclosure in any manner. The content of any individual section may be equally applicable to all sections.

REFERENCES

Alduaij W, Illidge T M (2011) The future of anti-CD20 monoclonal antibodies: are we making progress? Blood 117: 2993-3001

Alduaij W, Ivanov A, Honeychurch J, Cheadle E J, Potluri S, Lim S H, Shimada K, Chan C H T, Tutt A, Beers S A, Glennie M J, Cragg M S, Illidge T M (2011) Novel type II anti-CD20 monoclonal antibody (GA101) evokes homotypic adhesion and actin-dependent, lysosome-mediated cell death in B-cell malignancies. Blood 117: 4519-4529

Cang S D, Muhki N, Wang K M, Liu D L (2012) Novel CD20 monclonal antibodies for lymphoma therapy. Journal of Hematology & Oncology 5: 64

Cragg M S, Morgan S M, Chan H T C, Morgan B P, Filatov A V, Johnson P W M, French R R, Glennie M J (2003) Complement-mediated lysis by anti-CD20 mAb correlates with segregation into lipid rafts. Blood 101: 1045-1052

Dolk E, van Vliet C, Perez J M J, Vriend G, Darbon H, Ferrat G, Cambillau C, Frenken L G J, Verrips T (2005) Induced refolding of a temperature denatured llama heavy-chain antibody fragment by its antigen. Proteins—Structure, Function and Bioinformatics 59: 555-564

Einfield D A, Brown J P, Valentine M A, Clark E A, Ledbetter J A (1988) Molecular cloning of the human B-cell CD20 receptor predicts a hydrophobic protein with multiple transmembrane domains. EMBO Journal 7: 771

Glennie M J, French R R, Cragg M S, Talyor R P (2007) Mechanisms of killing by anti-CD20 monoclonal antibodies. Molecular Immunology 44: 3823-3837

Hamers-Casterman C, Atarhouch T, Muyldermans S, Robinson G, Hamers C, Songa E B, Bendahman N, Hamers R (1993) Naturally occurring antibodies devoid of light chains. Nature 363, 446-448

Harmsen M M and De Haard H J (2007) Properties, production, and applications of camelid single-domain antibody fragments. Applied Microbiology and Biotechnology 77: 13-22

Ishibashi K, Suzuki M, Sasaki S, Imai M (2001) Identification of a new multigene four-transmembrane family (MS4A) related to CD20, HTm4 and beta subunit of the high-affinity IgE receptor. Gene 264: 87-93

Lim S H, Beers S A, French R R, Johnson P W, Gelnnie M J, Cragg M S (2010) Anti-CD20 monoclonal antibodies: historical and future perspectives. Haematologica 95: 135-143

Muyldermans S (2013) Nanobodies: natural single-domain antibodies. Annual Review of Biochemistry 82: 775-779

Muyldermans S, Atarhouch T, Saldanha J, Barbosa J A, Hamers R (1994) Sequence and structure of V H domain from naturally occurring camel heavy chain immunoglobulins lacking light chains. Protein Engineering 7: 1129-1135

Niederfellner G, Lammens A, Mundigl O, Georges G J, Schaefer W, Schwaiger M, Franke A, Wiechmann K, Jenewein S, Slootstra J W, Timmerman P, Brannström A, Lindstrom F, Mössner E, Umana P, Hopfner K P, Klein C (2011) Epitope characterization and crystal structure of GA101 provide insights into the molecular basis for type I/II distinction of CD20 antibodies. Blood 118: 358-367

Oettgen H C, Bayard P J, Van Ewijk W, Nadler L M, Terhorst C P (1983) Further biochemical studies of the human B-cell differentiation antigens B1 and B2. Hybridoma 2: 17-28

O' Keefe T L, Williams G T, Davies S L, Neuberger M S (1998) Mice carrying CD20 gene disruption. Immunogenetics 48: 125-132

Robak T, Robak E. (2011) New anti-CD20 monoclonal antibodies for the treatment of B-cell lymphoid malignancies. Biodrugs 25: 13-25

Smith, M R (2003) Rituximab (monoclonal anti-CD20 antibody): mechanisms of action and resistance. Oncogene 22: 7359-7368

Stashenko P, Nadler L M, Hardy R, Schlossman S F (1980) Characterization of a human lymphocyte-B-specific antigen. Journal of Immunology 125: 1678-1685

Stashenko P, Nadler L M, Hardy R, Schlossman S F (1981) Expression of cell surface markers after human B lymphocyte activation. Proceedings of the National Academy of Sciences of the Unites States of America 78: 3848-3852

Townsend M J, Monroe J G, Chan A C (2010) B-cell targeted therapies in human autoimmune diseases: an updated perspective. Immunological Reviews 237: 264-283

Uchida J, Lee Y, Hasegawa M, Liang Y, Bradney A, Oliver J A, Bowen K, Steeber D A, Haas K M, Poe J C, Tedder T F (2004) Mouse CD20 expression and function. International Immunology 16: 119-129

Van Meerten T, Hagenbeek A (2010) CD20-targeted therapy: the next generation of antibodies. Seminars in Hematology 47: 199-210

Wesolowski J, Alzogaray V, Reyelt J, Unger M, Juarez K, Urrutia M, Cauerhff a, Danquah W, Rissiek B, Schueplein F, Schwarz N, Adriouch S, Boyer O, Seman M, Licea A, Serreze D V, Goldbaum F A, Haag F, Koch-Nolte F (2009) Single domain antibodies: promising experimental and therapeutic tools in infection and immunity. Medical Microbiology and Immunology 198: 157-174

What is claimed is:

1. A CD20 binding agent comprising at least one targeting moiety comprising a single-domain antibody comprising three complementarity determining regions (CDR1, CDR2, and CDR3), wherein:

(a) CDR1 comprises the amino acid sequence of SEQ ID NO: 35, CDR2 comprises the amino acid sequence of SEQ ID NO: 46, and CDR3 comprises the amino acid sequence of SEQ ID NO: 56;

(b) CDR1 comprises the amino acid sequence of SEQ ID NO: 35, CDR2 comprises the amino acid sequence of SEQ ID NO: 47, and CDR3 comprises the amino acid sequence of SEQ ID NO: 56;

(c) CDR1 comprises the amino acid sequence of SEQ ID NO: 36, CDR2 comprises the amino acid sequence of SEQ ID NO: 46, and CDR3 comprises the amino acid sequence of SEQ ID NO: 56;

(d) CDR1 comprises the amino acid sequence of SEQ ID NO: 37, CDR2 comprises the amino acid sequence of SEQ ID NO: 46, and CDR3 comprises the amino acid sequence of SEQ ID NO: 56;

(e) CDR1 comprises the amino acid sequence of SEQ ID NO: 38, CDR2 comprises the amino acid sequence of SEQ ID NO: 48, and CDR3 comprises the amino acid sequence of SEQ ID NO: 57;

(f) CDR1 comprises the amino acid sequence of SEQ ID NO: 39, CDR2 comprises the amino acid sequence of SEQ ID NO: 49, and CDR3 comprises the amino acid sequence of SEQ ID NO: 58;

(g) CDR1 comprises the amino acid sequence of SEQ ID NO: 40, CDR2 comprises the amino acid sequence of SEQ ID NO: 50, and CDR3 comprises the amino acid sequence of SEQ ID NO: 59; or (h) CDR1 comprises the amino acid sequence of SEQ ID NO: 41, CDR2 comprises the amino acid sequence of SEQ ID NO: 50, and CDR3 comprises the amino acid sequence of SEQ ID NO: 60.

2. The CD20 binding agent of claim 1, wherein the single-domain antibody is a recombinant heavy-chain-only antibody or a shark heavy-chain-only antibody.

3. The CD20 binding agent of claim 2, wherein the recombinant heavy-chain-only antibody is a humanized recombinant heavy-chain-only antibody.

4. The CD20 binding agent of claim 1, wherein the targeting moiety comprises a CDR1 comprising the amino acid sequence of SEQ ID NO:35, a CDR2 comprising the amino acid sequence of SEQ ID NO:46, and a CDR3 comprising the amino acid sequence of SEQ ID NO:56.

5. The CD20 binding agent of claim 1, wherein the targeting moiety comprises a CDR1 comprising the amino acid sequence of SEQ ID NO:35, a CDR2 comprising the amino acid sequence of SEQ ID NO:47, and a CDR3 comprising the amino acid sequence of SEQ ID NO:56.

6. The CD20 binding agent of claim 1, wherein the targeting moiety comprises a CDR1 comprising the amino acid sequence of SEQ ID NO:36, a CDR2 comprising the amino acid sequence of SEQ ID NO:46, and a CDR3 comprising the amino acid sequence of SEQ ID NO:56.

7. The CD20 binding agent of claim 1, wherein the targeting moiety comprises a CDR1 comprising the amino acid sequence of SEQ ID NO:37, a CDR2 comprising the amino acid sequence of SEQ ID NO:46, and a CDR3 comprising the amino acid sequence of SEQ ID NO:56.

8. The CD20 binding agent of claim 1, wherein the targeting moiety comprises a CDR1 comprising the amino acid sequence of SEQ ID NO:38, a CDR2 comprising the amino acid sequence of SEQ ID NO:48, and a CDR3 comprising the amino acid sequence of SEQ ID NO:57.

9. The CD20 binding agent of claim 1, wherein the targeting moiety comprises a CDR1 comprising the amino acid sequence of SEQ ID NO:39, a CDR2 comprising the amino acid sequence of SEQ ID NO:49, and a CDR3 comprising the amino acid sequence of SEQ ID NO:58.

10. The CD20 binding agent of claim 1, wherein the targeting moiety comprises a CDR1 comprising the amino acid sequence of SEQ ID NO:40, a CDR2 comprising the amino acid sequence of SEQ ID NO:50, and a CDR3 comprising the amino acid sequence of SEQ ID NO:59.

11. The CD20 binding agent of claim 1, wherein the targeting moiety comprises a CDR1 comprising the amino acid sequence of SEQ ID NO:41, a CDR2 comprising the amino acid sequence of SEQ ID NO:50, and a CDR3 comprising the amino acid sequence of SEQ ID NO:60.

12. The CD20 binding agent of claim 1, comprising an amino acid sequence having at least 90% identity to any one of SEQ ID NOs: 18-26, minus the linker sequence, the HA tag, and/or the $His_6$ tag.

13. The CD20 binding agent of claim 12, comprising the amino acid sequence of any one of SEQ ID NOs: 18-26, minus the linker sequence, the HA tag, and/or the $His_6$ tag.

14. The CD20 binding agent of claim 1, wherein the CD20 binding agent further comprises one or more signaling agents.

15. The CD20 binding agent of claim 14, wherein the one or more signaling agents is selected from the group consisting of an interferon, an interleukin, and a tumor necrosis factor, and a mutated form thereof.

16. The CD20 binding agent of claim 1, wherein the CD20 binding agent further comprises one or more additional targeting moieties.

* * * * *